US012698489B2

(12) United States Patent
Burleigh et al.

(10) Patent No.: US 12,698,489 B2
(45) Date of Patent: Aug. 4, 2026

(54) METHODS, COMPOSITIONS AND COMPONENTS FOR CRISPR-CAS9 EDITING OF TGFBR2 IN T CELLS FOR IMMUNOTHERAPY

(71) Applicants: EDITAS MEDICINE, INC., Cambridge, MA (US); JUNO THERAPEUTICS, INC., Seattle, WA (US)

(72) Inventors: Stephen Michael Burleigh, Seattle, WA (US); Melissa Chin, Cambridge, MA (US); Fred Harbinski, Cambridge, MA (US); Christopher Heath Nye, Seattle, WA (US); Blythe D. Sather, Seattle, WA (US); Queenie Vong, Seattle, WA (US); Gordon Grant Welstead, Cambridge, MA (US); Chris Wilson, Cambridge, MA (US)

(73) Assignees: EDITAS MEDICINE, INC., Cambridge, MA (US); JUNO THERAPEUTICS, INC., Seattle, WA (US)

( * ) Notice: Subject to any disclaimer, the term of this patent is extended or adjusted under 35 U.S.C. 154(b) by 1624 days.

(21) Appl. No.: 16/758,842

(22) PCT Filed: Nov. 1, 2018

(86) PCT No.: PCT/US2018/058635

§ 371 (c)(1),
(2) Date: Apr. 23, 2020

(87) PCT Pub. No.: WO2019/089884

PCT Pub. Date: May 9, 2019

(65) Prior Publication Data

US 2023/0061455 A1 Mar. 2, 2023

Related U.S. Application Data

(60) Provisional application No. 62/580,320, filed on Nov. 1, 2017.

(51) Int. Cl.

| | |
|---|---|
| ***C12N 9/22*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C12N 15/10*** | (2006.01) |

(52) U.S. Cl.

CPC ................ *C12N 9/22* (2013.01); *A61K 40/11* (2025.01); *A61K 40/31* (2025.01); *A61K 40/4215* (2025.01); *A61P 35/00* (2018.01); *C12N 15/102* (2013.01); *A61K 2239/38* (2023.05); *A61K 2239/48* (2023.05); *C07K 2319/03* (2013.01); *C12N 2310/20* (2017.05)

(58) Field of Classification Search

CPC ... C12N 2310/20; C12N 9/22; C07K 2319/03
See application file for complete search history.

(56) References Cited

U.S. PATENT DOCUMENTS

| | | | | |
|---|---|---|---|---|
| 4,690,915 | A | 9/1987 | Erkens | |
| 5,087,616 | A | 2/1992 | Myers et al. | |
| 5,219,740 | A | 6/1993 | Miller et al. | |
| 6,040,177 | A | 3/2000 | Riddell et al. | |
| 6,207,453 | B1 | 3/2001 | Maass et al. | |
| 6,410,319 | B1 | 6/2002 | Raubitschek et al. | |
| 6,451,995 | B1 | 9/2002 | Cheung et al. | |
| 7,070,995 | B2 | 7/2006 | Jensen | |
| 7,265,209 | B2 | 9/2007 | Jensen | |
| 7,354,762 | B2 | 4/2008 | Jensen | |
| 7,446,179 | B2 | 11/2008 | Jensen et al. | |
| 7,446,190 | B2 | 11/2008 | Sadelain et al. | |
| 7,446,191 | B2 | 11/2008 | Jensen | |
| 7,569,664 | B2 | 8/2009 | Jakobsen et al. | |
| 8,324,353 | B2 | 12/2012 | Jensen | |
| 8,389,282 | B2 | 3/2013 | Sadelain et al. | |
| 8,911,993 | B2 | 12/2014 | June et al. | |
| 2002/0131960 | A1 | 9/2002 | Latouche et al. | |
| 2003/0170238 | A1 | 9/2003 | Chavan et al. | |
| 2013/0149337 | A1 | 6/2013 | Cooper et al. | |
| 2013/0287748 | A1 | 10/2013 | June et al. | |
| 2014/0295556 | A1* | 10/2014 | Joung .................... | C12N 15/11 435/254.2 |

(Continued)

FOREIGN PATENT DOCUMENTS

| | | | |
|---|---|---|---|
| EP | 2537416 | A1 | 12/2012 |
| WO | WO/1992/008796 | | 5/1992 |

(Continued)

OTHER PUBLICATIONS

Annunziato, Stefano, et al. "Rapid in vivo testing of tumor suppressors in ILC by CRISPR-Cas9 mediated somatic gene editing of the mammary gland." Cancer Research 76.14_Supplement (2016): 2687-2687. (Year: 2016).*
Clements, Thomas P., et al. "RICE CRISPR: Rapidly increased cut ends by an exonuclease Cas9 fusion in zebrafish." genesis 55.8 (Jun. 27, 2017): e23044. (Year: 2017).*
Ran, F., Cong, L., Yan, W. et al. In vivo genome editing using *Staphylococcus aureus* Cas9. Nature 520, 186-191 (2015). (Year: 2015).*
Vidigal, Joana A., and Andrea Ventura. "Rapid and efficient one-step generation of paired gRNA CRISPR-Cas9 libraries." Nature communications 6.1 (2015): 8083. (Year: 2015).*

(Continued)

*Primary Examiner* — Robert M Kelly
*Assistant Examiner* — Allison Marie Johnson
(74) *Attorney, Agent, or Firm* — Lathrop GPM LLP; James H. Velema, Esq.; Lisa M. W. Hillman

(57) ABSTRACT

CRISPR/CAS-related genome editing systems, compositions and methods for targeting the TGFBR2 locus, as well as cells edited using these systems, compositions and methods are provided.

19 Claims, 25 Drawing Sheets

Specification includes a Sequence Listing.

(56) References Cited

U.S. PATENT DOCUMENTS

| | | | | |
|---|---|---|---|---|
| 2015/0232881 | A1 | 8/2015 | Glucksmann et al. | |
| 2016/0138029 | A1* | 5/2016 | Hossbach | A61P 25/18 536/24.5 |
| 2016/0168594 | A1 | 6/2016 | Zhang et al. | |
| 2016/0237455 | A1 | 8/2016 | Glucksmann et al. | |
| 2017/0087185 | A1* | 3/2017 | Crane | A61P 31/12 |

FOREIGN PATENT DOCUMENTS

| | | | |
|---|---|---|---|
| WO | WO/1994/028143 | | 12/1994 |
| WO | WO 1996/13593 | A2 | 5/1996 |
| WO | WO 1996/18105 | A1 | 6/1996 |
| WO | WO 1999/18129 | A1 | 4/1999 |
| WO | WO 1999/60120 | A2 | 11/1999 |
| WO | WO 2000/14257 | A1 | 3/2000 |
| WO | WO 2004/033685 | A1 | 4/2004 |
| WO | WO 2004/045543 | A2 | 6/2004 |
| WO | WO 2006/000830 | A2 | 1/2006 |
| WO | WO 2006/037960 | A2 | 4/2006 |
| WO | WO 2008/109546 | A2 | 9/2008 |
| WO | WO 2011/044186 | A1 | 4/2011 |
| WO | WO 2012/129514 | | 9/2012 |
| WO | W0 2013/071154 | A1 | 5/2013 |
| WO | W0 2013/166321 | A1 | 7/2013 |
| WO | W0 2013/123061 | | 8/2013 |
| WO | WO 2013/126726 | A1 | 8/2013 |
| WO | WO 2014/031687 | A1 | 2/2014 |
| WO | W02014/055668 | | 4/2014 |
| WO | WO 2014/055815 | A1 | 4/2014 |
| WO | WO 2015/070083 | A1 | 5/2015 |
| WO | WO 2015/138510 | A1 | 9/2015 |
| WO | WO 2016/073990 | A2 | 5/2016 |
| WO | WO2017/023801 | A1 | 9/2017 |

OTHER PUBLICATIONS

Wiles, Michael V., et al. "CRISPR-Cas9-mediated genome editing and guide RNA design." Mammalian Genome 26 (2015): 501-510. (Year: 2015).*

Montague, Tessa G., et al. "CHOPCHOP: a CRISPR/Cas9 and TALEN web tool for genome editing." Nucleic acids research 42.W1 (2014): W401-W407. (Year: 2014).*

Annunziato et al., "Abstract 2687: Rapid in vivo testing of tumor suppressors in ILC by CRISPR-Cas9 mediated somatic gene editing of the mammary gland", Proceedings of the 107th Annual Meeting of the American Association for Cancer Research; Apr. 16-20, 2016; New Orleans, LA. Philadelphia (PA): AACR; Cancer Res 2016;76(14 Suppl):Abstract nr 2687.

Brunner et al., "Cytotoxic T cells: Double-barreled shot guns", Nature Medicine, 1999, vol. 5, No. 1, abstract.

Cebrian-Serrano et al., CRISPR-Cas orthologues and variants: optimizing the repertoire, specificity, and delivery of genome engineering tools. Mamm Genome, Jun. 20, 2017, vol. 28, pp. 247-261.

Foster et al., Antitumor activity of EBV-specific T lymphocytes transduced with a dominant negative TGF-beta receptor. J. Immunother., Jun. 30, 2008, vol. 31, No. 5, pp. 500-505.

Lucas et al., "Disruption of T cell homeostasis in mice expressing T cell-specific dominant negative transforming growth factor beta II receptor" The Journal of Experimental Medicine, Apr. 3, 2000, vol. 191, No. 7, pp. 1187-1196.

Meisam et al., "Generation of Knock-out primary and Expanded Human NK Cells Using Cas9 Ribonucleoproteins", Journal of Visualized Experiments, Jun. 14, 2018, No. 136.

Roitt et al., Really Essential Medical Immunology, 2000, Moscow: MIR, pp. 4-6.

Singer et al., "Genes and Genomes", Moscow, MIR, Jan. 1998, vol. 1, pp. 63-64.

Zhang et al., "TGF-β signaling to T cells inhibits autoimmunity during lymphopenia-driven proliferation", Nature Immunology, May 27, 2012, vol. 13, No. 7, pp. 667-673.

Alonso-Camino, Vanesa et al., CARbodies: Human Antibodies Against Cell Surface Tumor Antigens Selected From Repertoires Displayed on T Cell Chimeric Antigen Receptors, Molecular Therapy—Nucleic Acids, 2013, pp. e93, vol. 2.

Anupama, Reddy et al: "Genetic and Functional Drivers of Diffuse Large B Cell Lymphoma", Cell, vol. 171, No. 2, Oct. 5, 2017 (Oct. 5, 2017), p. 481, XP085207526. ISSN: 0092-8674, DOI: 10.1016/J.CELL.2017.09.027 p. 486, left-hand column; figure 3.

Aref, Salah et al., Upregulation of CD200 is associated with regulatory T cell expansion and disease progression in multiple myeloma, Hematological Oncology, 2017, pp. 51-57, vol. 35.

Bae et al., Cas-OFFinder; a fast and versatile algorithm that searches for potential off-target sites of Cas9 RNA-guided endonucleases, Bioinformatics, 2014, pp. 1473-1475, vol. 30, No. 10.

Baum, Christopher et al., Retrovirus Vectors: Toward the Plentivirus? Molecular Therapy: The American Society of Gene Therapy, 2006, pp. 1050-1063, vol. 13.

Brash, Douglas E. et al., Strontium Phosphate Transfection of Human Cells in Primary Culture: Stable Expression of the Simian Virus 40 Large-T-Antigen Gene in Primary Human Bronchial Epithelial Cells, Molecular and Cellular Biology, May 1987, pp. 2031-2034, vol. 7, No. 5.

Brentjens et al., CD19-targeted T Cells rapidly induce molecular remissions in adults with chemotherapy-refractory acute lymphoblastic leukemia. Sci Transl Med. 2013, ,vol. 5, No. 177.

Briner et al., Guide RNA Functional Modules Direct Cas9 Activity and Orthogonality, Molecular Cell, Oct. 23, 2014 (Oct. 23, 2014), pp. 333-339, vol. 56, No. 2.

Bruns, Ingmar et al., Multiple myeloma-related deregulation of bone marrow-derived CD34+hematopoietic stem and progenitor cells, Blood: The American Society of Hematology, 2012, pp. 2620-2630, vol. 120, No. 13.

Burns, Jane C. et al., Vesicular stomatitis virus G glycoprotein pseudotyped retroviral vectors: Concentration to very high titer and efficient gene transfer into mammalian cells, Proc. Natl. Acad. Sci. USA, Sep. 1993, pp. 8033-8037, vol. 90.

Carlens, Stefans et al., Ex Vivo T lymphocyte expansion for retroviral transduction: Influence of serum-free media on variations in cell expansion rates and lymphocyte subset distribution, Experimental Hematology, 2000, pp. 1137-1146, vol. 28, No. 10.

Cavalieri, Simona et al., Human T lymphocytes transduced by lentiviral vectors in the absence of TCR activation maintain an intact immune competence, Blood, Jul. 2003, pp. 497-505, vol. 102, No. 2.

Chen, Wanjun et al., Conversion of Peripheral CD4+CD25− Naive T Cells to CD4+CD25+ Regulatory T Cells by TGF-B Induction of Transcription Factor FoxP3, The Journal of Experimental Medicine., 2003, pp. 1875-1886, vol. 198, No. 12.

Chervin, Adam S. et al., Engineering higher affinity T cell receptors using a T cell display system, The Journal of Immunological Methods, 2008, pp. 175-184, vol. 339.

Cohen, Cyrille J., Recognition of Fresh Human Tumor by Human Peripheral Blood Lymphocytes Transduced with a Bicistronic Retroviral Vector Encoding a Murine Anti-p53 TCR et al., J Immunology, 2005, pp. 5799-5808, vol. 175.

Cooper, Laurence J.N. et al., T-cell clones can be rendered specific for CD19: toward the selective augmentation of the graft-versus-B-lineage leukemia effect, Blood, 2003, pp. 1637-1644, vol. 101.

Davis, Luther et al, Homology-directed repair of DNA nicks via pathways distinct from canonical double-strand break repair, PNAS, 2014, pp. E924-E932, vol. 111, No. 10.

Doench, John G. et al: "Optimized sgRNA design to maximize activity and minimize off-target effects of CRISPR-Cas9", Nature Biotechnology,vol. 34, No. 2,Jan. 18, 2016 (Jan. 18, 2016), pp. 184-191, XP055551151,New York, ISSN:1087-0156, DOI: 10.1038/nbt.3437.

Doench, John G et al: "Optimized sgRNA design to maximize activity and minimize off-target effects of CRISPR-Cas9", Supplementary table 21, sgRNAs in the Brunello Library excerpt Jan. 18, 2016 (Jan. 18, 2016); XP055562042, Retrieved from the Internet: URL:https://www.nature.com/articles/nbt.34; 37#supplementary-information; [retrieved on Feb. 26, 2019] the whole document.

(56) References Cited

OTHER PUBLICATIONS

Doench, John G et al: "Optimized sgRNA design to maximize activity and minimize off-target effects of CRISPR-Cas9, Supplementary table 2, sgRNAs in the six subpools of Avana Library, excerpt", Jan. 18, 2016 (Jan. 18, 2016), XP055562242, Retrieved from the Internet: URL:https://www.nature.com/articles/nbt.34, 37#supplementary-information, [retrieved on Feb. 26, 2019], the whole document.
Fine et al., Trans-spliced Cas9 allows cleavage of HBB and CCR5 genes in human cells using compact expression cassettes, Scientific Reports., Jul. 1, 2015 (Jul. 1, 2015), pp. 10777, vol. 5.
Frecha, Cecilia et al., Advances in the Field of Lentivector-based Transduction of T and B lymphocytes for Gene Therapy, Molecular Therapy: The Journal of The American Society of Gene Therapy, 2010, pp. 1748-1757, vol. 18.
Frit, Philippe et al., Alternative end—Joining pathway(s): Bricolage at DNA breaks, DNA Repair, 2014, pp. 81-97, vol. 17.
Hackett, Perry B. et al., A transposon and Transposase System for Human Application, Molecular Therapy: The Journal of The American Society of Gene Therapy, 2010, pp. 674-683, vol. 18.
Heigwer, Florian et al., E-CRISP: fast CRISPR target site identification, Nature Methods, Feb. 2014, pp. 122-123, vol. 11, No. 2.
Holler et al., In vitro evolution of a T cell receptor with high affinity for peptide/MHC, PNAS, May 9, 2000, pp. 5387-5392, vol. 97., No. 10.
Holler, Phillip D. et al., TCRs with high affinity for foreign pMHC show self-reactivity, Nature Immunology, 2003, pp. 55-62, vol. 4.
Hsu, Patrick D. et al., DNA targeting specificity of RNA-guided Cas9 nucleases, Nature Biotechnology., Sep. 1, 2013 (Sep. 1, 2013), pp. 827-832, vol. 31, No. 9.
Huang, Guangcun et al: "TGF-[beta] signal rewiring sustains epithelial-mesenchymal transition of circulating tumor cells in prostate cancer xenograft hosts", Oncotarget, vol. 7, No. 47, Oct. 21, 2016 (Oct. 21, 2016), XP055561551, DOI: 10.18632/oncotarget.12808, p. 77125, left-hand column—p. 77126, left-hand column; figure 1.
Hudecek, Michael et al., Receptor Affinity and Extracellular Domain Modifications Affect Tumor Recognition by ROR1-Specific Chimeric Antigen Receptor T Cells, Clinical Cancer Research., 2013, pp. 3153, vol. 19.
Jinek, Martin et al., A Programmable Dual-RNA-Guided DNA Endonuclease in Adaptive Bacterial Immunity, Science Magazine, Aug. 17, 2012 (Aug. 17, 2012), pp. 816-821, vol. 337, No. 6096.
Kleinstiver, Benjamin P. et al., Broadening *Staphylococcus aureus* Caso Targeting Range by Modifying PAM Recognition, Nat Biotechnol., vol. 33, No. 12, Dec. 2015 (Dec. 1, 2015), pp. 1293-1298.
Kleinstiver, Benjamin P. et al., Engineered CRISPR-Cas9 nucleases with altered PAM specificities, Nature, Jul. 23, 2015, pp. 481-485, vol. 523, No. 7561.
Kleinstiver, Benjamin P. et al., High-fidelity CRISPR-Cas9 nucleases with no detectable genome-wide off-target effects, Nature, Jan. 28, 2016 (Jan. 28, 2016), pp. 490-495, vol. 529.
Kochenderfer, James N. et al., B-cell depletion and remissions of malignancy along with cytokine-associated toxicity in a clinical trial of anti-CD19 chimeric-antigen-receptor-transduced T cells, Blood, 2012, pp. 2709-2720, vol. 119.
Kochenderfer, James N. et al., Treating B-cell cancer with T cells expressing anti-CD19 chimeric antigen receptors, Nat Rev Clin Oncol. May 2013, pp. 267-276, vol. 10.
Kochenderfer, James N. et al., Construction and Pre-Clinical Evaluation of an Anti-CD19 Chrimeric Antigen Receptor, J. Immunothreapy, Sep. 2009, pp. 689-702, vol. 32, No. 7.
Komor, Alexis C. et al., Programmable editing of a target base in genomic DNA without double-stranded DNA cleavage, Nature, May 19, 2016, pp. 420-424, vol. 533.
Kosaka, Akemi et al: "Transgene-derived overexpression of miR-17-92 in CD8+ T-cells confers enhanced cytotoxic activity", Biochemical and Biophysical Research Communications, vol. 458, No. 3, Feb. 10, 2015 (Feb. 10, 2015), pp. 549-554, XP055561723, Amsterdam, NL, ISSN:0006-291X, DOI: 10.1016/j.bbrc.2015.02.003 p. 551, right-hand column; figure 3 abstract.
Li, Yi et al., Directed evolution of human T-cell receptors with picomolar affinities by phage display, Nature Biotechnology, Mar. 2005, pp. 349-354, vol. 23.
Makarova, Kira S. et al., Evolution and classification of the CRISPR-Cas systems, Nature Reviews: Microbiology, Jun. 2011, pp. 467-477, vol. 9, No. 6.
Mali, Prashant et al., RNA-Guided Human Genome Engineering via Cas9, ScienceMag, 2013, pp. 823-826, vol. 339, No. 6121.
Manuri et al., piggyBac Transposon/Transposase System to Generate CD19-Specific T Cells for the Treatment of B-Lineage Malignancies, Human Gene Therapy, 2010, pp. 427-437, vol. 21, No. 4.
Nishimasu et al., Crystal Structure of *Staphylococcus aureus* Cas9, Cell, Aug. 27, 2015, pp. 1113-1126, vol. 162.
Nishimasu, Hiroshi et al., Crystal Structure of Cas9 in Complex with Guide RNA and Target DNA, Cell, Feb. 27, 2014 (Feb. 27, 2014), pp. 935-949, vol. 156.
Park, Tristen S. et al., Treating cancer with genetically engineered T cells, Trends in Biotechnology, Nov. 2011, pp. 550-557, vol. 29, No. 11.
Parkhurst et al., Characterization of Genetically Modified T-Cell Receptors that Recognize the CEA: 691-699 Peptide in the Context of HLA-A2.1 on Human Colorectal Cancer Cells, Clin Cancer Res., 2009, pp. 169-180, vol. 15.
Ran, Ann F. et al., Double Nicking by RNA-Guided CRISPR Cas9 for Enhanced Genome Editing Specificity, Cell, Sep. 12, 2013 pp. 1380-1389, , vol. 154, No. 6.
Rosenberg, Cell transfer immunotherapy for metastatic solid cancer—what clinicians need to know, Nat Rev Clin Oncol, 2011, pp. 577-585, vol. 8, No. 10.
Scarpa et al., Characterization of Recombinant Helper Retroviruses from Moloney-Based Vectors in Ecotropic and Amphotropic Packaging Cell Lines, Virology, 1991, pp. 849-852, vol. 180.
Schlueter, Carol J. et al., Specificity and Binding Properties of a Single-chain T Cell Receptor, J. Mol. Biol., 1996, pp. 859, vol. 256.
Sharma et al., Efficient Sleeping Beauty DNA Transposition From DNA Minicircles, Molecular Therapy-Nucleic Acids, 2013, pp. e74, vol. 2.
Shmakov, Sergey et al., Discovery and Functional Characterization of Diverse Class 2 CRISPR-Cas Systems, Molecular Cell, Nov. 5, 2015 (Nov. 5, 2015), pp. 385-397, vol. 60.
Tamsin, Lannagan et al: "Genetic Editing of Colonic Organoids Provides a Molecularly Distinct and Orthotopic Mouse Model of Serrated Carcinogenesis", Gastroenterology, vol. 152, No. 5, Apr. 22, 2017 (Apr. 22, 2017), XP029979296, ISSN:0016-5085, DOI: 10.1016/S0016-5085(17)30685-6; abstract.
Terakura, Seitaro et al., Generation of CD19-chimeric antigen receptor modified CD8+ T cells derived from virus-specific central memory T cells, Blood, 2012, pp. 72-82, vol. 1.
Tiemessen, Machteld M. et al., Transforming growth factor-B inhibits human antigen-specific CD4+ T cell proliferation without modulating the cytokine response, International Immunology, May 2003, pp. 1495-1504, vol. 15.
Toledo, Chad M.: "Identification of Cancer-specific Therapeutic Targets and Tumor Suppressor Genes in Glioblastoma Multiforme by Functional Genetics", Ph.D. thesis, Sep. 28, 2016 (Sep. 28, 2016), pp. i-xvi, 1-182,XP055561603, Retrieved from the Internet: URL:https://digital.lib.washington.edu/res earchworks/handle/1773/34069 [retrieved on Feb. 26, 2019] abstract; figures 3.16, 3.17; tables 3.1, 3.5.
Tsukahara, Tomonori et al., CD19 target engineered T-cells accumulate at tumor lesions in human B-cell lymphoma xenograft mouse models, Biochem Biophys Res Commun, Aug. 2013, pp. 84-89, vol. 438, No. 1.
Turtle, Cameron J. et al., Engineered T cells for anti-cancer therapy, Current Opinion in Immunology, Oct. 2012, pp. 633-639, vol. 24, No. 5.
Van Tedeloo et al., High-level transgene expression in primary human T lyphocytes and adult bone marrow CD34+ cells via electroporation-mediated gene delivery, Gene Therapy, 2000, pp. 1431-1437, vol. 7, No. 16.
Varela-Rohena, Angel et al., Control of HIV-1 immune escape by CD8 T-cells expressing enhanced T-cell receptor, Nat Med., 2008, pp. 1390-1395, vol. 14.

(56) References Cited

OTHER PUBLICATIONS

Verhoeyen et al., Lentiviral Vector Gene Transfer into Human T Cells, Methods in Molecular Biology, Methods and Protocols, 2009, pp. 97-114, vol. 506.

Wang et al., Phenotypic and Functional Attributes of Lentivirus Modified CD19-specific Human CD8+ Central Memory T Cells Manufactured at Clinical Scale, J Immunother, Nov. 2012, pp. 689-701, vol. 35, No. 9.

Wigler et al., Transfer of Purified Herpes Virus Thymidine Kinase Gene to Cultured Mouse Cells, Cell II, 1977, pp. 223, vol. 11.

Wu, Richard et al., Adoptive T-cell Therapy Using Autologous Tumor-infiltrating Lymphocytes for Metastatic Melanoma: Current Status and Future Outlook, Cancer Journal, Mar. 2012 (Mar. 1, 2012), pp. 160-175, vol. 18, No. 2.

Xiao, An et al., CasOT: a genome-wide Cas0/gRNA off-target searching tool Bioinformatics, Jan. 2014, pp. 1180-1182, vol. 30, No. 8.

Yamano et al., Crystal Structure of CPf1 in Complex with Guide RNA and Target DNA, Cell, May 5, 2016 (May 5, 2016), pp. 949-962, vol. 165, No. 4.

Yang, Guo-Xiang et al: "Adoptive transfer of CD8+ T cells from transforming growth factor beta receptor type II (dominant negative form) induces autoimmune cholangitis in mice", Hepatology, vol. 47, No. 6, Jan. 21, 2008 (Jan. 21, 2008), pp. 1974-1982, XP055561792, US; ISSN: 0270-9139, DOI: 10.1002/hep.22226 p. 1975, right-hand column; figures 1,3.

Zetsche et al., A Split Cas9 Architecture for Inducible Genome Editing and Transcription Modulation, Nat Biotechnol., Feb. 2015 (Feb. 1, 2015), pp. 139-142, vol. 33, No. 2.

Zetsche, Bernd et al., Cpf1 Is a Single RNA-Guided Endonuclease of a Class 2 CRISPR-Cas System, Cell, Oct. 22, 2015, pp. 759-771, vol. 163, 22.

Fedorov et al., PD-1-and CTLA-4-Based Inhibitory Chimeric Antigen Receptors(iCARs) Divert Off-Target Immunotherapy Responses, Sci Transl Med., Dec. 2013 (Dec. 1, 2013), pp. 215, vol. 5.

Guilinger et al., Fusion of catalytically inactive Cas9 to Fokl nuclease improves the specificity of genome modification Nat Biotechnol, Jun. 2014, pp. 577-582, vol. 32, No. 6.

Huang et al., DNA Transposons for Modification of Human Primary T Lymphocytes, Methods in Molecular Biology, Methods and Protocols, 2009, pp. 115-126, vol. 506.

Johnson, Laura, A. et al., Gene therapy with human and mouse T-cell receptors mediates cancer regression and targets normal tissues expressing cognate antigen, Blood, 2009, pp. 535-546, vol. 114.

Leveen et al., "Induced disruption of the transforming growth factor beta type II receptor gene in mice causes a lethal inflammatory disorder that is transplantable", Blood, Immunobiology, Jul. 15, 2002, 100(2): 560-568.

Leveen et al., "TGF-β type II receptor-deficient thymocytes develop normally but demonstrate increased CD8+ proliferation in vivo", Blood, Immunobiology, Dec. 15, 2005, 106(13): 4234-4240.

Montague et al., "CHOPCHOP: a CRSIPR-Cas9 and TALEN web tool for genome editing", Nucl. Acids Res., May 26, 2014, 24: W401-407.

Vidigal et al., "Rapid and efficient one-step generation of pair gRNA CRSIPR-Cas8 libraries", Nat. Comm., Aug. 17, 2015, 6(8083): 1-7.

Wiles et al., "CRSIPR-Cas9-mediated genome editing and guide RNA design", Mammalian Genome, May 20, 2015, 26: 501-510.

* cited by examiner

| Spacer | % of indel |
|---|---|
| AAVS1 | 84.8±7.4 |
| 5050 | 82.75±8.9 |
| 5052 | 95.15±3.0 |
| 5043/5093 | 86.95±2.6 |

METHODS, COMPOSITIONS AND COMPONENTS FOR CRISPR-CAS9 EDITING OF TGFBR2 IN T CELLS FOR IMMUNOTHERAPY

RELATED APPLICATION

This application is a 35 U.S.C. § 371 filing of International Patent Application No. PCT/US2018/058635, filed Nov. 1, 2018, which claims the benefit of U.S. Provisional Application No. 62/580,320, filed on Nov. 1, 2017, which are incorporated herein by reference in their entirety.

SEQUENCE LISTING

The instant application contains a Sequence Listing which has been submitted electronically in ASCII format and is hereby incorporated by reference in its entirety. Said TXT file, created on Apr. 23, 2020, is named 705349_EDT9-002US_ST25.TXT and is 196,314 bytes in size.

FIELD

The present disclosure relates to CRISPR/Cas9-related methods and components for editing a target nucleic acid sequence, e.g., a Transforming Growth Factor β Receptor II (TGFBR2) gene, or modulating expression of a target nucleic acid sequence, e.g., a TGFBR2 gene.

BACKGROUND

Adoptive T cell transfer utilizing genetically modified T cells has entered clinical testing as a therapeutic for solid and hematologic malignancies. In phase I and II trials involving hematologic malignancies (e.g., lymphoma, Chronic Lymphocytic Leukemia (CLL) and Acute Lymphocytic Leukemia (ALL)), many patients have exhibited at least a partial response, with some exhibiting complete responses (Kochenderfer, J. N, et al., 2012 Blood 119, 2709-2720). However, responses observed in solid tumor types (including melanoma, renal cell carcinoma and colorectal cancer) have not always been as robust (Johnson, L. A, et al., 2009 Blood 114, 535-546; Lamers. C. H, et al., 2013 Mol. Ther. 21, 904-912; Warren, R. S, et al., 1998 Cancer Gene Ther. 5, S1-S2).

While not wishing to be bound by any particular theory, the efficacy of adoptive T cell therapies in solid tumor patients may be influenced by a number of factors, such as: (1) T cell proliferation, e.g., limited proliferation of T cells following adoptive transfer; (2) T cell survival, e.g., induction of T cell apoptosis by factors in the target cell, e.g., cancer cell, environment; and (3) T cell function, e.g., inhibition of cytotoxic T cell function by inhibitory factors secreted by host immune cells and target cells, e.g., cancer cells. These factors, in turn, may be influenced by the activity of transforming growth factor β (TGF-β), a cytokine produced by a wide variety of tumor types that has been shown to directly suppress tumor infiltrating lymphocytes, as well as inducing and promoting the function of regulatory T cells (Tregs) capable of preventing anti-tumor immunity.

TGFBR2 is a receptor for TGF-β that is expressed on a myriad of cell types including immune cells. Binding of TGF-β by TGFBR2 has been demonstrated to down-regulate T cell activation, proliferation and differentiation. Development of TGFBR2 inhibitors that may ameliorate TGFBR2 activity on tumor reactive T cells has been complicated by the lack of pre-clinical mouse models due to the severe autoimmune phenotype observed in mice containing T cells engineered to conditionally lack TGFBR2. Consequently, a need exists for effective strategies to reduce or eliminate the T cell inhibitory impact of TGF-β, including in the context of T cell mediated immunotherapy.

CRISPRs (Clustered Regularly Interspaced Short Palindromic Repeats) evolved in bacteria and archea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of an RNA-guided nuclease to a target sequence in the viral genome. The RNA-guided nuclease, in turn, cleaves and thereby silences the viral target.

Recently, the CRISPR/Cas9 system has been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR). CRISPR/Cas9 represents a promising avenue for addressing TGF-β-mediated inhibition of T-cells in the context of tumor therapy, but to date no viable approaches for addressing this issue in T-cells for use in tumor therapy have been identified.

SUMMARY

In certain aspects, provided herein are genome editing systems and related compositions and methods for the targeted editing of the nucleic acid sequence of TGFBR2. In certain embodiments, such targeted editing results in the alteration (e.g., down regulation) of TGFBR2 expression. In certain embodiments, such alteration of expression occurs in T cells. In certain embodiments, the alteration of TGFBR2 expression in T cells involves the use of a ribonucleoprotein (RNP) complex as a genome editing system comprising an RNA-guided nuclease protein complexed with a gRNA targeting the TGFBR2 gene. In certain embodiments, the alteration in TGFBR2 expression occurs as a result of a double-stranded break induced by the RNP and subsequent imperfect repair that leads to indels at and/or adjacent to the targeted TGFBR2 sequence.

In certain embodiments, the instant disclosure relates to genome editing systems that include a guide RNA with a targeting domain that is complementary to target sequence of a TGFBR2 gene and where the RNA-guided nuclease is a Cas9 nuclease. The targeting domain may be 70%, 80%, 85%, 90%, 95%, or 100% complementary.

In certain embodiments, the targeting domain has a length of 16, 17, 18, 19, 20, 21, 22, 23, 24, 25, or 26 nucleotides.

In certain embodiments, the targeting domain has at least 18 contiguous nucleotides that are complementary to the TGFBR2 gene.

In certain embodiments, the targeting domain comprises a nucleotide sequence that is identical to, or differs by no more than 3 nucleotides from, a nucleotide sequence selected from SEQ ID NOS: 5036 to 5096. In certain embodiments, the targeting domain is configured to form a double strand break or a single strand break within about 500 bp, about 450 bp, about 400 bp, about 350 bp, about 300 bp, about 250 bp, about 200 bp, about 150 bp, about 100 bp, about 50 bp, about 25 bp, or about 10 bp of the TGFBR2 target position.

In certain embodiments disclosed herein, the genome editing system is capable of altering TGFBR2 gene by knocking out the expression of the TGFBR2 gene or knocking down the expression of the TGFBR2 gene.

In certain embodiments, the genome editing systems disclosed herein incorporate a gRNA comprising a targeting domain configured to target a coding region or a non-coding region of the TGFBR2 gene, wherein said non-coding region comprises a promoter region, an enhancer region, an intron, the 3' UTR, the 5' UTR, or a polyadenylation signal region of said TGFBR2 gene; and the coding region comprises, e.g., an early coding region of said TGFBR2 gene.

In certain embodiments, the genome editing systems disclosed herein have a target sequence of the TGFBR2 gene comprising the sequence selected from the group consisting of SEQ ID NOs: 1, 2, and 3.

In certain embodiments, the genome editing systems disclosed herein have a target sequence of the TGFBR2 gene comprising the sequence selected from the group consisting of SEQ ID NOs: 4 to 10.

In certain embodiments, the genome editing systems disclosed herein incorporate a targeting domain comprising a nucleotide sequence that is identical to, or differs by no more than 3 nucleotides from, a nucleotide sequence selected from SEQ ID NOS: 5036 to 5096. In certain embodiments, the targeting domain comprises a nucleotide sequence that is identical to, or differs by no more than 3 nucleotides from, a nucleotide sequence selected from the group consisting of: (a) SEQ ID NO: 5041; (b) SEQ ID NO: 5042; (c) SEQ ID NO: 5047; (d) SEQ ID NO: 5050; (e) SEQ ID NO: 5052; (f) SEQ ID NO: 5092; and (g) SEQ ID NO: 5093. In certain embodiments, the genome editing system incorporates pairs of gRNA molecules, including, e.g., gRNA pairs having target sequences SEQ ID NOS: 5042 and 5041, or 5042 and 5092, or SEQ ID NOS: 5042 and 5093, or SEQ ID NOS: 5093 and 5041.

In certain embodiments, the present disclosure relates to a composition comprising a gRNA molecule comprising a targeting domain that is complementary with a target sequence of a TGFBR2 gene. In certain embodiments, the composition comprises one, two, three, or four gRNA molecules. In certain embodiments, the composition further comprises an RNA-guided nuclease, e.g., a Cas9 molecule. In certain embodiments, the targeting domain incorporated into such compositions comprises a nucleotide sequence that is identical to, or differs by no more than 3 nucleotides from, a nucleotide sequence selected from SEQ ID NOS: 5036 to 5096. In certain embodiments, the targeting domain comprises a nucleotide sequence that is identical to, or differs by no more than 3 nucleotides from, a nucleotide sequence selected from the group consisting of: (a) SEQ ID NO: 5041; (b) SEQ ID NO: 5042; (c) SEQ ID NO: 5047; (d) SEQ ID NO: 5050; (e) SEQ ID NO: 5052; (f) SEQ ID NO: 5092; and (g) SEQ ID NO: 5093. In certain embodiments, the composition incorporates pairs of gRNA molecules, including, e.g., gRNA pairs having target sequences SEQ ID NOS: 5042 and 5041, or 5042 and 5092, or SEQ ID NOS: 5042 and 5093, or SEQ ID NOS: 5093 and 5041.

In certain embodiments, the present disclosure relates to a vector encoding a gRNA molecule comprising a targeting domain that is complementary with a target sequence of a TGFBR2 gene. In certain embodiments, the vector further encodes for an RNA-guided nuclease, e.g., a Cas9 molecule. In certain embodiments, the targeting domain of the gRNA encoded by the vector comprises a nucleotide sequence that is identical to, or differs by no more than 3 nucleotides from, a nucleotide sequence selected from SEQ ID NOS: 5036 to 5096. In certain embodiments, the targeting domain comprises a nucleotide sequence that is identical to, or differs by no more than 3 nucleotides from, a nucleotide sequence selected from the group consisting of: (a) SEQ ID NO: 5041; (b) SEQ ID NO: 5042; (c) SEQ ID NO: 5047; (d) SEQ ID NO: 5050; (e) SEQ ID NO: 5052; (f) SEQ ID NO: 5092; and (g) SEQ ID NO: 5093. In certain embodiments the vector is a viral vector. In certain embodiments, the vector is an adeno-associated virus (AAV) vector or a lentivirus (LV) vector.

In certain embodiments, the present disclosure is directed to a method of altering a TGFBR2 gene in a cell, comprising administering to said cell one of: (i) a genome editing system comprising a gRNA molecule comprising a targeting domain that is complementary with a target sequence of said TGFBR2 gene, and a Cas9 molecule; (ii) a vector comprising a polynucleotide encoding a gRNA molecule comprising a targeting domain that is complementary with a target sequence of said TGFBR2 gene, and a polynucleotide encoding a Cas9 molecule; or (iii) a composition comprising a gRNA molecule comprising a targeting domain that that is complementary with a target sequence of said TGFBR2 gene, and a Cas9 molecule.

In certain embodiments, the present disclosure is directed to a cell comprising a genome editing system as described herein, a gRNA composition of as described herein, or a vector as described herein. In certain embodiments, the cell expresses TGFBR2. In certain embodiments, the cell is a T cell.

In certain embodiments, the present disclosure is directed to a gRNA and a RNA-guided nuclease comprising a ribonucleoprotein (RNP) complex.

In certain embodiments, the present disclosure is directed to administering to a cell two or more RNP complexes comprising gRNAs with different targeting domains.

In certain embodiments, the present disclosure is directed to RNP complexes comprising enzymatically active Cas9 (eaCas9) nucleases.

In certain embodiments, the present disclosure is directed to RNP complexes comprising eaCas9 nucleases that form double strand breaks in a target nucleic acid or single strand breaks in a target nucleic acid.

In certain embodiments, the present disclosure is directed to two RNP complexes comprising distinct gRNAs are used to form offset single strand breaks in the TGFBR2 gene in a cell.

In certain embodiments, the present disclosure is directed to a cell that is a T cell or a Natural Killer (NK) cell. In certain embodiments, the cell further comprises an engineered T cell receptor (eTCR) or a chimeric antigen receptor (CAR).

In certain embodiments, the present disclosure is directed to an RNA-guided nuclease-mediated method of altering TGFBR2 gene expression in a cell comprising: a) contacting the cell with a sufficient amount of a gRNA that targets TGFBR2 and an RNA-guided nuclease; and b) forming a first DNA double strand break near a TGFBR2 target position in a TGFBR2 gene of the cell, wherein the first DNA double strand break is repaired by NHEJ, wherein said repair alters the expression of the TGFBR2 gene.

In certain embodiments, the present disclosure is directed to forming a second DNA double strand break near the TGFBR2 target position. In certain embodiments, a first double strand break is formed within about 500 bp, about 450 bp, about 400 bp, about 350 bp, about 300 bp, about 250 bp, about 200 bp, about 150 bp, about 100 bp, about 50 bp, about 25 bp, or about 10 bp of the TGFBR2 target position. In certain embodiments, the first and second double strand breaks are formed within about 500 bp, about 450 bp, about 400 bp, about 350 bp, about 300 bp, about 250 bp, about 200 bp, about 150 bp, about 100 bp, about 50 bp, about 25 bp, or about 10 bp of the TGFBR2 target position. In certain embodiments, the first double strand break is formed in a coding region or a non-coding region of said TGFBR2 gene, wherein said non-coding region comprises a promoter region, an enhancer region, an intron, a 3' UTR, a 5' UTR, or a polyadenylation signal region of said TGFBR2 gene. In certain embodiments the first and second double strand breaks are formed in a coding region or a non-coding region of said TGFBR2 gene, wherein said non-coding region comprises a promoter region, an enhancer region, an intron, a 3' UTR, a 5' UTR, or a polyadenylation signal region of said TGFBR2 gene.

In certain embodiments, the coding region is selected from exon 3, exon 4, and exon 5.

In certain embodiments, the targeting domain comprises a nucleotide sequence that is identical to, or differs by no more than about 3 nucleotides from, a nucleotide sequence selected from the group consisting of SEQ ID NOS: 5036 to 5096.

In certain embodiments, the RNA-guided nuclease is an *S. pyogenes* Cas9 nuclease, and said targeting domain comprises a nucleotide sequence that is identical to, or differs by no more than about 3 nucleotides from, a nucleotide sequence selected from the group consisting of: (a) SEQ ID NO: 5041; (b) SEQ ID NO: 5042; (c) SEQ ID NO: 5047; (d) SEQ ID NO: 5050; (e) SEQ ID NO: 5052; (f) SEQ ID NO: 5092; and (g) SEQ ID NO: 5093.

In certain embodiments, the RNA-guided nuclease is an *S. aureus* Cas9 nuclease.

In certain embodiments, the RNA-guided nuclease is a mutant Cas9 nuclease.

In certain embodiments, the NHEJ repair produces an insertion or deletion with a frequency of greater than or equal to 20/o.

In certain embodiments, the insertion or deletion frequency is greater than or equal to 30%, 40%, or 50%.

In certain embodiments, the present disclosure is directed to a genome engineered cell comprising an insertion or deletion near or at a target position of a TGFBR2 gene, wherein said target position comprises a nucleotide sequence that is complementary to, or differs by no more than about 3 nucleotides from, a nucleotide sequence selected from SEQ ID NOS: 5036 to 5096.

In certain embodiments, the insertion or deletion is within about 500 bp, about 450 bp, about 400 bp, about 350 bp, about 300 bp, about 250 bp, about 200 bp, about 150 bp, about 100 bp, about 50 bp, about 25 bp, or about 10 bp of the TGFBR2 target position.

In certain embodiments, the cell is a T cell or NK cell. In certain embodiments, the cell further comprises a eTCR or CAR.

In certain embodiments, the present disclosure is directed to a composition comprising: a) a population of genome engineered cells comprising an insertion or deletion near or at a target position of a TGFBR2 gene, wherein said target position comprises a nucleotide sequence that is complementary to, or differs by no more than about 3 nucleotides from, a nucleotide sequence selected from SEQ ID NOS: 5036 to 5096; and b) a pharmaceutically acceptable buffer.

In certain embodiments, the population of cells comprises T cells or NK cells. In certain embodiments, the cell further comprises a eTCR or CAR.

In certain embodiments, the present disclosure is directed to a method of treating cancer in subject, comprising administering to the subject engineered immune cells, wherein the engineered immune cells have reduced expression of TGFBR2, and optionally expresses an engineered T Cell Receptor (eTCR) or a Chimeric Antigen Receptor (CAR), wherein the engineered immune cells have an insertion or a deletion near or at a target position of the TGFBR2 gene.

In certain embodiments, the engineered immune cells comprise T cells or NK cells. In certain embodiments, the cell further comprises a eTCR or CAR.

In certain embodiments, the cancer is selected from the group consisting of: leukemia, lymphoma, e.g., chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma. Hodgkin's lymphoma, cervical carcinoma, colorectal cancer, glioblastoma, neuroblastoma. Ewing's sarcoma, medulloblastoma, osteosarcoma, synovial sarcoma, mesothelioma, and/or any cancer type that expresses TGF-β.

In certain embodiments, the T cells are CD4+ and/or CD8+ T cells.

In certain embodiments, the engineered immune cells maintain or have enhanced lysis activity against a target cancer cell relative to a non-engineered immune cell.

In certain embodiments, the engineered immune cells maintain or have increased expression of granzyme B and/or interferon gamma in the presence of TGFβ relative to non-engineered immune cells.

In certain embodiments, the engineered immune cells maintain or have improved persistence against repeated antigen stimulation relative to non-engineered immune cells.

In certain embodiments, the engineered immune cells maintain or have increased expression of CD25 relative to non-engineered immune cells.

In certain embodiments, the engineered immune cells maintain or have decreased expression of PD-1 relative to non-engineered immune cells.

In certain embodiments, the engineered immune cells maintain or have increased proliferation relative to non-engineered immune cells.

In certain embodiments, the present disclosure is directed to a composition comprising a plurality of engineered T cells, wherein said engineered T cells exhibit reduced TGFBR2 gene expression relative to non-engineered T cells.

In certain embodiments, the engineered T cells exhibit a TGFBR2 gene expression level that is about 50%, about 40%, about 30%, about 20%, about 10% or about 5% the level of TGFBR2 expression in non-engineered T cells.

In certain embodiments, the engineered T cells further comprise expression of an eTCR or a CAR.

In certain embodiments, the T cells are CD4+ T cells and/or CD8+ T cells.

In certain embodiments, the engineered T cells are further characterized by possessing: a) enhanced lysis activity against a target cancer cell relative to non-engineered T cells; b) maintained or increased expression of granzyme B and/or interferon gamma in the presence of TGFβ relative to non-engineered T cells; c) maintained or increased persistence against repeated antigen stimulation relative to non-engineered T cells; d) maintained or increased expression of CD25 relative to non-engineered T cells; e) maintained or decreased expression of PD-1 relative to non-engineered T cells; and/or f) maintained or increased proliferation relative to non-engineered T cells.

In certain embodiments, the present disclosure is directed to a composition comprising a plurality of engineered T cells, wherein said engineered T cells exhibit reduced TGFBR2 gene expression relative to non-engineered T cells, said engineered T cells produced by contacting non-engineered T cells with a genome editing system comprising: a gRNA comprising a targeting domain that is complementary with a target sequence of a TGFBR2 gene; and an RNA-guided nuclease.

In certain embodiments, the engineered T cells are further transduced with a vector that expresses an eTCR or a CAR. In certain embodiments, the vector is a viral vector. In certain embodiments, the viral vector is an adeno-associated virus (AAV) vector or a lentivirus (LV) vector.

In certain embodiments, the RNA-guided nuclease is an *S. pyogenes* Cas9 nuclease, and said targeting domain comprises a nucleotide sequence that is identical to, or differs by no more than about 3 nucleotides from, a nucleotide sequence selected from the group consisting of: (a) SEQ ID NO: 5041; (b) SEQ ID NO: 5042; (c) SEQ ID NO: 5047; (d) SEQ ID NO: 5050; (e) SEQ ID NO: 5052; (f) SEQ ID NO: 5092; and (g) SEQ ID NO: 5093.

In certain embodiments, the present disclosure is directed to a composition comprising a plurality of engineered T cells, wherein said engineered T cells are deficient in TGFBR2 signaling.

In certain embodiments, the deficient TGFBR2 signaling is mediated by expressing a Dominant Negative (DN) form of the TGFBR2 in said engineered T cells.

In certain embodiments, the engineered T cells are further transduced with a vector that expresses an eTCR or a CAR. In certain embodiments, the vector is a viral vector. In certain embodiments, the viral vector is an adeno-associated virus (AAV) vector or a lentivirus (LV) vector.

In certain embodiments, the T cells are CD4+ T cells and/or CD8+ T cells.

In certain embodiments, the engineered T cells are further characterized by possessing: a) enhanced lysis activity against a target cancer cell relative to non-engineered T cells; b) maintained or increased expression of granzyme B and/or interferon gamma in the presence of TGFβ relative to non-engineered T cells; c) maintained or increased persistence against repeated antigen stimulation relative to non-engineered T cells; d) maintained or increased expression of CD25 relative to non-engineered T cells; e) maintained or decreased expression of PD-1 relative to non-engineered T cells; and/or f) maintained or increased proliferation relative to non-engineered T cells.

In certain embodiments, the engineered immune cells further comprise reduced expression of wild-type TGFBR2.

In certain embodiments, the wild-type TGFBR2 expression is reduced by contacting the engineered immune cells with a genome editing system comprising: a gRNA comprising a targeting domain that is complementary with a target sequence of a TGFBR2 gene; and an RNA-guided nuclease.

In certain embodiments, the present disclosure is directed to a ribonucleoprotein (RNP) complex comprising a gRNA that comprises a targeting domain that is complementary with a target sequence of a TGFBR2 gene and an RNA-guided nuclease.

In certain embodiments, the RNA-guided nuclease is a Cas9 nuclease.

In certain embodiments, the RNP is electroporated into cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Headings, including numeric and alphabetical headings and subheadings, are for organization and presentation and are not intended to be limiting.

Other features and advantages of the invention will be apparent from the detailed description, examples, drawings, and from the claims.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 15A-FIG. 15C show the projected cell number after stimulation with three different antigens. FIG. 15D-FIG. 15F show the % anti-BCMA CAR-expressing T cells over time with repeated TGFβ antigen stimulation.

DETAILED DESCRIPTION

Definitions and Abbreviations

Figure 1:
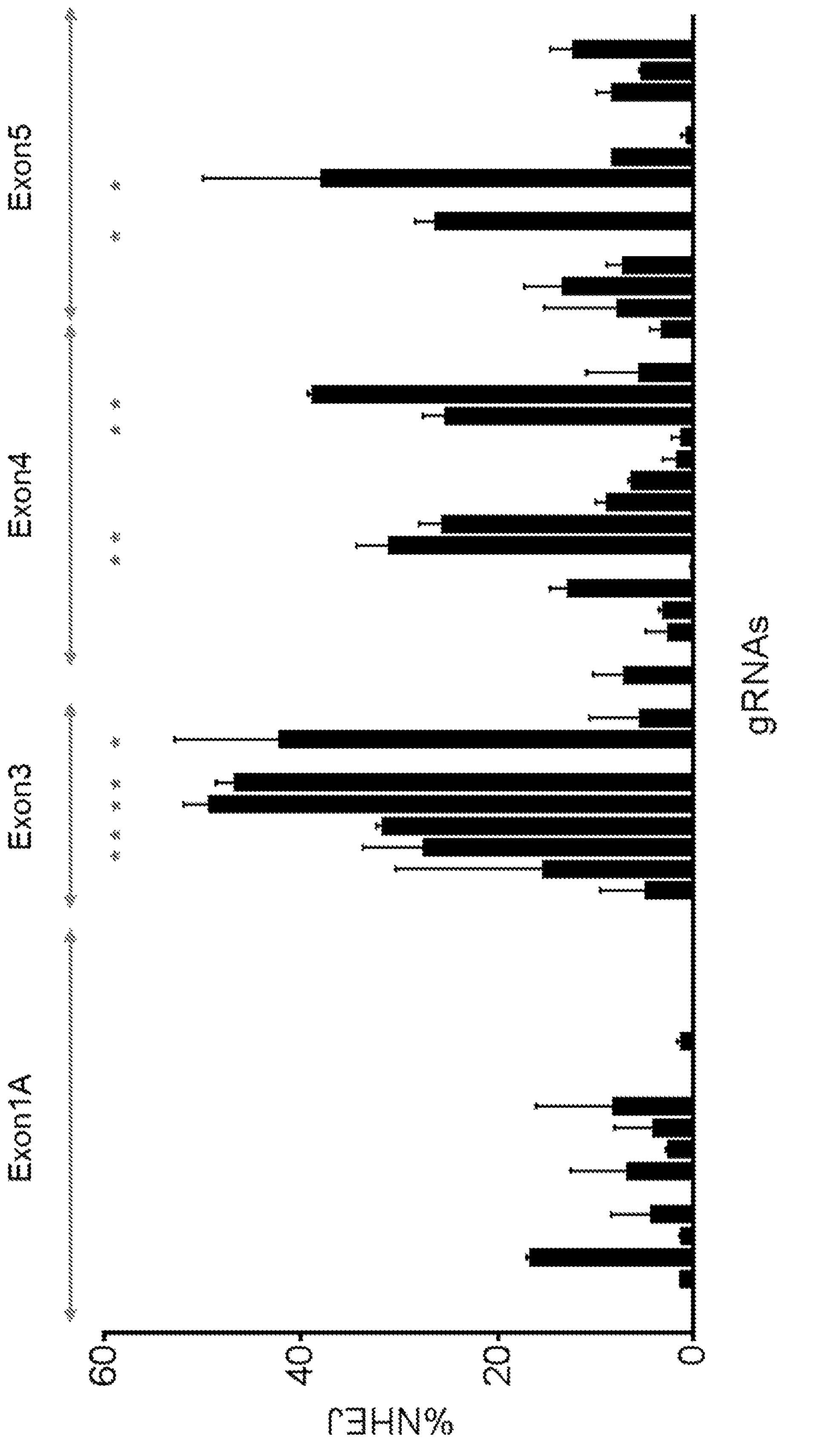
FIG. 1 depicts a list of exemplary gRNAs targeting Exons 1A-5 of Transforming Growth Factor β Receptor II (TGFBR2) and their associated % Non-Homologous End Joining (NHEJ) activity.

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

The phrase "consisting essentially of" means that the species recited are the predominant species, but that other species may be present in trace amounts or amounts that do not affect structure, function or behavior of the subject composition. For instance, a composition that consists essentially of a particular species will generally comprise 90%, 95%, 96%, or more of that species.

"Domain" is used to describe a segment of a protein or nucleic acid. Unless otherwise indicated, a domain is not required to have any specific functional property.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below. An indel may produce insertions or deletions creating in-frame or out-of-frame mutations in the target sequence.

"Gene conversion" refers to the alteration of a DNA sequence by incorporation of an endogenous homologous sequence (e.g., a homologous sequence within a gene array). "Gene correction" refers to the alteration of a DNA sequence by incorporation of an exogenous homologous sequence, such as an exogenous single- or double stranded donor template DNA. Gene conversion and gene correction are products of the repair of DNA double-strand breaks by HDR pathways such as those described below.

An indel, gene conversion, gene correction, and other genome editing outcome is typically assessed by sequencing (most commonly by "next-gen" or "sequencing-by-synthesis" methods, though Sanger sequencing may still be used) and is quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUTDEseq process described in Tsai et al. (Nat. Biotechnol. 34(5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Alt-HDR." "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Replacement" or "replaced," when used with reference to a modification of a molecule (e.g., a nucleic acid or protein), does not require a process limitation but merely indicates that the replacement entity is present.

"Subject" means a human or non-human animal. A human subject can be any age (e.g., an infant, child, young adult, or adult), and may suffer from a disease, or may be in need of alteration of a gene. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

"Treat." "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" refer to the prevention of a disease in a mammal. e.g., in a human, including (a) avoiding or precluding the disease; (b) affecting the predisposition toward the disease; or (c) preventing or delaying the onset of at least one symptom of the disease.

A "kit" refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g., suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

The terms "polynucleotide," "nucleotide sequence," "nucleic acid," "nucleic acid molecule." "nucleic acid sequence." and "oligonucleotide" refer to a series of nucleotide bases (also called "nucleotides") in DNA and RNA, and mean any chain of two or more nucleotides. The polynucleotides, nucleotide sequences, nucleic acids etc, can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 1, below (see also Cornish-Bowden A, Nucleic Acids Res. 1985 May 10; 13(9):3021-30, incorporated by reference herein). It should be noted, however, that "T" denotes "Thymine or Uracil" in those instances where a sequence may be encoded by either DNA or RNA, for example in gRNA targeting domains.

TABLE 1

IUPAC nucleic acid notation

| Character | Base |
|---|---|
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

The term "variant" refers to an entity such as a polypeptide, polynucleotide or small molecule that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity.

Overview

The genome editing systems described herein generally include one or more gRNAs comprising targeting domains that are complimentary to one or more TGFBR2 target sequences, which target sequences, in turn, include or are adjacent to protospacer adjacent motif (PAM) sequences recognized by one or more RNA-guided nucleases to which the one or more gRNAs can bind (e.g., complexed). Accordingly, the genome editing systems of this disclosure are directed, in a site-specific manner, to the one or more TGFBR2 target sequences, and operate to introduce an alteration within or proximate to those TGFBR2 target sequences.

Alterations introduced into, or proximate to, the TGFBR2 target sites by the genome editing systems of this disclosure will, most commonly, include DNA single-strand breaks (SSBs or "nicks") and/or double strand breaks (DSBs). Nicks and DSBs, in turn, are repaired by cells in a manner that may result in in the introduction of small indels or larger insertions or deletions at one or more TGFBR2 target sites, deletions of sequences between two TGFBR2 target sites, and/or insertions of sequences (particularly exogenous sequences introduced into cells via donor template oligonucleotides) into TGFBR2 sites, or between two TGFBR2 target sites in a manner that replaces an endogenous cellular DNA sequence between those target sites. However, in some cases, the genome editing systems introduce one or more of a point mutation (e.g., via cysteine deamination), a change in DNA marking (e.g., DNA methylation, histone acetylation or deacetylation, or other chromatin modifications), and/or recruitment of trans-acting factors such as transcription factors. Alternatively, genome editing systems of this disclosure may associate, in a durable (e.g., over an interval of weeks, months or longer) or transient (over an interval of seconds, minutes, hours, or days) manner, with one or more TGFBR2 target sequences, thereby preventing association of other factors (particularly RNA polymerases, but also DNA polymerases, transcription factors, and/or other cis- or trans-acting factors that influence gene expression) with the TGFBR2 target sequences. These and other modes of action of genome editing systems and their components are described in detail below under the headings "RNA-guided nucleases" and "Modifications of RNA-guided nucleases."

The TGFBR2 target sequences and corresponding gRNA targeting domain sequences are generally, but not necessarily, located in exons, where the introduction of a small indel, or a larger insertion or deletion may result in one or more mutations (e.g., a frameshift mutation, a nonsense mutation, introduction of a codon for an amino acid that disrupts the structure of the surrounding protein, and/or removal of a codon for an amino acid that is necessary for protein activity) that reduce or eliminate function of the TGFBR2 protein. FIG. 1 shows a mapping of cutting activity of various *S. pyogenes* guide RNAs to the locations they target within the exon structure of the TGFBR2 gene. These mutations are referred to throughout this specification as "knockout" mutations, and their functional effect is "knockout" of TGFBR2 protein function.

Certain TGFBR2 target sequences may be considered "hot spot" target sites for gRNA targeting domain sequences. As used herein, a "hot spot" refers to a site that is preferentially targeted because it produces high % indel frequencies or effective knock down or knock out of the TGFBR2 gene, gRNAs targeting one or more of these preferred sites may produce % indel frequencies of 30% or higher. For example, a preferred target site in the TGFBR2 gene may have complementary gRNA targeting domains that produce % indel frequencies of 30%, 40%, 50%, 60%, 70%, 80%, 85%, 90%, 95%, or higher. Hot spot target sites within the TGFBR2 gene are described herein.

Preferred hot spot TGFBR2 regions are shown in table x:

TABLE 2

Preferred TGFBR2 target sites

| TGFBR2 Exon | Sequence |
|---|---|
| Exon 3 | TTAATAACGACATGATAGTCACTGACAACAACGGTGCAGTCAAGTTTCCAC<br>AACTGTGTAAATTTTGTGATGTGAGATTTTCCACCTGTGACAACCAGAAATC<br>CTGCATGAGCAACTGCAGCATCACCTCCATCTGTGAGAAGCCACAGGAAGT<br>CTGTGTGGCTGTATG (SEQ ID NO: 1) |
| Exon 4 | GAGAAAGAATGACGAGAACATAACACTAGAGACAGTTTGCCATGACCCCAA<br>GCTCCCCTACCATGACTTTATTCTGGAAGATGCTGCTTCTCCAAAGTGCATT<br>ATGAAGGAAAAAAAAAAGCCTGGTGAGACTTTCTTCATGTGTTCCTGTAGCT<br>CTGATGAGTGCAATGACAACATCATCTTCTCAGAAG (SEQ ID NO: 2) |
| Exon 5 | AATATAACACCAGCAATCCTGACTTGTTGCTAGTCATATTTCAAGTGACAGG<br>CATCAGCCTCCTGCCACCACTGGGAGTTGCCATATCTGTCATCATCATCTTCT<br>ACTGCTACCGCGTTAACCGGCAGCAGAAGCTGAGTTCAACCTGGGAAACCG<br>GCAAGACGCGGAAGCTCATGGAGTTCAGCGAGCACTGTGCCATCATCCTGG<br>AAGATGACCGCTCTGACATCAGCTCCACGTGTGCCAACAACATCAACCACA<br>ACACAGAGCTGCTGCCCATTGAGCTGGACACCCTGGTGGGGAAAGGTCGCT<br>TTGCTGAGGTCTATAAGGCCAAGCTGAAGCAGAACACTTCAGAGCAGTTTG<br>AGACAGTGGCAGTCAAGATCTTTCCCTATGAGGAGTATGCCTCTTGGAAGAC<br>AGAGAAGGACATCTTCTCAGACATCAATCTGAAGCATGAGAACATACTCCA<br>GTTCCTGACGGCTGAGGAGCGGAAGACGGAGTTGGGGAAACAATACTGGCT<br>GATCACCGCCTTCCACGCCAAGGGCAACCTACAGGAGTACCTGACGCGGCA |

TABLE 2-continued

| Preferred TGFBR2 target sites | |
|---|---|
| TGFBR2 Exon | Sequence |
| | TGTCATCAGCTGGGAGGACCTGCGCAAGCTGGGCAGCTCCCTCGCCCGGGG GATTGCTCACCTCCACAGTGATCACACTCCATGTGGGAGGCCCAAGATGCCC ATCGTGCACAGGGACCTCAAGAGCTCCAATATCCTCGTGAAGAACGACCTA ACCTGCTGCCTGTGTGACTTTGGGCTTTCCCTGCGTCTGGACCCTACTCTGTC TGTGGATGACCTGGCTAACAGTGGGCAG (SEQ ID NO: 3) |

Particularly preferred hot spot TGFBR2 regions are shown in table 3:

| TGFBR2 Target | Sequence |
|---|---|
| SEQ ID NO: 4 | GTAGCTCTGATGAGTGCAAT |
| SEQ ID NO: 5 | ATGAATCTCTTCACTCTAGG |
| SEQ ID NO: 6 | ACAGGAGTACCTGACGCGGC |
| SEQ ID NO: 7 | CTGTTAGCCAGGTCATCCAC |
| SEQ ID NO: 8 | GGGTGTCCAGCTCAATGGGC |
| SEQ ID NO: 9 | TCATAATGCACTTTGGAGAA |
| SEQ ID NO: 10 | TGACTTTATTCTGGAAGATG |

A TGFBR2 target sequence can be, for example, located in exon 3, 4, or 5 of the TGFBR2 gene. A gRNA targeting domain sequence corresponding to a TGFBR2 target sequence present in exon 3, 4, or 5 of the TGFBR2 gene can comprise a nucleotide sequence that is identical to, or differs by no more than 1, 2, or 3 nucleotides from, a nucleotide sequence selected from SEQ ID NOS: 5036 to 5096. For example, but not by way of limitation, an exemplary targeting domain can comprise a nucleotide sequence that is identical to, or differs by no more than 1, 2, or 3 nucleotides from a nucleotide sequence selected from the group consisting of:

(a) SEQ ID NOS: 5041;

(b) SEQ ID NOS: 5042;

(c) SEQ ID NOS: 5047;

(d) SEQ ID NOS: 5050;

(c) SEQ ID NOS: 5052;

(f) SEQ ID NOS: 5092; and g) SEQ ID NOS: 5093.

TABLE 4

| Targeting sequences | | | |
|---|---|---|---|
| SEQ ID | targeting sequence | PAM | exon |
| 5041 | ATTGCACTCATCAGAGCTAC | AGG | 4 |
| 5043 | CCAATGAATCTCTTCACTCT | AGG | intronic - adjacent to 4 |
| 5047 | GCCGCGTCAGGTACTCCTGT | AGG | 5 |
| 5050 | GTGGATGACCTGGCTAACAG | TGG | 5 |
| 5052 | GCCCATTGAGCTGGACACCC | TGG | 5 |

TABLE 4-continued

| Targeting sequences | | | |
|---|---|---|---|
| SEQ ID | targeting sequence | PAM | exon |
| 5092 | TTCTCCAAAGTGCATTATGA | AGG | 4 |
| 5093 | CATCTTCCAGAATAAAGTCA | TGG | 4 |

As an alternative to knocking out TGFBR2 expression, a transcriptional regulatory region, e.g., a promoter region (e.g., a promoter region that controls the transcription of the TGFBR2 gene) can be targeted to alter (e.g., knock down) the expression of the gene. A targeted knockdown approach can be mediated by a CRISPR/Cas system comprising an enzymatically inactive Cas9 (eiCas9) molecule or an eiCas9 fusion protein (e.g., an eiCas9 fused to a transcription repressor domain or chromatin modifying protein), as described herein. For example, one or more gRN A molecules comprising a targeting domain can be configured to target an eiCas9 molecule or an eiCas9 fusion protein, sufficiently close to a transcriptional regulatory region, e.g., a promoter region (e.g., a promoter region that controls the transcription of TGFBR2 gene), such that transcription of the TGFBR2 gene is reduced and/or eliminated. In certain embodiments, an eiCas9 or an eiCas9 fusion protein can be used to knock down TGFBR2 expression in a T cell, e.g., a human T cell.

TGFBR2 knock-out and/or knock down can be assessed in any suitable way, including without limitation, the examination of the sequence of the TGFBR2 gene, assessment of TGFBR2 protein expression on the surface of cells (e.g., by immunostaining and cell sorting, particularly by fluorescence activated cell sorting or FACS including indirect intracellular staining flow cytometry), detection of cellular or molecular changes mediated by TGFBR2, assessment of the effect of TGF-β on cell proliferation or survival, or by western blot to detect TGFBR2 protein levels. With respect to T cells in particular, TGFBR2 knockout may be confirmed by (a) sequencing of the TGFBR2 locus or T7E1 primer extension assay, and/or (b) intracellular FACS assessment of SMAD2/3 phosphorylation. Sequencing and T7E1 are described in greater detail below, while intracellular SMAD2/3 phosphorylation assays are described in the literature, e.g., by Chen, et al., J. Experimental Med. Volume 198, Number 12, Dec. 15, 2003 1875-1886 (which reference is incorporated by reference in its entirety and for all purposes herein), particularly the Materials & Methods section at page 1877 and Supplemental Figure S2.

Knock out and/or knock down of TGFBR2 may correspond to a 10%, 20%, 30%, 40%, 50%, 60%, 70%, 80%, 85%, 90%, 95%, or 100% reduction in TGFBR2 expression relative to a baseline measurement or a wild-type cell.

In some aspects, the provided compositions and methods include those in which: at least or greater than about 50%, 60%, 65%, 70%, 75%, 80%, 85%, 90% or 95% of cells in a composition of cells into which an agent (e.g. gRNA/Cas9) for knockout or genetic disruption of a TGFBR2 gene was introduced contain the genetic disruption; do not express the endogenous TGFBR2 polypeptide; do not contain a contiguous TGFBR2 gene, a TGFBR2 gene, and/or a functional TGFBR2 gene. In some embodiments, the methods, compositions and cells according to the present disclosure include those in which at least or greater than about 50%, 60%, 65%, 70%, 75%, 80%, 85%, 90% or 95% of cells in a composition of cells into which an agent (e.g. gRNA/Cas9) for knockout or genetic disruption of a TGFBR2 gene was introduced do not express a TGFBR2 polypeptide, such as on the surface of the cells. In some embodiments, at least or greater than about 50%, 60%, 65%, 70%, 75%, 80%, 85%, 90% or 95% of cells in a composition of cells into which an agent (e.g. gRNA/Cas9) for knockout or genetic disruption of a TGFBR2 gene was introduced are knocked out in both alleles, i.e, comprise a biallelic deletion, in such percentage of cells.

Genome editing systems targeting TGFBR2 may be implemented in a variety of ways, and their implementation may be tailored to the setting in which cells will be edited. Certain embodiments of this disclosure involve the delivery of RNA-guided nucleases and guide RNAs targeting TGFBR2 to cells ex vivo in the form of ribonucleoprotein (RNP) complexes by means of electroporation, e.g., using electroporators and cuvettes available from commercial suppliers such as MaxCyte (Gaithersburg, MD) or Lonza (Basel. Switzerland). Other embodiments, however, may implement in vivo nucleic acids vectors, such as viral vectors or lipid nanoparticles, for either in vivo or ex vivo editing. Details of these implementations are described in greater detail below, under the heading “Implementation of genome editing systems.”

Knock-out and/or knock down of TGFBR2 may be useful in a variety of settings, including without limitation, in the context of adaptive T-cell therapy. According to certain embodiments of this disclosure, TGFBR2 is knocked out in an immune cell, such as a T-cell, that will be used in therapy. As one example, the T-cell may express an engineered receptor such as a chimeric antigen receptor (CAR) or a heterologous T-cell receptor (TCR), which receptor may be configured to recognize an antigen on a cell or tissue that is implicated in a pathology such as a tumor. Whether or not they express an engineered receptor. TGFBR2 knockout T-cells according the present disclosure may be employed in the targeting of a tissue or organ in which TGF-β is present in amounts sufficient to reduce the proliferation or activity of T cells expressing TGFBR2.

TGFBR2 knock-out and/or knock down cells may be employed in “autologous” cell therapies, in which cells are harvested from a subject, altered to knock-out or knock-down TGFBR2 expression, and then returned to the same subject; alternatively, these cells may be administered to a different subject in an “allogeneic” cell therapy. In either approach, between harvesting and administration TGFBR2 cells of this disclosure may be manipulated in a variety of ways, such as expanded, stimulated, purified or sorted, transduced with a transgene, frozen and/or thawed.

Knocking out or knocking down the presence of the TGFBR2 gene as described herein can: (1) improve T cell proliferation; (2) improve T cell survival; and/or (3) improve T cell function. Knocking down the expression of the TGFBR2 gene as described herein can similarly: (1) improve T cell proliferation; (2) improve T cell survival; and/or (3) improve T cell function.

Genome Editing Systems

The term “genome editing system” refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation. In certain embodiments, the double strand or single strand break is within about 500 bp, about 450 bp, about 400 bp, about 350 bp, about 300 bp, about 250 bp, about 200 bp, about 150 bp, about 100 bp, about 50 bp, about 25 bp, or about 10 bp of a TGFBR2 target position, thereby inducing an alteration in the expression of the TGFBR2 gene.

Naturally occurring CRISPR systems are organized evolutionarily into two classes and five types (Makarova et al. Nat Rev Microbiol. 2011 June; 9(6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types 11 and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e., target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g., administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as “multiplexing” throughout this disclosure, and can be employed to target multiple, unrelated target sequences of interest, or to form multiple SSBs or DSBs within a single target domain and, in some cases, to generate specific edits within such target domain. For example, International Patent Publication No, WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes two gRNAs in combination with a Cas9 nickase (a Cas9 that makes a single strand nick such as *S. pyogenes* D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant," incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932. Mar. 11, 2014 (Davis) (describing Alt-HDR); Frit et al. DNA Repair 17(2014) 81-97 (Frit) (describing Alt-NHEJ); and lyama and Wilson III, DNA Repair (Amst.) 2013-August; 12(8): 620-636 (lyama) (describing canonical HDR and NHEJ pathways generally).

Where genome editing systems operate by forming DSBs, such systems optionally include one or more components that promote or facilitate a particular mode of double-strand break repair or a particular repair outcome. For instance. Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell, gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing), gRNAs and their component parts are described throughout the literature, for instance in Briner et al. (Molecular Cell 56(2), 333-339, Oct. 23, 2014 (Briner), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science August 17; 337(6096): 816-821 ("Jinek"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832. ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949. Feb. 27, 2014 (Nishimasu 2014) and Nishimasu et al., Cell 162, 1113-1126, Aug. 27, 2015 (Nishimasu 2015), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains. Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain." (Cotta-Ramusino) "stem loop 1" (Nishimasu 2014 and 2015) and the "nexus" (Briner). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance. Cpf1 ("CRISPR from *Prevotella* and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate that, although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type 11 or type V or CRISPR system, or an RNA-guided nuclease derived or adapted therefrom.

Table 2, below, provides exemplary gRNAs for targeting TGFBR2 with an *S. pyogenes* Cas9.

TABLE 5

| SEQ ID | SEQUENCE |
|---|---|
| 5038 | AGTTGCTCATGCAGGATTTC |
| 5088 | CCAGAATAAAGTCATGGTAG |
| 5087 | CCCCTACCATGACTTTATTC |
| 5039 | AAGTCATGGTAGGGGAGCTT |
| 5040 | AGTCATGGTAGGGGAGCTTG |
| 5041 | ATTGCACTCATCAGAGCTAC |
| 5042 | CCTAGAGTGAAGAGATTCAT |
| 5043 | CCAATGAATCTCTTCACTCT |
| 5044 | AAAGTCATGGTAGGGGAGCT |
| 5045 | GTGAGCAATCCCCCGGGCGA |
| 5046 | GTCGTTCTTCACGAGGATAT |
| 5047 | GCCGCGTCAGGTACTCCTGT |
| 5048 | GACGCGGCATGTCATCAGCT |
| 5049 | GCTTCTGCTGCCGGTTAACG |
| 5050 | GTGGATGACCTGGCTAACAG |
| 5051 | GTGATCACACTCCATGTGGG |
| 5052 | GCCCATTGAGCTGGACACCC |
| 5053 | GCGGTCATCTTCCAGGATGA |
| 5054 | GGGAGCTGCCCAGCTTGCGC |
| 5055 | GTTGATGTTGTTGGCACACG |
| 5056 | GGCATCTTGGGCCTCCCACA |
| 5057 | GCGGCATGTCATCAGCTGGG |
| 5058 | GCTCCTCAGCCGTCAGGAAC |
| 5059 | GCTGGTGTTATATTCTGATG |
| 5060 | CCGACTTCTGAACGTGCGGT |
| 5061 | TGCTGGCGATACGCGTCCAC |
| 5062 | CCCGACTTCTGAACGTGCGG |
| 5063 | CCACCGCACGTTCAGAAGTC |
| 5064 | TCACCCGACTTCTGAACGTG |
| 5065 | CCCACCGCACGTTCAGAAGT |
| 5066 | CGAGCAGCGGGGTCTGCCAT |
| 5067 | ACGAGCAGCGGGGTCTGCCA |

TABLE 5-continued

| SEQ ID | SEQUENCE |
|---|---|
| 5068 | AGCGGGGTCTGCCATGGGTC |
| 5069 | CCTGAGCAGCCCCCGACCCA |
| 5074 | CCATGGGTCGGGGGCTGCTC |
| 5070 | AACGTGCGGTGGGATCGTGC |
| 5071 | GGACGATGTGCAGCGGCCAC |
| 5072 | GTCCACAGGACGATGTGCAG |
| 5073 | CATGGGTCGGGGGCTGCTCA |
| 5075 | CAGCGGGGTCTGCCATGGGT |
| 5076 | ATGGGTCGGGGGCTGCTCAG |
| 5077 | CGGGGTCTGCCATGGGTCGG |
| 5078 | AGGAAGTCTGTGTGGCTGTA |
| 5079 | CTCCATCTGTGAGAAGCCAC |
| 5080 | ATGATAGTCACTGACAACAA |
| 5081 | GATGCTGCAGTTGCTCATGC |
| 5082 | ACAGCCACACAGACTTCCTG |
| 5083 | GAAGCCACAGGAAGTCTGTG |
| 5084 | TTCCTGTGGCTTCTCACAGA |
| 5085 | CTGTGGCTTCTCACAGATGG |
| 5086 | TCACAAAATTTACACAGTTG |
| 5089 | GACAACATCATCTTCTCAGA |
| 5090 | TCCAGAATAAAGTCATGGTA |
| 5091 | GGTAGGGGAGCTTGGGGTCA |
| 5092 | TTCTCCAAAGTGCATTATGA |
| 5093 | CATCTTCCAGAATAAAGTCA |
| 5094 | CACATGAAGAAAGTCTCACC |
| 5095 | TTCCAGAATAAAGTCATGGT |
| 5096 | TTTTCCTTCATAATGCACTT |
| 5036 | GGCCGCTGCACATCGTCCTG |
| 5037 | GCGGGGTCTGCCATGGGTCG |

gRNA Design

Methods for selection and validation of target sequences as well as off-target analyses have been described previously, e.g., in Mali; Hsu. Fu et al., 2014 Nat Biotechnol 32(3): 279-84, Heigwer et al., 2014 Nat methods 11(2):122-3, Bae et al. (2014) Bioinformatics 30(10): 1473-5; and Xiao Acet al. (2014) Bioinformatics 30(8): 1180-1182. Each of these references is incorporated by reference herein. As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

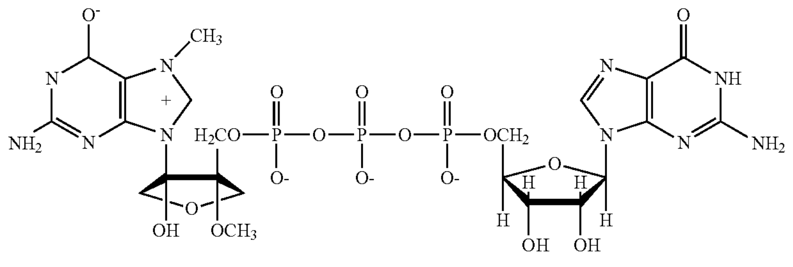

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., *E. coli* Poly(A)Polymerase), or in vivo by means of a polyadenylation sequence, as described in Maeder.

It should be noted that the modifications described herein can be combined in any suitable manner, e.g., a gRNA, whether transcribed in vivo from a DNA vector, or in vitro transcribed gRNA, can include either or both of a 5' cap structure or cap analog and a 3' poly A tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

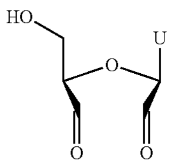

wherein "U" can be an unmodified or modified uridine.

The 3' terminal U ribose can be modified with a 2'3' cyclic phosphate as shown below:

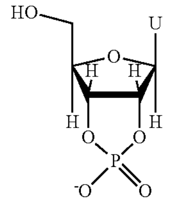

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo. —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aco), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'-+2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate. RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S, aureus*) or variation (e.g., full-length vs. truncated or split; naturally-occurring PAM specificity vs, engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers.

In addition to recognizing specific sequential orientations of PAMs and protospacers, RNA-guided nucleases can also recognize specific PAM sequences. *S. aureus* Cas9, for instance, recognizes a PAM sequence of NNGRRT or NNGRRV, wherein the N residues are immediately 3' of the region recognized by the gRNA targeting domain. *S. pyogenes* Cas9 recognizes NGG PAM sequences. And *F. novicida* Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389. Sep. 12, 2013 (Ran), incorporated by reference herein), or that that do not cut at all.

Cas9

Crystal structures have been determined for *S. pyogenes* Cas9 (Jinek 2014), and for *S, aureus* Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in *S. pyogenes* and *S. aureus*). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of Acidaminococcus sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity. PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand. On the other hand, inactivation of a Cas9 HNH domain results in a nickase that cleaves the bottom or non-complementary strand.

Modifications of PAM specificity relative to naturally occurring Cas9 reference molecules has been described by Kleinstiver et al, for both *S. pyogenes* (Kleinstiver et al., Nature. 2015 Jul. 23; 523(7561):481-5 (Kleinstiver I) and *S. aureus* (Kleinstiver et al., Nat Biotechnol. 2015 December; 33(12): 1293-1298 (Klienstiver II)). Kleinstiver et al. have also described modifications that improve the targeting fidelity of Cas9 (Nature, 2016 Jan. 28; 529, 490-495 (Kleinstiver III)). Each of these references is incorporated by reference herein.

RNA-guided nucleases have been split into two or more parts, as described by Zetsche et al. (Nat Biotechnol. 2015 February; 33(2):139-42 (Zetsche IT), incorporated by reference), and by Fine et al. (Sci Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Nucleic Acids Encoding RNA-Guided Nucleases

Nucleic acids encoding RNA-guided nucleases, e.g., Cas9. Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g., Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g., different stoichiometric ratios of gRNA: RNA-guided nuclease protein, different buffer solutions, etc.) to identify optimal conditions for RNP formation; and (b) testing modifications (e.g., chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g., 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g., 2 μM) of Cas9 in water+10× SYPRO Orange®-(Life Technologies cat #S-6650) is dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C., with a 1° C., increase in temperature every 10 seconds.

The second assay consists of mixing various concentrations of gRNA with fixed concentration (e.g., 2 μM) Cas9 in optimal buffer from assay 1 above and incubating (e.g., at RT for 10') in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C., with a 1° C., increase in temperature every 10 seconds.

Genome Editing Strategies

The genome editing systems described above are used, in various embodiments of the present disclosure, to generate edits in (i.e., to alter) targeted regions of DNA (e.g., TGFBR2 DNA) within or obtained from a cell. Various strategies are described herein to generate particular edits, and these strategies are generally described in terms of the desired repair outcome, the number and positioning of individual edits (e.g., SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double stranded, as described in greater detail below. Single or double stranded templates can be exogenous, in which case they will promote gene correction, or they can be endogenous (e.g., a homologous sequence within the cellular genome), to promote gene conversion. Exogenous templates can have asymmetric overhangs (i.e., the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g., a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g., ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of multiple DSBs, or SSBs, are described in, for instance. Cotta-Ramusino.

Donor Template Design

Donor template design is described in detail in the literature, for instance in Cotta-Ramusino. DNA oligomer donor templates (oligodeoxynucleotides or ODNs), which can be single stranded (ssODNs) or double-stranded (dsODNs), can be used to facilitate HDR-based repair of DSBs, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g., flanking or adjoining) a target sequence to be cleaved. These homologous regions are referred to here as "homology arms." and are illustrated schematically below:

[5' homology arm]-[replacement sequence]-[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or micro-homologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson et al. Nature Biotechnology 34, 339-344 (2016) (Richardson), which is incorporated by reference, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid. (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication. In certain embodiments, the cell is a T cell.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g., administered to a subject) immediately, or they can be maintained or stored for later use. Those of skill in the art will appreciate that cells can be maintained in culture or stored (e.g., frozen in liquid nitrogen) using any suitable method known in the art.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 3 and 4 set forth several, non-limiting examples of genome editing system implementations. Those of skill in the art will appreciate, however, that these listings are not comprehensive, and that other implementations are possible. With reference to Table 3 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 6

| Genome Editing System Components | | | |
|---|---|---|---|
| RNA-guided Nuclease | gRNA | Donor Template | Comments |
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |

TABLE 6-continued

| Genome Editing System Components | | | |
|---|---|---|---|
| RNA-guided Nuclease | gRNA | Donor Template | Comments |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | DNA | | A first DNA or DNA vector encoding an RNA-guided nuclease and second DNA or DNA vector encoding a gRNA and a donor template. |
| | DNA<br>DNA | | A first DNA or DNA vector encoding an RNA-guided nuclease and a donor template, and a second DNA or DNA vector encoding a gRNA |
| | DNA<br>RNA | | A DNA or DNA vector encoding an RNA-guided nuclease and a donor template, and a gRNA |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 7 summarizes various delivery methods for the components of genome editing systems, as described herein. Again, the listing is intended to be exemplary rather than limiting.

TABLE 7

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |

TABLE 7-continued

| Delivery Vector/Mode | Delivery into Non-Dividing Cells | Duration of Expression | Genome Integration | Type of Molecule Delivered |
|---|---|---|---|---|
| Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof Nucleic acids encoding elements of a genome editing system can include sequences that encode for one, two, three, four, or more gRNAs. For example, the nucleic acids can encode for both a first and a second gRNA molecule, e.g., where the second gRNA has a second targeting domain that is complementary to a second target sequence of the TGFBR2 gene. The nucleic acids disclosed herein can further comprise a nucleotide sequence that encodes a third gRNA molecule having a third targeting domain that is complementary to a third target sequence of the TGFBR2 gene. The nucleic acid compositions disclosed herein can further comprise a nucleotide sequence that encodes a fourth gRNA molecule described herein having a fourth targeting domain that is complementary to a fourth target sequence of the TGFBR2 gene. In certain embodiments, the second, third and/or fourth gRNA molecule comprises a targeting domain comprising a nucleotide sequence selected SEQ ID NOS: 5036 to 5096.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes. HSCs). Nucleic acid vectors, such as the vectors summarized in Table 4, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 7, and additional suitable viral vectors and their use and production are described in Cotta-Ramusino. In certain embodiments, the vector is a viral vector, e.g., an adeno-associated virus (AAV) vector or a lentivirus (LV) vector. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g., lipid and/or polymer) nanoparticles can be suitable for use as delivery vehicles in certain embodiments of this disclosure. Exemplary lipids for use in nanoparticle formulations, and/or gene transfer are shown in Table 8, and Table 9 lists exemplary polymers for use in gene transfer and/or nanoparticle formulations.

TABLE 8

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |

TABLE 8-continued

| Lipids Used for Gene Transfer | | |
|---|---|---|
| Lipid | Abbreviation | Feature |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl] trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 9

| Polymers Used for Gene Transfer | |
|---|---|
| Polymer | Abbreviation |
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases, i.e., ribonucleoprotein complexes) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure In certain embodiments, the RNP complexes of the present disclosure, including, e.g., RNP pharmaceutical compositions, can be used to: (1) improve T cell proliferation; (2) improve T cell survival; and/or (3) improve T cell function. For example, but not by way of limitation, two or more RNP complexes comprising distinct gRNAs can be employed concurrently or sequentially to alter TGFBR2 gene expression in a cell, e.g., a T cell. Such RNP complexes can comprise distinct gRNAs targeting distinct TGFBR2 gene sequences. The RNP complexes can, in certain instances, induce a cleavage event, e.g., a double strand or single strand break. For example, the RNP complexes can comprise enzymatically active Cas9 (eaCas9) molecules that form double strand breaks in a target nucleic acid or eaCas9 molecules that form single strand breaks in a target nucleic acid (e.g., nickase molecules). In certain embodiments, a dual-nickase RNP strategy can be used to form two offset single strand breaks that, in turn, form a single double strand break having an overhang (e.g., a 5' overhang).

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target. e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically, the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or non-simultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex will only be formed in the tissue that is targeted by both vectors.

Genetically Engineered Cells and Methods of Producing Cells Expressing a Recombinant Receptor Provided herein are cells for adoptive cell therapy, e.g., adoptive immunotherapy, and methods for producing or generating the cells. The cells include immune cells such as T cells. The cells generally are engineered by introducing one or more genetically engineered nucleic acids or products thereof. Among such products are genetically engineered antigen receptors, including engineered T cell receptors (TCRs) and functional non-TCR antigen receptors, such as chimeric antigen receptors (CARs), including activating, stimulatory, and costimulatory CARs, and combinations thereof. In some embodiments, the cells also are introduced, either simultaneously or sequentially, with the nucleic acid encoding the genetically engineered antigen receptor, with an agent (e.g., Cas9/gRNA RNP) that is capable of disrupting a gene encoding TGFBR2.

In some embodiments, the cells (e.g., T cells) can be incubated or cultivated prior to, during and/or subsequent to, introducing the nucleic acid molecule encoding the recombinant receptor and/or the agent (e.g., Cas9/gRNA RNP). In some embodiments, the cells (e.g., T cells) can be incubated or cultivated prior to, during or subsequent to, the introduction of the nucleic acid molecule encoding the recombinant receptor, such as prior to, during or subsequent to, the transduction of the cells with a viral vector (e.g., a lentiviral vector) encoding the recombinant receptor. In some embodiments, the cells (e.g., T cells) can be incubated or cultivated prior to, during or subsequent to, the introduction of the agent (e.g., Cas9/gRNA RNP), such as prior to, during or subsequent to, contacting the cells with the agent or prior to, during or subsequent to, delivering the agent into the cells, e.g., via electroporation. In some embodiments, the incubation can be both in the context of introducing the nucleic acid molecule encoding the recombinant receptor and introducing the agent, e.g., Cas9/gRNA RNP. In some embodiments, the incubation can be in the presence of a cytokine, such as IL-2, IL-7 or IL-15, or in the presence of a stimulating or activating agents that induces the proliferation or activation of cells, such as an anti-CD3/anti-CD28 antibodies.

In some embodiments, the method includes activating or stimulating cells with a stimulating or activating agent (e.g., anti-CD3/anti-CD28 antibodies) prior to introducing the nucleic acid molecule encoding the recombinant receptor and the agent, e.g., Cas9/gRNA RNP. In some embodiments, incubation also can be performed in the presence of a cytokine, such as IL-2 (e.g., 1 U/mL to 500 U/mL, such as 10 U/mL to 200 U/mL, for example at least or about 50 U/mL or 100 U/mL), IL-7 (e.g. 0.5 ng/mL to 50 ng/mL, such as 1 ng/mL to 20 ng/mL, for example, at least or about 5 ng/mL or 10 ng/mL) or IL-15 (e.g., 0.1 ng/mL to 50 ng/mL, such as 0.5 ng/mL to 25 ng/mL, for example, at least or about 1 ng/mL or 5 ng/mL). In some embodiments, the cells are incubated for 6 hours to 96 hours, such as 24-48 hours or 24-36 hours prior to introducing the nucleic acid molecule encoding the recombinant receptor (e.g., via transduction).

Cells and Preparation of Cells for Genetic Engineering

Recombinant receptors that bind to a specific antigen and agents (e.g., Cas9/gRNA RNP) for gene editing of a TGFBR2 gene encoding a TGFBR2 polypeptide can be introduced into a wide variety of cells. In some embodiments, a recombinant receptor is engineered and/or the TGFBR2 target gene is manipulated ex vivo and the resulting genetically engineered cells are administered to a subject. Sources of target cells for ex vivo manipulation may include, e.g., the subject's blood, the subject's cord blood, or the subject's bone marrow. Sources of target cells for ex vivo manipulation may also include, e.g., heterologous donor blood, cord blood, or bone marrow.

In some embodiments, the cells, e.g., engineered cells, are eukaryotic cells, such as mammalian cells, e.g., human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In some embodiments, the target cell is a T cell, e.g., a CD8+ T cell (e.g., a CD8+ naïve T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naïve T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

Among the subtypes and subpopulations of T cells and/or of CD4+ and/or of CD8+ T cells, are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells. TH2 cells, TH3 cells. TH17 cells. TH9 cells. TH22 cells, follicular helper T cells, alpha/beta T cells, and delta/gamma T cells.

In some embodiments, the methods include isolating cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from a mouse, a rat, a non-human primate, or a pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more properties, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes. B cells, other nucleated white blood cells, red blood cells, and/or platelets, and, in some aspects, contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor. Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++-free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation, in some aspects, includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 10(0% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker−) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Rα (CD127). In some examples, CD8+ T cells are enriched for cells positive for CD45RO (or negative for CD45RA) and for CD62L.

For example, CD3+, CD28+ T cells can be positively selected using CD3/CD28 conjugated magnetic beads (e.g., DYNABEADS® M-450 CD3/CD28 T Cell Expander).

In some embodiments. T cells are separated from a peripheral blood mononuclear cell (PBMC) sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. (See Terakura et al. (2012) Blood. 1:72-82; Wang et al. (2012) J Immunother. 35(9):689-701.) In some embodiments, combining TCM-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L. CCR7, CD28, CD3, and/or CD 127, in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections, in some aspects, are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+T helper cells are sorted into naïve, central memory, and effector cells by identifying cell populations that have cell surface antigens, CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L- and CD45RO.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher e Humana Press Inc., Totowa, NJ).

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660. Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing PBMCs (e.g., such that the resulting population of cells contains at least about 5, 10, 20, or 40 or more PBMC feeder cells for each T lymphocyte in the initial population to be expanded), and incubating the culture (e.g., for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees Celsius, and generally at or about 37 degrees Celsius. Optionally, the incubation may further comprise adding non-dividing EBV-transformed lymphoblastoid cells (LCLs) as feeder cells. LCLs can be irradiated with gamma rays in the range of about 6000 to 10,000 rads. The LCL feeder cells, in some aspects, are provided in any suitable amount, such as a ratio of LCL feeder cells to initial T lymphocytes of at least about 10:1.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters may be used in certain aspects. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C., at a rate of 1° per minute and stored in the vapor phase of a liquid nitrogen storage tank.

In some embodiments, the methods include re-introducing the engineered cells into the same patient, before or after cryopreservation.

Recombinant Receptors

In some embodiments, the cells comprise one or more nucleic acids encoding a recombinant receptor introduced via genetic engineering, and genetically engineered products of such nucleic acids. In some embodiments, the cells can be produced or generated by introducing into a cell (e.g., via transduction of a viral vector, such as a retroviral or lentiviral vector) a nucleic acid molecule encoding the recombinant receptor. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the target cell has been altered to bind to one or more target antigen, such as one or more tumor antigen. In some embodiments, the target antigen is selected from ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin. CEA, and hepatitis B surface antigen, anti-folate receptor, CD23, CD24, CD30, CD33, CD38, CD44. EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-A1 MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target cell has been altered to bind one or more of the following tumor antigens, e.g., by a TCR or a CAR, Tumor antigens may include, but are not limited to, AD034, AKT1, BRAP, CAGE, CDX2, CLP, CT-7, CT8/HOM-TES-85, cTAGE-1, Fibulin-1, HAGE, HCA587/MAGE-C2, hCAP-G, HCE661, HER2/neu, HLA-Cw, HOM-HD-21/Galectin9, HOM-MEEL-40/SSX2, HOM-RCC-3.1.3/CAXII, HOXA7, HOXB6, Hu, HUB1, KM-HN-3, KM-KN-1, KOC1, KOC2, KOC3, KOC3, LAGE-1, MAGE-1, MAGE-4a, MPP11, MSLN, NNP-1, NY-BR-I, NY-BR-62, NY-BR-85, NY-CO-37, NY-CO-38, NY-ESO-1, NY-ESO-5, NY-LU-12, NY-REN-10, NY-REN-19/LKB/STK1, NY-REN-21, NY-REN-26/BCR, NY-REN-3/NY-CO-38, NY-REN-33/SNC6, NY-REN-43, NY-REN-65, NY-REN-9, NY-SAR-35, OGFr, PLU-1, Rab38, RBPJkappa, RHAMM, SCP1, SCP-1, SSX3, SSX4, SSX5, TOP2A, TOP2B, or Tyrosinase, Antigen Receptors:

Chimeric Antigen Receptors (CARs)

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Cuff. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337. U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens that may be targeted by the receptors include, but are not limited to, αvβ6 integrin (avb6 integrin), B cell maturation antigen (BCMA). B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123. CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor. Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100). Her2/neu (receptor tyrosine kinase erbB2), Her3 (erb-B3). Her4 (erb-B4), erbB dimers, human high molecular weight-melanoma-associated antigen (HMW-MAA), hepatitis B surface antigen, Human leukocyte antigen A1 (HLA-AI), human leukocyte antigen A2 (HLA-A2), IL-22 receptor alpha(IL-22Ra), IL-13 receptor alpha 2 (IL-13Ra2), kinase insert domain receptor (kdr), kappa light chain. L1 cell adhesion molecule (L1CAM). CE7 epitope of L1-CAM. Leucine Rich Repeat Containing 8 Family Member A (LRRC8A). Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), and a pathogen-specific antigen.

In some embodiments, antigens targeted by the receptors in some embodiments include orphan tyrosine kinase receptor ROR1, tEGFR, Her2. L1-CAM, CD19, CD20, CD22, mesothelin, CEA, and hepatitis B surface antigen, anti-folate receptor, CD23, CD24, CD30, CD33, CD38, CD44, EGFR. EGP-2. EGP-4, 0EPHa2. ErbB2, 3, or 4, FBP, fetal acetylcholine e receptor, GD2, GD3, HMW-MAA, IL-22R-alpha, IL-13R-alpha2, kdr, kappa light chain. Lewis Y, L1-cell adhesion molecule. MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3. CE7, Wilms Tumor 1 (WT-1), a cyclin, such as cyclin A1 (CCNA1), and/or biotinylated molecules, and/or molecules expressed by HIV. HCV. HBV or other pathogens.

In some embodiments, the CAR has binding specificity for a tumor associated antigen, e.g., CD19, CD20, carbonic anhydrase IX (CAIX), CD171, CEA, ERBB2, GD2, alpha-folate receptor. Lewis Y antigen, prostate specific membrane antigen (PSMA) or tumor associated glycoprotein 72 (TAG72).

In some embodiments, the CAR binds a pathogen-specific antigen. In some embodiments, the CAR is specific for viral antigens (such as HIV, HCV. HBV, etc.), bacterial antigens, and/or parasitic antigens.

Among the chimeric receptors are chimeric antigen receptors (CARs). The chimeric receptors, such as CARs, generally include an extracellular antigen binding domain, such as a portion of an antibody molecule, generally a variable heavy (VH) chain region and/or variable light ($V_L$) chain region of the antibody, e.g., an scFv antibody fragment.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone. IgG4 hinge linked to CH2 and CH3 domains, or IgG4 hinge linked to the CH3 domain.

Exemplary spacers include, but are not limited to, those described in Hudecek et al. (2013) *Clin. Cancer Res.*, 19:3153 or international patent application publication number WO2014031687.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain, in some aspects, is derived from any membrane-bound or transmembrane protein. Transmembrane regions include those derived from (i.e., comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD134, CD137, CD154. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-Z) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects, also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is, in some aspects, described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from the CD3 zeta chain. FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-IBB, OX40, DAP10, and ICOS. In some aspects, the same CAR includes both the activating and costimulatory components.

In some embodiments, the activating domain is included within one CAR whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine. 5(215) (December 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687.

In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published Application No, WO 2014/031687. For example, the marker can be a truncated EGFR (tEGFR) that is optionally linked to a linker sequence, such as a T2A cleavable linker sequence.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases. CARs are referred to as first, second, and/or third generation CARs. In some aspects, a first-generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1).

In some embodiments, the chimeric antigen receptor contains an intracellular domain of a T cell costimulatory molecule. In some aspects, the T cell costimulatory molecule is CD28 or 41BB.

In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof.

In some embodiments, the intracellular signaling domain comprises a human CD3 zeta stimulatory signaling domain or functional variant thereof, such as a 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993.

In some aspects, the spacer contains only a hinge region of an IgG, such as only a hinge of IgG4 or IgG1. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes an antibody or fragment that specifically binds an antigen, a spacer such as any of the Ig-hinge containing spacers, a CD28 transmembrane domain, a CD28 intracellular signaling domain, and a CD3 zeta signaling domain. In some embodiments, the CAR includes an antibody or fragment that specifically binds an antigen, a spacer such as any of the Ig-hinge containing spacers, a CD28 transmembrane domain, a CD28 intracellular signaling domain, and a CD3 zeta signaling domain. In some embodiments, such CAR constructs further include a T2A ribosomal skip element and/or a tEGFR sequence, e.g., downstream of the CAR.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

T Cell Receptors

In some embodiments, the genetically engineered antigen receptors include recombinant T cell receptors (TCRs) and/or TCRs cloned from naturally occurring T cells. Thus, in some embodiments, the target cell has been altered to contain specific T cell receptor (TCR) genes (e.g., a TRAC and RBC gene). TCRs or antigen-binding portions thereof include those that recognize a peptide epitope or T cell epitope of a target polypeptide, such as an antigen of a tumor, viral or autoimmune protein. In some embodiments, the TCR has binding specificity for a tumor associated antigen, e.g., carcinoembryonic antigen (CEA), GP100, melanoma antigen recognized by T cells 1 (MARTI), melanoma antigen A3 (MAGEA3). NYESO1 or p53.

In some embodiments, a "T cell receptor" or "TCR" is a molecule that contains a variable α and β chains (also known as TCRα and TCRβ, respectively) or a variable γ and δ chains (also known as TCRγ and TCRδ, respectively), or antigen-binding portions thereof, and which is capable of specifically binding to a peptide bound to an MHC molecule. In some embodiments, the TCR is in the ap form. Typically, TCRs that exist in αβ and γδ forms are generally structurally similar, but T cells expressing them may have distinct anatomical locations or functions. Generally, a TCR is or can be expressed on the surface of T cells (or T lymphocytes) where it is generally responsible for recognizing antigens bound to major histocompatibility complex (MHC) molecules.

In some embodiments, the TCR is a full TCR or an antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In some embodiments, the variable domains of the TCR contain hypervariable loops, or CDRs, which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., *Proc. Nat'l Acad Sci. U.S.A.* 87:9138, 1990; Chothia et al., *EMBO J.* 7:3745, 1988; see also Lefranc et al., *Dev. Comp. Immunol.* 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in super-antigen binding and not antigen recognition (Kotb (1995) Clinical Microbiology Reviews, 8:411-426).

In some embodiments, a TCR contains a variable alpha domain ($V_\alpha$) and/or a variable beta domain ($V_\beta$) or antigen-binding fragments thereof. In some embodiments, the α-chain and/or β-chain of a TCR also can contain a constant domain, a transmembrane domain and/or a short cytoplasmic tail (see, e.g., Janeway et al., *Immunobiology: The Immune System in Health and Disease.* $3^{rd}$ Ed., Current Biology Publications, p. 4:33, 1997). In some embodiments, the α chain constant domain is encoded by the TRAC gene (IMGT nomenclature) or is a variant thereof. In some embodiments, the β chain constant region is encoded by TRBC1 or TRBC2 genes (IMGT nomenclature) or is a variant thereof. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In some aspects, residues of a TCR are known or can be identified according to the International Immunogenetics Information System (IMGT) numbering system (see e.g, www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Vα chains and/or Vβ chain correspond to the amino acids present between residue numbers 27-38, inclusive, the CDR2 sequences within a TCR Vα chain and/or Vβ chain correspond to the amino acids present between residue numbers 56-65, inclusive, and the CDR3 sequences within a TCR Vα chain and/or Vβ chain correspond to the amino acids present between residue numbers 105-117, inclusive.

In some embodiments, the TCR may be a heterodimer of two chains α and β (or optionally γ and δ) that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains. In some embodiments, each of the constant and variable domains contain disulfide bonds formed by cysteine residues.

In some embodiments, the TCR for engineering cells as described is one generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In some embodiments, the TCR is obtained from a biological source, such as from cells such as from a T cell (e.g, cytotoxic T cell), T-cell hybridomas or other publicly available source. In some embodiments, the T-cells can be obtained from in vivo isolated cells. In some embodiments, the T-cells can be a cultured T-cell hybridoma or clone. In some embodiments, the TCR or antigen-binding portion thereof can be synthetically generated from knowledge of the sequence of the TCR.

In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with a desired altered property, such as higher affinity for a desired target antigen, are selected.

In some embodiments as described, the TCR can contain an introduced disulfide bond or bonds. In some embodiments, the native disulfide bonds are not present. In some embodiments, the one or more of the native cysteines (e.g. in the constant domain of the α chain and β chain) that form a native inter-chain disulfide bond are substituted to another residue, such as to a serine or alanine. In some embodiments, an introduced disulfide bond can be formed by mutating non-cysteine residues on the alpha and beta chains, such as in the constant domain of the α chain and β chain, to cysteine. Exemplary non-native disulfide bonds of a TCR are described in published International PCT Nos, WO 2006/000830 and WO 2006/037960. In some embodiments, cysteines can be introduced at residue Thr48 of the α chain and Ser57 of the β chain, at residue Thr45 of the α chain and Ser77 of the β chain, at residue Tyr10 of the α chain and Ser17 of the β chain, at residue Thr45 of the α chain and Asp59 of the β chain and/or at residue Ser15 of the α chain and Glu15 of the β chain. In some embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In some embodiments, the TCR chains contain a transmembrane domain. In some embodiments, the transmembrane domain is positively charged. In some cases, the TCR chain contains a cytoplasmic tail. In some aspects, each chain (e.g. alpha or beta) of the TCR can possess one N-terminal immunoglobulin variable domain, one immunoglobulin constant domain, a transmembrane region, and a short cytoplasmic tail at the C-terminal end. In some embodiments, a TCR, for example via the cytoplasmic tail, is associated with invariant proteins of the CD3 complex involved in mediating signal transduction. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). A TCR may be cell-bound or in soluble form. In some embodiments, for purposes of the provided methods, the TCR is in cell-bound form expressed on the surface of a cell.

In some embodiments, a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second poly peptides being linked by a disulfide bond. In some embodiments, the bond can correspond to the native inter-chain disulfide bond present in native dimeric as TCRs. In some embodiments, the inter-chain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR, which is a single amino acid strand containing an α chain and a β chain that is able to bind to MHC-peptide complexes. Typically, a scTCR can be generated using methods known to those of skill in the art. See e.g., International published PCT Nos. WO 1996/13593, WO 1996/18105, WO 1999/18129, WO 2004/033685, WO 2006/037960, WO 2011/044186; U.S. Pat. No. 7,569,664; and Schlueter. C. J, et al. J. Mol. Biol. 256, 859 (1996).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an amino acid sequence corresponding to a TCR β chain variable region, a second segment constituted by an amino acid sequence corresponding to a TCR α chain variable region sequence fused to the N terminus of an amino acid sequence corresponding to a TCR α chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, for the scTCR to bind an MHC-peptide complex, the α and β chains must be paired so that the variable region sequences thereof are orientated for such binding. Various methods of promoting pairing of an α and β in a scTCR are well known in the art. In some embodiments, a linker sequence is included that links the α and β chains to form the single polypeptide strand. In some embodiments, the linker should have sufficient length to span the distance between the C terminus of the α chain and the N terminus of the β chain, or vice versa, while also ensuring that the linker length is not so long so that it blocks or reduces bonding of the scTCR to the target peptide-MHC complex.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P-, wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-$(SGGGG)_5$-P- or -PGGG-$(SGGGG)_6$-P-, wherein P is proline, G is glycine and S is serine. In some embodiments, the linker has the sequence GSADDAKKDAAKKDGKS (SEQ ID NO: 5102).

In some embodiments, a scTCR contains a disulfide bond between residues of the single amino acid strand, which, in some cases, can promote stability of the pairing between the α and β regions of the single chain molecule (see e.g. U.S. Pat. No. 7,569,664). In some embodiments, the scTCR contains a covalent disulfide bond linking a residue of the immunoglobulin region of the constant domain of the α chain to a residue of the immunoglobulin region of the constant domain of the β chain of the single chain molecule. In some embodiments, the disulfide bond corresponds to the native disulfide bond present in a native dTCR. In some embodiments, the disulfide bond in a native TCR is not present. In some embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In some embodiments, a scTCR is a non-disulfide linked truncated TCR in which heterologous leucine zippers fused to the C-termini thereof facilitate chain association (see e.g. International published PCT No, WO 1999/60120). In some embodiments, a scTCR contain a TCRα variable domain covalently linked to a TCRβ variable domain via a peptide linker (see e.g., International published PCT No, WO 1999/18129).

In some embodiments, any of the TCRs, including a dTCR or scTCR, can be linked to signaling domains that yield an active TCR on the surface of a T cell. In some embodiments, the TCR is expressed on the surface of cells. In some embodiments, the TCR does contain a sequence corresponding to a transmembrane sequence. In some embodiments, the transmembrane domain can be a Cα or Cβ transmembrane domain. In some embodiments, the transmembrane domain can be from a non-TCR origin, for example, a transmembrane region from CD3z, CD28 or B7.1. In some embodiments, the TCR does contain a sequence corresponding to cytoplasmic sequences. In some embodiments, the TCR contains a CD3z signaling domain. In some embodiments, the TCR is capable of forming a TCR complex with CD3.

In some embodiments, the TCR or antigen-binding fragment thereof exhibits an affinity with an equilibrium binding constant for a target antigen of between or between about $10^{-5}$ and $10^{-12}$ M and all individual values and ranges therein. In some embodiments, the target antigen is an MHC-peptide complex or ligand.

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. In some embodiments, to generate a vector encoding a TCR, the α and β chains can be PCR amplified from total cDNA isolated from a T cell clone expressing the TCR of interest and cloned into an expression vector. In some embodiments, the α and β chains can be synthetically generated.

In some embodiments, the TCR alpha and beta chains are isolated and cloned into a gene expression vector. In some embodiments, transcription units can be engineered as a bicistronic unit containing an IRES (internal ribosome entry site), which allows co-expression of gene products (e.g. encoding an α and β chains) by a message from a single promoter. Alternatively, in some cases, a single promoter may direct expression of an RNA that contains, in a single open reading frame (ORF), multiple genes (e.g. encoding an α and β chains) separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream. Examples of 2A cleavage peptides, including those that can induce ribosome skipping, are T2A, P2A. E2A and F2A. In some embodiments, the α and β chains are cloned into different vectors. In some embodiments, the generated α and β chains are incorporated into a retroviral, e.g., a lentiviral, vector.

In some embodiments, the TCR alpha and beta genes are linked via a picornavirus 2A ribosomal skip peptide so that both chains are co-expression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

Vectors and Methods of Engineering

The provided methods include expressing the recombinant receptors, including CARs or TCRs, for producing the genetically engineered cells expressing such binding molecules. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, nucleic acid encoding a recombinant receptor can be cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, La Jolla. Calif.), the pET series (Novagen, Madison, Wis.), the pGEX series (Pharmacia Biotech. Uppsala, Sweden), or the pEX series (Clontech, Palo Alto. Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-C1, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the recombinant receptor. In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller. A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known in the art. Exemplary methods are described in, e.g., Wang et al. (2012) *J. Immunother.* 35(9): 689-701; Cooper et al. (2003) *Blood.* 101:1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology. John Wiley & Sons. New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application Publication No, WO 2014/055668, and U.S. Pat. No. 7,446,190.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example, in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D, et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. Se, e.g., Riddell et al., U.S. Pat. No. 6,040,177, at columns 14-17.

Compositions and Formulations

Also provided are populations of such cells, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term “pharmaceutical formulation” refers to a preparation which is in such form as to permit the biological activity of an active ingredient contained therein to be effective, and which contains no additional components which are unacceptably toxic to a subject to which the formulation would be administered.

A “pharmaceutically acceptable carrier” refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin. gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents, in some aspects, are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro-derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may, in some aspects, be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may, in some aspects, be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

Methods of Administration and Uses in Adoptive Cell Therapy

Provided herein are methods of administering cells, populations, and compositions described herein, and uses of such cells, populations, and compositions described herein, to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg. Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount. In the context of lower tumor burden, the prophylactically effective amount, in some aspects, will be higher than the therapeutically effective amount.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super-type as the first subject.

In some embodiments, the subject has been treated with a therapeutic agent targeting the disease or condition, e.g., the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse.

In some aspects, the subject has not received prior treatment with another therapeutic agent.

Among the diseases, conditions, and disorders for treatment with the provided compositions, cells, methods and uses are tumors, including solid tumors, hematologic malignancies, and melanomas, and infectious diseases, such as infection with a virus or other pathogen, e.g., HIV, HCV, HBV, CMV, and parasitic disease. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma. Hodgkin's lymphoma, cervical carcinoma, colorectal cancer, glioblastoma, neuroblastoma, Ewing's sarcoma, medulloblastoma, osteosarcoma, synovial sarcoma, and/or mesothelioma.

In some embodiments, the disease or condition is an infectious disease or condition, such as, but not limited to, viral, retroviral, bacterial, and protozoal infections, immunodeficiency. Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease. Grave's disease, Crohn's disease, multiple sclerosis, asthma, and/or a disease or condition associated with transplant.

In some embodiments, antigen associated with the disease, disorder or condition is selected from ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin. CEA, and hepatitis B surface antigen, anti-folate receptor, CD23, CD24, CD30, CD33, CD38, CD44. EGFR, epithelial glycoprotein 2 (EPG-2), epithelial glycoprotein 40 (EPG-40). EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain. Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin. TAG72, B7-H6, IL-13 receptor alpha 2 (IL-13Ra2), CA9. GD3. HMW-MAA, CD171. G250/CAIX, HLA-A1 MAGE A1, HLA-A2 NY-ESO-1, PSCA, folate receptor-a, CD44v6, CD44v7/8, avb6 integrin, 8H9. NCAM. VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1. MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met. GD-2. O-acetylated GD2 (OGD2), CE7, Wilms Tumor 1 (WT-1), a cyclin, cyclin A2. CCL-1, CD138, a pathogen-specific antigen.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3 and/or biotinylated molecules, and/or molecules expressed by HIV, HCV, HBV or other pathogens.

In some embodiments, the cells are administered at a desired dosage, which, in some aspects, includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4' to CD8' ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 80) million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about 10' and at or about 10' T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight.

In some embodiments, the cells are administered at or within a certain range of error of, greater than, and/or at least about $1\times10^6$, about $2.5\times10^6$, about $5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1. 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

The cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example. Kochenderfer et al., J. Immunotherapy. 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects, the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

EXAMPLES

The following Examples are merely illustrative and are not intended to limit the scope or content of the invention in any way.

Example 1—Initial Screening of gRNAs

Guide RNAs were screened by complexing commercially synthesized gRNAs with Cas9 in vitro and delivering the gRNA/Cas9 ribonucleoprotein (RNP) to cells via electroporation.

Figure 2:
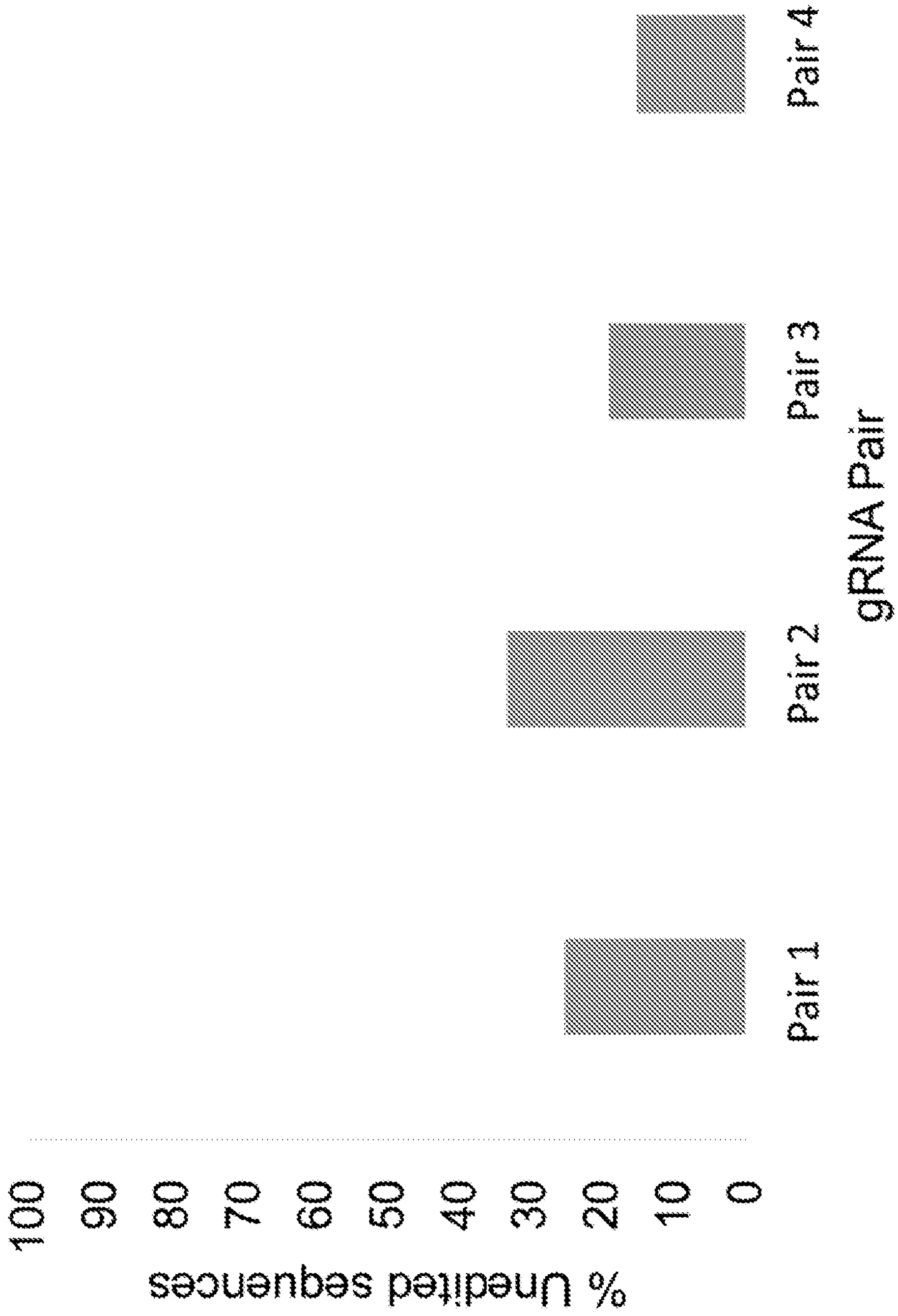
FIG. 2 depicts the genome editing efficiency of certain exemplary gRNA pairs.

FIG. 1 depicts % indel frequency of test gRNAs. FIG. 2 depicts the genome editing efficiency of certain exemplary gRNA pairs.

Example 2—Analysis of gRNA Candidates Against TGFBR2 in T Cells

Figure 3:
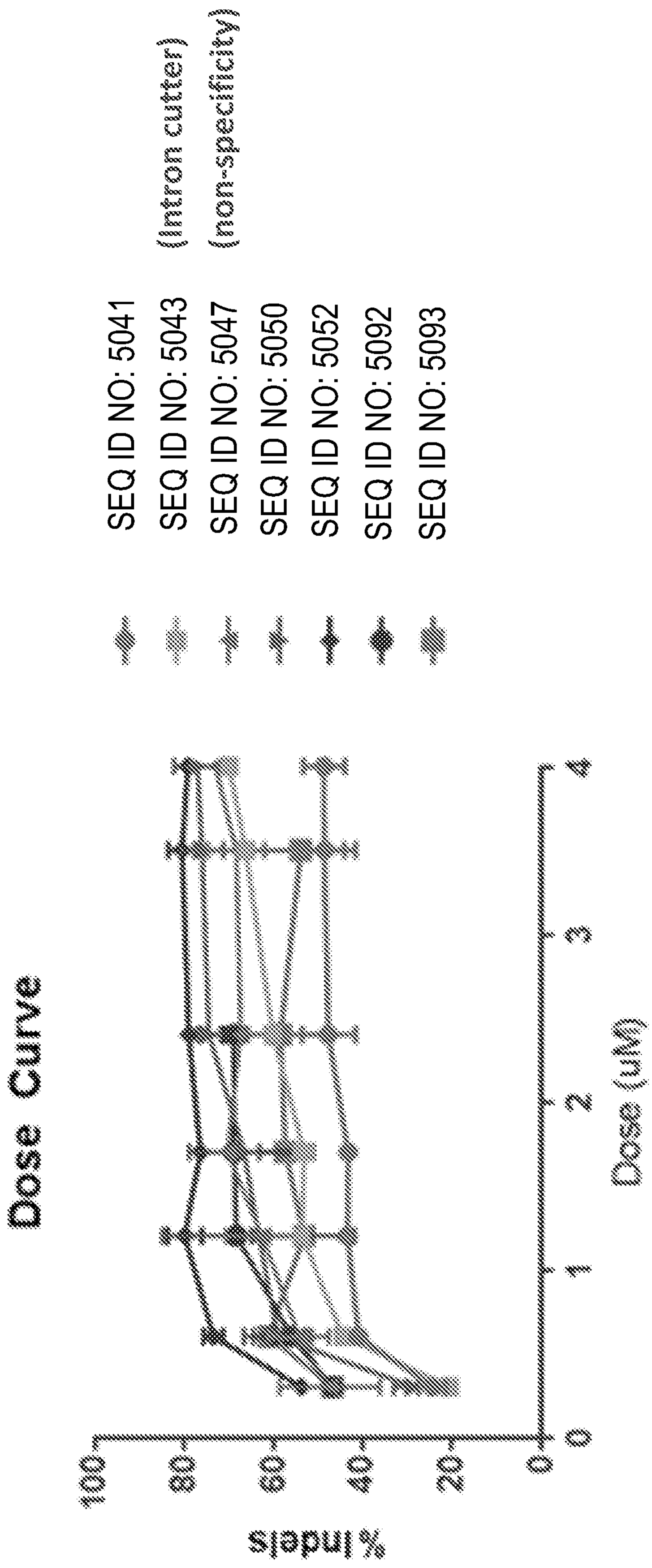
FIG. 3 depicts % indel formation as determined by miSeq in the TGFBR2 gene. Seven gRNAs were tested at various concentrations of RNPs to produce a dose response curve.

The goal of CRISPR-Cas9 editing of cells is to achieve the highest percent knock out of the target gene using the lowest possible concentration of the gRNA/Cas9 complex and the least number of off-target cutting events. To determine the best possible gRNA candidates for TGFBR2 gene editing, seven potential gRNAs were tested. T cells were transfected with gRNA/Cas9 RNPs at various concentrations. The percent indel frequency was then determined using Illumina miSeq analysis. The results show % indel frequency for different gRNAs ranged from 20% to 80%, with all gRNAs achieving their highest % indel frequency at a RNP concentration of 2 μM (FIG. 3). The 2 μM RNP concentration was subsequently used for all experiments.

Figure 4A:
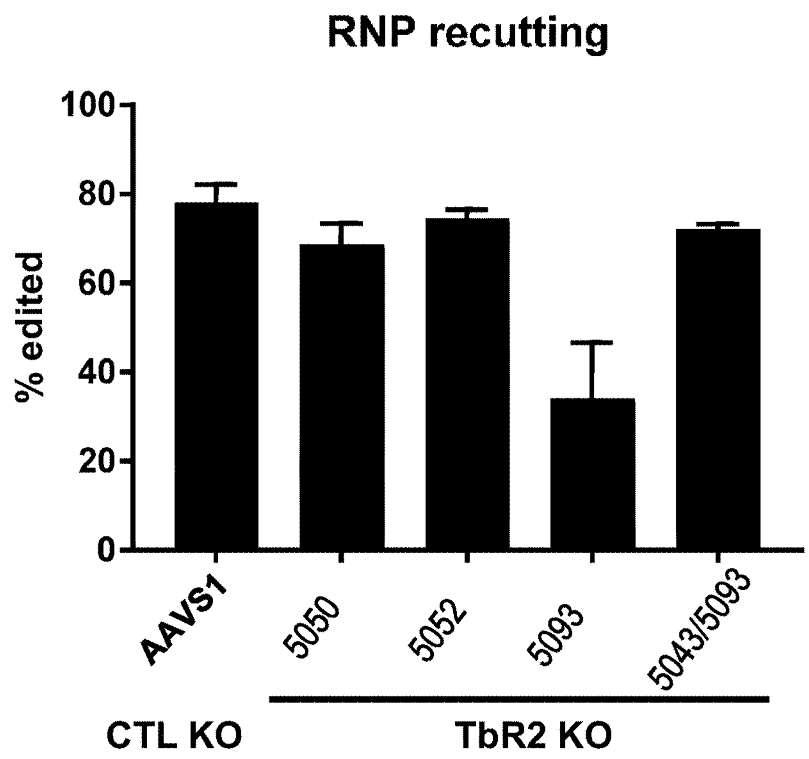
FIG. 4A-FIG. 4B depicts % edited cells (FIG. 4A) and % indel frequency (FIG. 4B) with several tested gRNAs targeting TGFBR2 and a control gRNA targeting the AAVS1 locus.

Select gRNAs from the miSeq analysis were chosen for further analysis in BCMA CART cells. The gRNAs of SEQ ID Nos: 5050, 5052, 5093, and 5043 were used in an RNP re-cutting assay to determine the % editing of the TGFBR2 gene. A dual gRNA approach was also tested using the combination of SEQ ID N05043/5093. While the individual gRNAs of SEQ ID NO: 5043 and 5093 only achieved 20-40% editing, the combination was found to be more efficacious, producing a % edited value of approximately 80% (FIG. 4A).

Figure 4B:
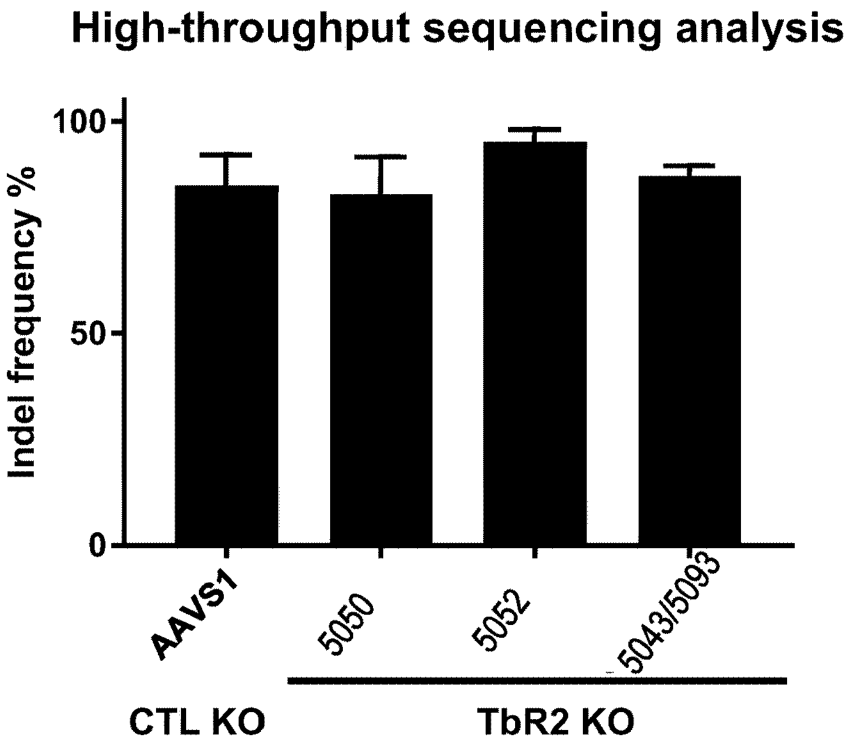

High-throughput sequencing analysis was performed with select gRNAs to determine the % indel frequency. The gRNAs of SEQ ID NO: a and b and the dual gRNA combination of c/d were tested. Remarkably. % indel frequencies as high as 95% were achieved from the selected gRNAs (FIG. 4B).

Figure 5:
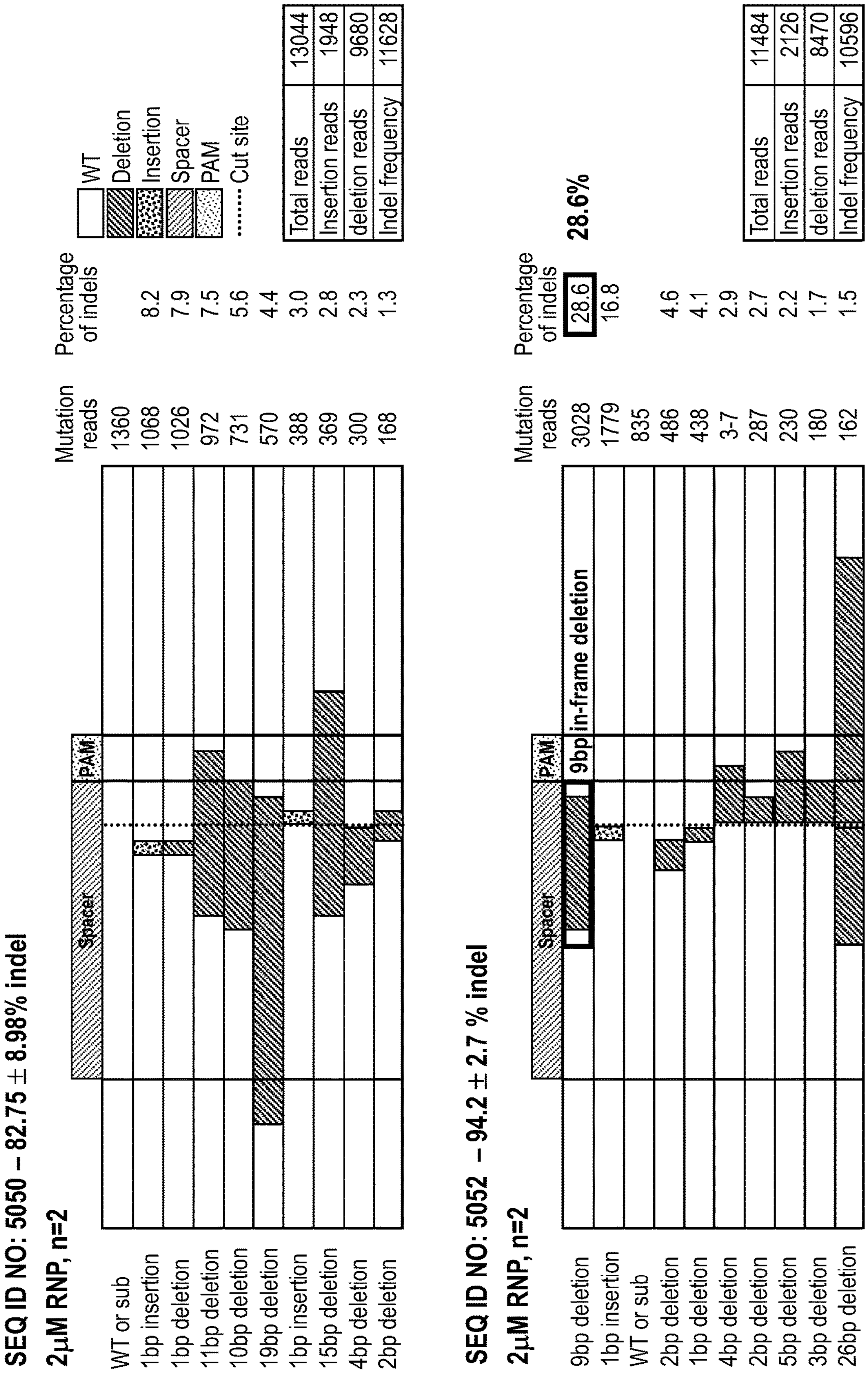
FIG. 5 depicts a comparison of two TGFBR2 targeting gRNAs in their ability to produce out-of-frame indel mutations.

While % indel frequency is a useful measure of a gRNA's effectiveness, some portion of the indels produced may be in-frame insertions or deletions. Such in-frame indels may produce a modified gene whose protein product retains some activity. When attempting to produce a gene knock out, out-of-frame indels are preferred. To ensure the gRNAs tested were, in fact, producing the desired out-of-frame indels, the sequencing results were analyzed for the specific types of indels produced. The results show that while SEQ ID NO: 5052 produced the highest % indel frequency. SEQ ID NO: 5050 generated the higher % out-of-frame indel frequency (FIG. 5).

Example 3—In Vitro Efficacy of Gene Editing in Primary and Engineered T Cells

Figure 6:
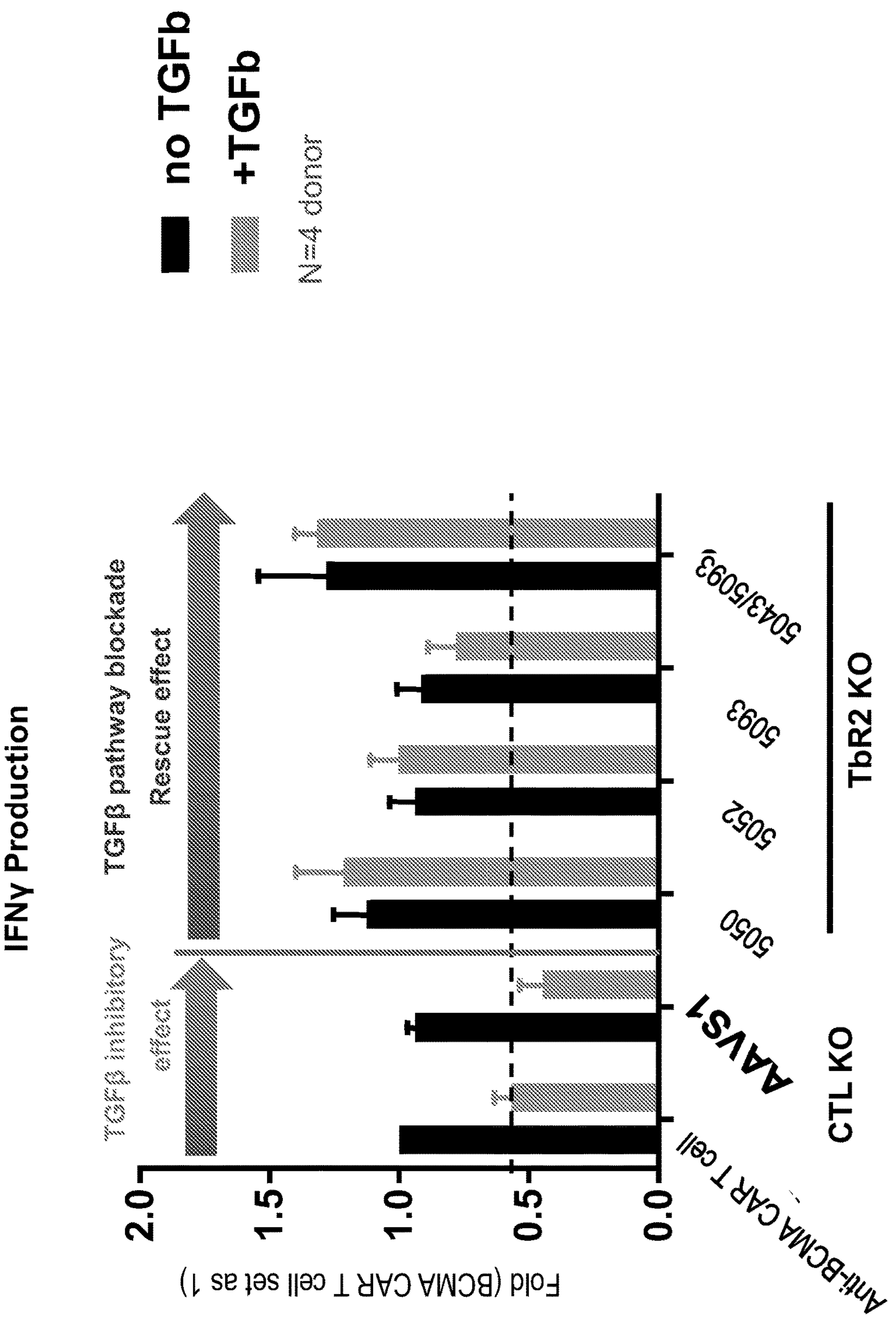
FIG. 6 depicts relative IFN-gamma production in primary T cells transduced to express anti-BCMA CAR in a TGFBR2 gene edited background, with (10 ng/ml) or without TGFβ. Single or paired gRNAs were compared.

The inhibitory effects of TGFβ were analyzed in primary T cells modified to expresses a BCMA-targeting CAR. The anti-BCMA CAR T cells were additionally modified to have the TGFBR2 gene edited via the CRISPR-Cas9 system using select gRNAs. AAVS1 control for gene editing and anti-BCMA CAR-expressing T cells with unedited TGFBR2 gene were used as controls. The cell lines were co-cultured with the RPMI 8226 multiple myeloma cell line with or without 10 ng/ml TGFβ, in the presence of excess TGFβ, primary T cells and anti-BCMA CAR T cells display the expected inhibitory effects of reduced production of Interferon-gamma (IFNγ). However, in the gene-edited anti-BCMA CAR T cells, the inhibitory effects of TGFβ are rescued, restoring IFNγ production to levels found without TGFβ addition (FIG. 6).

Figure 7:
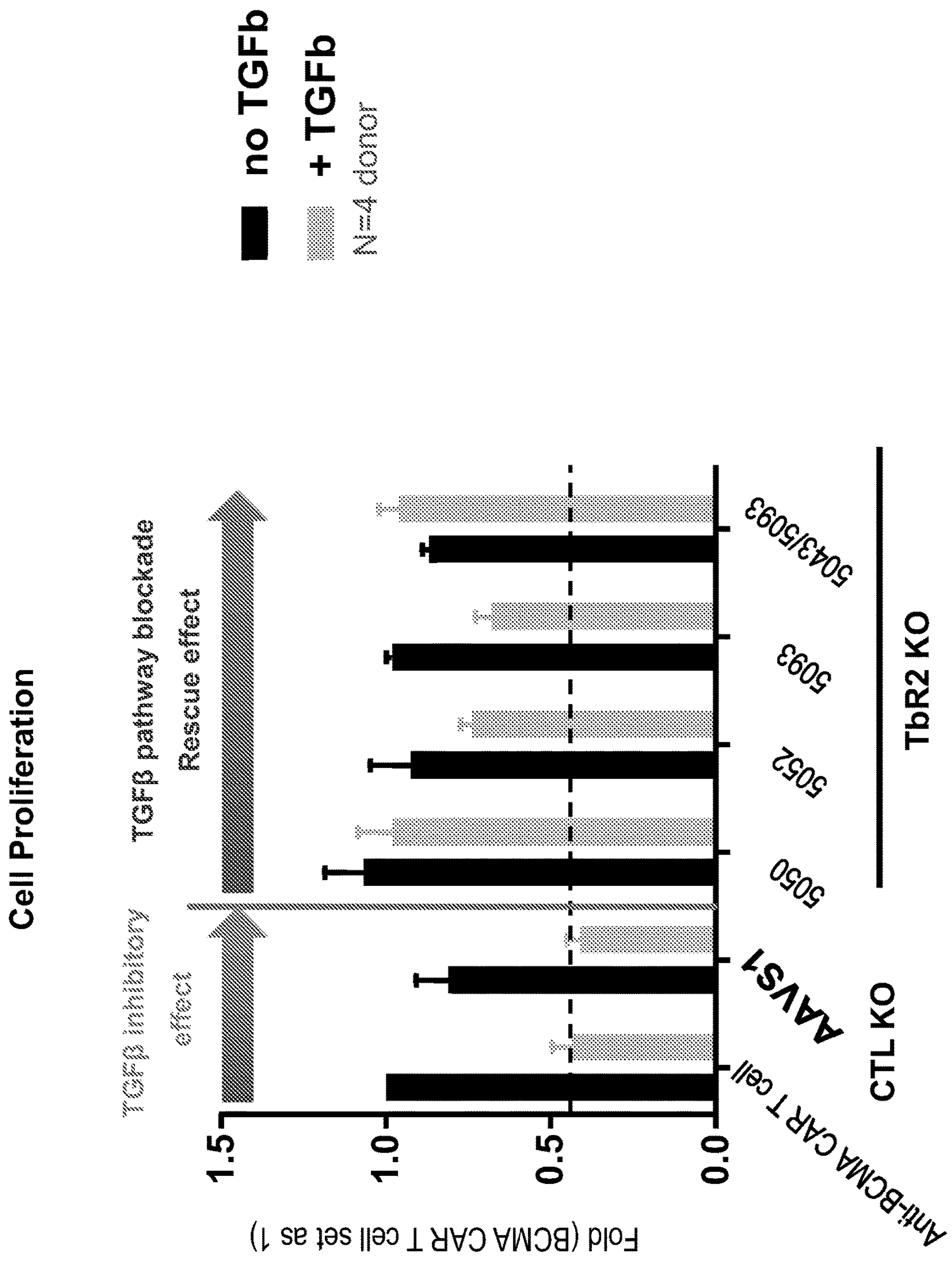
FIG. 7 depicts relative cell proliferation in primary T cells transduced to express anti-BCMA CAR in a TGFBR2 gene edited background, with (10 ng/ml) or without TGFβ. Single or paired gRNAs were compared.

Inhibition of T cell proliferation is one of the effects caused by TGFβ signaling (Tiemessen et al. Int. Immunol. 15:1495-1504, 2003). To address the effects of TGFβ signaling on cell proliferation, anti-BCMA CAR T cell proliferation was monitored in a TGFBR2 gene-edited background using several gRNAs. With the TGFBR2 gene edited, anti-BCMA CAR T cells were able to proliferate in the presence of excess TGFβ (FIG. 7).

Figure 8A:
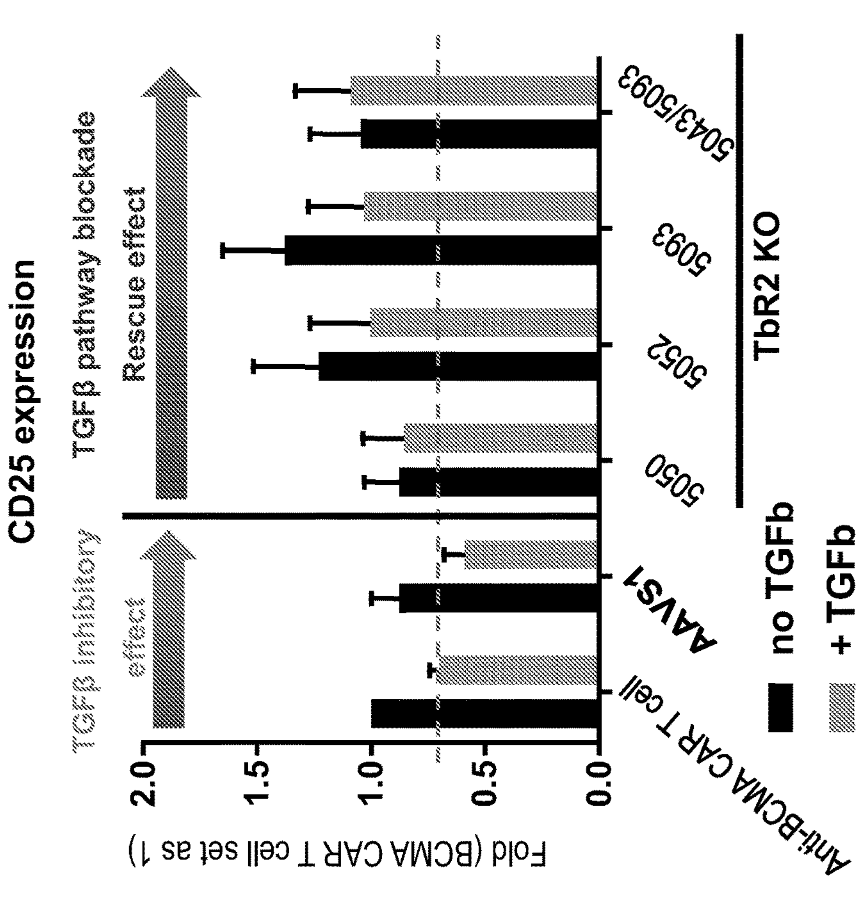
FIG. 8A-FIG. 8B depicts CD25 (FIG. 8A) and PD-1 (FIG. 8B) expression in primary T cells transduced to express anti-BCMA CAR in a TGFBR2 gene edited background, with (10 ng/ml) or without TGFβ. Single or paired gRNAs were compared. The cells were stimulated with RPMI 8226 cells for 48 hours as well.
Figure 8B:
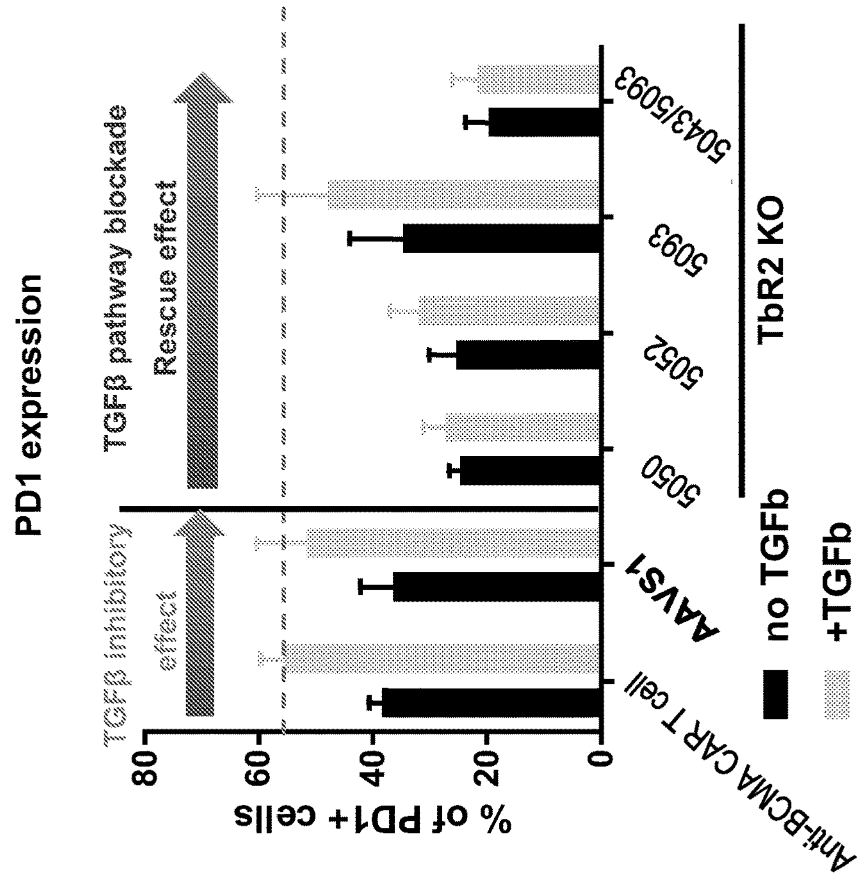

T cell activity is influenced by the expression of various stimulatory and inhibitory receptors. CD25 expression was assessed in the TGFBR2 gene-edited anti-BCMA CAR T cells. TGFBR2 gene-editing lead to higher expression levels of CD25 compared to control cells when exposed to TGFβ (FIG. 8A). The expression of the inhibitory receptor, PD-1, was also assessed by measuring the % of PD-1+ cells with and without excess TGFβ. The TGFBR2 gene-edited anti-BCMA CAR T cells showed a lower increase of PD-1 relative to control cells. Surprisingly, the gene-edited cells also led to fewer PD-1+ cells even when TGFβ was not added (FIG. 8B).

Figure 9:
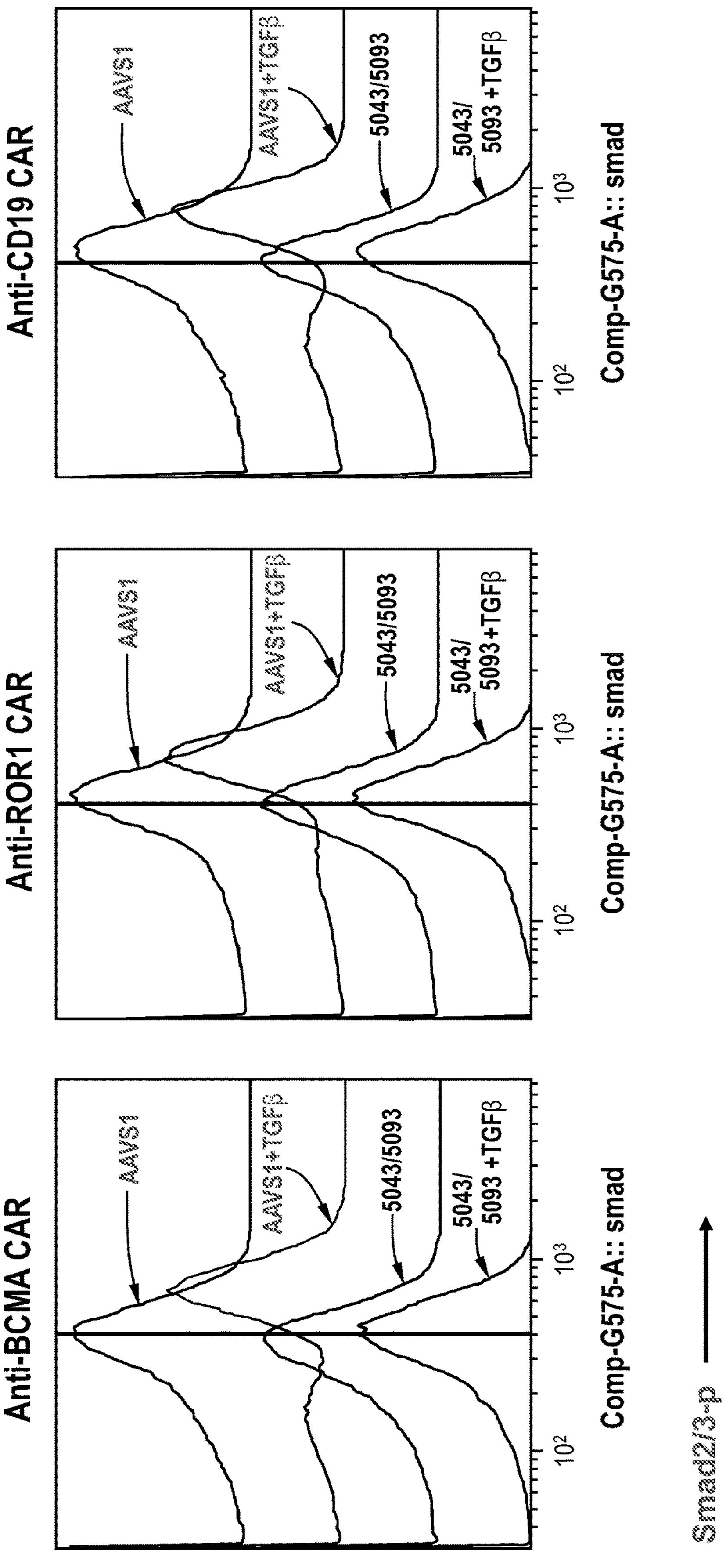
FIG. 9 depicts Smad 2/3 phosphorylation in T cells transduced to express different CARs in a TGFBR2 gene edited background, with (10 ng/ml) or without TGFβ.

Activation of the TGFβ signaling pathway leads to phosphorylation of the Smad 2/3 complex, which in turn regulates many of the downstream processes of the TGFβ signaling pathway. For this reason, phosphorylated Smad 2/3 is often used as a measure of TGFβ signaling in cells. Phospho Smad2/3 was detected in T cells transduced to express different CARs, with or without TGFBR2 gene-editing. CAR expressing T cells including AAVS1 gene editing control, with (10 ng/ml) or without TGFβ, were used as controls. While excess TGFβ lead to the expected increase in Smad 2/3 phosphorylation in the unedited cells, the TGFBR2 gene-edited cells maintained the same level of Smad 2/3 phosphorylation with and without the addition of TGFβ (FIG. 9). The results demonstrate that the TGFBR2 CRISPR gene editing approach is effective at silencing the TGFβ signaling pathway.

To further analyze the effects of TGFBR2 gene-editing in different CAR T cell backgrounds, GzmB levels were detected with and without TGFβ. CAR expressing T cells including AAVS1 gene editing control, with (10 ng/ml) or without TGFβ, were used as controls. The results of GzmB intracellular staining reveal that TGFBR2 gene-editing maintains GzmB expression in the presence of TGFβ (FIG. 10).

Figure 10:
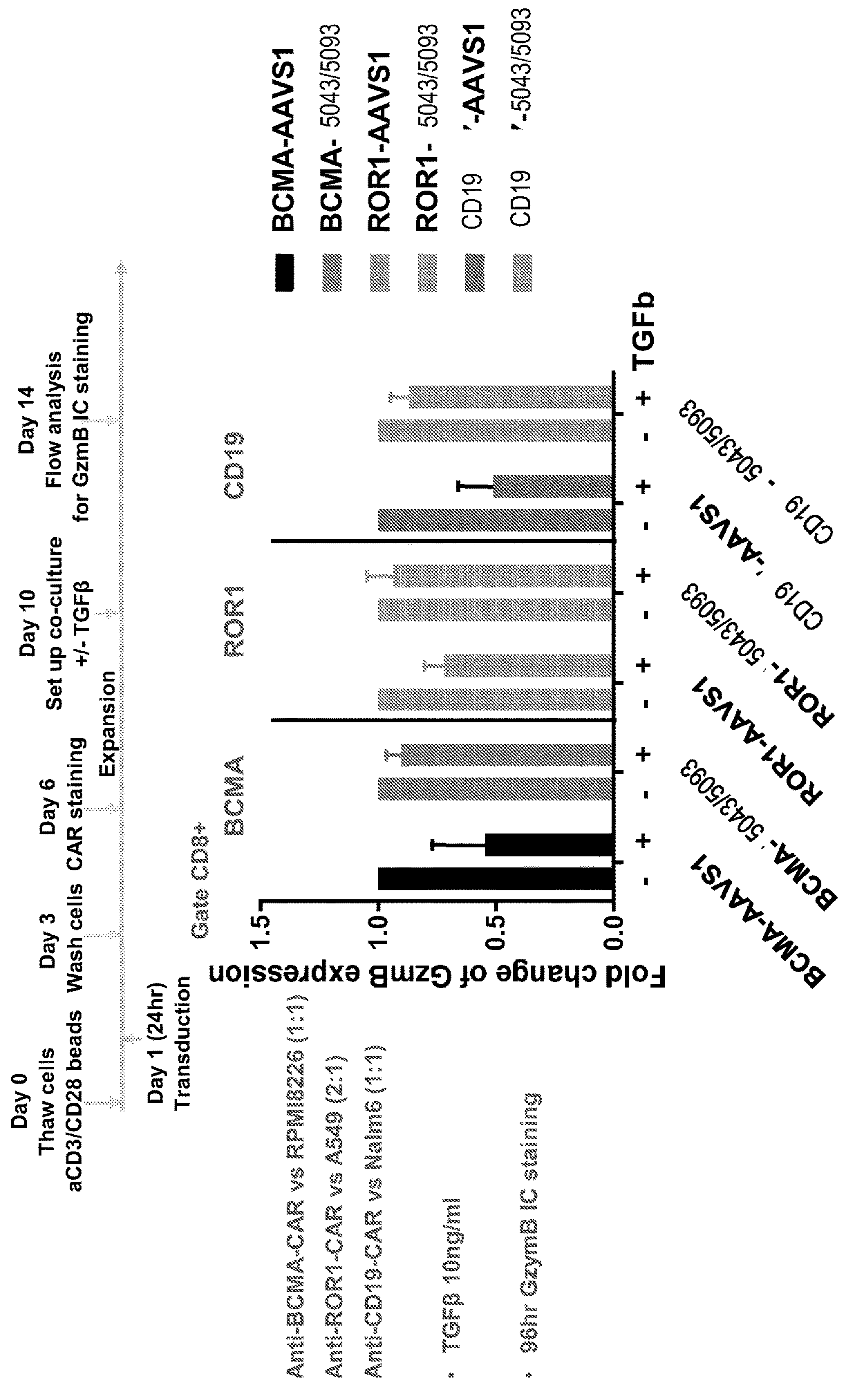
FIG. 10 depicts relative Granzyme B expression in T cells transduced to express different CARs in a TGFBR2 gene edited background, with (10 ng/ml) or without TGFβ.

IFNγ production was analyzed in a similar experiment as described in FIG. 10 using a cytokine detection assay. Consistent with the previous results of GzmB expression, IFNγ production was maintained and even increased in the TGFBR2 gene-edited background relative to controls in conditions of excess TGFβ (FIG. 11).

Figure 11:
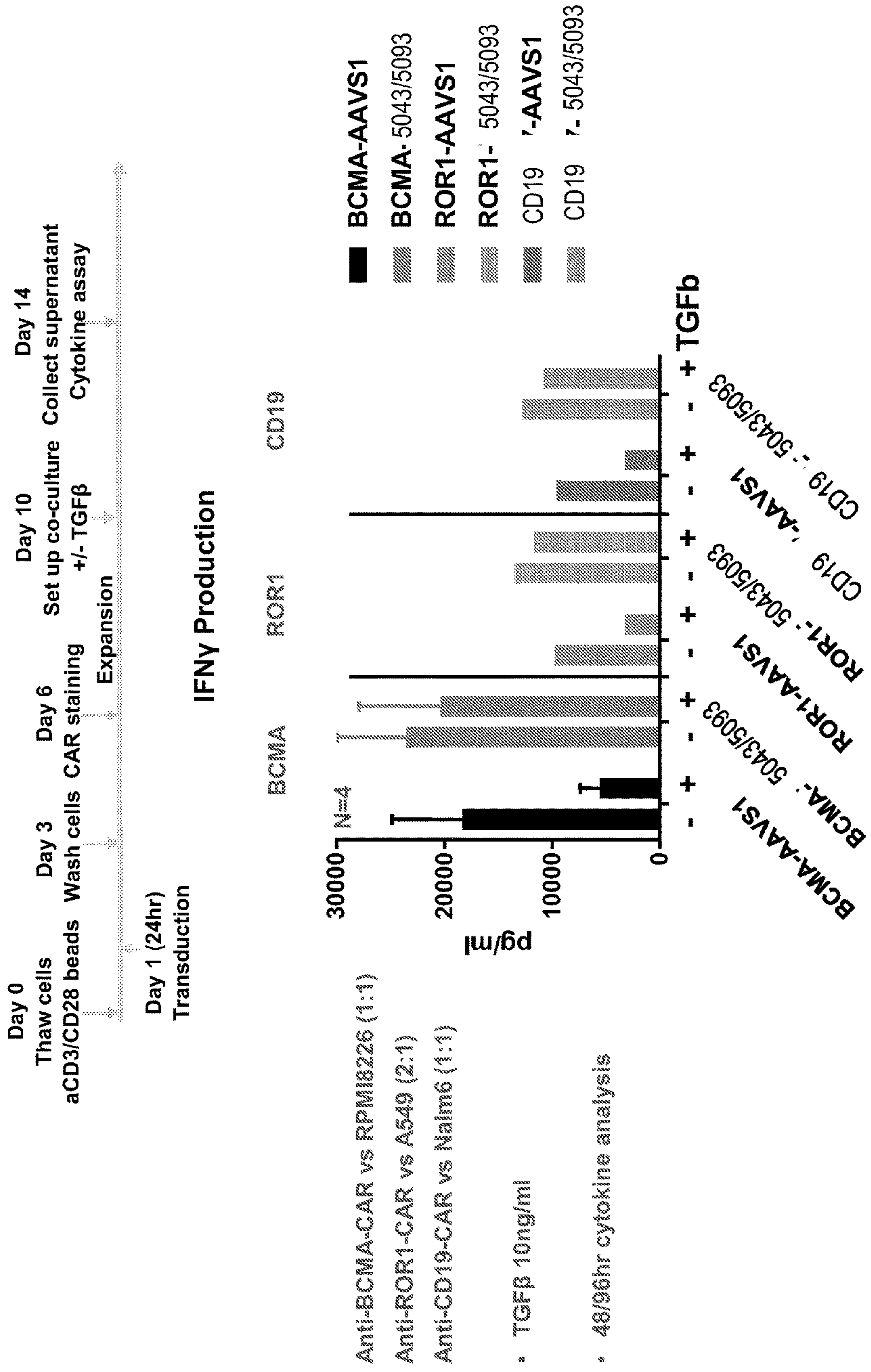
FIG. 11 depicts IFN-gamma production in T cells transduced to express different CARs in a TGFBR2 gene edited background, with (10 ng/ml) or without TGFβ.
Figure 12:
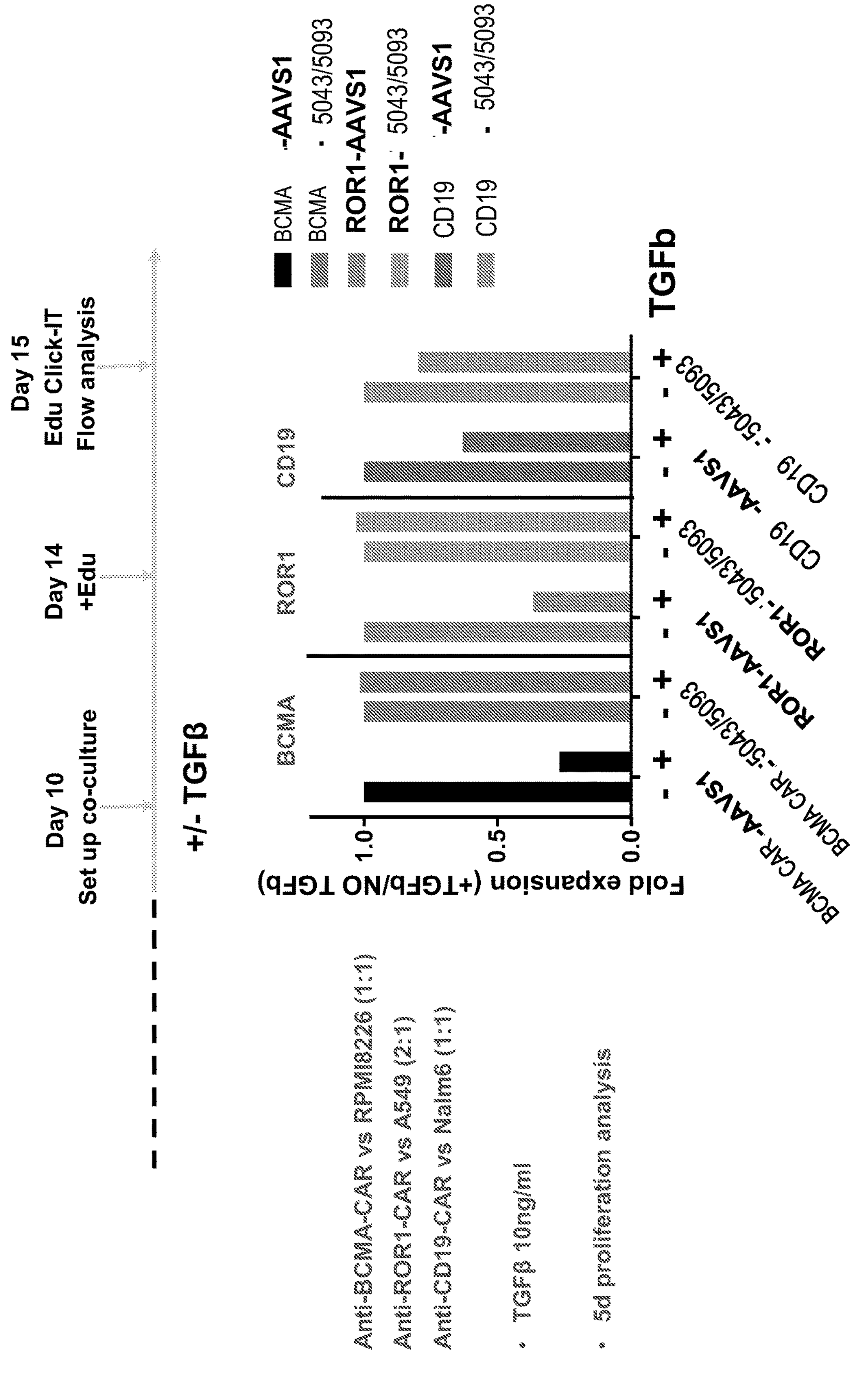
FIG. 12 depicts relative T cell proliferation in T cells transduced to express different CARs in a TGFBR2 gene edited background, with (10 ng/ml) or without TGFβ.

Cell proliferation was analyzed in a similar experiment as described in FIG. 10 and FIG. 11 using the Edu Click-It assay from ThermoFisher. Cell proliferation was maintained in the TGFBR2 gene-edited background relative to controls in conditions of excess TGFβ (FIG. 12).

The collective results of Example 3 demonstrate the advantages of employing the CRISPR-Cas9 gene-editing system to edit the TGFBR2 gene. Using the single and dual gRNA approach, the TGFβ signaling pathway can be effectively suppressed in a CAR T cell background.

Example 4—Comparison of the TGFBR2 Dominant Negative Approach to the CRISPR-Cas9 Gene Editing Approach An alternative approach to abrogating TGFβ signaling is to express a dominant negative form of TGFBR2 (DN). This version of TGFBR2 competes with the wild-type TGFBR2 for TGFβ binding, thus minimizing the effective signaling response.

Figure 13B:
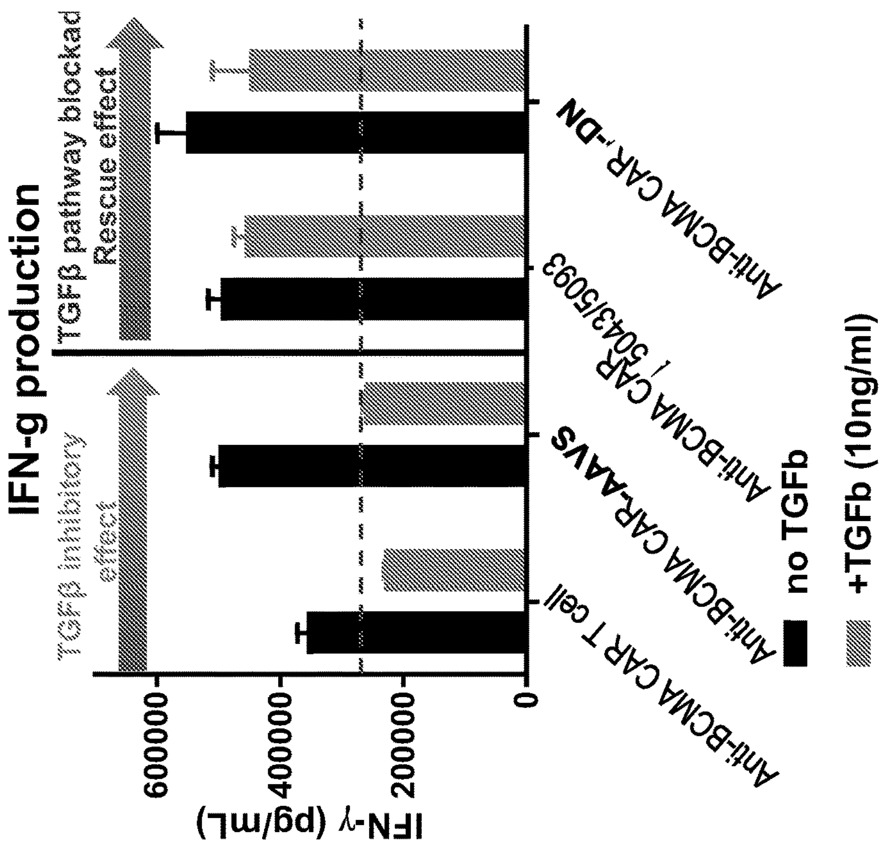
FIG. 13A-FIG. 13B depicts Granzyme B (FIG. 13A) and Interferon gamma (FIG. 13B) production in primary T cells transduced to express anti-BCMA CAR in a TGFBR2 gene edited or TGFBR2 DN background, with (10 ng/ml) or without TGFβ.
Figure 13A:
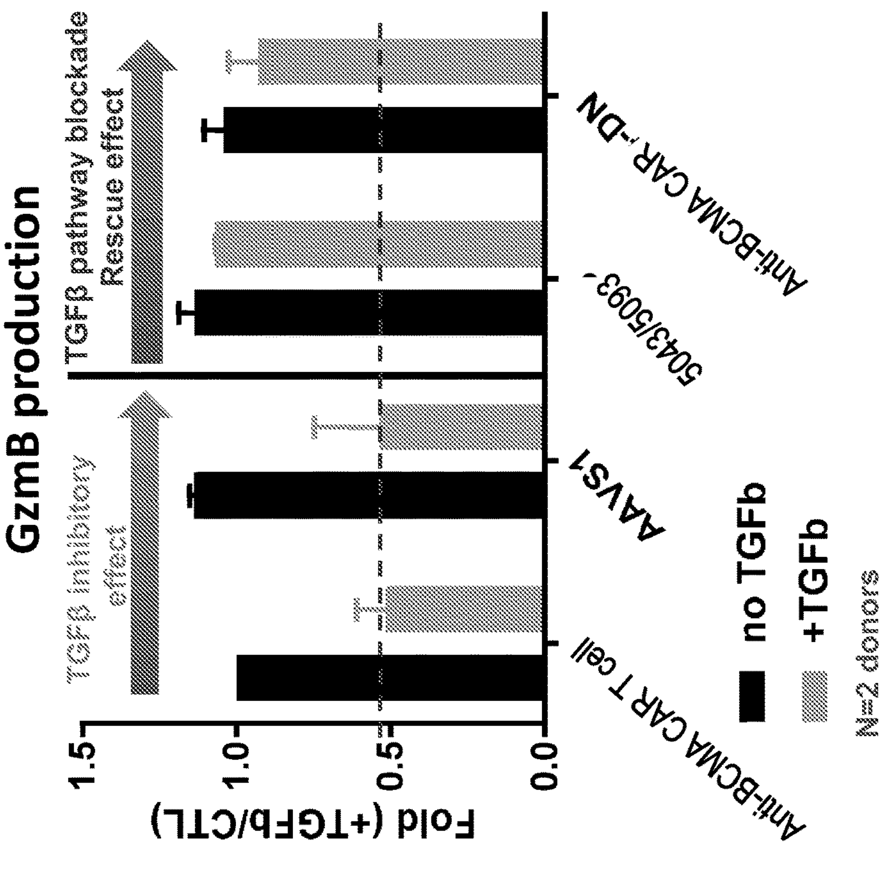

The inhibitory effects of TGFβ were analyzed in primary T cells transduced to express anti-BCMA CAR. The anti-BCMA CAR-expressing T cells were additionally modified to either express the DN or to have the TGFBR2 gene edited via the CRISPR-Cas9 system. The CRISPR-Cas9 edited cells were edited with dual gRNAs of SEQ ID Nos: 5043 and 5M03. AAVS1 control for gene editing, anti-BCMA CAR-expressing T cells with unedited TGFBR2 gene, and anti-BCMA CAR-expressing T cells including AAVS1 gene editing control were used as controls. The cell lines were co-cultured with the RPMI 8226 multiple myeloma cell line with or without 10 ng/ml TGFβ. In the presence of excess TGFβ, primary T cells and anti-BCMA CAR T cells display the expected inhibitory effects of reduced production of GzmB (FIG. 13A) and IFNγ (FIG. 13B). However, in the DN or CRISPR-edited anti-BCMA CAR T cells, the inhibitory effects of TGFβ are rescued, restoring GzmB and IFNγ production to levels found without TGFβ addition.

Figure 14:
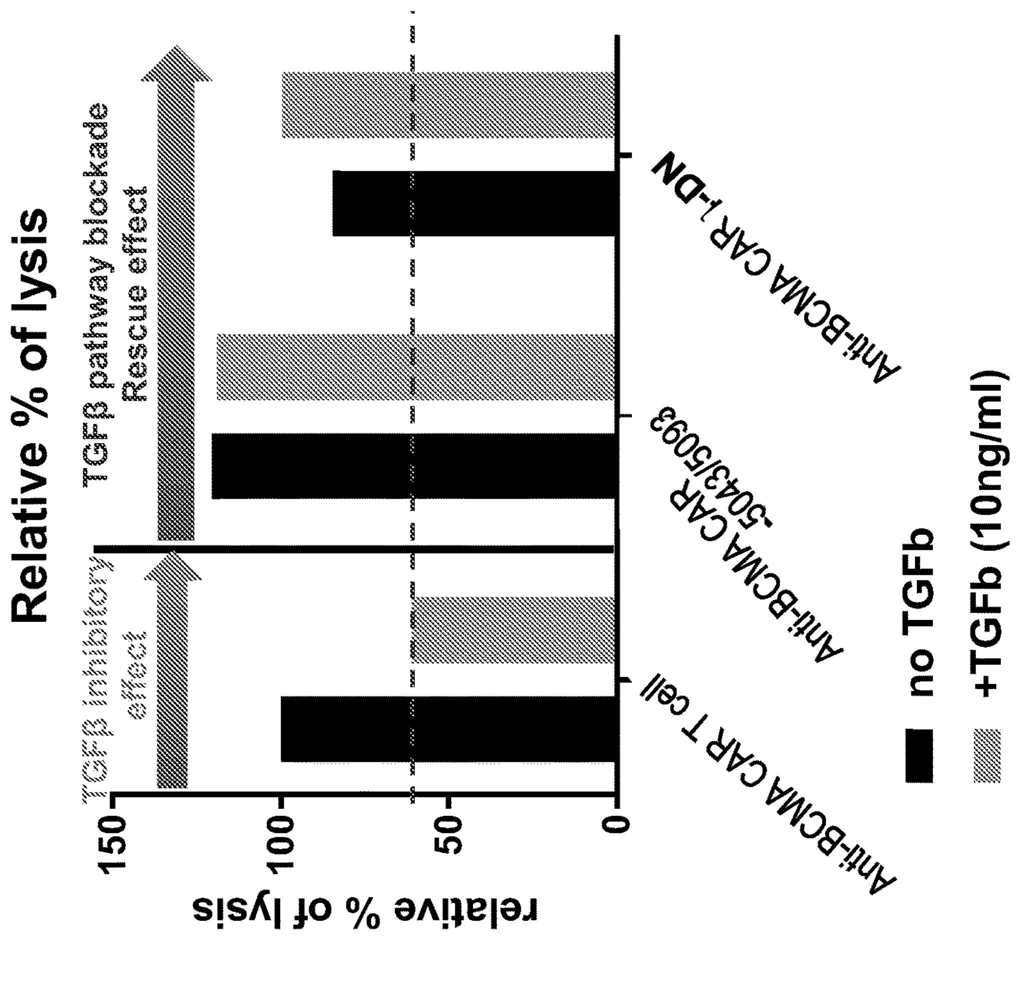
FIG. 14 depicts relative % lysis of RPMI 8226 cells by anti-BCMA CAR-expressing T cells in a TGFBR2 gene edited or TGFBR2 DN background, with (10 ng/ml) or without TGFβ.

To further demonstrate the utility of rescuing the inhibitory effects of TGFβ signaling, the anti-BCMA CAR T cells in the DN or CRISPR-edited background were analyzed for their killing activity. Anti-BCMA CAR-expressing T cells with unedited TGFBR2 gene were used as control. Anti-BCMA CAR T cells were co-cultured with RPMI 8226 cells at a ratio of 1 anti-BCMA CAR T cells to 4 RPMI cells, with or without 10 ng/ml TGFβ. The lytic activity of the anti-BCMA CAR T cells was maintained in both the DN and CRISPR-edited background in the presence of TGFβ. Surprisingly, the CRISPR-edited anti-BCMA CAR T cells displayed superior lytic activity when compared to the DN cells (FIG. 14). The lytic activity of the CRISPR-edited anti-BCMA CAR T cells was higher than the control cells even without excess TGFβ added.

Figure 15A:
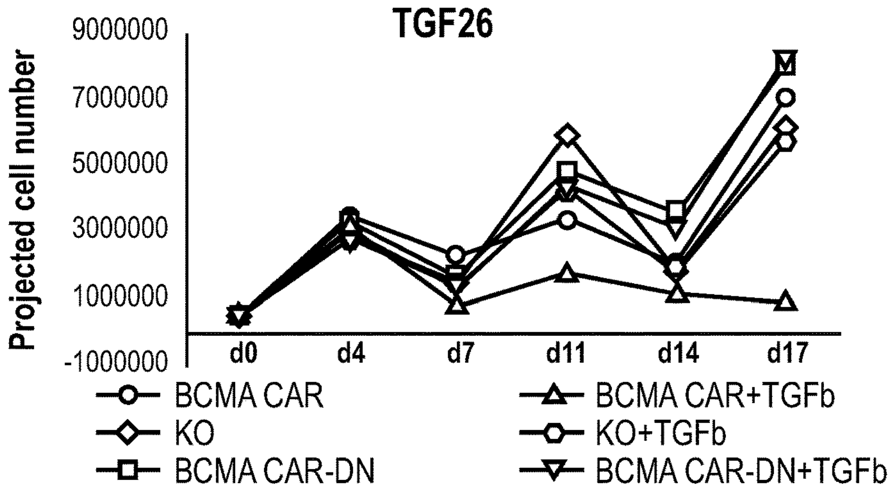
FIG. 15A-FIG. 15F depicts anti-BCMA CAR-expressing T cells in a TGFBR2 unedited, TGFBR2 gene edited, or TGFBR2 DN background with repeated TGFβ antigen stimulation.
Figure 15B:
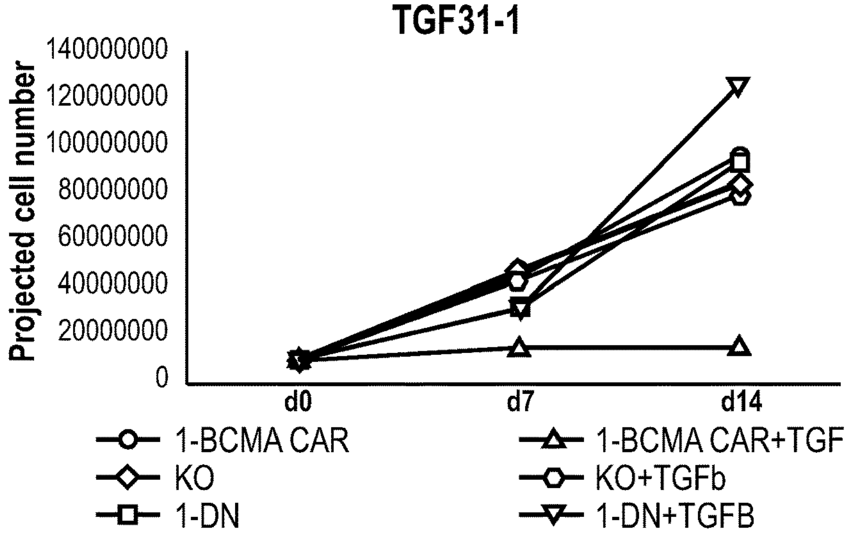
Figure 15C:
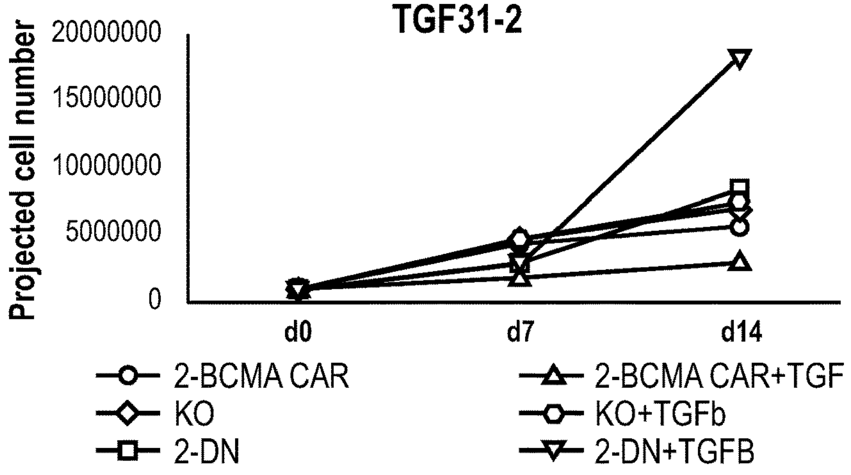
Figure 15D:
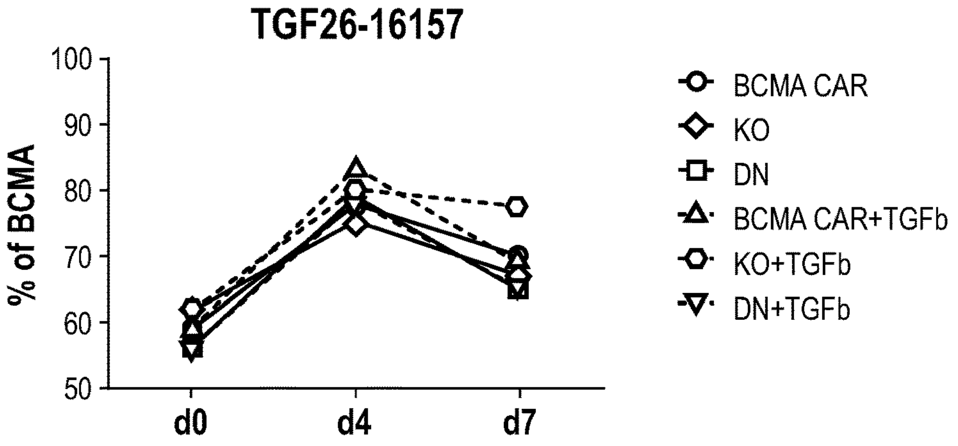
Figure 15E:
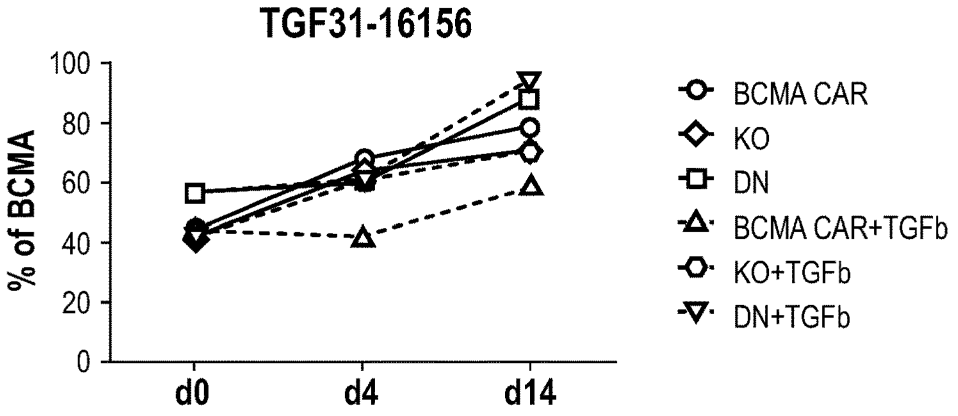
Figure 15F:
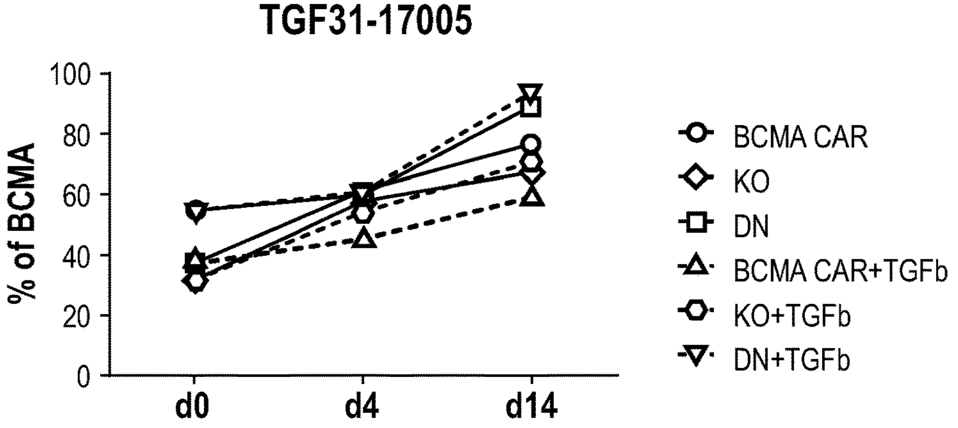

Repeated antigen stimulation of T cells, including CAR T cells, leads to diminished T cell persistence and can cause Activation-induced cell death (AICD) (Gargett et al. Mol. Ther. 24: 1135-1149. 2016). Strategies to maintain T cell activity against a specific antigen are of great importance to improve the efficacy of T cell-based therapies. The anti-BCMA CAR T cells in the DN or CRISPR-edited background were analyzed for their proliferative ability in presence of repeated stimulation with TGFβ. Anti-BCMA CAR-expressing T cells with unedited TGFBR2 gene were used as control. While the unmodified anti-BCMA CAR T cells did not proliferate over multiple days of TGFβ stimulation, the TGBR2 DN or CRISPR-edited cells continue to proliferate over time in the presence TGFβ (FIG. 15A-FIG. 15C). The percentage of anti-BCMA CAR T cells is also not diminished during the repeated stimulation with TGFβ (FIG. 15D-FIG. 15F).

Figures 16A, 16B:
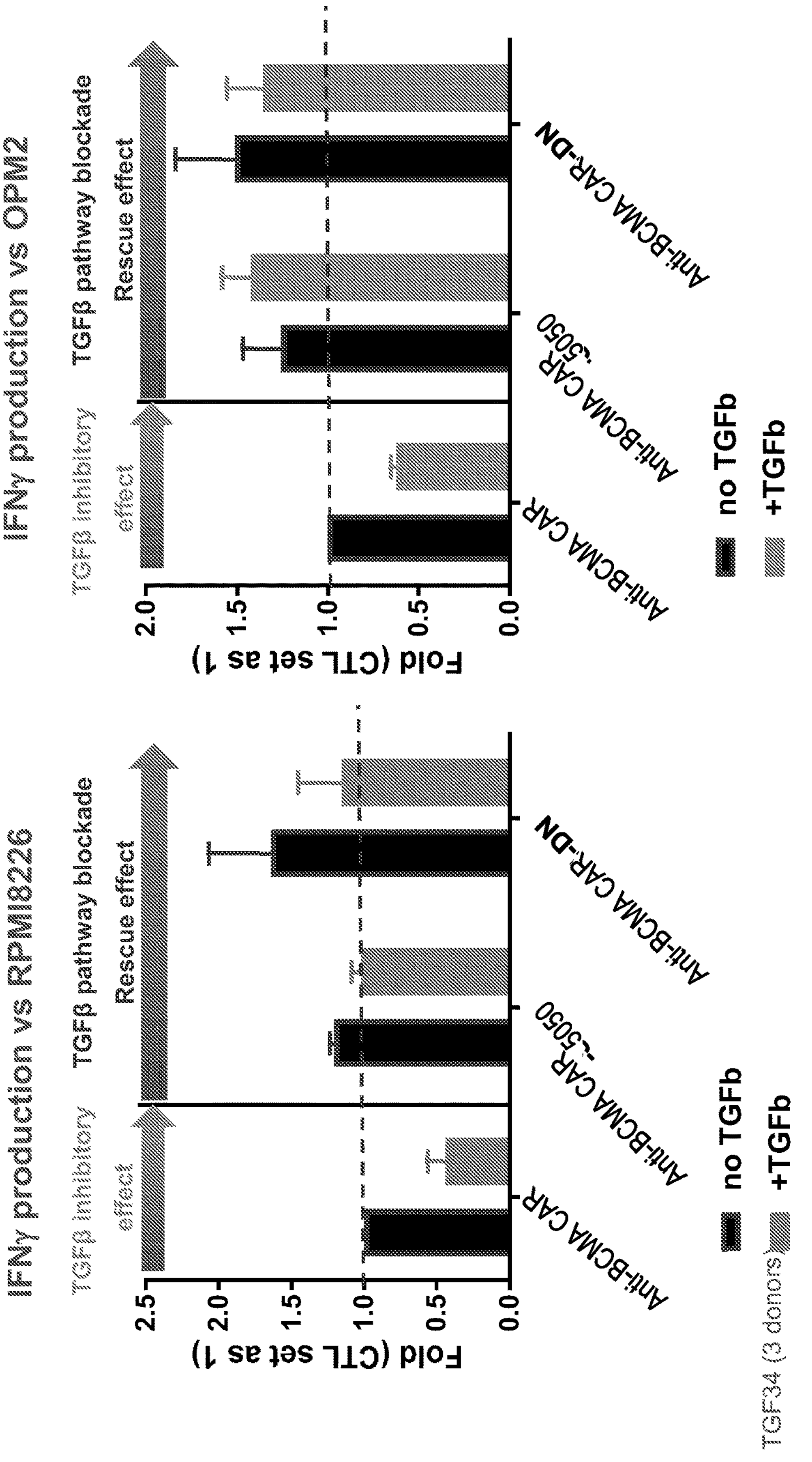
FIG. 16A-FIG. 16B depicts INF-gamma production in primary T cells transduced to express anti-BCMA CAR in a TGFBR2 gene edited or TGFBR2 DN background, with (10 ng/ml) or without TGFβ. The T cells were co-incubated with either RPMI 8226 cells (FIG. 16A) or OPM2 cells (FIG. 16B).

IFNγ production was analyzed again in the DN and gene-edited background using a single, rather than dual, gRNA approach. An additional multiple myeloma cell line, OPM2, was used as a comparison to the previously used RPMI 8226 cell line as described in FIG. 13. Consistent with the previous results, inhibition TGFβ signaling effectively maintained IFNγ production in the presence of excess TGFβ. This held true in both the RPMI (FIG. 16A) and OPM2 (FIG. 16B) cell lines.

Figure 17A:
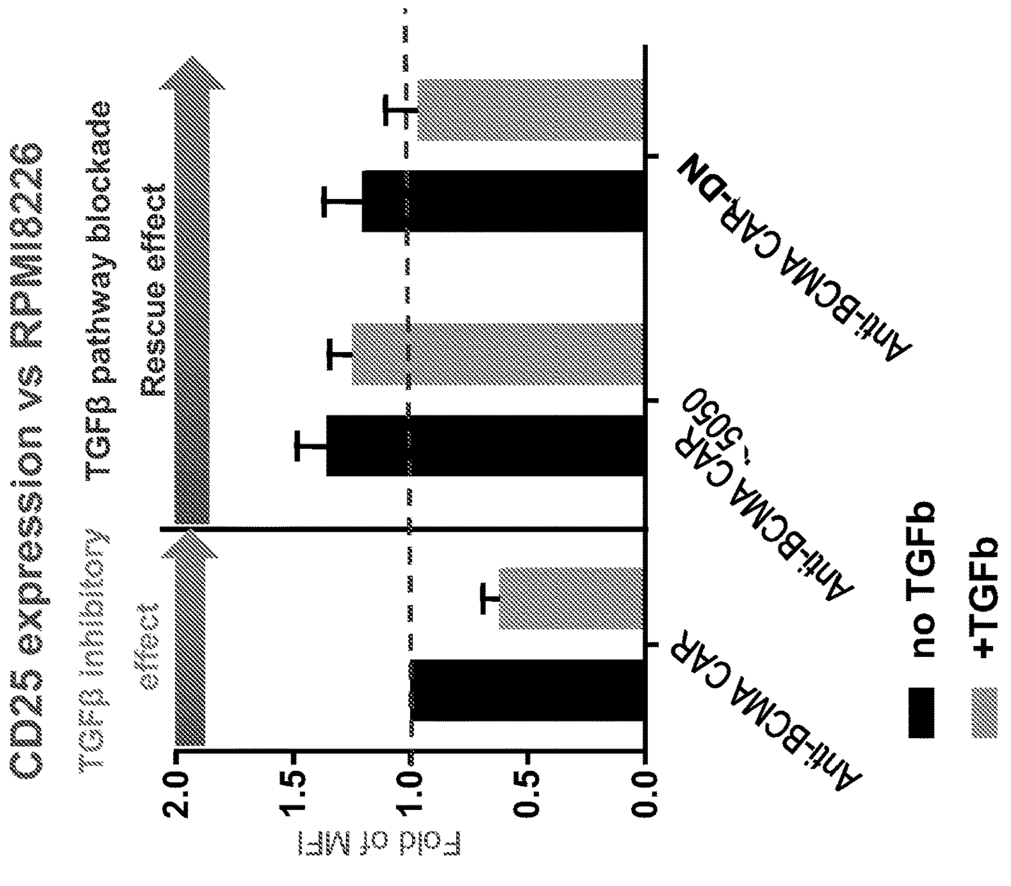
FIG. 17A-FIG. 17B depicts CD25 expression in primary T cells transduced to express anti-BCMA CAR in a TGFBR2 gene edited or TGFBR2 DN background, with (10 ng/ml) or without TGFβ. The T cells were co-incubated with either RPMI 8226 cells (FIG. 17A) or OPM2 cells (FIG. 17B).
Figure 17B:
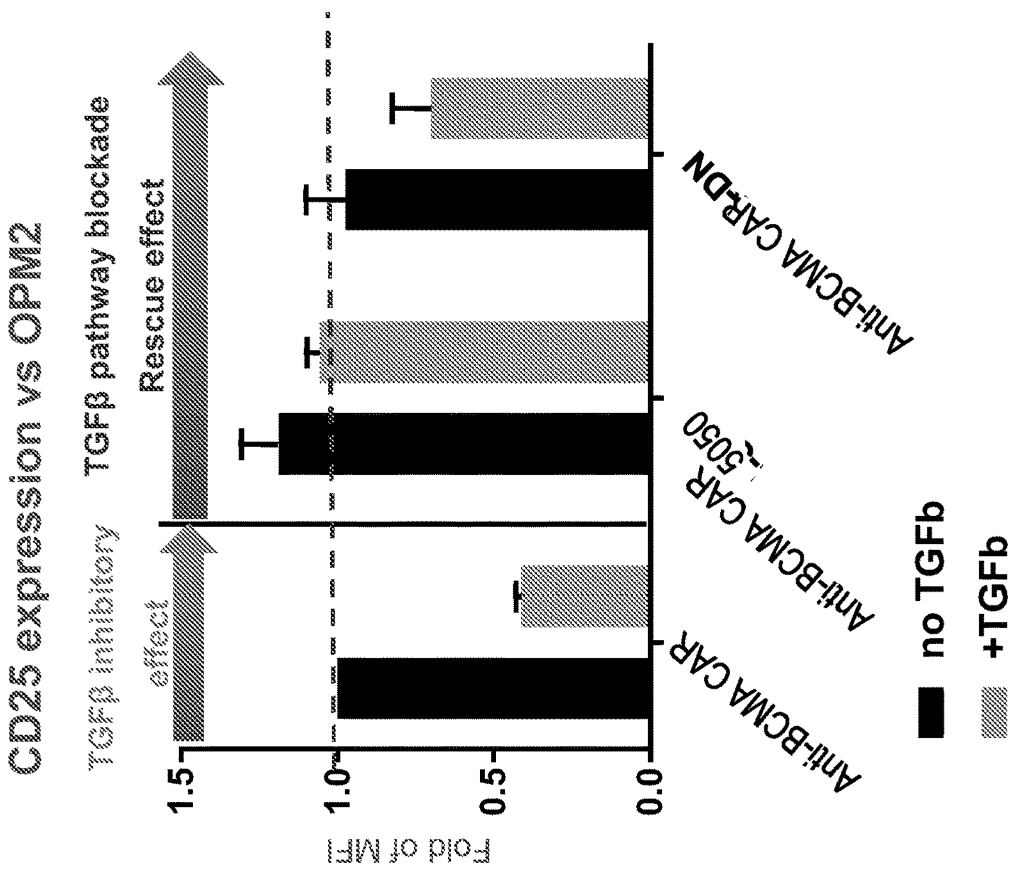

CD25 expression was also analyzed in the DN and gene-edited background using a single gRNA approach, CD25 expression was maintained in the presence of excess TGFβ in the RPMI (FIG. 17A) and OPM2 (FIG. 17B) cell lines. Surprisingly, CD25 expression in the DN and gene-edited cells was increased relative to the unmodified T cells.

Figure 18B:
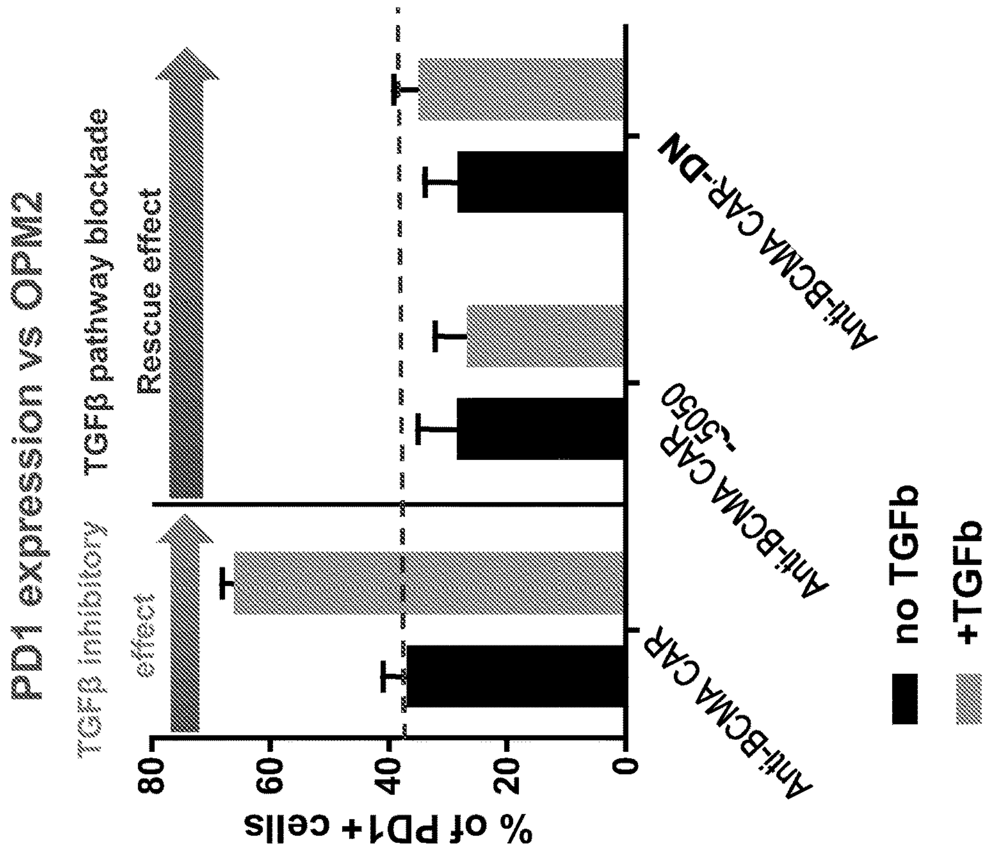
FIG. 18A-FIG. 18B depicts PD-1 expression in primary T cells transduced to express anti-BCMA CAR in a TGFBR2 gene edited or TGFBR2 DN background, with (10 ng/ml) or without TGFβ. The T cells were co-incubated with either RPMI 8226 cells (FIG. 18A) or OPM2 cells (FIG. 18B).
Figure 18A:
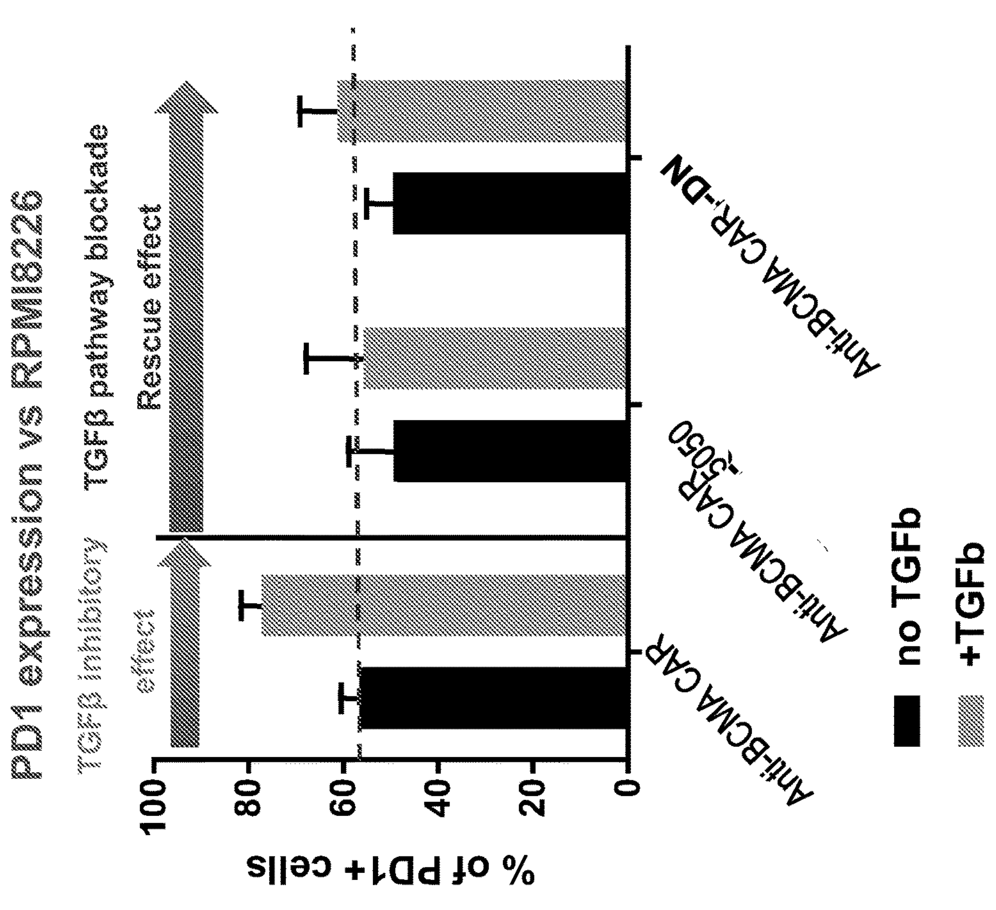

PD-1 expression was similarly detected in the DN and gene-edited background. Repression of TGFβ signaling with either approach effectively prevented increased PD-1 expression in the presence of excess TGFβ (FIGS. 18A and 18B).

Figure 19B:
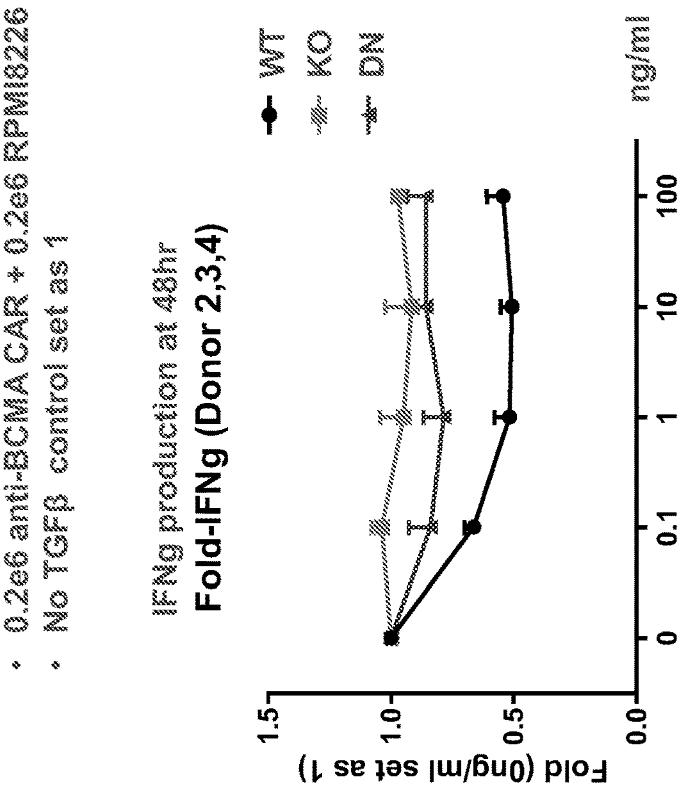
FIG. 19A-FIG. 19B depicts relative cell proliferation (FIG. 19A) and relative IFN-gamma production (FIG. 19B) of anti-BCMA CAR-expressing T cells in a TGFBR2 gene edited or TGFBR2 DN background, with (10 ng/ml) or without TGFβ. The cells were stimulated with RPMI 8226 cells as well.
Figure 19A:
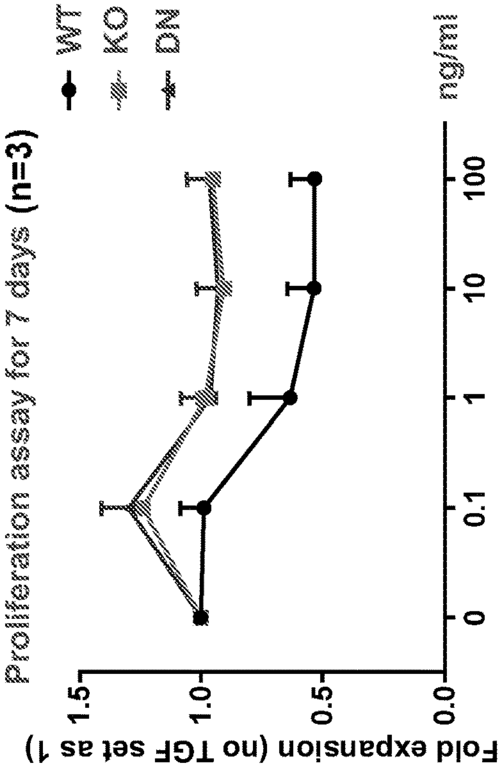

The previous experiments used TGFβ at a set dose of 10 ng/ml for stimulation. To better understand how TGFBR2 gene-editing affects TGFβ signaling under physiological conditions, a range of 0 to 100 ng/ml TGFβ was used. This range is based on previous work demonstrating that TGFβ serum levels range from approximately 3 to 88 ng/ml (Aref et al. Hematological Oncology. 35: 51-57, 2017) and approximately 3 to 10 ng/ml in multiple myeloma bone marrow (Bruns et al. Blood. 120: 2620-2630, 2012). A cell proliferation assay was used to determine relative fold expansion of cells in the DN and gene-edited background. Anti-BCMA CAR T cells were co-cultured with RPMI 8226 cells at a ratio of 1:1. Unexpectedly, the positive effects on cell proliferation can be seen at concentrations as low as 0.1 ng/ml TGFβ, well below the physiological levels in a normal or cancer setting (FIG. 19A). This responsiveness is further demonstrated by the increased production of IFNγ (FIG. 19B).

Figure 20B:
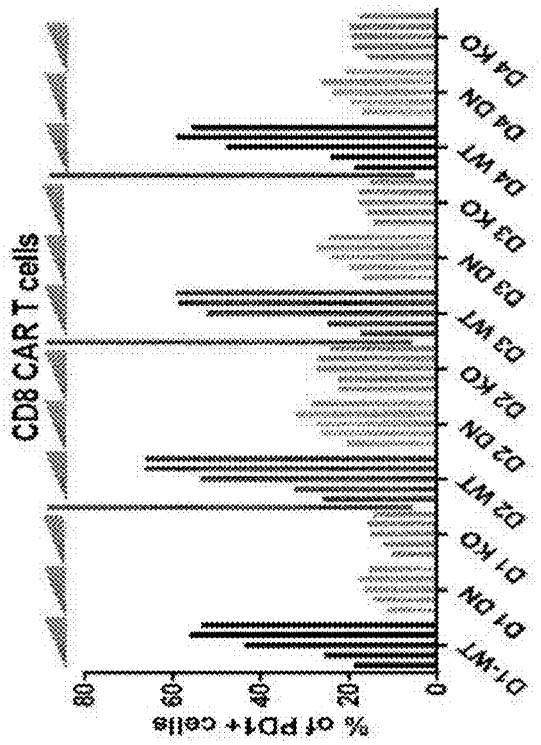
FIG. 20A-FIG. 20B depicts % of PD-1+ cells in several CD4+(FIG. 20A) and CD8+(FIG. 20B) anti-BCMA CAR-expressing T cells in a TGFBR2 gene edited or TGFBR2 DN background, with increasing concentrations of TGFβ. The cells were stimulated with RPMI 8226 cells for 48 hours as well.
Figure 20A:
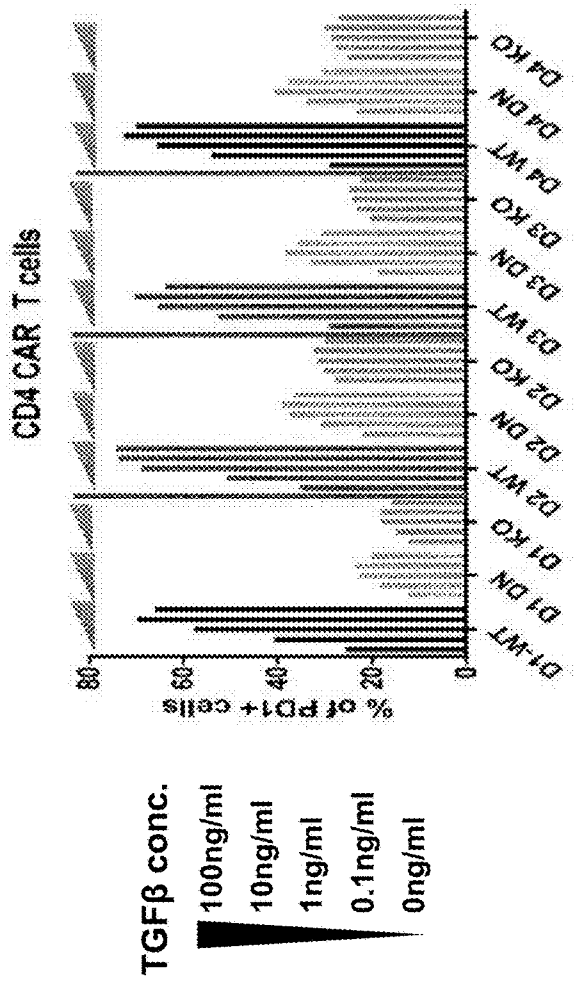

The same range of TGFβ concentrations was used to analyze PD-1 expression on CD4+ and CD8+ CAR T cells. Once again, the TGFBR2 DN and gene-edited background were able to maintain low levels of PD-1 expression as low as 0.1 ng/ml TGFβ (FIGS. 20A and 20B).

Figure 22:
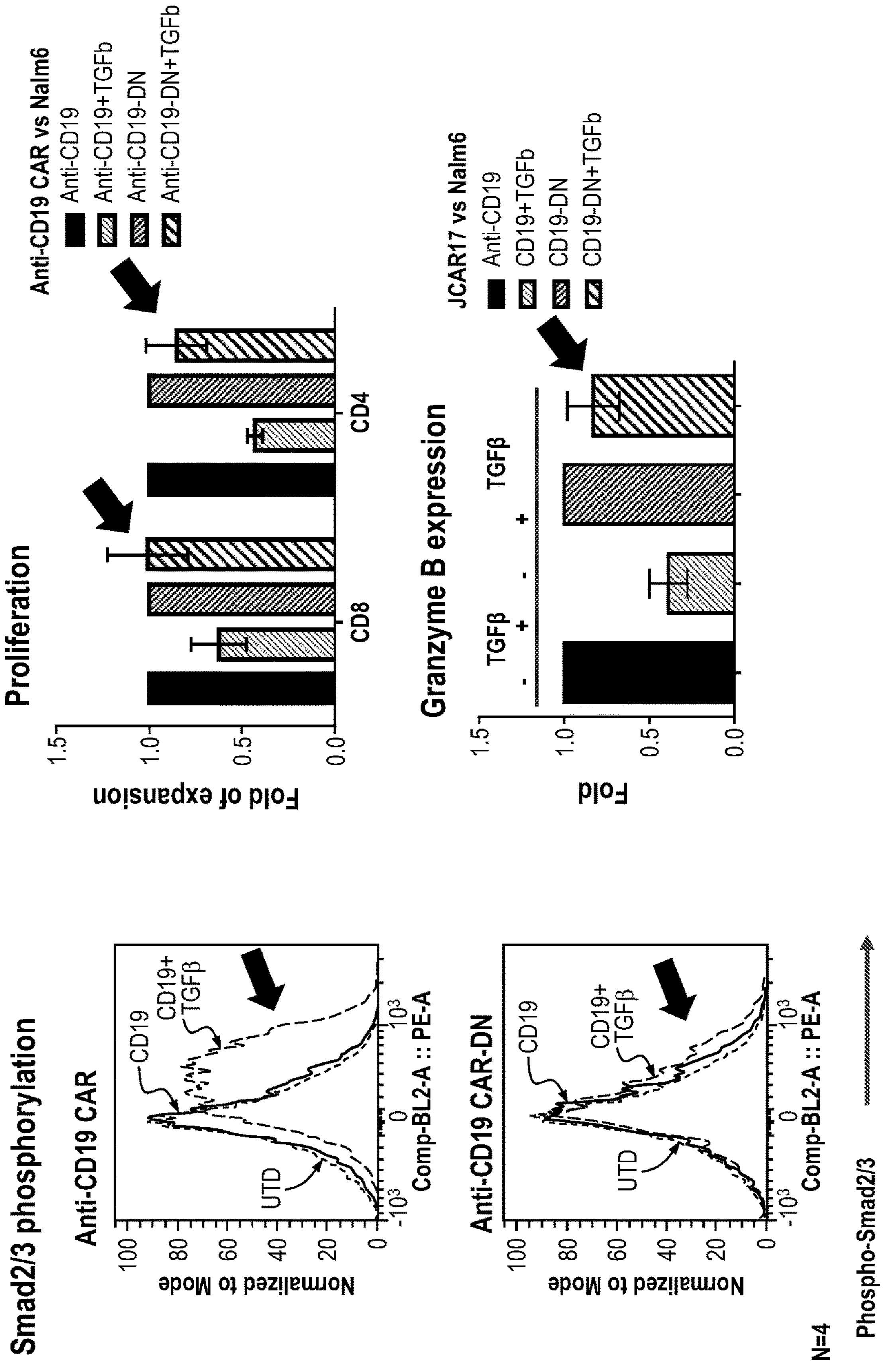
FIG. 22 depicts Smad 2/3 phosphorylation levels, proliferation, and Granzyme B expression in anti-CD19 CAR-expressing T cells in a TGFBR2 DN background, with and without TGFβ.

The DN TGFBR2 strategy was used to access cell proliferation. Granzyme B expression, and Smad 2/3 phosphorylation in T cells transduced to express three different CARs. The DN TGFBR2 was able to rescue the anti-proliferative effects of excess TGFβ in the tested CAR T cell backgrounds. The DN was able to maintain Granzyme B expression in the presence of excess TGFβ in the tested CAR T cell backgrounds. Finally, the DN was able to effectively suppress TGFβ signaling in the presence of excess TGFβ as measured by reduced Smad 2/3 phosphorylation in the tested CAR T cell backgrounds (FIG. 22). Data for only one of the three CAR T cell backgrounds is shown, however similar results were observed for the other two CAR T cell backgrounds as well.

Example 5—Transcriptional Profiling of BCMA CAR T Cells In Vivo

In order for the TGFBR2 gene-editing strategy disclosed herein to form an effective therapy, the TGFβ immunosuppressive pathway must be present in an in vivo setting. If said TGFβ immunosuppressive pathway is present, then the TGFBR2 gene-editing strategy must effectively release T cells from the TGFβ immunosuppressive effects. To address both of these concerns, transcriptional profiling of anti-BCMA CAR T cells was performed from anti-BCMA CAR T cells isolated from the tumor microenvironment in mice. The tumor xenograft model was generated by implanting mice with the multiple myeloma RPMI 8226 cells and allowed to propagate/form a tumor for 21 days. After the 21-day incubation period, anti-BCMA CAR T cells of a wild-type, AAVS gene editing control. TGFBR2 DN, or TGFBR2 gene-edited background were injected into the tumor-bearing mice. The tumor was allowed to regress for 14 days before Tumor Infiltrating Leukocytes (TILs) and CAR T cells were isolated from the tumor and the spleen (a non-cancerous negative control tissue). After isolation. RNAseq analysis was performed on the cells to determine gene expression profiles of TGFβ signaling pathway members.

Figure 21:
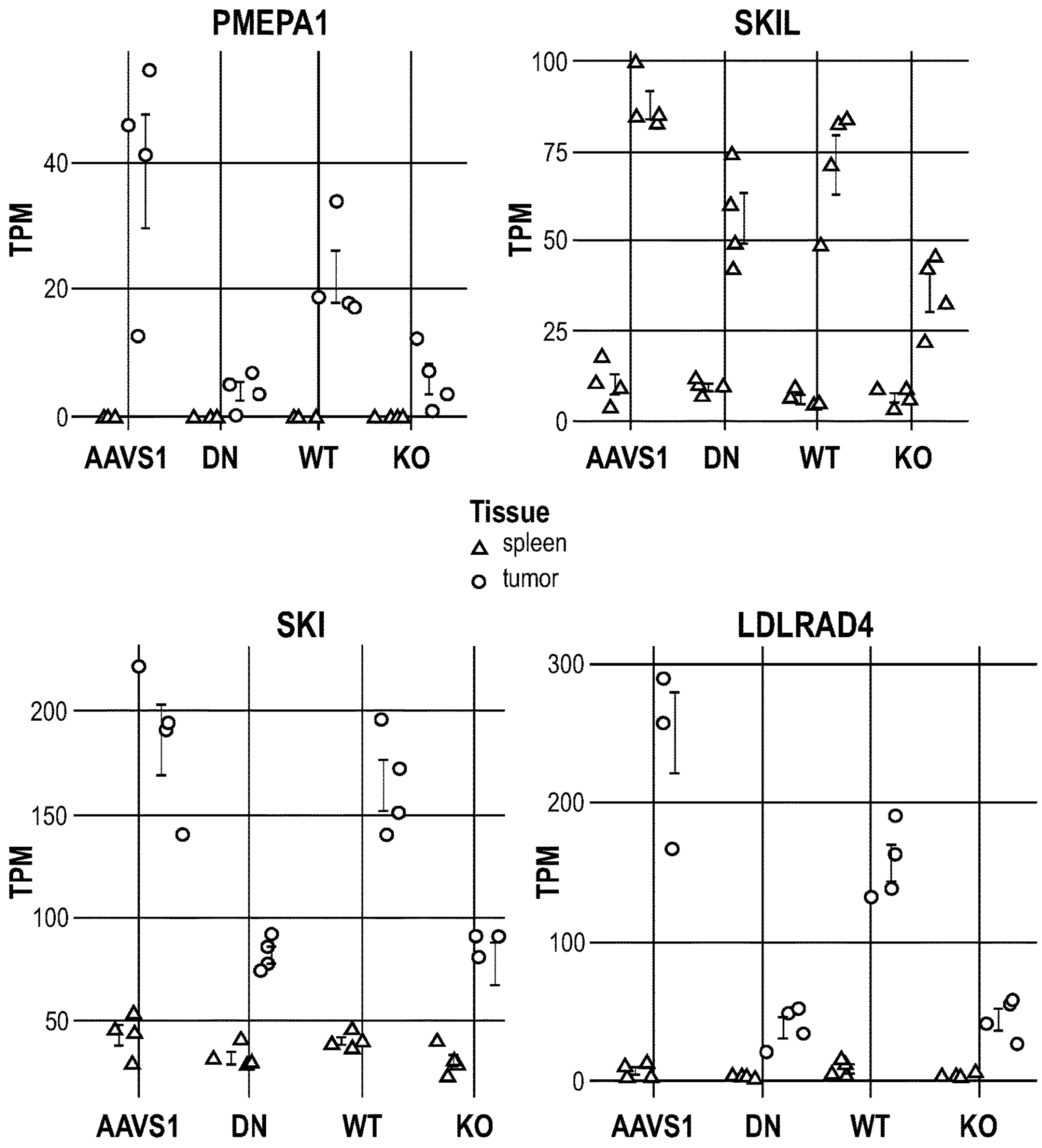
FIG. 21 depicts the expression level of TGFβ signaling pathway genes PMEPA1, SKIL, SKI, and LDLRAD4 in anti-BCMA CAR-expressing T cells in a TGFBR2 gene edited or TGFBR2 DN background. T cells were isolated from the mouse spleen or from the RPMI 8226 cell-derived tumor.

The results of the transcriptional profiling reveal that TGFBR2 gene-editing in CAR T cells successfully limits the expression of several TGFβ signaling pathway members in the tumor, where TGFβ repressive signaling occurs (FIG. 21). As shown in FIG. 21. TGFβ signaling pathway members are upregulated in anti-BCMA CAR-expressing T cells isolated from tumor but not spleen. Data indicates that anti-BCMA CAR-expressing T cells are exposed in TGFβ-enriched tumor micro-environment (TME). Further, anti-BCMA CAR-expressing T cells with TGFBR2 DN or TGFBR2 gene-edited background, reverse the upregulation of TGFβ signaling pathway members. Data indicates that the TGFβ signaling pathway was abolished effectively.

Example 6—Selective Advantage of TGFBR2 Gene-Editing Strategy

Figure 23:
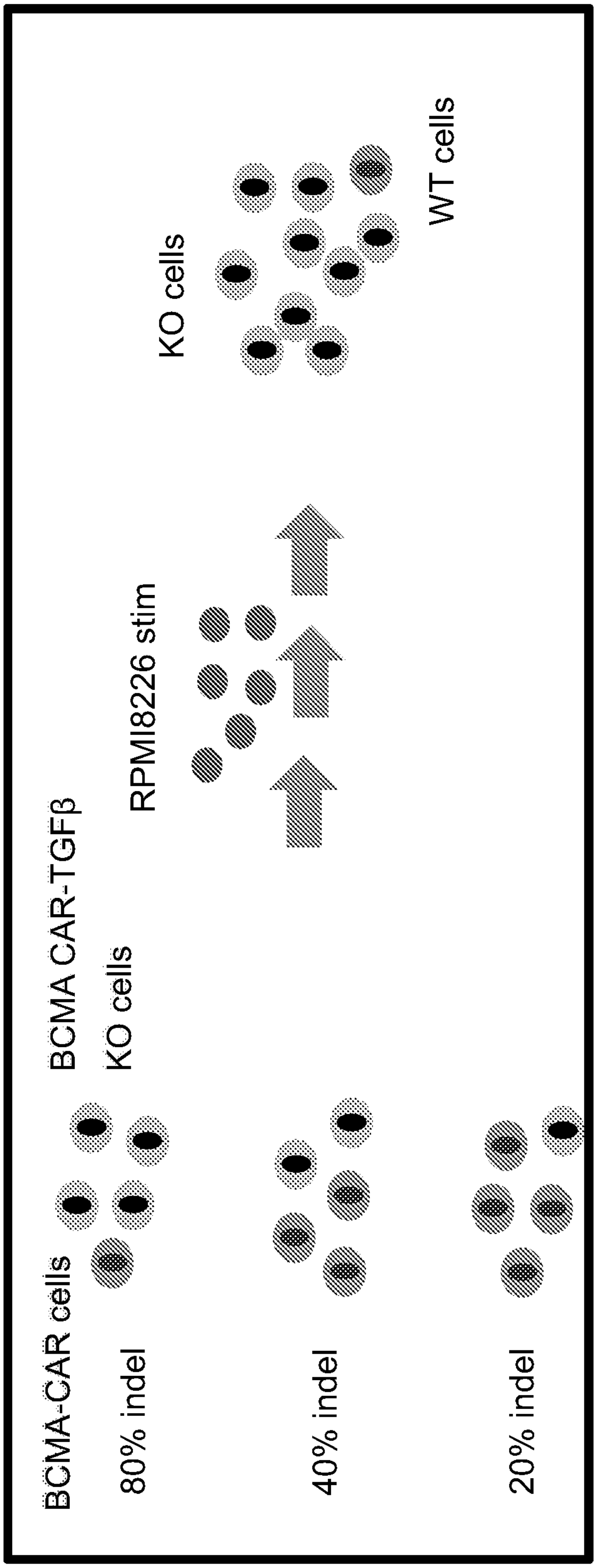
FIG. 23 depicts a schematic for determining if TGFBR2 gene-editing in T cells confers a selective advantage over wild-type cells.
Figure 24:
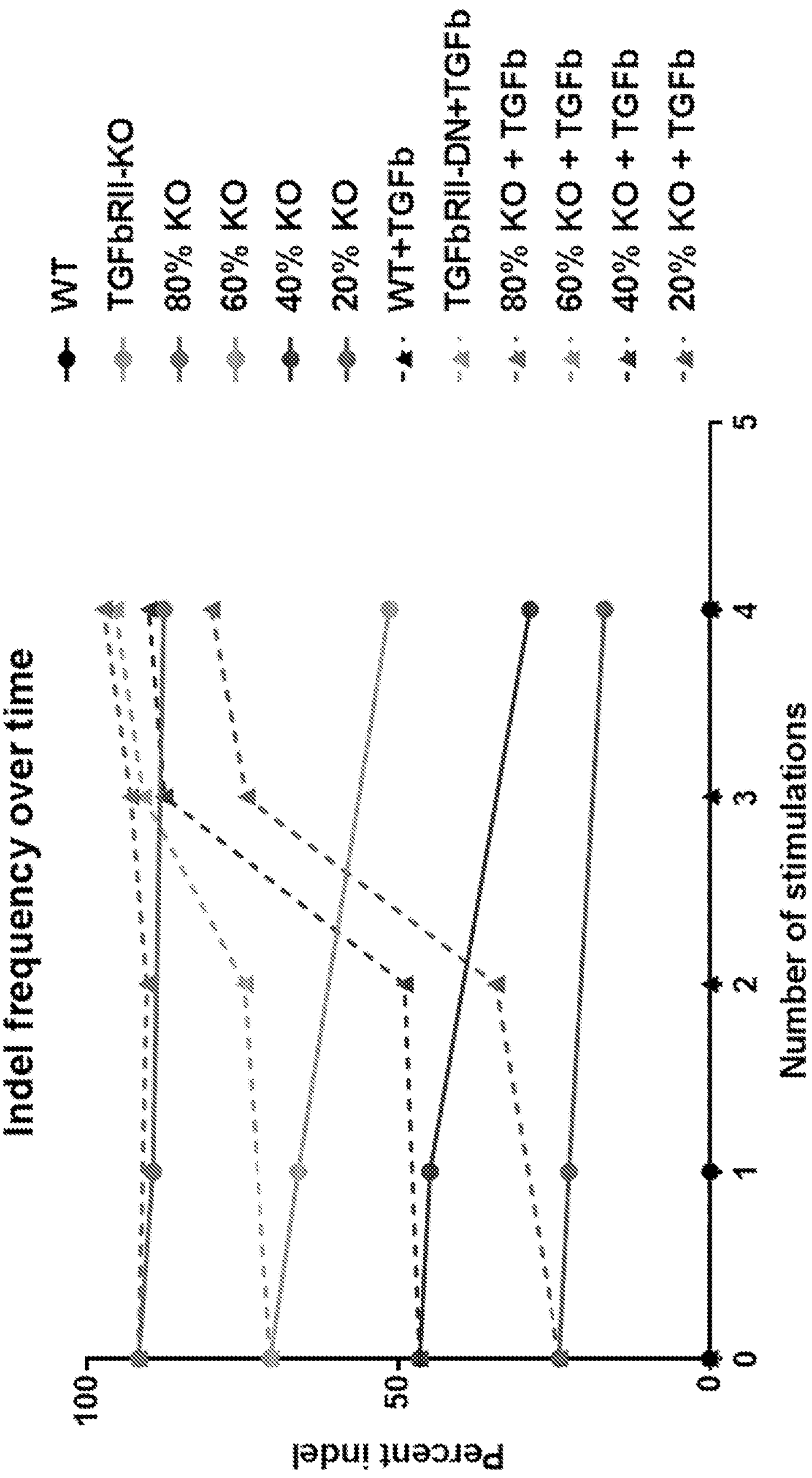
FIG. 24 depicts different ratios of anti-BCMA CAR, TGFBR2-KO cells with WT cells (1, 0.75, 0.5, 0.25). The cells were co-cultured with RPMI8226 cells in a 1:1 Effector to Target ratio±10 ng/ml TGFβ. Cells were collected every 7 days for analyzing the % of indel by high throughput sequencing. Cells were re-stimulated with fresh RPM18226 and re-adjusted to 1:1 Effector to Target ratio weekly.

To determine if TGFBR2 gene-edited CAR T cells have a selective proliferation advantage, anti-BCMA CAR T cells were gene edited to produce different % indel frequencies. These separate % indel populations of CAR T cells were co-cultured with RPMI 8226 cells in a 1:1 ratio for stimulation, with or without 10 ng/ml TGFβ. Cells were evaluated, using high throughput sequencing, approximately every 7 days to determine which portion of the cells are gene-edited and which portion are still wild-type (FIG. 23). Cells are re-stimulated with fresh RPMI cells, and readjusted to 1:1 ratio weekly. The results show that TGFBR2 gene-editing confers a selective proliferation advantage over wild-type cells in an immune-stimulatory environment (see FIG. 24).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A genome editing system comprising:

a guide RNA (gRNA) comprising a targeting domain that is complementary with a target sequence of a Transforming Growth Factor β Receptor II (TGFBR2) gene; and an RNA-guided nuclease, wherein the targeting domain comprises a nucleotide sequence that is identical to, or differs by no more than 3 nucleotides from, a nucleotide sequence selected from the group consisting of:

(a) SEQ ID NO: 5041;

(b) SEQ ID NO: 5042;

(c) SEQ ID NO: 5047;

(d) SEQ ID NO: 5050;

(e) SEQ ID NO: 5052;

(f) SEQ ID NO: 5092; and (g) SEQ ID NO: 5093.

2. The genome editing system of claim 1, wherein the target sequence of the TGFBR2 gene comprises a sequence selected from the group consisting of SEQ ID NOs: 1, 2, and 3.

3. The genome editing system of claim 1, wherein the RNA-guided nuclease is a Cas9 nuclease.

4. The genome editing system of claim 3, wherein the Cas9 nuclease is a *Streptococcus pyogenes* Cas9 nuclease.

5. The genome editing system of claim 3, wherein the Cas9 nuclease recognizes a Protospacer Adjacent Motif (PAM) of NGG.

6. The genome editing system of claim 1, wherein the RNA-guided nuclease is a *Staphylococcus aureus* Cas9 nuclease.

7. The genome editing system of claim 6, wherein the RNA-guided nuclease is a mutant Cas9 nuclease.

8. The genome editing system of claim 1, wherein the gRNA is a modular gRNA or a chimeric gRNA.

9. The genome editing system of claim 1, wherein the targeting domain comprises at least 18 contiguous nucleotides that are complementary to the TGFBR2 gene.

10. The genome editing system of claim 1, wherein the genome editing system comprises two, three or four gRNAs.

11. A composition comprising a guide RNA (gRNA) or a vector comprising a polynucleotide encoding the gRNA, wherein the gRNA comprises a targeting domain that is complementary with a target sequence of a Transforming Growth Factor β Receptor II (TGFBR2) gene, and wherein the targeting domain comprises a nucleotide sequence that is identical to, or differs by no more than 3 nucleotides from, a nucleotide sequence selected from the group consisting of:

(a) SEQ ID NO: 5041;

(b) SEQ ID NO: 5042;

(c) SEQ ID NO: 5047;

(d) SEQ ID NO: 5050;

(e) SEQ ID NO: 5052;

(f) SEQ ID NO: 5092; and (g) SEQ ID NO: 5093.

12. The composition of claim 11, wherein:

the target sequence of the TGFBR2 gene comprises a sequence selected from the group consisting of SEQ ID NOs: 1, 2, and 3.

13. The composition of claim 11, further comprising a Cas9 nuclease or a polynucleotide encoding the Cas9 nuclease.

14. The composition of claim 13, wherein:

the Cas9 nuclease is a *Staphylococcus aureus* Cas9 nuclease, optionally wherein the *Staphylococcus aureus* Cas9 nuclease recognizes a Protospacer Adjacent Motif (PAM) of either NNNRRT or NNNRRV; or the Cas9 nuclease is a *Streptococcus pyogenes* Cas9 nuclease, optionally wherein the *Streptococcus pyogenes* Cas9 nuclease recognizes a Protospacer Adjacent Motif (PAM) of NGG.

15. The composition of claim 13, wherein the composition further comprises one or both of a wild-type Cas9 nuclease and a mutant Cas9 nuclease.

16. The composition of claim 11, wherein the targeting domain comprises at least 18 contiguous nucleotides that are complementary to the TGFBR2 gene.

17. The composition of claim 11, wherein the composition comprises one, two, three, or four gRNAs.

18. The composition of claim 11, wherein the vector is a viral vector.

19. The composition of claim 18, wherein the viral vector is an adeno-associated virus (AAV) vector or a lentivirus (LV) vector.

* * * * *

SEQUENCE LISTING

```
<160> NUMBER OF SEQ ID NOS: 5102

<210> SEQ ID NO 1
<211> LENGTH: 169
<212> TYPE: DNA
<213> ORGANISM: Unknown
<220> FEATURE:
<221> NAME/KEY: source
<223> OTHER INFORMATION: /note="Description of Unknown:
      TGFBR2 Exon 3 sequence"

<400> SEQUENCE: 1

ttaataacga catgatagtc actgacaaca acggtgcagt caagtttcca caactgtgta     60

aattttgtga tgtgagattt tccacctgtg acaaccagaa atcctgcatg agcaactgca    120

gcatcacctc catctgtgag aagccacagg aagtctgtgt ggctgtatg                169


<210> SEQ ID NO 2
<211> LENGTH: 191
<212> TYPE: DNA
<213> ORGANISM: Unknown
<220> FEATURE:
<221> NAME/KEY: source
<223> OTHER INFORMATION: /note="Description of Unknown:
      TGFBR2 Exon 4 sequence"

<400> SEQUENCE: 2

gagaaagaat gacgagaaca taacactaga gacagtttgc catgacccca agctccccta     60

ccatgacttt attctggaag atgctgcttc tccaaagtgc attatgaagg aaaaaaaaaa    120

gcctggtgag actttcttca tgtgttcctg tagctctgat gagtgcaatg acaacatcat    180

cttctcagaa g                                                         191


<210> SEQ ID NO 3
<211> LENGTH: 800
<212> TYPE: DNA
<213> ORGANISM: Unknown
<220> FEATURE:
<221> NAME/KEY: source
<223> OTHER INFORMATION: /note="Description of Unknown:
```

TGFBR2 Exon 5 sequence"

<400> SEQUENCE: 3
aatataacac cagcaatcct gacttgttgc tagtcatatt tcaagtgaca ggcatcagcc 60
tcctgccacc actgggagtt gccatatctg tcatcatcat cttctactgc taccgcgtta 120
accggcagca gaagctgagt tcaacctggg aaaccggcaa gacgcggaag ctcatggagt 180
tcagcgagca ctgtgccatc atcctggaag atgaccgctc tgacatcagc tccacgtgtg 240
ccaacaacat caaccacaac acagagctgc tgcccattga gctggacacc ctggtgggga 300
aaggtcgctt tgctgaggtc tataaggcca agctgaagca gaacacttca gagcagtttg 360
agacagtggc agtcaagatc tttccctatg aggagtatgc ctcttggaag acagagaagg 420
acatcttctc agacatcaat ctgaagcatg agaacatact ccagttcctg acggctgagg 480
agcggaagac ggagttgggg aaacaatact ggctgatcac cgccttccac gccaagggca 540
acctacagga gtacctgacg cggcatgtca tcagctggga ggacctgcgc aagctgggca 600
gctccctcgc ccgggggatt gctcacctcc acagtgatca cactccatgt gggaggccca 660
agatgcccat cgtgcacagg gacctcaaga gctccaatat cctcgtgaag aacgacctaa 720
cctgctgcct gtgtgacttt gggctttccc tgcgtctgga ccctactctg tctgtggatg 780
acctggctaa cagtgggcag 800

<210> SEQ ID NO 4
<211> LENGTH: 20
<212> TYPE: DNA
<213> ORGANISM: Unknown
<220> FEATURE:
<221> NAME/KEY: source
<223> OTHER INFORMATION: /note="Description of Unknown:
TGFBR2 Target sequence"

<400> SEQUENCE: 4
gtagctctga tgagtgcaat 20

<210> SEQ ID NO 5
<211> LENGTH: 20
<212> TYPE: DNA
<213> ORGANISM: Unknown
<220> FEATURE:
<221> NAME/KEY: source
<223> OTHER INFORMATION: /note="Description of Unknown:
TGFBR2 Target sequence"

<400> SEQUENCE: 5
atgaatctct tcactctagg 20

<210> SEQ ID NO 6
<211> LENGTH: 20
<212> TYPE: DNA
<213> ORGANISM: Unknown
<220> FEATURE:
<221> NAME/KEY: source
<223> OTHER INFORMATION: /note="Description of Unknown:
TGFBR2 Target sequence"

<400> SEQUENCE: 6
acaggagtac ctgacgcggc 20

<210> SEQ ID NO 7
<211> LENGTH: 20
<212> TYPE: DNA
<213> ORGANISM: Unknown

-continued

<220> FEATURE:
<221> NAME/KEY: source
<223> OTHER INFORMATION: /note="Description of Unknown:
      TGFBR2 Target sequence"

<400> SEQUENCE: 7
ctgttagcca ggtcatccac 20

<210> SEQ ID NO 8
<211> LENGTH: 20
<212> TYPE: DNA
<213> ORGANISM: Unknown
<220> FEATURE:
<221> NAME/KEY: source
<223> OTHER INFORMATION: /note="Description of Unknown:
      TGFBR2 Target sequence"

<400> SEQUENCE: 8
gggtgtccag ctcaatgggc 20

<210> SEQ ID NO 9
<211> LENGTH: 20
<212> TYPE: DNA
<213> ORGANISM: Unknown
<220> FEATURE:
<221> NAME/KEY: source
<223> OTHER INFORMATION: /note="Description of Unknown:
      TGFBR2 Target sequence"

<400> SEQUENCE: 9
tcataatgca ctttggagaa 20

<210> SEQ ID NO 10
<211> LENGTH: 20
<212> TYPE: DNA
<213> ORGANISM: Unknown
<220> FEATURE:
<221> NAME/KEY: source
<223> OTHER INFORMATION: /note="Description of Unknown:
      TGFBR2 Target sequence"

<400> SEQUENCE: 10
tgactttatt ctggaagatg 20

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

-continued

000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

-continued

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

-continued

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

-continued

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

-continued

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

-continued

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

-continued

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

-continued

000

<210> SEQ ID NO 433
<400> SEQUENCE: 433
000

<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000

<210> SEQ ID NO 438
<400> SEQUENCE: 438
000

<210> SEQ ID NO 439
<400> SEQUENCE: 439
000

<210> SEQ ID NO 440
<400> SEQUENCE: 440
000

<210> SEQ ID NO 441
<400> SEQUENCE: 441
000

<210> SEQ ID NO 442
<400> SEQUENCE: 442
000

<210> SEQ ID NO 443
<400> SEQUENCE: 443
000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512
<400> SEQUENCE: 512
000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

-continued

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

-continued

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

-continued

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770
<400> SEQUENCE: 770
000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801

<400> SEQUENCE: 801

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

-continued

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907
<400> SEQUENCE: 907
000

<210> SEQ ID NO 908
<400> SEQUENCE: 908
000

<210> SEQ ID NO 909
<400> SEQUENCE: 909
000

<210> SEQ ID NO 910
<400> SEQUENCE: 910
000

<210> SEQ ID NO 911
<400> SEQUENCE: 911
000

<210> SEQ ID NO 912
<400> SEQUENCE: 912
000

<210> SEQ ID NO 913
<400> SEQUENCE: 913
000

<210> SEQ ID NO 914
<400> SEQUENCE: 914
000

<210> SEQ ID NO 915
<400> SEQUENCE: 915
000

<210> SEQ ID NO 916
<400> SEQUENCE: 916
000

<210> SEQ ID NO 917
<400> SEQUENCE: 917
000

<210> SEQ ID NO 918
<400> SEQUENCE: 918
000

<210> SEQ ID NO 919
<400> SEQUENCE: 919
000

<210> SEQ ID NO 920
<400> SEQUENCE: 920
000

<210> SEQ ID NO 921
<400> SEQUENCE: 921
000

<210> SEQ ID NO 922
<400> SEQUENCE: 922
000

<210> SEQ ID NO 923
<400> SEQUENCE: 923
000

<210> SEQ ID NO 924
<400> SEQUENCE: 924
000

<210> SEQ ID NO 925
<400> SEQUENCE: 925
000

<210> SEQ ID NO 926
<400> SEQUENCE: 926
000

<210> SEQ ID NO 927
<400> SEQUENCE: 927
000

<210> SEQ ID NO 928
<400> SEQUENCE: 928
000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

-continued

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111

<400> SEQUENCE: 1111

000

<210> SEQ ID NO 1112

<400> SEQUENCE: 1112

000

<210> SEQ ID NO 1113

<400> SEQUENCE: 1113

000

<210> SEQ ID NO 1114

<400> SEQUENCE: 1114

000

<210> SEQ ID NO 1115

<400> SEQUENCE: 1115

000

<210> SEQ ID NO 1116

<400> SEQUENCE: 1116

000

<210> SEQ ID NO 1117

<400> SEQUENCE: 1117

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131

<400> SEQUENCE: 1131

000

<210> SEQ ID NO 1132

<400> SEQUENCE: 1132

000

<210> SEQ ID NO 1133

<400> SEQUENCE: 1133

000

<210> SEQ ID NO 1134

<400> SEQUENCE: 1134

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

<210> SEQ ID NO 1140

<400> SEQUENCE: 1140

000

<210> SEQ ID NO 1141

<400> SEQUENCE: 1141

000

<210> SEQ ID NO 1142

<400> SEQUENCE: 1142

000

<210> SEQ ID NO 1143

<400> SEQUENCE: 1143

000

<210> SEQ ID NO 1144
<400> SEQUENCE: 1144
000

<210> SEQ ID NO 1145
<400> SEQUENCE: 1145
000

<210> SEQ ID NO 1146
<400> SEQUENCE: 1146
000

<210> SEQ ID NO 1147
<400> SEQUENCE: 1147
000

<210> SEQ ID NO 1148
<400> SEQUENCE: 1148
000

<210> SEQ ID NO 1149
<400> SEQUENCE: 1149
000

<210> SEQ ID NO 1150
<400> SEQUENCE: 1150
000

<210> SEQ ID NO 1151
<400> SEQUENCE: 1151
000

<210> SEQ ID NO 1152
<400> SEQUENCE: 1152
000

<210> SEQ ID NO 1153
<400> SEQUENCE: 1153
000

<210> SEQ ID NO 1154
<400> SEQUENCE: 1154
000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218

000

<210> SEQ ID NO 1219

<400> SEQUENCE: 1219

000

<210> SEQ ID NO 1220

<400> SEQUENCE: 1220

000

<210> SEQ ID NO 1221

<400> SEQUENCE: 1221

000

<210> SEQ ID NO 1222

<400> SEQUENCE: 1222

000

<210> SEQ ID NO 1223
<400> SEQUENCE: 1223
000

<210> SEQ ID NO 1224
<400> SEQUENCE: 1224
000

<210> SEQ ID NO 1225
<400> SEQUENCE: 1225
000

<210> SEQ ID NO 1226
<400> SEQUENCE: 1226
000

<210> SEQ ID NO 1227
<400> SEQUENCE: 1227
000

<210> SEQ ID NO 1228
<400> SEQUENCE: 1228
000

<210> SEQ ID NO 1229
<400> SEQUENCE: 1229
000

<210> SEQ ID NO 1230
<400> SEQUENCE: 1230
000

<210> SEQ ID NO 1231
<400> SEQUENCE: 1231
000

<210> SEQ ID NO 1232
<400> SEQUENCE: 1232
000

<210> SEQ ID NO 1233
<400> SEQUENCE: 1233
000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241

<400> SEQUENCE: 1241

000

<210> SEQ ID NO 1242

<400> SEQUENCE: 1242

000

<210> SEQ ID NO 1243

<400> SEQUENCE: 1243

000

<210> SEQ ID NO 1244

<400> SEQUENCE: 1244

000

<210> SEQ ID NO 1245

<400> SEQUENCE: 1245

000

<210> SEQ ID NO 1246

<400> SEQUENCE: 1246

000

<210> SEQ ID NO 1247

<400> SEQUENCE: 1247

000

<210> SEQ ID NO 1248

<400> SEQUENCE: 1248

000

<210> SEQ ID NO 1249

<400> SEQUENCE: 1249

000

<210> SEQ ID NO 1250

<400> SEQUENCE: 1250

000

<210> SEQ ID NO 1251

<400> SEQUENCE: 1251

000

<210> SEQ ID NO 1252

<400> SEQUENCE: 1252

000

<210> SEQ ID NO 1253

<400> SEQUENCE: 1253

000

<210> SEQ ID NO 1254

<400> SEQUENCE: 1254

000

<210> SEQ ID NO 1255

<400> SEQUENCE: 1255

000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264

<400> SEQUENCE: 1264

000

<210> SEQ ID NO 1265

<400> SEQUENCE: 1265

000

<210> SEQ ID NO 1266

<400> SEQUENCE: 1266

000

<210> SEQ ID NO 1267

<400> SEQUENCE: 1267

000

<210> SEQ ID NO 1268

<400> SEQUENCE: 1268

000

<210> SEQ ID NO 1269

<400> SEQUENCE: 1269

000

<210> SEQ ID NO 1270

<400> SEQUENCE: 1270

000

<210> SEQ ID NO 1271

<400> SEQUENCE: 1271

000

<210> SEQ ID NO 1272

<400> SEQUENCE: 1272

000

<210> SEQ ID NO 1273

<400> SEQUENCE: 1273

000

<210> SEQ ID NO 1274

<400> SEQUENCE: 1274

000

<210> SEQ ID NO 1275

<400> SEQUENCE: 1275

000

<210> SEQ ID NO 1276

<400> SEQUENCE: 1276

000

<210> SEQ ID NO 1277

<400> SEQUENCE: 1277

000

<210> SEQ ID NO 1278

<400> SEQUENCE: 1278

000

<210> SEQ ID NO 1279

<400> SEQUENCE: 1279

000

<210> SEQ ID NO 1280

<400> SEQUENCE: 1280

000

<210> SEQ ID NO 1281

<400> SEQUENCE: 1281

000

<210> SEQ ID NO 1282

<400> SEQUENCE: 1282

000

<210> SEQ ID NO 1283

<400> SEQUENCE: 1283

000

<210> SEQ ID NO 1284

<400> SEQUENCE: 1284

000

<210> SEQ ID NO 1285

<400> SEQUENCE: 1285

000

<210> SEQ ID NO 1286

<400> SEQUENCE: 1286

000

<210> SEQ ID NO 1287

<400> SEQUENCE: 1287

000

<210> SEQ ID NO 1288

<400> SEQUENCE: 1288

000

<210> SEQ ID NO 1289

<400> SEQUENCE: 1289

000

<210> SEQ ID NO 1290

<400> SEQUENCE: 1290

000

<210> SEQ ID NO 1291

<400> SEQUENCE: 1291

000

<210> SEQ ID NO 1292

<400> SEQUENCE: 1292

000

<210> SEQ ID NO 1293

<400> SEQUENCE: 1293

000

<210> SEQ ID NO 1294

<400> SEQUENCE: 1294

000

<210> SEQ ID NO 1295

<400> SEQUENCE: 1295

000

<210> SEQ ID NO 1296

<400> SEQUENCE: 1296

000

<210> SEQ ID NO 1297

<400> SEQUENCE: 1297

000

<210> SEQ ID NO 1298

<400> SEQUENCE: 1298

000

<210> SEQ ID NO 1299

<400> SEQUENCE: 1299

000

<210> SEQ ID NO 1300

<400> SEQUENCE: 1300

000

<210> SEQ ID NO 1301

<400> SEQUENCE: 1301

-continued

000

<210> SEQ ID NO 1302

<400> SEQUENCE: 1302

000

<210> SEQ ID NO 1303

<400> SEQUENCE: 1303

000

<210> SEQ ID NO 1304

<400> SEQUENCE: 1304

000

<210> SEQ ID NO 1305

<400> SEQUENCE: 1305

000

<210> SEQ ID NO 1306

<400> SEQUENCE: 1306

000

<210> SEQ ID NO 1307

<400> SEQUENCE: 1307

000

<210> SEQ ID NO 1308

<400> SEQUENCE: 1308

000

<210> SEQ ID NO 1309

<400> SEQUENCE: 1309

000

<210> SEQ ID NO 1310

<400> SEQUENCE: 1310

000

<210> SEQ ID NO 1311

<400> SEQUENCE: 1311

000

<210> SEQ ID NO 1312

<400> SEQUENCE: 1312

000

<210> SEQ ID NO 1313

<400> SEQUENCE: 1313

000

<210> SEQ ID NO 1314

<400> SEQUENCE: 1314

000

<210> SEQ ID NO 1315

<400> SEQUENCE: 1315

000

<210> SEQ ID NO 1316

<400> SEQUENCE: 1316

000

<210> SEQ ID NO 1317

<400> SEQUENCE: 1317

000

<210> SEQ ID NO 1318

<400> SEQUENCE: 1318

000

<210> SEQ ID NO 1319

<400> SEQUENCE: 1319

000

<210> SEQ ID NO 1320

<400> SEQUENCE: 1320

000

<210> SEQ ID NO 1321

<400> SEQUENCE: 1321

000

<210> SEQ ID NO 1322

<400> SEQUENCE: 1322

000

<210> SEQ ID NO 1323

<400> SEQUENCE: 1323

000

<210> SEQ ID NO 1324

<400> SEQUENCE: 1324

000

<210> SEQ ID NO 1325

<400> SEQUENCE: 1325

000

<210> SEQ ID NO 1326

<400> SEQUENCE: 1326

000

<210> SEQ ID NO 1327

<400> SEQUENCE: 1327

000

<210> SEQ ID NO 1328

<400> SEQUENCE: 1328

000

<210> SEQ ID NO 1329

<400> SEQUENCE: 1329

000

<210> SEQ ID NO 1330

<400> SEQUENCE: 1330

000

<210> SEQ ID NO 1331

<400> SEQUENCE: 1331

000

<210> SEQ ID NO 1332

<400> SEQUENCE: 1332

000

<210> SEQ ID NO 1333

<400> SEQUENCE: 1333

000

<210> SEQ ID NO 1334

<400> SEQUENCE: 1334

000

<210> SEQ ID NO 1335

<400> SEQUENCE: 1335

000

<210> SEQ ID NO 1336

<400> SEQUENCE: 1336

000

<210> SEQ ID NO 1337

<400> SEQUENCE: 1337

000

<210> SEQ ID NO 1338

<400> SEQUENCE: 1338

000

<210> SEQ ID NO 1339

<400> SEQUENCE: 1339

000

<210> SEQ ID NO 1340

<400> SEQUENCE: 1340

000

<210> SEQ ID NO 1341

<400> SEQUENCE: 1341

000

<210> SEQ ID NO 1342

<400> SEQUENCE: 1342

000

<210> SEQ ID NO 1343

<400> SEQUENCE: 1343

000

<210> SEQ ID NO 1344

<400> SEQUENCE: 1344

000

<210> SEQ ID NO 1345

<400> SEQUENCE: 1345

000

<210> SEQ ID NO 1346

<400> SEQUENCE: 1346

000

<210> SEQ ID NO 1347

<400> SEQUENCE: 1347

000

<210> SEQ ID NO 1348

<400> SEQUENCE: 1348

000

<210> SEQ ID NO 1349

<400> SEQUENCE: 1349

000

<210> SEQ ID NO 1350

<400> SEQUENCE: 1350

000

<210> SEQ ID NO 1351

<400> SEQUENCE: 1351

000

<210> SEQ ID NO 1352

<400> SEQUENCE: 1352

000

<210> SEQ ID NO 1353

<400> SEQUENCE: 1353

000

<210> SEQ ID NO 1354

<400> SEQUENCE: 1354

000

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

<210> SEQ ID NO 1359

<400> SEQUENCE: 1359

000

<210> SEQ ID NO 1360

<400> SEQUENCE: 1360

000

<210> SEQ ID NO 1361

<400> SEQUENCE: 1361

000

<210> SEQ ID NO 1362

<400> SEQUENCE: 1362

000

<210> SEQ ID NO 1363

<400> SEQUENCE: 1363

000

<210> SEQ ID NO 1364

<400> SEQUENCE: 1364

000

<210> SEQ ID NO 1365

<400> SEQUENCE: 1365

000

<210> SEQ ID NO 1366

<400> SEQUENCE: 1366

000

<210> SEQ ID NO 1367

<400> SEQUENCE: 1367

000

<210> SEQ ID NO 1368

<400> SEQUENCE: 1368

000

<210> SEQ ID NO 1369

<400> SEQUENCE: 1369

000

<210> SEQ ID NO 1370

<400> SEQUENCE: 1370

000

<210> SEQ ID NO 1371

<400> SEQUENCE: 1371

000

<210> SEQ ID NO 1372

<400> SEQUENCE: 1372

000

<210> SEQ ID NO 1373

<400> SEQUENCE: 1373

000

<210> SEQ ID NO 1374

<400> SEQUENCE: 1374

000

<210> SEQ ID NO 1375

<400> SEQUENCE: 1375

000

<210> SEQ ID NO 1376

<400> SEQUENCE: 1376

000

<210> SEQ ID NO 1377

<400> SEQUENCE: 1377

000

<210> SEQ ID NO 1378

<400> SEQUENCE: 1378

000

<210> SEQ ID NO 1379

<400> SEQUENCE: 1379

000

<210> SEQ ID NO 1380

<400> SEQUENCE: 1380

000

<210> SEQ ID NO 1381

<400> SEQUENCE: 1381

000

<210> SEQ ID NO 1382

<400> SEQUENCE: 1382

000

<210> SEQ ID NO 1383

<400> SEQUENCE: 1383

000

<210> SEQ ID NO 1384

<400> SEQUENCE: 1384

000

<210> SEQ ID NO 1385

<400> SEQUENCE: 1385

000

<210> SEQ ID NO 1386

<400> SEQUENCE: 1386

000

<210> SEQ ID NO 1387

<400> SEQUENCE: 1387

000

<210> SEQ ID NO 1388

<400> SEQUENCE: 1388

000

<210> SEQ ID NO 1389

<400> SEQUENCE: 1389

000

<210> SEQ ID NO 1390

<400> SEQUENCE: 1390

000

<210> SEQ ID NO 1391

<400> SEQUENCE: 1391

000

<210> SEQ ID NO 1392

<400> SEQUENCE: 1392

000

<210> SEQ ID NO 1393

<400> SEQUENCE: 1393

000

<210> SEQ ID NO 1394

<400> SEQUENCE: 1394

000

<210> SEQ ID NO 1395

<400> SEQUENCE: 1395

000

<210> SEQ ID NO 1396

<400> SEQUENCE: 1396

000

<210> SEQ ID NO 1397

<400> SEQUENCE: 1397

000

<210> SEQ ID NO 1398

<400> SEQUENCE: 1398

000

<210> SEQ ID NO 1399

<400> SEQUENCE: 1399

000

<210> SEQ ID NO 1400

<400> SEQUENCE: 1400

000

<210> SEQ ID NO 1401

<400> SEQUENCE: 1401

000

<210> SEQ ID NO 1402

<400> SEQUENCE: 1402

000

<210> SEQ ID NO 1403

<400> SEQUENCE: 1403

000

<210> SEQ ID NO 1404

<400> SEQUENCE: 1404

000

<210> SEQ ID NO 1405

<400> SEQUENCE: 1405

000

<210> SEQ ID NO 1406

<400> SEQUENCE: 1406

000

<210> SEQ ID NO 1407

<400> SEQUENCE: 1407

000

<210> SEQ ID NO 1408

<400> SEQUENCE: 1408

000

<210> SEQ ID NO 1409

<400> SEQUENCE: 1409

000

<210> SEQ ID NO 1410

<400> SEQUENCE: 1410

000

<210> SEQ ID NO 1411

<400> SEQUENCE: 1411

000

<210> SEQ ID NO 1412

<400> SEQUENCE: 1412

000

<210> SEQ ID NO 1413

<400> SEQUENCE: 1413

000

<210> SEQ ID NO 1414

<400> SEQUENCE: 1414

000

<210> SEQ ID NO 1415

<400> SEQUENCE: 1415

000

<210> SEQ ID NO 1416

<400> SEQUENCE: 1416

000

<210> SEQ ID NO 1417

<400> SEQUENCE: 1417

000

<210> SEQ ID NO 1418

<400> SEQUENCE: 1418

000

<210> SEQ ID NO 1419

<400> SEQUENCE: 1419

000

<210> SEQ ID NO 1420

<400> SEQUENCE: 1420

000

<210> SEQ ID NO 1421

<400> SEQUENCE: 1421

000

<210> SEQ ID NO 1422

<400> SEQUENCE: 1422

000

<210> SEQ ID NO 1423

<400> SEQUENCE: 1423

000

<210> SEQ ID NO 1424

<400> SEQUENCE: 1424

000

<210> SEQ ID NO 1425

<400> SEQUENCE: 1425

000

<210> SEQ ID NO 1426

<400> SEQUENCE: 1426

000

<210> SEQ ID NO 1427

<400> SEQUENCE: 1427

000

<210> SEQ ID NO 1428

<400> SEQUENCE: 1428

000

<210> SEQ ID NO 1429

<400> SEQUENCE: 1429

000

<210> SEQ ID NO 1430

<400> SEQUENCE: 1430

000

<210> SEQ ID NO 1431

<400> SEQUENCE: 1431

000

<210> SEQ ID NO 1432

<400> SEQUENCE: 1432

000

<210> SEQ ID NO 1433

<400> SEQUENCE: 1433

000

<210> SEQ ID NO 1434

<400> SEQUENCE: 1434

000

<210> SEQ ID NO 1435

<400> SEQUENCE: 1435

000

<210> SEQ ID NO 1436

<400> SEQUENCE: 1436

000

<210> SEQ ID NO 1437

<400> SEQUENCE: 1437

000

<210> SEQ ID NO 1438

<400> SEQUENCE: 1438

000

<210> SEQ ID NO 1439

<400> SEQUENCE: 1439

000

<210> SEQ ID NO 1440

<400> SEQUENCE: 1440

000

<210> SEQ ID NO 1441

<400> SEQUENCE: 1441

000

<210> SEQ ID NO 1442

<400> SEQUENCE: 1442

000

<210> SEQ ID NO 1443

<400> SEQUENCE: 1443

000

<210> SEQ ID NO 1444

<400> SEQUENCE: 1444

000

<210> SEQ ID NO 1445

<400> SEQUENCE: 1445

000

<210> SEQ ID NO 1446

<400> SEQUENCE: 1446

000

<210> SEQ ID NO 1447

<400> SEQUENCE: 1447

000

<210> SEQ ID NO 1448

<400> SEQUENCE: 1448

000

<210> SEQ ID NO 1449

<400> SEQUENCE: 1449

000

<210> SEQ ID NO 1450

<400> SEQUENCE: 1450

000

<210> SEQ ID NO 1451

<400> SEQUENCE: 1451

000

<210> SEQ ID NO 1452

<400> SEQUENCE: 1452

000

<210> SEQ ID NO 1453

<400> SEQUENCE: 1453

000

<210> SEQ ID NO 1454

<400> SEQUENCE: 1454

000

<210> SEQ ID NO 1455

<400> SEQUENCE: 1455

000

<210> SEQ ID NO 1456

<400> SEQUENCE: 1456

000

<210> SEQ ID NO 1457

<400> SEQUENCE: 1457

000

<210> SEQ ID NO 1458

<400> SEQUENCE: 1458

000

<210> SEQ ID NO 1459

<400> SEQUENCE: 1459

000

<210> SEQ ID NO 1460
<400> SEQUENCE: 1460
000

<210> SEQ ID NO 1461
<400> SEQUENCE: 1461
000

<210> SEQ ID NO 1462
<400> SEQUENCE: 1462
000

<210> SEQ ID NO 1463
<400> SEQUENCE: 1463
000

<210> SEQ ID NO 1464
<400> SEQUENCE: 1464
000

<210> SEQ ID NO 1465
<400> SEQUENCE: 1465
000

<210> SEQ ID NO 1466
<400> SEQUENCE: 1466
000

<210> SEQ ID NO 1467
<400> SEQUENCE: 1467
000

<210> SEQ ID NO 1468
<400> SEQUENCE: 1468
000

<210> SEQ ID NO 1469
<400> SEQUENCE: 1469
000

<210> SEQ ID NO 1470
<400> SEQUENCE: 1470
000

<210> SEQ ID NO 1471

<400> SEQUENCE: 1471

000

<210> SEQ ID NO 1472

<400> SEQUENCE: 1472

000

<210> SEQ ID NO 1473

<400> SEQUENCE: 1473

000

<210> SEQ ID NO 1474

<400> SEQUENCE: 1474

000

<210> SEQ ID NO 1475

<400> SEQUENCE: 1475

000

<210> SEQ ID NO 1476

<400> SEQUENCE: 1476

000

<210> SEQ ID NO 1477

<400> SEQUENCE: 1477

000

<210> SEQ ID NO 1478

<400> SEQUENCE: 1478

000

<210> SEQ ID NO 1479

<400> SEQUENCE: 1479

000

<210> SEQ ID NO 1480

<400> SEQUENCE: 1480

000

<210> SEQ ID NO 1481

<400> SEQUENCE: 1481

000

<210> SEQ ID NO 1482

<400> SEQUENCE: 1482

000

<210> SEQ ID NO 1483

<400> SEQUENCE: 1483

000

<210> SEQ ID NO 1484

<400> SEQUENCE: 1484

000

<210> SEQ ID NO 1485

<400> SEQUENCE: 1485

000

<210> SEQ ID NO 1486

<400> SEQUENCE: 1486

000

<210> SEQ ID NO 1487

<400> SEQUENCE: 1487

000

<210> SEQ ID NO 1488

<400> SEQUENCE: 1488

000

<210> SEQ ID NO 1489

<400> SEQUENCE: 1489

000

<210> SEQ ID NO 1490

<400> SEQUENCE: 1490

000

<210> SEQ ID NO 1491

<400> SEQUENCE: 1491

000

<210> SEQ ID NO 1492

<400> SEQUENCE: 1492

000

<210> SEQ ID NO 1493

<400> SEQUENCE: 1493

000

<210> SEQ ID NO 1494

<400> SEQUENCE: 1494

000

<210> SEQ ID NO 1495

<400> SEQUENCE: 1495

000

<210> SEQ ID NO 1496

<400> SEQUENCE: 1496

000

<210> SEQ ID NO 1497

<400> SEQUENCE: 1497

000

<210> SEQ ID NO 1498

<400> SEQUENCE: 1498

000

<210> SEQ ID NO 1499

<400> SEQUENCE: 1499

000

<210> SEQ ID NO 1500

<400> SEQUENCE: 1500

000

<210> SEQ ID NO 1501

<400> SEQUENCE: 1501

000

<210> SEQ ID NO 1502

<400> SEQUENCE: 1502

000

<210> SEQ ID NO 1503

<400> SEQUENCE: 1503

000

<210> SEQ ID NO 1504

<400> SEQUENCE: 1504

000

<210> SEQ ID NO 1505

<400> SEQUENCE: 1505

000

<210> SEQ ID NO 1506

<400> SEQUENCE: 1506

000

<210> SEQ ID NO 1507

<400> SEQUENCE: 1507

000

<210> SEQ ID NO 1508

<400> SEQUENCE: 1508

000

<210> SEQ ID NO 1509

<400> SEQUENCE: 1509

000

<210> SEQ ID NO 1510

<400> SEQUENCE: 1510

000

<210> SEQ ID NO 1511

<400> SEQUENCE: 1511

000

<210> SEQ ID NO 1512

<400> SEQUENCE: 1512

000

<210> SEQ ID NO 1513

<400> SEQUENCE: 1513

000

<210> SEQ ID NO 1514

<400> SEQUENCE: 1514

000

<210> SEQ ID NO 1515

<400> SEQUENCE: 1515

000

<210> SEQ ID NO 1516

<400> SEQUENCE: 1516

000

<210> SEQ ID NO 1517

<400> SEQUENCE: 1517

000

<210> SEQ ID NO 1518

<400> SEQUENCE: 1518

000

<210> SEQ ID NO 1519

<400> SEQUENCE: 1519

000

<210> SEQ ID NO 1520

<400> SEQUENCE: 1520

000

<210> SEQ ID NO 1521

<400> SEQUENCE: 1521

000

<210> SEQ ID NO 1522

<400> SEQUENCE: 1522

000

<210> SEQ ID NO 1523

<400> SEQUENCE: 1523

000

<210> SEQ ID NO 1524

<400> SEQUENCE: 1524

000

<210> SEQ ID NO 1525

<400> SEQUENCE: 1525

000

<210> SEQ ID NO 1526

<400> SEQUENCE: 1526

000

<210> SEQ ID NO 1527

<400> SEQUENCE: 1527

000

<210> SEQ ID NO 1528

<400> SEQUENCE: 1528

000

<210> SEQ ID NO 1529

<400> SEQUENCE: 1529

000

<210> SEQ ID NO 1530

<400> SEQUENCE: 1530

000

<210> SEQ ID NO 1531

<400> SEQUENCE: 1531

000

<210> SEQ ID NO 1532

<400> SEQUENCE: 1532

000

<210> SEQ ID NO 1533

<400> SEQUENCE: 1533

000

<210> SEQ ID NO 1534

<400> SEQUENCE: 1534

000

<210> SEQ ID NO 1535

<400> SEQUENCE: 1535

000

<210> SEQ ID NO 1536

<400> SEQUENCE: 1536

000

<210> SEQ ID NO 1537

<400> SEQUENCE: 1537

000

<210> SEQ ID NO 1538

<400> SEQUENCE: 1538

-continued

000

<210> SEQ ID NO 1539

<400> SEQUENCE: 1539

000

<210> SEQ ID NO 1540

<400> SEQUENCE: 1540

000

<210> SEQ ID NO 1541

<400> SEQUENCE: 1541

000

<210> SEQ ID NO 1542

<400> SEQUENCE: 1542

000

<210> SEQ ID NO 1543

<400> SEQUENCE: 1543

000

<210> SEQ ID NO 1544

<400> SEQUENCE: 1544

000

<210> SEQ ID NO 1545

<400> SEQUENCE: 1545

000

<210> SEQ ID NO 1546

<400> SEQUENCE: 1546

000

<210> SEQ ID NO 1547

<400> SEQUENCE: 1547

000

<210> SEQ ID NO 1548

<400> SEQUENCE: 1548

000

<210> SEQ ID NO 1549

<400> SEQUENCE: 1549

000

<210> SEQ ID NO 1550

<400> SEQUENCE: 1550

000

<210> SEQ ID NO 1551

<400> SEQUENCE: 1551

000

<210> SEQ ID NO 1552

<400> SEQUENCE: 1552

000

<210> SEQ ID NO 1553

<400> SEQUENCE: 1553

000

<210> SEQ ID NO 1554

<400> SEQUENCE: 1554

000

<210> SEQ ID NO 1555

<400> SEQUENCE: 1555

000

<210> SEQ ID NO 1556

<400> SEQUENCE: 1556

000

<210> SEQ ID NO 1557

<400> SEQUENCE: 1557

000

<210> SEQ ID NO 1558

<400> SEQUENCE: 1558

000

<210> SEQ ID NO 1559

<400> SEQUENCE: 1559

000

<210> SEQ ID NO 1560

<400> SEQUENCE: 1560

000

<210> SEQ ID NO 1561

<400> SEQUENCE: 1561

000

<210> SEQ ID NO 1562

<400> SEQUENCE: 1562

000

<210> SEQ ID NO 1563

<400> SEQUENCE: 1563

000

<210> SEQ ID NO 1564

<400> SEQUENCE: 1564

000

<210> SEQ ID NO 1565

<400> SEQUENCE: 1565

000

<210> SEQ ID NO 1566

<400> SEQUENCE: 1566

000

<210> SEQ ID NO 1567

<400> SEQUENCE: 1567

000

<210> SEQ ID NO 1568

<400> SEQUENCE: 1568

000

<210> SEQ ID NO 1569

<400> SEQUENCE: 1569

000

<210> SEQ ID NO 1570

<400> SEQUENCE: 1570

000

<210> SEQ ID NO 1571

<400> SEQUENCE: 1571

000

<210> SEQ ID NO 1572

<400> SEQUENCE: 1572

000

<210> SEQ ID NO 1573

<400> SEQUENCE: 1573

000

<210> SEQ ID NO 1574

<400> SEQUENCE: 1574

000

<210> SEQ ID NO 1575

<400> SEQUENCE: 1575

000

<210> SEQ ID NO 1576

<400> SEQUENCE: 1576

000

<210> SEQ ID NO 1577

<400> SEQUENCE: 1577

000

<210> SEQ ID NO 1578

<400> SEQUENCE: 1578

000

<210> SEQ ID NO 1579

<400> SEQUENCE: 1579

000

<210> SEQ ID NO 1580

<400> SEQUENCE: 1580

000

<210> SEQ ID NO 1581

<400> SEQUENCE: 1581

000

<210> SEQ ID NO 1582

<400> SEQUENCE: 1582

000

<210> SEQ ID NO 1583

<400> SEQUENCE: 1583

000

<210> SEQ ID NO 1584

<400> SEQUENCE: 1584

000

<210> SEQ ID NO 1585

<400> SEQUENCE: 1585

000

<210> SEQ ID NO 1586

<400> SEQUENCE: 1586

000

<210> SEQ ID NO 1587

<400> SEQUENCE: 1587

000

<210> SEQ ID NO 1588

<400> SEQUENCE: 1588

000

<210> SEQ ID NO 1589

<400> SEQUENCE: 1589

000

<210> SEQ ID NO 1590

<400> SEQUENCE: 1590

000

<210> SEQ ID NO 1591

<400> SEQUENCE: 1591

000

<210> SEQ ID NO 1592

<400> SEQUENCE: 1592

000

<210> SEQ ID NO 1593

<400> SEQUENCE: 1593

000

<210> SEQ ID NO 1594

<400> SEQUENCE: 1594

000

<210> SEQ ID NO 1595

<400> SEQUENCE: 1595

000

<210> SEQ ID NO 1596

<400> SEQUENCE: 1596

000

<210> SEQ ID NO 1597

<400> SEQUENCE: 1597

000

<210> SEQ ID NO 1598

<400> SEQUENCE: 1598

000

<210> SEQ ID NO 1599

<400> SEQUENCE: 1599

000

<210> SEQ ID NO 1600

<400> SEQUENCE: 1600

000

<210> SEQ ID NO 1601

<400> SEQUENCE: 1601

000

<210> SEQ ID NO 1602

<400> SEQUENCE: 1602

000

<210> SEQ ID NO 1603

<400> SEQUENCE: 1603

000

<210> SEQ ID NO 1604

<400> SEQUENCE: 1604

000

<210> SEQ ID NO 1605

<400> SEQUENCE: 1605

000

<210> SEQ ID NO 1606

<400> SEQUENCE: 1606

000

<210> SEQ ID NO 1607

<400> SEQUENCE: 1607

000

<210> SEQ ID NO 1608

<400> SEQUENCE: 1608

000

<210> SEQ ID NO 1609

<400> SEQUENCE: 1609

000

<210> SEQ ID NO 1610

<400> SEQUENCE: 1610

000

<210> SEQ ID NO 1611

<400> SEQUENCE: 1611

000

<210> SEQ ID NO 1612

<400> SEQUENCE: 1612

000

<210> SEQ ID NO 1613

<400> SEQUENCE: 1613

000

<210> SEQ ID NO 1614

<400> SEQUENCE: 1614

000

<210> SEQ ID NO 1615

<400> SEQUENCE: 1615

000

<210> SEQ ID NO 1616

<400> SEQUENCE: 1616

000

<210> SEQ ID NO 1617

<400> SEQUENCE: 1617

000

<210> SEQ ID NO 1618
<400> SEQUENCE: 1618
000

<210> SEQ ID NO 1619
<400> SEQUENCE: 1619
000

<210> SEQ ID NO 1620
<400> SEQUENCE: 1620
000

<210> SEQ ID NO 1621
<400> SEQUENCE: 1621
000

<210> SEQ ID NO 1622
<400> SEQUENCE: 1622
000

<210> SEQ ID NO 1623
<400> SEQUENCE: 1623
000

<210> SEQ ID NO 1624
<400> SEQUENCE: 1624
000

<210> SEQ ID NO 1625
<400> SEQUENCE: 1625
000

<210> SEQ ID NO 1626
<400> SEQUENCE: 1626
000

<210> SEQ ID NO 1627
<400> SEQUENCE: 1627
000

<210> SEQ ID NO 1628
<400> SEQUENCE: 1628
000

<210> SEQ ID NO 1629

<400> SEQUENCE: 1629

000

<210> SEQ ID NO 1630

<400> SEQUENCE: 1630

000

<210> SEQ ID NO 1631

<400> SEQUENCE: 1631

000

<210> SEQ ID NO 1632

<400> SEQUENCE: 1632

000

<210> SEQ ID NO 1633

<400> SEQUENCE: 1633

000

<210> SEQ ID NO 1634

<400> SEQUENCE: 1634

000

<210> SEQ ID NO 1635

<400> SEQUENCE: 1635

000

<210> SEQ ID NO 1636

<400> SEQUENCE: 1636

000

<210> SEQ ID NO 1637

<400> SEQUENCE: 1637

000

<210> SEQ ID NO 1638

<400> SEQUENCE: 1638

000

<210> SEQ ID NO 1639

<400> SEQUENCE: 1639

000

<210> SEQ ID NO 1640

<400> SEQUENCE: 1640

000

<210> SEQ ID NO 1641

<400> SEQUENCE: 1641

000

<210> SEQ ID NO 1642

<400> SEQUENCE: 1642

000

<210> SEQ ID NO 1643

<400> SEQUENCE: 1643

000

<210> SEQ ID NO 1644

<400> SEQUENCE: 1644

000

<210> SEQ ID NO 1645

<400> SEQUENCE: 1645

000

<210> SEQ ID NO 1646

<400> SEQUENCE: 1646

000

<210> SEQ ID NO 1647

<400> SEQUENCE: 1647

000

<210> SEQ ID NO 1648

<400> SEQUENCE: 1648

000

<210> SEQ ID NO 1649

<400> SEQUENCE: 1649

000

<210> SEQ ID NO 1650

<400> SEQUENCE: 1650

000

<210> SEQ ID NO 1651

<400> SEQUENCE: 1651

000

<210> SEQ ID NO 1652

<400> SEQUENCE: 1652

000

<210> SEQ ID NO 1653

<400> SEQUENCE: 1653

000

<210> SEQ ID NO 1654

<400> SEQUENCE: 1654

000

<210> SEQ ID NO 1655

<400> SEQUENCE: 1655

000

<210> SEQ ID NO 1656

<400> SEQUENCE: 1656

000

<210> SEQ ID NO 1657

<400> SEQUENCE: 1657

000

<210> SEQ ID NO 1658

<400> SEQUENCE: 1658

000

<210> SEQ ID NO 1659

<400> SEQUENCE: 1659

000

<210> SEQ ID NO 1660

<400> SEQUENCE: 1660

000

<210> SEQ ID NO 1661

<400> SEQUENCE: 1661

000

<210> SEQ ID NO 1662

<400> SEQUENCE: 1662

000

<210> SEQ ID NO 1663

<400> SEQUENCE: 1663

000

<210> SEQ ID NO 1664

<400> SEQUENCE: 1664

000

<210> SEQ ID NO 1665

<400> SEQUENCE: 1665

000

<210> SEQ ID NO 1666

<400> SEQUENCE: 1666

000

<210> SEQ ID NO 1667

<400> SEQUENCE: 1667

000

<210> SEQ ID NO 1668

<400> SEQUENCE: 1668

000

<210> SEQ ID NO 1669

<400> SEQUENCE: 1669

000

<210> SEQ ID NO 1670

<400> SEQUENCE: 1670

000

<210> SEQ ID NO 1671

<400> SEQUENCE: 1671

000

<210> SEQ ID NO 1672

<400> SEQUENCE: 1672

000

<210> SEQ ID NO 1673

<400> SEQUENCE: 1673

000

<210> SEQ ID NO 1674

<400> SEQUENCE: 1674

000

<210> SEQ ID NO 1675

<400> SEQUENCE: 1675

000

<210> SEQ ID NO 1676

<400> SEQUENCE: 1676

000

<210> SEQ ID NO 1677

<400> SEQUENCE: 1677

000

<210> SEQ ID NO 1678

<400> SEQUENCE: 1678

000

<210> SEQ ID NO 1679

<400> SEQUENCE: 1679

000

<210> SEQ ID NO 1680

<400> SEQUENCE: 1680

000

<210> SEQ ID NO 1681

<400> SEQUENCE: 1681

000

<210> SEQ ID NO 1682

<400> SEQUENCE: 1682

000

<210> SEQ ID NO 1683

<400> SEQUENCE: 1683

000

<210> SEQ ID NO 1684

<400> SEQUENCE: 1684

000

<210> SEQ ID NO 1685

<400> SEQUENCE: 1685

000

<210> SEQ ID NO 1686

<400> SEQUENCE: 1686

000

<210> SEQ ID NO 1687

<400> SEQUENCE: 1687

000

<210> SEQ ID NO 1688

<400> SEQUENCE: 1688

000

<210> SEQ ID NO 1689

<400> SEQUENCE: 1689

000

<210> SEQ ID NO 1690

<400> SEQUENCE: 1690

000

<210> SEQ ID NO 1691

<400> SEQUENCE: 1691

000

<210> SEQ ID NO 1692

<400> SEQUENCE: 1692

000

<210> SEQ ID NO 1693

<400> SEQUENCE: 1693

000

<210> SEQ ID NO 1694

<400> SEQUENCE: 1694

000

<210> SEQ ID NO 1695

<400> SEQUENCE: 1695

000

<210> SEQ ID NO 1696

<400> SEQUENCE: 1696

000

<210> SEQ ID NO 1697

<400> SEQUENCE: 1697

000

<210> SEQ ID NO 1698

<400> SEQUENCE: 1698

000

<210> SEQ ID NO 1699

<400> SEQUENCE: 1699

000

<210> SEQ ID NO 1700

<400> SEQUENCE: 1700

000

<210> SEQ ID NO 1701

<400> SEQUENCE: 1701

000

<210> SEQ ID NO 1702

<400> SEQUENCE: 1702

000

<210> SEQ ID NO 1703

<400> SEQUENCE: 1703

000

<210> SEQ ID NO 1704

<400> SEQUENCE: 1704

000

<210> SEQ ID NO 1705

<400> SEQUENCE: 1705

000

<210> SEQ ID NO 1706

<400> SEQUENCE: 1706

000

<210> SEQ ID NO 1707

<400> SEQUENCE: 1707

000

<210> SEQ ID NO 1708

<400> SEQUENCE: 1708

000

<210> SEQ ID NO 1709

<400> SEQUENCE: 1709

000

<210> SEQ ID NO 1710

<400> SEQUENCE: 1710

000

<210> SEQ ID NO 1711

<400> SEQUENCE: 1711

000

<210> SEQ ID NO 1712

<400> SEQUENCE: 1712

000

<210> SEQ ID NO 1713

<400> SEQUENCE: 1713

000

<210> SEQ ID NO 1714

<400> SEQUENCE: 1714

000

<210> SEQ ID NO 1715

<400> SEQUENCE: 1715

000

<210> SEQ ID NO 1716

<400> SEQUENCE: 1716

000

<210> SEQ ID NO 1717

<400> SEQUENCE: 1717

000

<210> SEQ ID NO 1718

<400> SEQUENCE: 1718

000

<210> SEQ ID NO 1719

<400> SEQUENCE: 1719

000

<210> SEQ ID NO 1720

<400> SEQUENCE: 1720

000

<210> SEQ ID NO 1721

<400> SEQUENCE: 1721

000

<210> SEQ ID NO 1722

<400> SEQUENCE: 1722

000

<210> SEQ ID NO 1723

<400> SEQUENCE: 1723

000

<210> SEQ ID NO 1724

<400> SEQUENCE: 1724

000

<210> SEQ ID NO 1725

<400> SEQUENCE: 1725

000

<210> SEQ ID NO 1726

<400> SEQUENCE: 1726

000

<210> SEQ ID NO 1727

<400> SEQUENCE: 1727

000

<210> SEQ ID NO 1728

<400> SEQUENCE: 1728

000

<210> SEQ ID NO 1729

<400> SEQUENCE: 1729

000

<210> SEQ ID NO 1730

<400> SEQUENCE: 1730

000

<210> SEQ ID NO 1731

<400> SEQUENCE: 1731

000

<210> SEQ ID NO 1732

<400> SEQUENCE: 1732

000

<210> SEQ ID NO 1733

<400> SEQUENCE: 1733

000

<210> SEQ ID NO 1734

<400> SEQUENCE: 1734

000

<210> SEQ ID NO 1735

<400> SEQUENCE: 1735

000

<210> SEQ ID NO 1736

<400> SEQUENCE: 1736

000

<210> SEQ ID NO 1737

<400> SEQUENCE: 1737

000

<210> SEQ ID NO 1738

<400> SEQUENCE: 1738

000

<210> SEQ ID NO 1739

<400> SEQUENCE: 1739

000

<210> SEQ ID NO 1740

<400> SEQUENCE: 1740

000

<210> SEQ ID NO 1741

<400> SEQUENCE: 1741

000

<210> SEQ ID NO 1742

<400> SEQUENCE: 1742

000

<210> SEQ ID NO 1743

<400> SEQUENCE: 1743

000

<210> SEQ ID NO 1744

<400> SEQUENCE: 1744

000

<210> SEQ ID NO 1745

<400> SEQUENCE: 1745

000

<210> SEQ ID NO 1746

<400> SEQUENCE: 1746

000

<210> SEQ ID NO 1747

<400> SEQUENCE: 1747

000

<210> SEQ ID NO 1748

<400> SEQUENCE: 1748

000

<210> SEQ ID NO 1749

<400> SEQUENCE: 1749

000

<210> SEQ ID NO 1750

<400> SEQUENCE: 1750

000

<210> SEQ ID NO 1751

<400> SEQUENCE: 1751

000

<210> SEQ ID NO 1752

<400> SEQUENCE: 1752

000

<210> SEQ ID NO 1753

<400> SEQUENCE: 1753

000

<210> SEQ ID NO 1754

<400> SEQUENCE: 1754

000

<210> SEQ ID NO 1755

<400> SEQUENCE: 1755

000

<210> SEQ ID NO 1756

<400> SEQUENCE: 1756

000

<210> SEQ ID NO 1757

<400> SEQUENCE: 1757

000

<210> SEQ ID NO 1758

<400> SEQUENCE: 1758

000

<210> SEQ ID NO 1759

<400> SEQUENCE: 1759

000

<210> SEQ ID NO 1760

<400> SEQUENCE: 1760

000

<210> SEQ ID NO 1761

<400> SEQUENCE: 1761

000

<210> SEQ ID NO 1762

<400> SEQUENCE: 1762

000

<210> SEQ ID NO 1763

<400> SEQUENCE: 1763

000

<210> SEQ ID NO 1764

<400> SEQUENCE: 1764

000

<210> SEQ ID NO 1765

<400> SEQUENCE: 1765

000

<210> SEQ ID NO 1766

<400> SEQUENCE: 1766

000

<210> SEQ ID NO 1767

<400> SEQUENCE: 1767

000

<210> SEQ ID NO 1768

<400> SEQUENCE: 1768

000

<210> SEQ ID NO 1769

<400> SEQUENCE: 1769

000

<210> SEQ ID NO 1770

<400> SEQUENCE: 1770

000

<210> SEQ ID NO 1771

<400> SEQUENCE: 1771

000

<210> SEQ ID NO 1772

<400> SEQUENCE: 1772

000

<210> SEQ ID NO 1773

<400> SEQUENCE: 1773

000

<210> SEQ ID NO 1774

<400> SEQUENCE: 1774

000

<210> SEQ ID NO 1775

<400> SEQUENCE: 1775

000

<210> SEQ ID NO 1776

<400> SEQUENCE: 1776

000

<210> SEQ ID NO 1777

<400> SEQUENCE: 1777

000

<210> SEQ ID NO 1778

<400> SEQUENCE: 1778

000

<210> SEQ ID NO 1779

<400> SEQUENCE: 1779

000

<210> SEQ ID NO 1780

<400> SEQUENCE: 1780

000

<210> SEQ ID NO 1781

<400> SEQUENCE: 1781

000

<210> SEQ ID NO 1782

<400> SEQUENCE: 1782

000

<210> SEQ ID NO 1783

<400> SEQUENCE: 1783

000

<210> SEQ ID NO 1784

<400> SEQUENCE: 1784

000

<210> SEQ ID NO 1785

<400> SEQUENCE: 1785

000

<210> SEQ ID NO 1786

<400> SEQUENCE: 1786

000

<210> SEQ ID NO 1787

<400> SEQUENCE: 1787

000

<210> SEQ ID NO 1788

<400> SEQUENCE: 1788

000

<210> SEQ ID NO 1789

<400> SEQUENCE: 1789

000

<210> SEQ ID NO 1790

<400> SEQUENCE: 1790

000

<210> SEQ ID NO 1791

<400> SEQUENCE: 1791

000

<210> SEQ ID NO 1792

<400> SEQUENCE: 1792

000

<210> SEQ ID NO 1793

<400> SEQUENCE: 1793

000

<210> SEQ ID NO 1794

<400> SEQUENCE: 1794

000

<210> SEQ ID NO 1795

<400> SEQUENCE: 1795

000

<210> SEQ ID NO 1796

<400> SEQUENCE: 1796

000

<210> SEQ ID NO 1797

<400> SEQUENCE: 1797

000

<210> SEQ ID NO 1798

<400> SEQUENCE: 1798

000

<210> SEQ ID NO 1799

<400> SEQUENCE: 1799

000

<210> SEQ ID NO 1800

<400> SEQUENCE: 1800

000

<210> SEQ ID NO 1801

<400> SEQUENCE: 1801

000

<210> SEQ ID NO 1802

<400> SEQUENCE: 1802

000

<210> SEQ ID NO 1803

<400> SEQUENCE: 1803

000

<210> SEQ ID NO 1804

<400> SEQUENCE: 1804

000

<210> SEQ ID NO 1805

<400> SEQUENCE: 1805

000

<210> SEQ ID NO 1806

<400> SEQUENCE: 1806

000

<210> SEQ ID NO 1807

<400> SEQUENCE: 1807

000

<210> SEQ ID NO 1808

<400> SEQUENCE: 1808

000

<210> SEQ ID NO 1809

<400> SEQUENCE: 1809

000

<210> SEQ ID NO 1810

<400> SEQUENCE: 1810

000

<210> SEQ ID NO 1811

<400> SEQUENCE: 1811

000

<210> SEQ ID NO 1812

<400> SEQUENCE: 1812

000

<210> SEQ ID NO 1813

<400> SEQUENCE: 1813

000

<210> SEQ ID NO 1814

<400> SEQUENCE: 1814

000

<210> SEQ ID NO 1815

<400> SEQUENCE: 1815

000

<210> SEQ ID NO 1816

<400> SEQUENCE: 1816

000

<210> SEQ ID NO 1817

<400> SEQUENCE: 1817

000

<210> SEQ ID NO 1818

<400> SEQUENCE: 1818

000

<210> SEQ ID NO 1819

<400> SEQUENCE: 1819

000

<210> SEQ ID NO 1820

<400> SEQUENCE: 1820

000

<210> SEQ ID NO 1821

<400> SEQUENCE: 1821

000

<210> SEQ ID NO 1822

<400> SEQUENCE: 1822

000

<210> SEQ ID NO 1823

<400> SEQUENCE: 1823

000

<210> SEQ ID NO 1824

<400> SEQUENCE: 1824

000

<210> SEQ ID NO 1825

<400> SEQUENCE: 1825

000

<210> SEQ ID NO 1826

<400> SEQUENCE: 1826

000

<210> SEQ ID NO 1827

<400> SEQUENCE: 1827

000

<210> SEQ ID NO 1828

<400> SEQUENCE: 1828

000

<210> SEQ ID NO 1829

<400> SEQUENCE: 1829

000

<210> SEQ ID NO 1830

<400> SEQUENCE: 1830

000

<210> SEQ ID NO 1831

<400> SEQUENCE: 1831

000

<210> SEQ ID NO 1832

<400> SEQUENCE: 1832

000

<210> SEQ ID NO 1833

<400> SEQUENCE: 1833

000

<210> SEQ ID NO 1834

<400> SEQUENCE: 1834

000

<210> SEQ ID NO 1835

<400> SEQUENCE: 1835

000

<210> SEQ ID NO 1836

<400> SEQUENCE: 1836

000

<210> SEQ ID NO 1837

<400> SEQUENCE: 1837

000

<210> SEQ ID NO 1838

<400> SEQUENCE: 1838

000

<210> SEQ ID NO 1839

<400> SEQUENCE: 1839

000

<210> SEQ ID NO 1840

<400> SEQUENCE: 1840

000

<210> SEQ ID NO 1841

<400> SEQUENCE: 1841

000

<210> SEQ ID NO 1842

<400> SEQUENCE: 1842

000

<210> SEQ ID NO 1843

<400> SEQUENCE: 1843

000

<210> SEQ ID NO 1844

<400> SEQUENCE: 1844

000

<210> SEQ ID NO 1845

<400> SEQUENCE: 1845

000

<210> SEQ ID NO 1846

<400> SEQUENCE: 1846

000

<210> SEQ ID NO 1847

<400> SEQUENCE: 1847

000

<210> SEQ ID NO 1848

<400> SEQUENCE: 1848

000

<210> SEQ ID NO 1849

<400> SEQUENCE: 1849

000

<210> SEQ ID NO 1850

<400> SEQUENCE: 1850

000

<210> SEQ ID NO 1851

<400> SEQUENCE: 1851

000

<210> SEQ ID NO 1852

<400> SEQUENCE: 1852

000

<210> SEQ ID NO 1853

<400> SEQUENCE: 1853

000

<210> SEQ ID NO 1854

<400> SEQUENCE: 1854

000

<210> SEQ ID NO 1855

<400> SEQUENCE: 1855

000

<210> SEQ ID NO 1856

<400> SEQUENCE: 1856

000

<210> SEQ ID NO 1857

<400> SEQUENCE: 1857

000

<210> SEQ ID NO 1858

<400> SEQUENCE: 1858

000

<210> SEQ ID NO 1859

<400> SEQUENCE: 1859

000

<210> SEQ ID NO 1860

<400> SEQUENCE: 1860

000

<210> SEQ ID NO 1861

<400> SEQUENCE: 1861

000

<210> SEQ ID NO 1862

<400> SEQUENCE: 1862

000

<210> SEQ ID NO 1863

<400> SEQUENCE: 1863

000

<210> SEQ ID NO 1864

<400> SEQUENCE: 1864

000

<210> SEQ ID NO 1865

<400> SEQUENCE: 1865

000

<210> SEQ ID NO 1866
<400> SEQUENCE: 1866
000

<210> SEQ ID NO 1867
<400> SEQUENCE: 1867
000

<210> SEQ ID NO 1868
<400> SEQUENCE: 1868
000

<210> SEQ ID NO 1869
<400> SEQUENCE: 1869
000

<210> SEQ ID NO 1870
<400> SEQUENCE: 1870
000

<210> SEQ ID NO 1871
<400> SEQUENCE: 1871
000

<210> SEQ ID NO 1872
<400> SEQUENCE: 1872
000

<210> SEQ ID NO 1873
<400> SEQUENCE: 1873
000

<210> SEQ ID NO 1874
<400> SEQUENCE: 1874
000

<210> SEQ ID NO 1875
<400> SEQUENCE: 1875
000

<210> SEQ ID NO 1876
<400> SEQUENCE: 1876
000

<210> SEQ ID NO 1877

<400> SEQUENCE: 1877

000

<210> SEQ ID NO 1878

<400> SEQUENCE: 1878

000

<210> SEQ ID NO 1879

<400> SEQUENCE: 1879

000

<210> SEQ ID NO 1880

<400> SEQUENCE: 1880

000

<210> SEQ ID NO 1881

<400> SEQUENCE: 1881

000

<210> SEQ ID NO 1882

<400> SEQUENCE: 1882

000

<210> SEQ ID NO 1883

<400> SEQUENCE: 1883

000

<210> SEQ ID NO 1884

<400> SEQUENCE: 1884

000

<210> SEQ ID NO 1885

<400> SEQUENCE: 1885

000

<210> SEQ ID NO 1886

<400> SEQUENCE: 1886

000

<210> SEQ ID NO 1887

<400> SEQUENCE: 1887

000

<210> SEQ ID NO 1888

<400> SEQUENCE: 1888

000

<210> SEQ ID NO 1889

<400> SEQUENCE: 1889

000

<210> SEQ ID NO 1890

<400> SEQUENCE: 1890

000

<210> SEQ ID NO 1891

<400> SEQUENCE: 1891

000

<210> SEQ ID NO 1892

<400> SEQUENCE: 1892

000

<210> SEQ ID NO 1893

<400> SEQUENCE: 1893

000

<210> SEQ ID NO 1894

<400> SEQUENCE: 1894

000

<210> SEQ ID NO 1895

<400> SEQUENCE: 1895

000

<210> SEQ ID NO 1896

<400> SEQUENCE: 1896

000

<210> SEQ ID NO 1897

<400> SEQUENCE: 1897

000

<210> SEQ ID NO 1898

<400> SEQUENCE: 1898

000

<210> SEQ ID NO 1899

<400> SEQUENCE: 1899

000

<210> SEQ ID NO 1900

<400> SEQUENCE: 1900

000

<210> SEQ ID NO 1901

<400> SEQUENCE: 1901

000

<210> SEQ ID NO 1902

<400> SEQUENCE: 1902

000

<210> SEQ ID NO 1903

<400> SEQUENCE: 1903

000

<210> SEQ ID NO 1904

<400> SEQUENCE: 1904

000

<210> SEQ ID NO 1905

<400> SEQUENCE: 1905

000

<210> SEQ ID NO 1906

<400> SEQUENCE: 1906

000

<210> SEQ ID NO 1907

<400> SEQUENCE: 1907

000

<210> SEQ ID NO 1908

<400> SEQUENCE: 1908

000

<210> SEQ ID NO 1909

<400> SEQUENCE: 1909

000

<210> SEQ ID NO 1910

<400> SEQUENCE: 1910

000

<210> SEQ ID NO 1911
<400> SEQUENCE: 1911
000

<210> SEQ ID NO 1912
<400> SEQUENCE: 1912
000

<210> SEQ ID NO 1913
<400> SEQUENCE: 1913
000

<210> SEQ ID NO 1914
<400> SEQUENCE: 1914
000

<210> SEQ ID NO 1915
<400> SEQUENCE: 1915
000

<210> SEQ ID NO 1916
<400> SEQUENCE: 1916
000

<210> SEQ ID NO 1917
<400> SEQUENCE: 1917
000

<210> SEQ ID NO 1918
<400> SEQUENCE: 1918
000

<210> SEQ ID NO 1919
<400> SEQUENCE: 1919
000

<210> SEQ ID NO 1920
<400> SEQUENCE: 1920
000

<210> SEQ ID NO 1921
<400> SEQUENCE: 1921
000

<210> SEQ ID NO 1922

<400> SEQUENCE: 1922

000

<210> SEQ ID NO 1923

<400> SEQUENCE: 1923

000

<210> SEQ ID NO 1924

<400> SEQUENCE: 1924

000

<210> SEQ ID NO 1925

<400> SEQUENCE: 1925

000

<210> SEQ ID NO 1926

<400> SEQUENCE: 1926

000

<210> SEQ ID NO 1927

<400> SEQUENCE: 1927

000

<210> SEQ ID NO 1928

<400> SEQUENCE: 1928

000

<210> SEQ ID NO 1929

<400> SEQUENCE: 1929

000

<210> SEQ ID NO 1930

<400> SEQUENCE: 1930

000

<210> SEQ ID NO 1931

<400> SEQUENCE: 1931

000

<210> SEQ ID NO 1932

<400> SEQUENCE: 1932

000

<210> SEQ ID NO 1933

<400> SEQUENCE: 1933

000

<210> SEQ ID NO 1934

<400> SEQUENCE: 1934

000

<210> SEQ ID NO 1935

<400> SEQUENCE: 1935

000

<210> SEQ ID NO 1936

<400> SEQUENCE: 1936

000

<210> SEQ ID NO 1937

<400> SEQUENCE: 1937

000

<210> SEQ ID NO 1938

<400> SEQUENCE: 1938

000

<210> SEQ ID NO 1939

<400> SEQUENCE: 1939

000

<210> SEQ ID NO 1940

<400> SEQUENCE: 1940

000

<210> SEQ ID NO 1941

<400> SEQUENCE: 1941

000

<210> SEQ ID NO 1942

<400> SEQUENCE: 1942

000

<210> SEQ ID NO 1943

<400> SEQUENCE: 1943

000

<210> SEQ ID NO 1944

<400> SEQUENCE: 1944

000

<210> SEQ ID NO 1945

<400> SEQUENCE: 1945

000

<210> SEQ ID NO 1946

<400> SEQUENCE: 1946

000

<210> SEQ ID NO 1947

<400> SEQUENCE: 1947

000

<210> SEQ ID NO 1948

<400> SEQUENCE: 1948

000

<210> SEQ ID NO 1949

<400> SEQUENCE: 1949

000

<210> SEQ ID NO 1950

<400> SEQUENCE: 1950

000

<210> SEQ ID NO 1951

<400> SEQUENCE: 1951

000

<210> SEQ ID NO 1952

<400> SEQUENCE: 1952

000

<210> SEQ ID NO 1953

<400> SEQUENCE: 1953

000

<210> SEQ ID NO 1954

<400> SEQUENCE: 1954

000

<210> SEQ ID NO 1955

<400> SEQUENCE: 1955

000

-continued

<210> SEQ ID NO 1956

<400> SEQUENCE: 1956

000

<210> SEQ ID NO 1957

<400> SEQUENCE: 1957

000

<210> SEQ ID NO 1958

<400> SEQUENCE: 1958

000

<210> SEQ ID NO 1959

<400> SEQUENCE: 1959

000

<210> SEQ ID NO 1960

<400> SEQUENCE: 1960

000

<210> SEQ ID NO 1961

<400> SEQUENCE: 1961

000

<210> SEQ ID NO 1962

<400> SEQUENCE: 1962

000

<210> SEQ ID NO 1963

<400> SEQUENCE: 1963

000

<210> SEQ ID NO 1964

<400> SEQUENCE: 1964

000

<210> SEQ ID NO 1965

<400> SEQUENCE: 1965

000

<210> SEQ ID NO 1966

<400> SEQUENCE: 1966

000

<210> SEQ ID NO 1967

<400> SEQUENCE: 1967

000

<210> SEQ ID NO 1968

<400> SEQUENCE: 1968

000

<210> SEQ ID NO 1969

<400> SEQUENCE: 1969

000

<210> SEQ ID NO 1970

<400> SEQUENCE: 1970

000

<210> SEQ ID NO 1971

<400> SEQUENCE: 1971

000

<210> SEQ ID NO 1972

<400> SEQUENCE: 1972

000

<210> SEQ ID NO 1973

<400> SEQUENCE: 1973

000

<210> SEQ ID NO 1974

<400> SEQUENCE: 1974

000

<210> SEQ ID NO 1975

<400> SEQUENCE: 1975

000

<210> SEQ ID NO 1976

<400> SEQUENCE: 1976

000

<210> SEQ ID NO 1977

<400> SEQUENCE: 1977

000

<210> SEQ ID NO 1978

<400> SEQUENCE: 1978

000

<210> SEQ ID NO 1979

<400> SEQUENCE: 1979

000

<210> SEQ ID NO 1980

<400> SEQUENCE: 1980

000

<210> SEQ ID NO 1981

<400> SEQUENCE: 1981

000

<210> SEQ ID NO 1982

<400> SEQUENCE: 1982

000

<210> SEQ ID NO 1983

<400> SEQUENCE: 1983

000

<210> SEQ ID NO 1984

<400> SEQUENCE: 1984

000

<210> SEQ ID NO 1985

<400> SEQUENCE: 1985

000

<210> SEQ ID NO 1986

<400> SEQUENCE: 1986

000

<210> SEQ ID NO 1987

<400> SEQUENCE: 1987

000

<210> SEQ ID NO 1988

<400> SEQUENCE: 1988

000

<210> SEQ ID NO 1989

<400> SEQUENCE: 1989

000

<210> SEQ ID NO 1990
<400> SEQUENCE: 1990
000

<210> SEQ ID NO 1991
<400> SEQUENCE: 1991
000

<210> SEQ ID NO 1992
<400> SEQUENCE: 1992
000

<210> SEQ ID NO 1993
<400> SEQUENCE: 1993
000

<210> SEQ ID NO 1994
<400> SEQUENCE: 1994
000

<210> SEQ ID NO 1995
<400> SEQUENCE: 1995
000

<210> SEQ ID NO 1996
<400> SEQUENCE: 1996
000

<210> SEQ ID NO 1997
<400> SEQUENCE: 1997
000

<210> SEQ ID NO 1998
<400> SEQUENCE: 1998
000

<210> SEQ ID NO 1999
<400> SEQUENCE: 1999
000

<210> SEQ ID NO 2000
<400> SEQUENCE: 2000
000

<210> SEQ ID NO 2001

<400> SEQUENCE: 2001

000

<210> SEQ ID NO 2002

<400> SEQUENCE: 2002

000

<210> SEQ ID NO 2003

<400> SEQUENCE: 2003

000

<210> SEQ ID NO 2004

<400> SEQUENCE: 2004

000

<210> SEQ ID NO 2005

<400> SEQUENCE: 2005

000

<210> SEQ ID NO 2006

<400> SEQUENCE: 2006

000

<210> SEQ ID NO 2007

<400> SEQUENCE: 2007

000

<210> SEQ ID NO 2008

<400> SEQUENCE: 2008

000

<210> SEQ ID NO 2009

<400> SEQUENCE: 2009

000

<210> SEQ ID NO 2010

<400> SEQUENCE: 2010

000

<210> SEQ ID NO 2011

<400> SEQUENCE: 2011

000

<210> SEQ ID NO 2012

<400> SEQUENCE: 2012

000

<210> SEQ ID NO 2013

<400> SEQUENCE: 2013

000

<210> SEQ ID NO 2014

<400> SEQUENCE: 2014

000

<210> SEQ ID NO 2015

<400> SEQUENCE: 2015

000

<210> SEQ ID NO 2016

<400> SEQUENCE: 2016

000

<210> SEQ ID NO 2017

<400> SEQUENCE: 2017

000

<210> SEQ ID NO 2018

<400> SEQUENCE: 2018

000

<210> SEQ ID NO 2019

<400> SEQUENCE: 2019

000

<210> SEQ ID NO 2020

<400> SEQUENCE: 2020

000

<210> SEQ ID NO 2021

<400> SEQUENCE: 2021

000

<210> SEQ ID NO 2022

<400> SEQUENCE: 2022

000

<210> SEQ ID NO 2023

<400> SEQUENCE: 2023

000

<210> SEQ ID NO 2024

<400> SEQUENCE: 2024

000

<210> SEQ ID NO 2025

<400> SEQUENCE: 2025

000

<210> SEQ ID NO 2026

<400> SEQUENCE: 2026

000

<210> SEQ ID NO 2027

<400> SEQUENCE: 2027

000

<210> SEQ ID NO 2028

<400> SEQUENCE: 2028

000

<210> SEQ ID NO 2029

<400> SEQUENCE: 2029

000

<210> SEQ ID NO 2030

<400> SEQUENCE: 2030

000

<210> SEQ ID NO 2031

<400> SEQUENCE: 2031

000

<210> SEQ ID NO 2032

<400> SEQUENCE: 2032

000

<210> SEQ ID NO 2033

<400> SEQUENCE: 2033

000

<210> SEQ ID NO 2034

<400> SEQUENCE: 2034

000

<210> SEQ ID NO 2035
<400> SEQUENCE: 2035
000

<210> SEQ ID NO 2036
<400> SEQUENCE: 2036
000

<210> SEQ ID NO 2037
<400> SEQUENCE: 2037
000

<210> SEQ ID NO 2038
<400> SEQUENCE: 2038
000

<210> SEQ ID NO 2039
<400> SEQUENCE: 2039
000

<210> SEQ ID NO 2040
<400> SEQUENCE: 2040
000

<210> SEQ ID NO 2041
<400> SEQUENCE: 2041
000

<210> SEQ ID NO 2042
<400> SEQUENCE: 2042
000

<210> SEQ ID NO 2043
<400> SEQUENCE: 2043
000

<210> SEQ ID NO 2044
<400> SEQUENCE: 2044
000

<210> SEQ ID NO 2045
<400> SEQUENCE: 2045
000

<210> SEQ ID NO 2046

<400> SEQUENCE: 2046

000

<210> SEQ ID NO 2047

<400> SEQUENCE: 2047

000

<210> SEQ ID NO 2048

<400> SEQUENCE: 2048

000

<210> SEQ ID NO 2049

<400> SEQUENCE: 2049

000

<210> SEQ ID NO 2050

<400> SEQUENCE: 2050

000

<210> SEQ ID NO 2051

<400> SEQUENCE: 2051

000

<210> SEQ ID NO 2052

<400> SEQUENCE: 2052

000

<210> SEQ ID NO 2053

<400> SEQUENCE: 2053

000

<210> SEQ ID NO 2054

<400> SEQUENCE: 2054

000

<210> SEQ ID NO 2055

<400> SEQUENCE: 2055

000

<210> SEQ ID NO 2056

<400> SEQUENCE: 2056

000

<210> SEQ ID NO 2057

<400> SEQUENCE: 2057

000

<210> SEQ ID NO 2058

<400> SEQUENCE: 2058

000

<210> SEQ ID NO 2059

<400> SEQUENCE: 2059

000

<210> SEQ ID NO 2060

<400> SEQUENCE: 2060

000

<210> SEQ ID NO 2061

<400> SEQUENCE: 2061

000

<210> SEQ ID NO 2062

<400> SEQUENCE: 2062

000

<210> SEQ ID NO 2063

<400> SEQUENCE: 2063

000

<210> SEQ ID NO 2064

<400> SEQUENCE: 2064

000

<210> SEQ ID NO 2065

<400> SEQUENCE: 2065

000

<210> SEQ ID NO 2066

<400> SEQUENCE: 2066

000

<210> SEQ ID NO 2067

<400> SEQUENCE: 2067

000

<210> SEQ ID NO 2068

<400> SEQUENCE: 2068

000

<210> SEQ ID NO 2069

<400> SEQUENCE: 2069

000

<210> SEQ ID NO 2070

<400> SEQUENCE: 2070

000

<210> SEQ ID NO 2071

<400> SEQUENCE: 2071

000

<210> SEQ ID NO 2072

<400> SEQUENCE: 2072

000

<210> SEQ ID NO 2073

<400> SEQUENCE: 2073

000

<210> SEQ ID NO 2074

<400> SEQUENCE: 2074

000

<210> SEQ ID NO 2075

<400> SEQUENCE: 2075

000

<210> SEQ ID NO 2076

<400> SEQUENCE: 2076

000

<210> SEQ ID NO 2077

<400> SEQUENCE: 2077

000

<210> SEQ ID NO 2078

<400> SEQUENCE: 2078

000

<210> SEQ ID NO 2079

<400> SEQUENCE: 2079

000

<210> SEQ ID NO 2080

<400> SEQUENCE: 2080

000

<210> SEQ ID NO 2081

<400> SEQUENCE: 2081

000

<210> SEQ ID NO 2082

<400> SEQUENCE: 2082

000

<210> SEQ ID NO 2083

<400> SEQUENCE: 2083

000

<210> SEQ ID NO 2084

<400> SEQUENCE: 2084

000

<210> SEQ ID NO 2085

<400> SEQUENCE: 2085

000

<210> SEQ ID NO 2086

<400> SEQUENCE: 2086

000

<210> SEQ ID NO 2087

<400> SEQUENCE: 2087

000

<210> SEQ ID NO 2088

<400> SEQUENCE: 2088

000

<210> SEQ ID NO 2089

<400> SEQUENCE: 2089

000

<210> SEQ ID NO 2090

<400> SEQUENCE: 2090

000

<210> SEQ ID NO 2091

<400> SEQUENCE: 2091

000

<210> SEQ ID NO 2092
<400> SEQUENCE: 2092
000

<210> SEQ ID NO 2093
<400> SEQUENCE: 2093
000

<210> SEQ ID NO 2094
<400> SEQUENCE: 2094
000

<210> SEQ ID NO 2095
<400> SEQUENCE: 2095
000

<210> SEQ ID NO 2096
<400> SEQUENCE: 2096
000

<210> SEQ ID NO 2097
<400> SEQUENCE: 2097
000

<210> SEQ ID NO 2098
<400> SEQUENCE: 2098
000

<210> SEQ ID NO 2099
<400> SEQUENCE: 2099
000

<210> SEQ ID NO 2100
<400> SEQUENCE: 2100
000

<210> SEQ ID NO 2101
<400> SEQUENCE: 2101
000

<210> SEQ ID NO 2102
<400> SEQUENCE: 2102
000

<210> SEQ ID NO 2103

<400> SEQUENCE: 2103

000

<210> SEQ ID NO 2104

<400> SEQUENCE: 2104

000

<210> SEQ ID NO 2105

<400> SEQUENCE: 2105

000

<210> SEQ ID NO 2106

<400> SEQUENCE: 2106

000

<210> SEQ ID NO 2107

<400> SEQUENCE: 2107

000

<210> SEQ ID NO 2108

<400> SEQUENCE: 2108

000

<210> SEQ ID NO 2109

<400> SEQUENCE: 2109

000

<210> SEQ ID NO 2110

<400> SEQUENCE: 2110

000

<210> SEQ ID NO 2111

<400> SEQUENCE: 2111

000

<210> SEQ ID NO 2112

<400> SEQUENCE: 2112

000

<210> SEQ ID NO 2113

<400> SEQUENCE: 2113

000

<210> SEQ ID NO 2114

<400> SEQUENCE: 2114

000

<210> SEQ ID NO 2115

<400> SEQUENCE: 2115

000

<210> SEQ ID NO 2116

<400> SEQUENCE: 2116

000

<210> SEQ ID NO 2117

<400> SEQUENCE: 2117

000

<210> SEQ ID NO 2118

<400> SEQUENCE: 2118

000

<210> SEQ ID NO 2119

<400> SEQUENCE: 2119

000

<210> SEQ ID NO 2120

<400> SEQUENCE: 2120

000

<210> SEQ ID NO 2121

<400> SEQUENCE: 2121

000

<210> SEQ ID NO 2122

<400> SEQUENCE: 2122

000

<210> SEQ ID NO 2123

<400> SEQUENCE: 2123

000

<210> SEQ ID NO 2124

<400> SEQUENCE: 2124

000

<210> SEQ ID NO 2125

<400> SEQUENCE: 2125

000

<210> SEQ ID NO 2126

<400> SEQUENCE: 2126

000

<210> SEQ ID NO 2127

<400> SEQUENCE: 2127

000

<210> SEQ ID NO 2128

<400> SEQUENCE: 2128

000

<210> SEQ ID NO 2129

<400> SEQUENCE: 2129

000

<210> SEQ ID NO 2130

<400> SEQUENCE: 2130

000

<210> SEQ ID NO 2131

<400> SEQUENCE: 2131

000

<210> SEQ ID NO 2132

<400> SEQUENCE: 2132

000

<210> SEQ ID NO 2133

<400> SEQUENCE: 2133

000

<210> SEQ ID NO 2134

<400> SEQUENCE: 2134

000

<210> SEQ ID NO 2135

<400> SEQUENCE: 2135

000

<210> SEQ ID NO 2136

<400> SEQUENCE: 2136

000

<210> SEQ ID NO 2137

<400> SEQUENCE: 2137

000

<210> SEQ ID NO 2138

<400> SEQUENCE: 2138

000

<210> SEQ ID NO 2139

<400> SEQUENCE: 2139

000

<210> SEQ ID NO 2140

<400> SEQUENCE: 2140

000

<210> SEQ ID NO 2141

<400> SEQUENCE: 2141

000

<210> SEQ ID NO 2142

<400> SEQUENCE: 2142

000

<210> SEQ ID NO 2143

<400> SEQUENCE: 2143

000

<210> SEQ ID NO 2144

<400> SEQUENCE: 2144

000

<210> SEQ ID NO 2145

<400> SEQUENCE: 2145

000

<210> SEQ ID NO 2146

<400> SEQUENCE: 2146

000

<210> SEQ ID NO 2147

<400> SEQUENCE: 2147

000

<210> SEQ ID NO 2148

<400> SEQUENCE: 2148

000

<210> SEQ ID NO 2149

<400> SEQUENCE: 2149

000

<210> SEQ ID NO 2150

<400> SEQUENCE: 2150

000

<210> SEQ ID NO 2151

<400> SEQUENCE: 2151

000

<210> SEQ ID NO 2152

<400> SEQUENCE: 2152

000

<210> SEQ ID NO 2153

<400> SEQUENCE: 2153

000

<210> SEQ ID NO 2154

<400> SEQUENCE: 2154

000

<210> SEQ ID NO 2155

<400> SEQUENCE: 2155

000

<210> SEQ ID NO 2156

<400> SEQUENCE: 2156

000

<210> SEQ ID NO 2157

<400> SEQUENCE: 2157

000

<210> SEQ ID NO 2158

<400> SEQUENCE: 2158

000

<210> SEQ ID NO 2159

<400> SEQUENCE: 2159

000

<210> SEQ ID NO 2160

<400> SEQUENCE: 2160

000

<210> SEQ ID NO 2161

<400> SEQUENCE: 2161

000

<210> SEQ ID NO 2162

<400> SEQUENCE: 2162

000

<210> SEQ ID NO 2163

<400> SEQUENCE: 2163

000

<210> SEQ ID NO 2164

<400> SEQUENCE: 2164

000

<210> SEQ ID NO 2165

<400> SEQUENCE: 2165

000

<210> SEQ ID NO 2166

<400> SEQUENCE: 2166

000

<210> SEQ ID NO 2167

<400> SEQUENCE: 2167

000

<210> SEQ ID NO 2168

<400> SEQUENCE: 2168

000

<210> SEQ ID NO 2169

<400> SEQUENCE: 2169

000

<210> SEQ ID NO 2170

<400> SEQUENCE: 2170

000

<210> SEQ ID NO 2171

<400> SEQUENCE: 2171

000

<210> SEQ ID NO 2172

<400> SEQUENCE: 2172

000

<210> SEQ ID NO 2173

<400> SEQUENCE: 2173

000

<210> SEQ ID NO 2174

<400> SEQUENCE: 2174

000

<210> SEQ ID NO 2175

<400> SEQUENCE: 2175

000

<210> SEQ ID NO 2176

<400> SEQUENCE: 2176

000

<210> SEQ ID NO 2177

<400> SEQUENCE: 2177

000

<210> SEQ ID NO 2178

<400> SEQUENCE: 2178

000

<210> SEQ ID NO 2179

<400> SEQUENCE: 2179

000

<210> SEQ ID NO 2180

<400> SEQUENCE: 2180

000

<210> SEQ ID NO 2181

<400> SEQUENCE: 2181

000

<210> SEQ ID NO 2182

<400> SEQUENCE: 2182

000

<210> SEQ ID NO 2183

<400> SEQUENCE: 2183

000

<210> SEQ ID NO 2184

<400> SEQUENCE: 2184

000

<210> SEQ ID NO 2185

<400> SEQUENCE: 2185

000

<210> SEQ ID NO 2186

<400> SEQUENCE: 2186

000

<210> SEQ ID NO 2187

<400> SEQUENCE: 2187

000

<210> SEQ ID NO 2188

<400> SEQUENCE: 2188

000

<210> SEQ ID NO 2189

<400> SEQUENCE: 2189

000

<210> SEQ ID NO 2190

<400> SEQUENCE: 2190

000

<210> SEQ ID NO 2191

<400> SEQUENCE: 2191

000

<210> SEQ ID NO 2192

<400> SEQUENCE: 2192

000

-continued

<210> SEQ ID NO 2193

<400> SEQUENCE: 2193

000

<210> SEQ ID NO 2194

<400> SEQUENCE: 2194

000

<210> SEQ ID NO 2195

<400> SEQUENCE: 2195

000

<210> SEQ ID NO 2196

<400> SEQUENCE: 2196

000

<210> SEQ ID NO 2197

<400> SEQUENCE: 2197

000

<210> SEQ ID NO 2198

<400> SEQUENCE: 2198

000

<210> SEQ ID NO 2199

<400> SEQUENCE: 2199

000

<210> SEQ ID NO 2200

<400> SEQUENCE: 2200

000

<210> SEQ ID NO 2201

<400> SEQUENCE: 2201

000

<210> SEQ ID NO 2202

<400> SEQUENCE: 2202

000

<210> SEQ ID NO 2203

<400> SEQUENCE: 2203

000

<210> SEQ ID NO 2204

<400> SEQUENCE: 2204

000

<210> SEQ ID NO 2205

<400> SEQUENCE: 2205

000

<210> SEQ ID NO 2206

<400> SEQUENCE: 2206

000

<210> SEQ ID NO 2207

<400> SEQUENCE: 2207

000

<210> SEQ ID NO 2208

<400> SEQUENCE: 2208

000

<210> SEQ ID NO 2209

<400> SEQUENCE: 2209

000

<210> SEQ ID NO 2210

<400> SEQUENCE: 2210

000

<210> SEQ ID NO 2211

<400> SEQUENCE: 2211

000

<210> SEQ ID NO 2212

<400> SEQUENCE: 2212

000

<210> SEQ ID NO 2213

<400> SEQUENCE: 2213

000

<210> SEQ ID NO 2214

<400> SEQUENCE: 2214

000

<210> SEQ ID NO 2215

<400> SEQUENCE: 2215

000

<210> SEQ ID NO 2216

<400> SEQUENCE: 2216

000

<210> SEQ ID NO 2217

<400> SEQUENCE: 2217

000

<210> SEQ ID NO 2218

<400> SEQUENCE: 2218

000

<210> SEQ ID NO 2219

<400> SEQUENCE: 2219

000

<210> SEQ ID NO 2220

<400> SEQUENCE: 2220

000

<210> SEQ ID NO 2221

<400> SEQUENCE: 2221

000

<210> SEQ ID NO 2222

<400> SEQUENCE: 2222

000

<210> SEQ ID NO 2223

<400> SEQUENCE: 2223

000

<210> SEQ ID NO 2224

<400> SEQUENCE: 2224

000

<210> SEQ ID NO 2225

<400> SEQUENCE: 2225

000

<210> SEQ ID NO 2226

<400> SEQUENCE: 2226

000

<210> SEQ ID NO 2227

<400> SEQUENCE: 2227

000

<210> SEQ ID NO 2228

<400> SEQUENCE: 2228

000

<210> SEQ ID NO 2229

<400> SEQUENCE: 2229

000

<210> SEQ ID NO 2230

<400> SEQUENCE: 2230

000

<210> SEQ ID NO 2231

<400> SEQUENCE: 2231

000

<210> SEQ ID NO 2232

<400> SEQUENCE: 2232

000

<210> SEQ ID NO 2233

<400> SEQUENCE: 2233

000

<210> SEQ ID NO 2234

<400> SEQUENCE: 2234

000

<210> SEQ ID NO 2235

<400> SEQUENCE: 2235

000

<210> SEQ ID NO 2236

<400> SEQUENCE: 2236

000

<210> SEQ ID NO 2237

<400> SEQUENCE: 2237

000

<210> SEQ ID NO 2238

<400> SEQUENCE: 2238

000

<210> SEQ ID NO 2239

<400> SEQUENCE: 2239

000

<210> SEQ ID NO 2240

<400> SEQUENCE: 2240

000

<210> SEQ ID NO 2241

<400> SEQUENCE: 2241

000

<210> SEQ ID NO 2242

<400> SEQUENCE: 2242

000

<210> SEQ ID NO 2243

<400> SEQUENCE: 2243

000

<210> SEQ ID NO 2244

<400> SEQUENCE: 2244

000

<210> SEQ ID NO 2245

<400> SEQUENCE: 2245

000

<210> SEQ ID NO 2246

<400> SEQUENCE: 2246

000

<210> SEQ ID NO 2247

<400> SEQUENCE: 2247

000

<210> SEQ ID NO 2248

<400> SEQUENCE: 2248

000

<210> SEQ ID NO 2249

<400> SEQUENCE: 2249

000

<210> SEQ ID NO 2250
<400> SEQUENCE: 2250
000

<210> SEQ ID NO 2251
<400> SEQUENCE: 2251
000

<210> SEQ ID NO 2252
<400> SEQUENCE: 2252
000

<210> SEQ ID NO 2253
<400> SEQUENCE: 2253
000

<210> SEQ ID NO 2254
<400> SEQUENCE: 2254
000

<210> SEQ ID NO 2255
<400> SEQUENCE: 2255
000

<210> SEQ ID NO 2256
<400> SEQUENCE: 2256
000

<210> SEQ ID NO 2257
<400> SEQUENCE: 2257
000

<210> SEQ ID NO 2258
<400> SEQUENCE: 2258
000

<210> SEQ ID NO 2259
<400> SEQUENCE: 2259
000

<210> SEQ ID NO 2260
<400> SEQUENCE: 2260
000

<210> SEQ ID NO 2261

<400> SEQUENCE: 2261

000

<210> SEQ ID NO 2262

<400> SEQUENCE: 2262

000

<210> SEQ ID NO 2263

<400> SEQUENCE: 2263

000

<210> SEQ ID NO 2264

<400> SEQUENCE: 2264

000

<210> SEQ ID NO 2265

<400> SEQUENCE: 2265

000

<210> SEQ ID NO 2266

<400> SEQUENCE: 2266

000

<210> SEQ ID NO 2267

<400> SEQUENCE: 2267

000

<210> SEQ ID NO 2268

<400> SEQUENCE: 2268

000

<210> SEQ ID NO 2269

<400> SEQUENCE: 2269

000

<210> SEQ ID NO 2270

<400> SEQUENCE: 2270

000

<210> SEQ ID NO 2271

<400> SEQUENCE: 2271

000

<210> SEQ ID NO 2272

<400> SEQUENCE: 2272

000

<210> SEQ ID NO 2273

<400> SEQUENCE: 2273

000

<210> SEQ ID NO 2274

<400> SEQUENCE: 2274

000

<210> SEQ ID NO 2275

<400> SEQUENCE: 2275

000

<210> SEQ ID NO 2276

<400> SEQUENCE: 2276

000

<210> SEQ ID NO 2277

<400> SEQUENCE: 2277

000

<210> SEQ ID NO 2278

<400> SEQUENCE: 2278

000

<210> SEQ ID NO 2279

<400> SEQUENCE: 2279

000

<210> SEQ ID NO 2280

<400> SEQUENCE: 2280

000

<210> SEQ ID NO 2281

<400> SEQUENCE: 2281

000

<210> SEQ ID NO 2282

<400> SEQUENCE: 2282

000

<210> SEQ ID NO 2283

<400> SEQUENCE: 2283

000

<210> SEQ ID NO 2284

<400> SEQUENCE: 2284

000

<210> SEQ ID NO 2285

<400> SEQUENCE: 2285

000

<210> SEQ ID NO 2286

<400> SEQUENCE: 2286

000

<210> SEQ ID NO 2287

<400> SEQUENCE: 2287

000

<210> SEQ ID NO 2288

<400> SEQUENCE: 2288

000

<210> SEQ ID NO 2289

<400> SEQUENCE: 2289

000

<210> SEQ ID NO 2290

<400> SEQUENCE: 2290

000

<210> SEQ ID NO 2291

<400> SEQUENCE: 2291

000

<210> SEQ ID NO 2292

<400> SEQUENCE: 2292

000

<210> SEQ ID NO 2293

<400> SEQUENCE: 2293

000

<210> SEQ ID NO 2294

<400> SEQUENCE: 2294

000

<210> SEQ ID NO 2295

<400> SEQUENCE: 2295

000

<210> SEQ ID NO 2296

<400> SEQUENCE: 2296

000

<210> SEQ ID NO 2297

<400> SEQUENCE: 2297

000

<210> SEQ ID NO 2298

<400> SEQUENCE: 2298

000

<210> SEQ ID NO 2299

<400> SEQUENCE: 2299

000

<210> SEQ ID NO 2300

<400> SEQUENCE: 2300

000

<210> SEQ ID NO 2301

<400> SEQUENCE: 2301

000

<210> SEQ ID NO 2302

<400> SEQUENCE: 2302

000

<210> SEQ ID NO 2303

<400> SEQUENCE: 2303

000

<210> SEQ ID NO 2304

<400> SEQUENCE: 2304

000

<210> SEQ ID NO 2305

<400> SEQUENCE: 2305

000

<210> SEQ ID NO 2306

<400> SEQUENCE: 2306

000

<210> SEQ ID NO 2307

<400> SEQUENCE: 2307

000

<210> SEQ ID NO 2308

<400> SEQUENCE: 2308

000

<210> SEQ ID NO 2309

<400> SEQUENCE: 2309

000

<210> SEQ ID NO 2310

<400> SEQUENCE: 2310

000

<210> SEQ ID NO 2311

<400> SEQUENCE: 2311

000

<210> SEQ ID NO 2312

<400> SEQUENCE: 2312

000

<210> SEQ ID NO 2313

<400> SEQUENCE: 2313

000

<210> SEQ ID NO 2314

<400> SEQUENCE: 2314

000

<210> SEQ ID NO 2315

<400> SEQUENCE: 2315

000

<210> SEQ ID NO 2316

<400> SEQUENCE: 2316

000

<210> SEQ ID NO 2317

<400> SEQUENCE: 2317

000

<210> SEQ ID NO 2318

<400> SEQUENCE: 2318

000

<210> SEQ ID NO 2319

<400> SEQUENCE: 2319

000

<210> SEQ ID NO 2320

<400> SEQUENCE: 2320

000

<210> SEQ ID NO 2321

<400> SEQUENCE: 2321

000

<210> SEQ ID NO 2322

<400> SEQUENCE: 2322

000

<210> SEQ ID NO 2323

<400> SEQUENCE: 2323

000

<210> SEQ ID NO 2324

<400> SEQUENCE: 2324

000

<210> SEQ ID NO 2325

<400> SEQUENCE: 2325

000

<210> SEQ ID NO 2326

<400> SEQUENCE: 2326

000

<210> SEQ ID NO 2327

<400> SEQUENCE: 2327

000

<210> SEQ ID NO 2328

<400> SEQUENCE: 2328

000

<210> SEQ ID NO 2329
<400> SEQUENCE: 2329
000

<210> SEQ ID NO 2330
<400> SEQUENCE: 2330
000

<210> SEQ ID NO 2331
<400> SEQUENCE: 2331
000

<210> SEQ ID NO 2332
<400> SEQUENCE: 2332
000

<210> SEQ ID NO 2333
<400> SEQUENCE: 2333
000

<210> SEQ ID NO 2334
<400> SEQUENCE: 2334
000

<210> SEQ ID NO 2335
<400> SEQUENCE: 2335
000

<210> SEQ ID NO 2336
<400> SEQUENCE: 2336
000

<210> SEQ ID NO 2337
<400> SEQUENCE: 2337
000

<210> SEQ ID NO 2338
<400> SEQUENCE: 2338
000

<210> SEQ ID NO 2339
<400> SEQUENCE: 2339
000

<210> SEQ ID NO 2340
<400> SEQUENCE: 2340
000

<210> SEQ ID NO 2341
<400> SEQUENCE: 2341
000

<210> SEQ ID NO 2342
<400> SEQUENCE: 2342
000

<210> SEQ ID NO 2343
<400> SEQUENCE: 2343
000

<210> SEQ ID NO 2344
<400> SEQUENCE: 2344
000

<210> SEQ ID NO 2345
<400> SEQUENCE: 2345
000

<210> SEQ ID NO 2346
<400> SEQUENCE: 2346
000

<210> SEQ ID NO 2347
<400> SEQUENCE: 2347
000

<210> SEQ ID NO 2348
<400> SEQUENCE: 2348
000

<210> SEQ ID NO 2349
<400> SEQUENCE: 2349
000

<210> SEQ ID NO 2350
<400> SEQUENCE: 2350
000

<210> SEQ ID NO 2351

<400> SEQUENCE: 2351

000

<210> SEQ ID NO 2352

<400> SEQUENCE: 2352

000

<210> SEQ ID NO 2353

<400> SEQUENCE: 2353

000

<210> SEQ ID NO 2354

<400> SEQUENCE: 2354

000

<210> SEQ ID NO 2355

<400> SEQUENCE: 2355

000

<210> SEQ ID NO 2356

<400> SEQUENCE: 2356

000

<210> SEQ ID NO 2357

<400> SEQUENCE: 2357

000

<210> SEQ ID NO 2358

<400> SEQUENCE: 2358

000

<210> SEQ ID NO 2359

<400> SEQUENCE: 2359

000

<210> SEQ ID NO 2360

<400> SEQUENCE: 2360

000

<210> SEQ ID NO 2361

<400> SEQUENCE: 2361

000

<210> SEQ ID NO 2362

<400> SEQUENCE: 2362

000

<210> SEQ ID NO 2363

<400> SEQUENCE: 2363

000

<210> SEQ ID NO 2364

<400> SEQUENCE: 2364

000

<210> SEQ ID NO 2365

<400> SEQUENCE: 2365

000

<210> SEQ ID NO 2366

<400> SEQUENCE: 2366

000

<210> SEQ ID NO 2367

<400> SEQUENCE: 2367

000

<210> SEQ ID NO 2368

<400> SEQUENCE: 2368

000

<210> SEQ ID NO 2369

<400> SEQUENCE: 2369

000

<210> SEQ ID NO 2370

<400> SEQUENCE: 2370

000

<210> SEQ ID NO 2371

<400> SEQUENCE: 2371

000

<210> SEQ ID NO 2372

<400> SEQUENCE: 2372

000

<210> SEQ ID NO 2373

<400> SEQUENCE: 2373

000

<210> SEQ ID NO 2374

<400> SEQUENCE: 2374

000

<210> SEQ ID NO 2375

<400> SEQUENCE: 2375

000

<210> SEQ ID NO 2376

<400> SEQUENCE: 2376

000

<210> SEQ ID NO 2377

<400> SEQUENCE: 2377

000

<210> SEQ ID NO 2378

<400> SEQUENCE: 2378

000

<210> SEQ ID NO 2379

<400> SEQUENCE: 2379

000

<210> SEQ ID NO 2380

<400> SEQUENCE: 2380

000

<210> SEQ ID NO 2381

<400> SEQUENCE: 2381

000

<210> SEQ ID NO 2382

<400> SEQUENCE: 2382

000

<210> SEQ ID NO 2383

<400> SEQUENCE: 2383

000

<210> SEQ ID NO 2384

<400> SEQUENCE: 2384

000

<210> SEQ ID NO 2385

<400> SEQUENCE: 2385

000

<210> SEQ ID NO 2386

<400> SEQUENCE: 2386

000

<210> SEQ ID NO 2387

<400> SEQUENCE: 2387

000

<210> SEQ ID NO 2388

<400> SEQUENCE: 2388

000

<210> SEQ ID NO 2389

<400> SEQUENCE: 2389

000

<210> SEQ ID NO 2390

<400> SEQUENCE: 2390

000

<210> SEQ ID NO 2391

<400> SEQUENCE: 2391

000

<210> SEQ ID NO 2392

<400> SEQUENCE: 2392

000

<210> SEQ ID NO 2393

<400> SEQUENCE: 2393

000

<210> SEQ ID NO 2394

<400> SEQUENCE: 2394

000

<210> SEQ ID NO 2395

<400> SEQUENCE: 2395

000

<210> SEQ ID NO 2396

<400> SEQUENCE: 2396

000

<210> SEQ ID NO 2397

<400> SEQUENCE: 2397

000

<210> SEQ ID NO 2398

<400> SEQUENCE: 2398

000

<210> SEQ ID NO 2399

<400> SEQUENCE: 2399

000

<210> SEQ ID NO 2400

<400> SEQUENCE: 2400

000

<210> SEQ ID NO 2401

<400> SEQUENCE: 2401

000

<210> SEQ ID NO 2402

<400> SEQUENCE: 2402

000

<210> SEQ ID NO 2403

<400> SEQUENCE: 2403

000

<210> SEQ ID NO 2404

<400> SEQUENCE: 2404

000

<210> SEQ ID NO 2405

<400> SEQUENCE: 2405

000

<210> SEQ ID NO 2406

<400> SEQUENCE: 2406

000

<210> SEQ ID NO 2407

<400> SEQUENCE: 2407

000

<210> SEQ ID NO 2408
<400> SEQUENCE: 2408
000

<210> SEQ ID NO 2409
<400> SEQUENCE: 2409
000

<210> SEQ ID NO 2410
<400> SEQUENCE: 2410
000

<210> SEQ ID NO 2411
<400> SEQUENCE: 2411
000

<210> SEQ ID NO 2412
<400> SEQUENCE: 2412
000

<210> SEQ ID NO 2413
<400> SEQUENCE: 2413
000

<210> SEQ ID NO 2414
<400> SEQUENCE: 2414
000

<210> SEQ ID NO 2415
<400> SEQUENCE: 2415
000

<210> SEQ ID NO 2416
<400> SEQUENCE: 2416
000

<210> SEQ ID NO 2417
<400> SEQUENCE: 2417
000

<210> SEQ ID NO 2418
<400> SEQUENCE: 2418
000

<210> SEQ ID NO 2419

<400> SEQUENCE: 2419

000

<210> SEQ ID NO 2420

<400> SEQUENCE: 2420

000

<210> SEQ ID NO 2421

<400> SEQUENCE: 2421

000

<210> SEQ ID NO 2422

<400> SEQUENCE: 2422

000

<210> SEQ ID NO 2423

<400> SEQUENCE: 2423

000

<210> SEQ ID NO 2424

<400> SEQUENCE: 2424

000

<210> SEQ ID NO 2425

<400> SEQUENCE: 2425

000

<210> SEQ ID NO 2426

<400> SEQUENCE: 2426

000

<210> SEQ ID NO 2427

<400> SEQUENCE: 2427

000

<210> SEQ ID NO 2428

<400> SEQUENCE: 2428

000

<210> SEQ ID NO 2429

<400> SEQUENCE: 2429

000

<210> SEQ ID NO 2430

<400> SEQUENCE: 2430

000

<210> SEQ ID NO 2431

<400> SEQUENCE: 2431

000

<210> SEQ ID NO 2432

<400> SEQUENCE: 2432

000

<210> SEQ ID NO 2433

<400> SEQUENCE: 2433

000

<210> SEQ ID NO 2434

<400> SEQUENCE: 2434

000

<210> SEQ ID NO 2435

<400> SEQUENCE: 2435

000

<210> SEQ ID NO 2436

<400> SEQUENCE: 2436

000

<210> SEQ ID NO 2437

<400> SEQUENCE: 2437

000

<210> SEQ ID NO 2438

<400> SEQUENCE: 2438

000

<210> SEQ ID NO 2439

<400> SEQUENCE: 2439

000

<210> SEQ ID NO 2440

<400> SEQUENCE: 2440

000

<210> SEQ ID NO 2441

<400> SEQUENCE: 2441

000

<210> SEQ ID NO 2442

<400> SEQUENCE: 2442

000

<210> SEQ ID NO 2443

<400> SEQUENCE: 2443

000

<210> SEQ ID NO 2444

<400> SEQUENCE: 2444

000

<210> SEQ ID NO 2445

<400> SEQUENCE: 2445

000

<210> SEQ ID NO 2446

<400> SEQUENCE: 2446

000

<210> SEQ ID NO 2447

<400> SEQUENCE: 2447

000

<210> SEQ ID NO 2448

<400> SEQUENCE: 2448

000

<210> SEQ ID NO 2449

<400> SEQUENCE: 2449

000

<210> SEQ ID NO 2450

<400> SEQUENCE: 2450

000

<210> SEQ ID NO 2451

<400> SEQUENCE: 2451

000

<210> SEQ ID NO 2452

<400> SEQUENCE: 2452

000

<210> SEQ ID NO 2453

<400> SEQUENCE: 2453

000

<210> SEQ ID NO 2454

<400> SEQUENCE: 2454

000

<210> SEQ ID NO 2455

<400> SEQUENCE: 2455

000

<210> SEQ ID NO 2456

<400> SEQUENCE: 2456

000

<210> SEQ ID NO 2457

<400> SEQUENCE: 2457

000

<210> SEQ ID NO 2458

<400> SEQUENCE: 2458

000

<210> SEQ ID NO 2459

<400> SEQUENCE: 2459

000

<210> SEQ ID NO 2460

<400> SEQUENCE: 2460

000

<210> SEQ ID NO 2461

<400> SEQUENCE: 2461

000

<210> SEQ ID NO 2462

<400> SEQUENCE: 2462

000

<210> SEQ ID NO 2463

<400> SEQUENCE: 2463

000

-continued

<210> SEQ ID NO 2464

<400> SEQUENCE: 2464

000

<210> SEQ ID NO 2465

<400> SEQUENCE: 2465

000

<210> SEQ ID NO 2466

<400> SEQUENCE: 2466

000

<210> SEQ ID NO 2467

<400> SEQUENCE: 2467

000

<210> SEQ ID NO 2468

<400> SEQUENCE: 2468

000

<210> SEQ ID NO 2469

<400> SEQUENCE: 2469

000

<210> SEQ ID NO 2470

<400> SEQUENCE: 2470

000

<210> SEQ ID NO 2471

<400> SEQUENCE: 2471

000

<210> SEQ ID NO 2472

<400> SEQUENCE: 2472

000

<210> SEQ ID NO 2473

<400> SEQUENCE: 2473

000

<210> SEQ ID NO 2474

<400> SEQUENCE: 2474

000

<210> SEQ ID NO 2475

<400> SEQUENCE: 2475

000

<210> SEQ ID NO 2476

<400> SEQUENCE: 2476

000

<210> SEQ ID NO 2477

<400> SEQUENCE: 2477

000

<210> SEQ ID NO 2478

<400> SEQUENCE: 2478

000

<210> SEQ ID NO 2479

<400> SEQUENCE: 2479

000

<210> SEQ ID NO 2480

<400> SEQUENCE: 2480

000

<210> SEQ ID NO 2481

<400> SEQUENCE: 2481

000

<210> SEQ ID NO 2482

<400> SEQUENCE: 2482

000

<210> SEQ ID NO 2483

<400> SEQUENCE: 2483

000

<210> SEQ ID NO 2484

<400> SEQUENCE: 2484

000

<210> SEQ ID NO 2485

<400> SEQUENCE: 2485

000

<210> SEQ ID NO 2486

<400> SEQUENCE: 2486

000

<210> SEQ ID NO 2487
<400> SEQUENCE: 2487
000

<210> SEQ ID NO 2488
<400> SEQUENCE: 2488
000

<210> SEQ ID NO 2489
<400> SEQUENCE: 2489
000

<210> SEQ ID NO 2490
<400> SEQUENCE: 2490
000

<210> SEQ ID NO 2491
<400> SEQUENCE: 2491
000

<210> SEQ ID NO 2492
<400> SEQUENCE: 2492
000

<210> SEQ ID NO 2493
<400> SEQUENCE: 2493
000

<210> SEQ ID NO 2494
<400> SEQUENCE: 2494
000

<210> SEQ ID NO 2495
<400> SEQUENCE: 2495
000

<210> SEQ ID NO 2496
<400> SEQUENCE: 2496
000

<210> SEQ ID NO 2497
<400> SEQUENCE: 2497
000

<210> SEQ ID NO 2498

<400> SEQUENCE: 2498

000

<210> SEQ ID NO 2499

<400> SEQUENCE: 2499

000

<210> SEQ ID NO 2500

<400> SEQUENCE: 2500

000

<210> SEQ ID NO 2501

<400> SEQUENCE: 2501

000

<210> SEQ ID NO 2502

<400> SEQUENCE: 2502

000

<210> SEQ ID NO 2503

<400> SEQUENCE: 2503

000

<210> SEQ ID NO 2504

<400> SEQUENCE: 2504

000

<210> SEQ ID NO 2505

<400> SEQUENCE: 2505

000

<210> SEQ ID NO 2506

<400> SEQUENCE: 2506

000

<210> SEQ ID NO 2507

<400> SEQUENCE: 2507

000

<210> SEQ ID NO 2508

<400> SEQUENCE: 2508

000

<210> SEQ ID NO 2509

<400> SEQUENCE: 2509

000

<210> SEQ ID NO 2510

<400> SEQUENCE: 2510

000

<210> SEQ ID NO 2511

<400> SEQUENCE: 2511

000

<210> SEQ ID NO 2512

<400> SEQUENCE: 2512

000

<210> SEQ ID NO 2513

<400> SEQUENCE: 2513

000

<210> SEQ ID NO 2514

<400> SEQUENCE: 2514

000

<210> SEQ ID NO 2515

<400> SEQUENCE: 2515

000

<210> SEQ ID NO 2516

<400> SEQUENCE: 2516

000

<210> SEQ ID NO 2517

<400> SEQUENCE: 2517

000

<210> SEQ ID NO 2518

<400> SEQUENCE: 2518

000

<210> SEQ ID NO 2519

<400> SEQUENCE: 2519

000

<210> SEQ ID NO 2520

<400> SEQUENCE: 2520

000

<210> SEQ ID NO 2521

<400> SEQUENCE: 2521

000

<210> SEQ ID NO 2522

<400> SEQUENCE: 2522

000

<210> SEQ ID NO 2523

<400> SEQUENCE: 2523

000

<210> SEQ ID NO 2524

<400> SEQUENCE: 2524

000

<210> SEQ ID NO 2525

<400> SEQUENCE: 2525

000

<210> SEQ ID NO 2526

<400> SEQUENCE: 2526

000

<210> SEQ ID NO 2527

<400> SEQUENCE: 2527

000

<210> SEQ ID NO 2528

<400> SEQUENCE: 2528

000

<210> SEQ ID NO 2529

<400> SEQUENCE: 2529

000

<210> SEQ ID NO 2530

<400> SEQUENCE: 2530

000

<210> SEQ ID NO 2531

<400> SEQUENCE: 2531

000

<210> SEQ ID NO 2532

<400> SEQUENCE: 2532

000

<210> SEQ ID NO 2533

<400> SEQUENCE: 2533

000

<210> SEQ ID NO 2534

<400> SEQUENCE: 2534

000

<210> SEQ ID NO 2535

<400> SEQUENCE: 2535

000

<210> SEQ ID NO 2536

<400> SEQUENCE: 2536

000

<210> SEQ ID NO 2537

<400> SEQUENCE: 2537

000

<210> SEQ ID NO 2538

<400> SEQUENCE: 2538

000

<210> SEQ ID NO 2539

<400> SEQUENCE: 2539

000

<210> SEQ ID NO 2540

<400> SEQUENCE: 2540

000

<210> SEQ ID NO 2541

<400> SEQUENCE: 2541

000

<210> SEQ ID NO 2542

<400> SEQUENCE: 2542

000

<210> SEQ ID NO 2543

<400> SEQUENCE: 2543

000

<210> SEQ ID NO 2544

<400> SEQUENCE: 2544

000

<210> SEQ ID NO 2545

<400> SEQUENCE: 2545

000

<210> SEQ ID NO 2546

<400> SEQUENCE: 2546

000

<210> SEQ ID NO 2547

<400> SEQUENCE: 2547

000

<210> SEQ ID NO 2548

<400> SEQUENCE: 2548

000

<210> SEQ ID NO 2549

<400> SEQUENCE: 2549

000

<210> SEQ ID NO 2550

<400> SEQUENCE: 2550

000

<210> SEQ ID NO 2551

<400> SEQUENCE: 2551

000

<210> SEQ ID NO 2552

<400> SEQUENCE: 2552

000

<210> SEQ ID NO 2553

<400> SEQUENCE: 2553

000

<210> SEQ ID NO 2554

<400> SEQUENCE: 2554

000

<210> SEQ ID NO 2555

<400> SEQUENCE: 2555

000

<210> SEQ ID NO 2556

<400> SEQUENCE: 2556

000

<210> SEQ ID NO 2557

<400> SEQUENCE: 2557

000

<210> SEQ ID NO 2558

<400> SEQUENCE: 2558

000

<210> SEQ ID NO 2559

<400> SEQUENCE: 2559

000

<210> SEQ ID NO 2560

<400> SEQUENCE: 2560

000

<210> SEQ ID NO 2561

<400> SEQUENCE: 2561

000

<210> SEQ ID NO 2562

<400> SEQUENCE: 2562

000

<210> SEQ ID NO 2563

<400> SEQUENCE: 2563

000

<210> SEQ ID NO 2564

<400> SEQUENCE: 2564

000

<210> SEQ ID NO 2565

<400> SEQUENCE: 2565

000

<210> SEQ ID NO 2566

<400> SEQUENCE: 2566

000

<210> SEQ ID NO 2567

<400> SEQUENCE: 2567

000

<210> SEQ ID NO 2568

<400> SEQUENCE: 2568

000

<210> SEQ ID NO 2569

<400> SEQUENCE: 2569

000

<210> SEQ ID NO 2570

<400> SEQUENCE: 2570

000

<210> SEQ ID NO 2571

<400> SEQUENCE: 2571

000

<210> SEQ ID NO 2572

<400> SEQUENCE: 2572

000

<210> SEQ ID NO 2573

<400> SEQUENCE: 2573

000

<210> SEQ ID NO 2574

<400> SEQUENCE: 2574

000

<210> SEQ ID NO 2575

<400> SEQUENCE: 2575

000

<210> SEQ ID NO 2576

<400> SEQUENCE: 2576

000

<210> SEQ ID NO 2577

<400> SEQUENCE: 2577

000

<210> SEQ ID NO 2578

<400> SEQUENCE: 2578

000

<210> SEQ ID NO 2579

<400> SEQUENCE: 2579

000

<210> SEQ ID NO 2580

<400> SEQUENCE: 2580

000

<210> SEQ ID NO 2581

<400> SEQUENCE: 2581

000

<210> SEQ ID NO 2582

<400> SEQUENCE: 2582

000

<210> SEQ ID NO 2583

<400> SEQUENCE: 2583

000

<210> SEQ ID NO 2584

<400> SEQUENCE: 2584

000

<210> SEQ ID NO 2585

<400> SEQUENCE: 2585

000

<210> SEQ ID NO 2586

<400> SEQUENCE: 2586

000

<210> SEQ ID NO 2587

<400> SEQUENCE: 2587

000

<210> SEQ ID NO 2588

<400> SEQUENCE: 2588

000

<210> SEQ ID NO 2589

<400> SEQUENCE: 2589

000

<210> SEQ ID NO 2590

<400> SEQUENCE: 2590

000

<210> SEQ ID NO 2591

<400> SEQUENCE: 2591

000

<210> SEQ ID NO 2592

<400> SEQUENCE: 2592

000

<210> SEQ ID NO 2593

<400> SEQUENCE: 2593

000

<210> SEQ ID NO 2594

<400> SEQUENCE: 2594

000

<210> SEQ ID NO 2595

<400> SEQUENCE: 2595

000

<210> SEQ ID NO 2596

<400> SEQUENCE: 2596

000

<210> SEQ ID NO 2597

<400> SEQUENCE: 2597

000

<210> SEQ ID NO 2598

<400> SEQUENCE: 2598

000

<210> SEQ ID NO 2599

<400> SEQUENCE: 2599

000

<210> SEQ ID NO 2600

<400> SEQUENCE: 2600

000

<210> SEQ ID NO 2601

<400> SEQUENCE: 2601

000

<210> SEQ ID NO 2602

<400> SEQUENCE: 2602

000

<210> SEQ ID NO 2603

<400> SEQUENCE: 2603

000

<210> SEQ ID NO 2604

<400> SEQUENCE: 2604

000

<210> SEQ ID NO 2605

<400> SEQUENCE: 2605

000

<210> SEQ ID NO 2606

<400> SEQUENCE: 2606

000

<210> SEQ ID NO 2607

<400> SEQUENCE: 2607

000

<210> SEQ ID NO 2608

<400> SEQUENCE: 2608

000

<210> SEQ ID NO 2609

<400> SEQUENCE: 2609

000

<210> SEQ ID NO 2610

<400> SEQUENCE: 2610

000

<210> SEQ ID NO 2611

<400> SEQUENCE: 2611

000

<210> SEQ ID NO 2612

<400> SEQUENCE: 2612

000

<210> SEQ ID NO 2613

<400> SEQUENCE: 2613

000

<210> SEQ ID NO 2614

<400> SEQUENCE: 2614

000

<210> SEQ ID NO 2615

<400> SEQUENCE: 2615

000

<210> SEQ ID NO 2616

<400> SEQUENCE: 2616

000

<210> SEQ ID NO 2617

<400> SEQUENCE: 2617

000

<210> SEQ ID NO 2618

<400> SEQUENCE: 2618

000

<210> SEQ ID NO 2619

<400> SEQUENCE: 2619

000

<210> SEQ ID NO 2620

<400> SEQUENCE: 2620

000

<210> SEQ ID NO 2621

<400> SEQUENCE: 2621

000

<210> SEQ ID NO 2622

<400> SEQUENCE: 2622

000

<210> SEQ ID NO 2623

<400> SEQUENCE: 2623

000

<210> SEQ ID NO 2624

<400> SEQUENCE: 2624

000

<210> SEQ ID NO 2625

<400> SEQUENCE: 2625

000

<210> SEQ ID NO 2626

<400> SEQUENCE: 2626

000

<210> SEQ ID NO 2627

<400> SEQUENCE: 2627

000

<210> SEQ ID NO 2628

<400> SEQUENCE: 2628

000

<210> SEQ ID NO 2629

<400> SEQUENCE: 2629

000

<210> SEQ ID NO 2630

<400> SEQUENCE: 2630

000

<210> SEQ ID NO 2631

<400> SEQUENCE: 2631

000

<210> SEQ ID NO 2632

<400> SEQUENCE: 2632

000

<210> SEQ ID NO 2633

<400> SEQUENCE: 2633

000

<210> SEQ ID NO 2634

<400> SEQUENCE: 2634

000

<210> SEQ ID NO 2635

<400> SEQUENCE: 2635

000

<210> SEQ ID NO 2636

<400> SEQUENCE: 2636

000

<210> SEQ ID NO 2637

<400> SEQUENCE: 2637

000

<210> SEQ ID NO 2638

<400> SEQUENCE: 2638

000

<210> SEQ ID NO 2639

<400> SEQUENCE: 2639

000

<210> SEQ ID NO 2640

<400> SEQUENCE: 2640

000

<210> SEQ ID NO 2641

<400> SEQUENCE: 2641

000

<210> SEQ ID NO 2642

<400> SEQUENCE: 2642

000

<210> SEQ ID NO 2643

<400> SEQUENCE: 2643

000

<210> SEQ ID NO 2644

<400> SEQUENCE: 2644

000

<210> SEQ ID NO 2645

<400> SEQUENCE: 2645

000

<210> SEQ ID NO 2646

<400> SEQUENCE: 2646

000

<210> SEQ ID NO 2647

<400> SEQUENCE: 2647

000

<210> SEQ ID NO 2648

<400> SEQUENCE: 2648

000

<210> SEQ ID NO 2649

<400> SEQUENCE: 2649

000

<210> SEQ ID NO 2650

<400> SEQUENCE: 2650

000

<210> SEQ ID NO 2651

<400> SEQUENCE: 2651

000

<210> SEQ ID NO 2652

<400> SEQUENCE: 2652

000

<210> SEQ ID NO 2653

<400> SEQUENCE: 2653

000

<210> SEQ ID NO 2654

<400> SEQUENCE: 2654

000

<210> SEQ ID NO 2655

<400> SEQUENCE: 2655

000

<210> SEQ ID NO 2656
<400> SEQUENCE: 2656
000

<210> SEQ ID NO 2657
<400> SEQUENCE: 2657
000

<210> SEQ ID NO 2658
<400> SEQUENCE: 2658
000

<210> SEQ ID NO 2659
<400> SEQUENCE: 2659
000

<210> SEQ ID NO 2660
<400> SEQUENCE: 2660
000

<210> SEQ ID NO 2661
<400> SEQUENCE: 2661
000

<210> SEQ ID NO 2662
<400> SEQUENCE: 2662
000

<210> SEQ ID NO 2663
<400> SEQUENCE: 2663
000

<210> SEQ ID NO 2664
<400> SEQUENCE: 2664
000

<210> SEQ ID NO 2665
<400> SEQUENCE: 2665
000

<210> SEQ ID NO 2666
<400> SEQUENCE: 2666
000

<210> SEQ ID NO 2667

<400> SEQUENCE: 2667

000

<210> SEQ ID NO 2668

<400> SEQUENCE: 2668

000

<210> SEQ ID NO 2669

<400> SEQUENCE: 2669

000

<210> SEQ ID NO 2670

<400> SEQUENCE: 2670

000

<210> SEQ ID NO 2671

<400> SEQUENCE: 2671

000

<210> SEQ ID NO 2672

<400> SEQUENCE: 2672

000

<210> SEQ ID NO 2673

<400> SEQUENCE: 2673

000

<210> SEQ ID NO 2674

<400> SEQUENCE: 2674

000

<210> SEQ ID NO 2675

<400> SEQUENCE: 2675

000

<210> SEQ ID NO 2676

<400> SEQUENCE: 2676

000

<210> SEQ ID NO 2677

<400> SEQUENCE: 2677

000

<210> SEQ ID NO 2678

<400> SEQUENCE: 2678

000

<210> SEQ ID NO 2679

<400> SEQUENCE: 2679

000

<210> SEQ ID NO 2680

<400> SEQUENCE: 2680

000

<210> SEQ ID NO 2681

<400> SEQUENCE: 2681

000

<210> SEQ ID NO 2682

<400> SEQUENCE: 2682

000

<210> SEQ ID NO 2683

<400> SEQUENCE: 2683

000

<210> SEQ ID NO 2684

<400> SEQUENCE: 2684

000

<210> SEQ ID NO 2685

<400> SEQUENCE: 2685

000

<210> SEQ ID NO 2686

<400> SEQUENCE: 2686

000

<210> SEQ ID NO 2687

<400> SEQUENCE: 2687

000

<210> SEQ ID NO 2688

<400> SEQUENCE: 2688

000

<210> SEQ ID NO 2689

<400> SEQUENCE: 2689

-continued

000

<210> SEQ ID NO 2690

<400> SEQUENCE: 2690

000

<210> SEQ ID NO 2691

<400> SEQUENCE: 2691

000

<210> SEQ ID NO 2692

<400> SEQUENCE: 2692

000

<210> SEQ ID NO 2693

<400> SEQUENCE: 2693

000

<210> SEQ ID NO 2694

<400> SEQUENCE: 2694

000

<210> SEQ ID NO 2695

<400> SEQUENCE: 2695

000

<210> SEQ ID NO 2696

<400> SEQUENCE: 2696

000

<210> SEQ ID NO 2697

<400> SEQUENCE: 2697

000

<210> SEQ ID NO 2698

<400> SEQUENCE: 2698

000

<210> SEQ ID NO 2699

<400> SEQUENCE: 2699

000

<210> SEQ ID NO 2700

<400> SEQUENCE: 2700

000

<210> SEQ ID NO 2701

<400> SEQUENCE: 2701

000

<210> SEQ ID NO 2702

<400> SEQUENCE: 2702

000

<210> SEQ ID NO 2703

<400> SEQUENCE: 2703

000

<210> SEQ ID NO 2704

<400> SEQUENCE: 2704

000

<210> SEQ ID NO 2705

<400> SEQUENCE: 2705

000

<210> SEQ ID NO 2706

<400> SEQUENCE: 2706

000

<210> SEQ ID NO 2707

<400> SEQUENCE: 2707

000

<210> SEQ ID NO 2708

<400> SEQUENCE: 2708

000

<210> SEQ ID NO 2709

<400> SEQUENCE: 2709

000

<210> SEQ ID NO 2710

<400> SEQUENCE: 2710

000

<210> SEQ ID NO 2711

<400> SEQUENCE: 2711

000

<210> SEQ ID NO 2712

<400> SEQUENCE: 2712

000

<210> SEQ ID NO 2713

<400> SEQUENCE: 2713

000

<210> SEQ ID NO 2714

<400> SEQUENCE: 2714

000

<210> SEQ ID NO 2715

<400> SEQUENCE: 2715

000

<210> SEQ ID NO 2716

<400> SEQUENCE: 2716

000

<210> SEQ ID NO 2717

<400> SEQUENCE: 2717

000

<210> SEQ ID NO 2718

<400> SEQUENCE: 2718

000

<210> SEQ ID NO 2719

<400> SEQUENCE: 2719

000

<210> SEQ ID NO 2720

<400> SEQUENCE: 2720

000

<210> SEQ ID NO 2721

<400> SEQUENCE: 2721

000

<210> SEQ ID NO 2722

<400> SEQUENCE: 2722

000

<210> SEQ ID NO 2723

<400> SEQUENCE: 2723

000

<210> SEQ ID NO 2724
<400> SEQUENCE: 2724
000

<210> SEQ ID NO 2725
<400> SEQUENCE: 2725
000

<210> SEQ ID NO 2726
<400> SEQUENCE: 2726
000

<210> SEQ ID NO 2727
<400> SEQUENCE: 2727
000

<210> SEQ ID NO 2728
<400> SEQUENCE: 2728
000

<210> SEQ ID NO 2729
<400> SEQUENCE: 2729
000

<210> SEQ ID NO 2730
<400> SEQUENCE: 2730
000

<210> SEQ ID NO 2731
<400> SEQUENCE: 2731
000

<210> SEQ ID NO 2732
<400> SEQUENCE: 2732
000

<210> SEQ ID NO 2733
<400> SEQUENCE: 2733
000

<210> SEQ ID NO 2734
<400> SEQUENCE: 2734
000

<210> SEQ ID NO 2735
<400> SEQUENCE: 2735
000

<210> SEQ ID NO 2736
<400> SEQUENCE: 2736
000

<210> SEQ ID NO 2737
<400> SEQUENCE: 2737
000

<210> SEQ ID NO 2738
<400> SEQUENCE: 2738
000

<210> SEQ ID NO 2739
<400> SEQUENCE: 2739
000

<210> SEQ ID NO 2740
<400> SEQUENCE: 2740
000

<210> SEQ ID NO 2741
<400> SEQUENCE: 2741
000

<210> SEQ ID NO 2742
<400> SEQUENCE: 2742
000

<210> SEQ ID NO 2743
<400> SEQUENCE: 2743
000

<210> SEQ ID NO 2744
<400> SEQUENCE: 2744
000

<210> SEQ ID NO 2745
<400> SEQUENCE: 2745
000

<210> SEQ ID NO 2746

<400> SEQUENCE: 2746

000

<210> SEQ ID NO 2747

<400> SEQUENCE: 2747

000

<210> SEQ ID NO 2748

<400> SEQUENCE: 2748

000

<210> SEQ ID NO 2749

<400> SEQUENCE: 2749

000

<210> SEQ ID NO 2750

<400> SEQUENCE: 2750

000

<210> SEQ ID NO 2751

<400> SEQUENCE: 2751

000

<210> SEQ ID NO 2752

<400> SEQUENCE: 2752

000

<210> SEQ ID NO 2753

<400> SEQUENCE: 2753

000

<210> SEQ ID NO 2754

<400> SEQUENCE: 2754

000

<210> SEQ ID NO 2755

<400> SEQUENCE: 2755

000

<210> SEQ ID NO 2756

<400> SEQUENCE: 2756

000

<210> SEQ ID NO 2757

<400> SEQUENCE: 2757

000

<210> SEQ ID NO 2758

<400> SEQUENCE: 2758

000

<210> SEQ ID NO 2759

<400> SEQUENCE: 2759

000

<210> SEQ ID NO 2760

<400> SEQUENCE: 2760

000

<210> SEQ ID NO 2761

<400> SEQUENCE: 2761

000

<210> SEQ ID NO 2762

<400> SEQUENCE: 2762

000

<210> SEQ ID NO 2763

<400> SEQUENCE: 2763

000

<210> SEQ ID NO 2764

<400> SEQUENCE: 2764

000

<210> SEQ ID NO 2765

<400> SEQUENCE: 2765

000

<210> SEQ ID NO 2766

<400> SEQUENCE: 2766

000

<210> SEQ ID NO 2767

<400> SEQUENCE: 2767

000

<210> SEQ ID NO 2768

<400> SEQUENCE: 2768

000

<210> SEQ ID NO 2769

<400> SEQUENCE: 2769

000

<210> SEQ ID NO 2770

<400> SEQUENCE: 2770

000

<210> SEQ ID NO 2771

<400> SEQUENCE: 2771

000

<210> SEQ ID NO 2772

<400> SEQUENCE: 2772

000

<210> SEQ ID NO 2773

<400> SEQUENCE: 2773

000

<210> SEQ ID NO 2774

<400> SEQUENCE: 2774

000

<210> SEQ ID NO 2775

<400> SEQUENCE: 2775

000

<210> SEQ ID NO 2776

<400> SEQUENCE: 2776

000

<210> SEQ ID NO 2777

<400> SEQUENCE: 2777

000

<210> SEQ ID NO 2778

<400> SEQUENCE: 2778

000

<210> SEQ ID NO 2779

<400> SEQUENCE: 2779

000

<210> SEQ ID NO 2780

<400> SEQUENCE: 2780

000

<210> SEQ ID NO 2781

<400> SEQUENCE: 2781

000

<210> SEQ ID NO 2782

<400> SEQUENCE: 2782

000

<210> SEQ ID NO 2783

<400> SEQUENCE: 2783

000

<210> SEQ ID NO 2784

<400> SEQUENCE: 2784

000

<210> SEQ ID NO 2785

<400> SEQUENCE: 2785

000

<210> SEQ ID NO 2786

<400> SEQUENCE: 2786

000

<210> SEQ ID NO 2787

<400> SEQUENCE: 2787

000

<210> SEQ ID NO 2788

<400> SEQUENCE: 2788

000

<210> SEQ ID NO 2789

<400> SEQUENCE: 2789

000

<210> SEQ ID NO 2790

<400> SEQUENCE: 2790

000

<210> SEQ ID NO 2791

<400> SEQUENCE: 2791

000

<210> SEQ ID NO 2792

<400> SEQUENCE: 2792

000

<210> SEQ ID NO 2793

<400> SEQUENCE: 2793

000

<210> SEQ ID NO 2794

<400> SEQUENCE: 2794

000

<210> SEQ ID NO 2795

<400> SEQUENCE: 2795

000

<210> SEQ ID NO 2796

<400> SEQUENCE: 2796

000

<210> SEQ ID NO 2797

<400> SEQUENCE: 2797

000

<210> SEQ ID NO 2798

<400> SEQUENCE: 2798

000

<210> SEQ ID NO 2799

<400> SEQUENCE: 2799

000

<210> SEQ ID NO 2800

<400> SEQUENCE: 2800

000

<210> SEQ ID NO 2801

<400> SEQUENCE: 2801

000

<210> SEQ ID NO 2802

<400> SEQUENCE: 2802

000

<210> SEQ ID NO 2803
<400> SEQUENCE: 2803
000

<210> SEQ ID NO 2804
<400> SEQUENCE: 2804
000

<210> SEQ ID NO 2805
<400> SEQUENCE: 2805
000

<210> SEQ ID NO 2806
<400> SEQUENCE: 2806
000

<210> SEQ ID NO 2807
<400> SEQUENCE: 2807
000

<210> SEQ ID NO 2808
<400> SEQUENCE: 2808
000

<210> SEQ ID NO 2809
<400> SEQUENCE: 2809
000

<210> SEQ ID NO 2810
<400> SEQUENCE: 2810
000

<210> SEQ ID NO 2811
<400> SEQUENCE: 2811
000

<210> SEQ ID NO 2812
<400> SEQUENCE: 2812
000

<210> SEQ ID NO 2813
<400> SEQUENCE: 2813
000

<210> SEQ ID NO 2814

<400> SEQUENCE: 2814

000

<210> SEQ ID NO 2815

<400> SEQUENCE: 2815

000

<210> SEQ ID NO 2816

<400> SEQUENCE: 2816

000

<210> SEQ ID NO 2817

<400> SEQUENCE: 2817

000

<210> SEQ ID NO 2818

<400> SEQUENCE: 2818

000

<210> SEQ ID NO 2819

<400> SEQUENCE: 2819

000

<210> SEQ ID NO 2820

<400> SEQUENCE: 2820

000

<210> SEQ ID NO 2821

<400> SEQUENCE: 2821

000

<210> SEQ ID NO 2822

<400> SEQUENCE: 2822

000

<210> SEQ ID NO 2823

<400> SEQUENCE: 2823

000

<210> SEQ ID NO 2824

<400> SEQUENCE: 2824

000

<210> SEQ ID NO 2825

<400> SEQUENCE: 2825

000

<210> SEQ ID NO 2826

<400> SEQUENCE: 2826

000

<210> SEQ ID NO 2827

<400> SEQUENCE: 2827

000

<210> SEQ ID NO 2828

<400> SEQUENCE: 2828

000

<210> SEQ ID NO 2829

<400> SEQUENCE: 2829

000

<210> SEQ ID NO 2830

<400> SEQUENCE: 2830

000

<210> SEQ ID NO 2831

<400> SEQUENCE: 2831

000

<210> SEQ ID NO 2832

<400> SEQUENCE: 2832

000

<210> SEQ ID NO 2833

<400> SEQUENCE: 2833

000

<210> SEQ ID NO 2834

<400> SEQUENCE: 2834

000

<210> SEQ ID NO 2835

<400> SEQUENCE: 2835

000

<210> SEQ ID NO 2836

<400> SEQUENCE: 2836

000

<210> SEQ ID NO 2837

<400> SEQUENCE: 2837

000

<210> SEQ ID NO 2838

<400> SEQUENCE: 2838

000

<210> SEQ ID NO 2839

<400> SEQUENCE: 2839

000

<210> SEQ ID NO 2840

<400> SEQUENCE: 2840

000

<210> SEQ ID NO 2841

<400> SEQUENCE: 2841

000

<210> SEQ ID NO 2842

<400> SEQUENCE: 2842

000

<210> SEQ ID NO 2843

<400> SEQUENCE: 2843

000

<210> SEQ ID NO 2844

<400> SEQUENCE: 2844

000

<210> SEQ ID NO 2845

<400> SEQUENCE: 2845

000

<210> SEQ ID NO 2846

<400> SEQUENCE: 2846

000

<210> SEQ ID NO 2847

<400> SEQUENCE: 2847

000

<210> SEQ ID NO 2848

<400> SEQUENCE: 2848

000

<210> SEQ ID NO 2849

<400> SEQUENCE: 2849

000

<210> SEQ ID NO 2850

<400> SEQUENCE: 2850

000

<210> SEQ ID NO 2851

<400> SEQUENCE: 2851

000

<210> SEQ ID NO 2852

<400> SEQUENCE: 2852

000

<210> SEQ ID NO 2853

<400> SEQUENCE: 2853

000

<210> SEQ ID NO 2854

<400> SEQUENCE: 2854

000

<210> SEQ ID NO 2855

<400> SEQUENCE: 2855

000

<210> SEQ ID NO 2856

<400> SEQUENCE: 2856

000

<210> SEQ ID NO 2857

<400> SEQUENCE: 2857

000

<210> SEQ ID NO 2858

<400> SEQUENCE: 2858

000

<210> SEQ ID NO 2859

<400> SEQUENCE: 2859

000

<210> SEQ ID NO 2860

<400> SEQUENCE: 2860

000

<210> SEQ ID NO 2861

<400> SEQUENCE: 2861

000

<210> SEQ ID NO 2862

<400> SEQUENCE: 2862

000

<210> SEQ ID NO 2863

<400> SEQUENCE: 2863

000

<210> SEQ ID NO 2864

<400> SEQUENCE: 2864

000

<210> SEQ ID NO 2865

<400> SEQUENCE: 2865

000

<210> SEQ ID NO 2866

<400> SEQUENCE: 2866

000

<210> SEQ ID NO 2867

<400> SEQUENCE: 2867

000

<210> SEQ ID NO 2868

<400> SEQUENCE: 2868

000

<210> SEQ ID NO 2869

<400> SEQUENCE: 2869

000

<210> SEQ ID NO 2870

<400> SEQUENCE: 2870

000

<210> SEQ ID NO 2871

<400> SEQUENCE: 2871

000

<210> SEQ ID NO 2872

<400> SEQUENCE: 2872

000

<210> SEQ ID NO 2873

<400> SEQUENCE: 2873

000

<210> SEQ ID NO 2874

<400> SEQUENCE: 2874

000

<210> SEQ ID NO 2875

<400> SEQUENCE: 2875

000

<210> SEQ ID NO 2876

<400> SEQUENCE: 2876

000

<210> SEQ ID NO 2877

<400> SEQUENCE: 2877

000

<210> SEQ ID NO 2878

<400> SEQUENCE: 2878

000

<210> SEQ ID NO 2879

<400> SEQUENCE: 2879

000

<210> SEQ ID NO 2880

<400> SEQUENCE: 2880

000

<210> SEQ ID NO 2881

<400> SEQUENCE: 2881

000

<210> SEQ ID NO 2882

<400> SEQUENCE: 2882

000

<210> SEQ ID NO 2883

<400> SEQUENCE: 2883

000

<210> SEQ ID NO 2884

<400> SEQUENCE: 2884

000

<210> SEQ ID NO 2885

<400> SEQUENCE: 2885

000

<210> SEQ ID NO 2886

<400> SEQUENCE: 2886

000

<210> SEQ ID NO 2887

<400> SEQUENCE: 2887

000

<210> SEQ ID NO 2888

<400> SEQUENCE: 2888

000

<210> SEQ ID NO 2889

<400> SEQUENCE: 2889

000

<210> SEQ ID NO 2890

<400> SEQUENCE: 2890

000

<210> SEQ ID NO 2891

<400> SEQUENCE: 2891

000

<210> SEQ ID NO 2892

<400> SEQUENCE: 2892

000

<210> SEQ ID NO 2893
<400> SEQUENCE: 2893
000

<210> SEQ ID NO 2894
<400> SEQUENCE: 2894
000

<210> SEQ ID NO 2895
<400> SEQUENCE: 2895
000

<210> SEQ ID NO 2896
<400> SEQUENCE: 2896
000

<210> SEQ ID NO 2897
<400> SEQUENCE: 2897
000

<210> SEQ ID NO 2898
<400> SEQUENCE: 2898
000

<210> SEQ ID NO 2899
<400> SEQUENCE: 2899
000

<210> SEQ ID NO 2900
<400> SEQUENCE: 2900
000

<210> SEQ ID NO 2901
<400> SEQUENCE: 2901
000

<210> SEQ ID NO 2902
<400> SEQUENCE: 2902
000

<210> SEQ ID NO 2903
<400> SEQUENCE: 2903
000

<210> SEQ ID NO 2904

<400> SEQUENCE: 2904

000

<210> SEQ ID NO 2905

<400> SEQUENCE: 2905

000

<210> SEQ ID NO 2906

<400> SEQUENCE: 2906

000

<210> SEQ ID NO 2907

<400> SEQUENCE: 2907

000

<210> SEQ ID NO 2908

<400> SEQUENCE: 2908

000

<210> SEQ ID NO 2909

<400> SEQUENCE: 2909

000

<210> SEQ ID NO 2910

<400> SEQUENCE: 2910

000

<210> SEQ ID NO 2911

<400> SEQUENCE: 2911

000

<210> SEQ ID NO 2912

<400> SEQUENCE: 2912

000

<210> SEQ ID NO 2913

<400> SEQUENCE: 2913

000

<210> SEQ ID NO 2914

<400> SEQUENCE: 2914

000

<210> SEQ ID NO 2915

<400> SEQUENCE: 2915

000

<210> SEQ ID NO 2916

<400> SEQUENCE: 2916

000

<210> SEQ ID NO 2917

<400> SEQUENCE: 2917

000

<210> SEQ ID NO 2918

<400> SEQUENCE: 2918

000

<210> SEQ ID NO 2919

<400> SEQUENCE: 2919

000

<210> SEQ ID NO 2920

<400> SEQUENCE: 2920

000

<210> SEQ ID NO 2921

<400> SEQUENCE: 2921

000

<210> SEQ ID NO 2922

<400> SEQUENCE: 2922

000

<210> SEQ ID NO 2923

<400> SEQUENCE: 2923

000

<210> SEQ ID NO 2924

<400> SEQUENCE: 2924

000

<210> SEQ ID NO 2925

<400> SEQUENCE: 2925

000

<210> SEQ ID NO 2926

<400> SEQUENCE: 2926

000

<210> SEQ ID NO 2927

<400> SEQUENCE: 2927

000

<210> SEQ ID NO 2928

<400> SEQUENCE: 2928

000

<210> SEQ ID NO 2929

<400> SEQUENCE: 2929

000

<210> SEQ ID NO 2930

<400> SEQUENCE: 2930

000

<210> SEQ ID NO 2931

<400> SEQUENCE: 2931

000

<210> SEQ ID NO 2932

<400> SEQUENCE: 2932

000

<210> SEQ ID NO 2933

<400> SEQUENCE: 2933

000

<210> SEQ ID NO 2934

<400> SEQUENCE: 2934

000

<210> SEQ ID NO 2935

<400> SEQUENCE: 2935

000

<210> SEQ ID NO 2936

<400> SEQUENCE: 2936

000

<210> SEQ ID NO 2937

<400> SEQUENCE: 2937

000

<210> SEQ ID NO 2938

<400> SEQUENCE: 2938

000

<210> SEQ ID NO 2939

<400> SEQUENCE: 2939

000

<210> SEQ ID NO 2940

<400> SEQUENCE: 2940

000

<210> SEQ ID NO 2941

<400> SEQUENCE: 2941

000

<210> SEQ ID NO 2942

<400> SEQUENCE: 2942

000

<210> SEQ ID NO 2943

<400> SEQUENCE: 2943

000

<210> SEQ ID NO 2944

<400> SEQUENCE: 2944

000

<210> SEQ ID NO 2945

<400> SEQUENCE: 2945

000

<210> SEQ ID NO 2946

<400> SEQUENCE: 2946

000

<210> SEQ ID NO 2947

<400> SEQUENCE: 2947

000

<210> SEQ ID NO 2948

<400> SEQUENCE: 2948

000

<210> SEQ ID NO 2949

<400> SEQUENCE: 2949

000

<210> SEQ ID NO 2950

<400> SEQUENCE: 2950

000

<210> SEQ ID NO 2951

<400> SEQUENCE: 2951

000

<210> SEQ ID NO 2952

<400> SEQUENCE: 2952

000

<210> SEQ ID NO 2953

<400> SEQUENCE: 2953

000

<210> SEQ ID NO 2954

<400> SEQUENCE: 2954

000

<210> SEQ ID NO 2955

<400> SEQUENCE: 2955

000

<210> SEQ ID NO 2956

<400> SEQUENCE: 2956

000

<210> SEQ ID NO 2957

<400> SEQUENCE: 2957

000

<210> SEQ ID NO 2958

<400> SEQUENCE: 2958

000

<210> SEQ ID NO 2959

<400> SEQUENCE: 2959

000

<210> SEQ ID NO 2960

<400> SEQUENCE: 2960

000

<210> SEQ ID NO 2961
<400> SEQUENCE: 2961
000

<210> SEQ ID NO 2962
<400> SEQUENCE: 2962
000

<210> SEQ ID NO 2963
<400> SEQUENCE: 2963
000

<210> SEQ ID NO 2964
<400> SEQUENCE: 2964
000

<210> SEQ ID NO 2965
<400> SEQUENCE: 2965
000

<210> SEQ ID NO 2966
<400> SEQUENCE: 2966
000

<210> SEQ ID NO 2967
<400> SEQUENCE: 2967
000

<210> SEQ ID NO 2968
<400> SEQUENCE: 2968
000

<210> SEQ ID NO 2969
<400> SEQUENCE: 2969
000

<210> SEQ ID NO 2970
<400> SEQUENCE: 2970
000

<210> SEQ ID NO 2971
<400> SEQUENCE: 2971
000

<210> SEQ ID NO 2972

<400> SEQUENCE: 2972

000

<210> SEQ ID NO 2973

<400> SEQUENCE: 2973

000

<210> SEQ ID NO 2974

<400> SEQUENCE: 2974

000

<210> SEQ ID NO 2975

<400> SEQUENCE: 2975

000

<210> SEQ ID NO 2976

<400> SEQUENCE: 2976

000

<210> SEQ ID NO 2977

<400> SEQUENCE: 2977

000

<210> SEQ ID NO 2978

<400> SEQUENCE: 2978

000

<210> SEQ ID NO 2979

<400> SEQUENCE: 2979

000

<210> SEQ ID NO 2980

<400> SEQUENCE: 2980

000

<210> SEQ ID NO 2981

<400> SEQUENCE: 2981

000

<210> SEQ ID NO 2982

<400> SEQUENCE: 2982

000

<210> SEQ ID NO 2983

<400> SEQUENCE: 2983

000

<210> SEQ ID NO 2984

<400> SEQUENCE: 2984

000

<210> SEQ ID NO 2985

<400> SEQUENCE: 2985

000

<210> SEQ ID NO 2986

<400> SEQUENCE: 2986

000

<210> SEQ ID NO 2987

<400> SEQUENCE: 2987

000

<210> SEQ ID NO 2988

<400> SEQUENCE: 2988

000

<210> SEQ ID NO 2989

<400> SEQUENCE: 2989

000

<210> SEQ ID NO 2990

<400> SEQUENCE: 2990

000

<210> SEQ ID NO 2991

<400> SEQUENCE: 2991

000

<210> SEQ ID NO 2992

<400> SEQUENCE: 2992

000

<210> SEQ ID NO 2993

<400> SEQUENCE: 2993

000

<210> SEQ ID NO 2994

<400> SEQUENCE: 2994

000

<210> SEQ ID NO 2995

<400> SEQUENCE: 2995

000

<210> SEQ ID NO 2996

<400> SEQUENCE: 2996

000

<210> SEQ ID NO 2997

<400> SEQUENCE: 2997

000

<210> SEQ ID NO 2998

<400> SEQUENCE: 2998

000

<210> SEQ ID NO 2999

<400> SEQUENCE: 2999

000

<210> SEQ ID NO 3000

<400> SEQUENCE: 3000

000

<210> SEQ ID NO 3001

<400> SEQUENCE: 3001

000

<210> SEQ ID NO 3002

<400> SEQUENCE: 3002

000

<210> SEQ ID NO 3003

<400> SEQUENCE: 3003

000

<210> SEQ ID NO 3004

<400> SEQUENCE: 3004

000

<210> SEQ ID NO 3005

<400> SEQUENCE: 3005

000

<210> SEQ ID NO 3006

<400> SEQUENCE: 3006

000

<210> SEQ ID NO 3007

<400> SEQUENCE: 3007

000

<210> SEQ ID NO 3008

<400> SEQUENCE: 3008

000

<210> SEQ ID NO 3009

<400> SEQUENCE: 3009

000

<210> SEQ ID NO 3010

<400> SEQUENCE: 3010

000

<210> SEQ ID NO 3011

<400> SEQUENCE: 3011

000

<210> SEQ ID NO 3012

<400> SEQUENCE: 3012

000

<210> SEQ ID NO 3013

<400> SEQUENCE: 3013

000

<210> SEQ ID NO 3014

<400> SEQUENCE: 3014

000

<210> SEQ ID NO 3015

<400> SEQUENCE: 3015

000

<210> SEQ ID NO 3016

<400> SEQUENCE: 3016

000

<210> SEQ ID NO 3017

<400> SEQUENCE: 3017

000

<210> SEQ ID NO 3018

<400> SEQUENCE: 3018

000

<210> SEQ ID NO 3019

<400> SEQUENCE: 3019

000

<210> SEQ ID NO 3020

<400> SEQUENCE: 3020

000

<210> SEQ ID NO 3021

<400> SEQUENCE: 3021

000

<210> SEQ ID NO 3022

<400> SEQUENCE: 3022

000

<210> SEQ ID NO 3023

<400> SEQUENCE: 3023

000

<210> SEQ ID NO 3024

<400> SEQUENCE: 3024

000

<210> SEQ ID NO 3025

<400> SEQUENCE: 3025

000

<210> SEQ ID NO 3026

<400> SEQUENCE: 3026

000

<210> SEQ ID NO 3027

<400> SEQUENCE: 3027

000

<210> SEQ ID NO 3028

<400> SEQUENCE: 3028

000

<210> SEQ ID NO 3029

<400> SEQUENCE: 3029

000

<210> SEQ ID NO 3030

<400> SEQUENCE: 3030

000

<210> SEQ ID NO 3031

<400> SEQUENCE: 3031

000

<210> SEQ ID NO 3032

<400> SEQUENCE: 3032

000

<210> SEQ ID NO 3033

<400> SEQUENCE: 3033

000

<210> SEQ ID NO 3034

<400> SEQUENCE: 3034

000

<210> SEQ ID NO 3035

<400> SEQUENCE: 3035

000

<210> SEQ ID NO 3036

<400> SEQUENCE: 3036

000

<210> SEQ ID NO 3037

<400> SEQUENCE: 3037

000

<210> SEQ ID NO 3038

<400> SEQUENCE: 3038

000

<210> SEQ ID NO 3039

<400> SEQUENCE: 3039

000

<210> SEQ ID NO 3040

<400> SEQUENCE: 3040

000

<210> SEQ ID NO 3041

<400> SEQUENCE: 3041

000

<210> SEQ ID NO 3042

<400> SEQUENCE: 3042

000

<210> SEQ ID NO 3043

<400> SEQUENCE: 3043

000

<210> SEQ ID NO 3044

<400> SEQUENCE: 3044

000

<210> SEQ ID NO 3045

<400> SEQUENCE: 3045

000

<210> SEQ ID NO 3046

<400> SEQUENCE: 3046

000

<210> SEQ ID NO 3047

<400> SEQUENCE: 3047

000

<210> SEQ ID NO 3048

<400> SEQUENCE: 3048

000

<210> SEQ ID NO 3049

<400> SEQUENCE: 3049

000

<210> SEQ ID NO 3050

<400> SEQUENCE: 3050

000

<210> SEQ ID NO 3051

<400> SEQUENCE: 3051

000

<210> SEQ ID NO 3052

<400> SEQUENCE: 3052

000

<210> SEQ ID NO 3053

<400> SEQUENCE: 3053

000

<210> SEQ ID NO 3054

<400> SEQUENCE: 3054

000

<210> SEQ ID NO 3055

<400> SEQUENCE: 3055

000

<210> SEQ ID NO 3056

<400> SEQUENCE: 3056

000

<210> SEQ ID NO 3057

<400> SEQUENCE: 3057

000

<210> SEQ ID NO 3058

<400> SEQUENCE: 3058

000

<210> SEQ ID NO 3059

<400> SEQUENCE: 3059

000

<210> SEQ ID NO 3060

<400> SEQUENCE: 3060

000

<210> SEQ ID NO 3061

<400> SEQUENCE: 3061

000

<210> SEQ ID NO 3062

<400> SEQUENCE: 3062

000

<210> SEQ ID NO 3063

<400> SEQUENCE: 3063

000

<210> SEQ ID NO 3064

<400> SEQUENCE: 3064

000

<210> SEQ ID NO 3065

<400> SEQUENCE: 3065

000

<210> SEQ ID NO 3066

<400> SEQUENCE: 3066

000

<210> SEQ ID NO 3067

<400> SEQUENCE: 3067

000

<210> SEQ ID NO 3068

<400> SEQUENCE: 3068

000

<210> SEQ ID NO 3069

<400> SEQUENCE: 3069

000

<210> SEQ ID NO 3070

<400> SEQUENCE: 3070

000

<210> SEQ ID NO 3071

<400> SEQUENCE: 3071

000

<210> SEQ ID NO 3072

<400> SEQUENCE: 3072

000

<210> SEQ ID NO 3073

<400> SEQUENCE: 3073

000

<210> SEQ ID NO 3074

<400> SEQUENCE: 3074

000

<210> SEQ ID NO 3075

<400> SEQUENCE: 3075

000

<210> SEQ ID NO 3076

<400> SEQUENCE: 3076

000

<210> SEQ ID NO 3077

<400> SEQUENCE: 3077

000

<210> SEQ ID NO 3078

<400> SEQUENCE: 3078

000

<210> SEQ ID NO 3079

<400> SEQUENCE: 3079

000

<210> SEQ ID NO 3080

<400> SEQUENCE: 3080

000

<210> SEQ ID NO 3081

<400> SEQUENCE: 3081

000

<210> SEQ ID NO 3082

<400> SEQUENCE: 3082

000

<210> SEQ ID NO 3083

<400> SEQUENCE: 3083

000

<210> SEQ ID NO 3084

<400> SEQUENCE: 3084

000

<210> SEQ ID NO 3085

<400> SEQUENCE: 3085

000

<210> SEQ ID NO 3086

<400> SEQUENCE: 3086

000

<210> SEQ ID NO 3087

<400> SEQUENCE: 3087

000

<210> SEQ ID NO 3088

<400> SEQUENCE: 3088

000

<210> SEQ ID NO 3089

<400> SEQUENCE: 3089

000

<210> SEQ ID NO 3090

<400> SEQUENCE: 3090

000

<210> SEQ ID NO 3091

<400> SEQUENCE: 3091

000

<210> SEQ ID NO 3092

<400> SEQUENCE: 3092

000

<210> SEQ ID NO 3093

<400> SEQUENCE: 3093

000

<210> SEQ ID NO 3094

<400> SEQUENCE: 3094

000

<210> SEQ ID NO 3095

<400> SEQUENCE: 3095

000

<210> SEQ ID NO 3096

<400> SEQUENCE: 3096

000

<210> SEQ ID NO 3097

<400> SEQUENCE: 3097

000

<210> SEQ ID NO 3098

<400> SEQUENCE: 3098

000

<210> SEQ ID NO 3099

<400> SEQUENCE: 3099

000

<210> SEQ ID NO 3100

<400> SEQUENCE: 3100

000

<210> SEQ ID NO 3101

<400> SEQUENCE: 3101

000

<210> SEQ ID NO 3102

<400> SEQUENCE: 3102

000

<210> SEQ ID NO 3103

<400> SEQUENCE: 3103

000

<210> SEQ ID NO 3104

<400> SEQUENCE: 3104

000

<210> SEQ ID NO 3105

<400> SEQUENCE: 3105

000

<210> SEQ ID NO 3106

<400> SEQUENCE: 3106

000

<210> SEQ ID NO 3107

<400> SEQUENCE: 3107

000

<210> SEQ ID NO 3108

<400> SEQUENCE: 3108

000

<210> SEQ ID NO 3109

<400> SEQUENCE: 3109

000

<210> SEQ ID NO 3110

<400> SEQUENCE: 3110

000

<210> SEQ ID NO 3111

<400> SEQUENCE: 3111

000

<210> SEQ ID NO 3112

<400> SEQUENCE: 3112

000

<210> SEQ ID NO 3113

<400> SEQUENCE: 3113

000

<210> SEQ ID NO 3114

<400> SEQUENCE: 3114

000

<210> SEQ ID NO 3115

<400> SEQUENCE: 3115

000

<210> SEQ ID NO 3116

<400> SEQUENCE: 3116

000

<210> SEQ ID NO 3117

<400> SEQUENCE: 3117

000

<210> SEQ ID NO 3118

<400> SEQUENCE: 3118

000

<210> SEQ ID NO 3119

<400> SEQUENCE: 3119

000

<210> SEQ ID NO 3120

<400> SEQUENCE: 3120

000

<210> SEQ ID NO 3121

<400> SEQUENCE: 3121

000

<210> SEQ ID NO 3122

<400> SEQUENCE: 3122

000

<210> SEQ ID NO 3123

<400> SEQUENCE: 3123

000

<210> SEQ ID NO 3124

<400> SEQUENCE: 3124

000

<210> SEQ ID NO 3125

<400> SEQUENCE: 3125

000

<210> SEQ ID NO 3126

<400> SEQUENCE: 3126

000

<210> SEQ ID NO 3127

<400> SEQUENCE: 3127

000

<210> SEQ ID NO 3128

<400> SEQUENCE: 3128

000

<210> SEQ ID NO 3129

<400> SEQUENCE: 3129

000

<210> SEQ ID NO 3130

<400> SEQUENCE: 3130

000

<210> SEQ ID NO 3131

<400> SEQUENCE: 3131

000

<210> SEQ ID NO 3132

<400> SEQUENCE: 3132

000

<210> SEQ ID NO 3133

<400> SEQUENCE: 3133

000

<210> SEQ ID NO 3134

<400> SEQUENCE: 3134

000

<210> SEQ ID NO 3135

<400> SEQUENCE: 3135

000

<210> SEQ ID NO 3136

<400> SEQUENCE: 3136

000

<210> SEQ ID NO 3137

<400> SEQUENCE: 3137

000

<210> SEQ ID NO 3138

<400> SEQUENCE: 3138

000

<210> SEQ ID NO 3139

<400> SEQUENCE: 3139

000

<210> SEQ ID NO 3140

<400> SEQUENCE: 3140

000

<210> SEQ ID NO 3141

<400> SEQUENCE: 3141

000

<210> SEQ ID NO 3142

<400> SEQUENCE: 3142

000

<210> SEQ ID NO 3143

<400> SEQUENCE: 3143

000

<210> SEQ ID NO 3144

<400> SEQUENCE: 3144

000

<210> SEQ ID NO 3145

<400> SEQUENCE: 3145

000

<210> SEQ ID NO 3146

<400> SEQUENCE: 3146

000

<210> SEQ ID NO 3147

<400> SEQUENCE: 3147

000

<210> SEQ ID NO 3148

<400> SEQUENCE: 3148

000

<210> SEQ ID NO 3149

<400> SEQUENCE: 3149

000

<210> SEQ ID NO 3150

<400> SEQUENCE: 3150

000

<210> SEQ ID NO 3151

<400> SEQUENCE: 3151

000

<210> SEQ ID NO 3152

<400> SEQUENCE: 3152

000

<210> SEQ ID NO 3153

<400> SEQUENCE: 3153

000

<210> SEQ ID NO 3154

<400> SEQUENCE: 3154

000

<210> SEQ ID NO 3155

<400> SEQUENCE: 3155

000

<210> SEQ ID NO 3156

<400> SEQUENCE: 3156

000

<210> SEQ ID NO 3157

<400> SEQUENCE: 3157

000

<210> SEQ ID NO 3158

<400> SEQUENCE: 3158

000

<210> SEQ ID NO 3159

<400> SEQUENCE: 3159

000

<210> SEQ ID NO 3160

<400> SEQUENCE: 3160

000

<210> SEQ ID NO 3161

<400> SEQUENCE: 3161

000

<210> SEQ ID NO 3162

<400> SEQUENCE: 3162

000

<210> SEQ ID NO 3163

<400> SEQUENCE: 3163

000

<210> SEQ ID NO 3164

<400> SEQUENCE: 3164

000

<210> SEQ ID NO 3165

<400> SEQUENCE: 3165

000

<210> SEQ ID NO 3166

<400> SEQUENCE: 3166

000

<210> SEQ ID NO 3167

<400> SEQUENCE: 3167

000

<210> SEQ ID NO 3168

<400> SEQUENCE: 3168

000

<210> SEQ ID NO 3169

<400> SEQUENCE: 3169

000

<210> SEQ ID NO 3170

<400> SEQUENCE: 3170

000

<210> SEQ ID NO 3171

<400> SEQUENCE: 3171

000

<210> SEQ ID NO 3172

<400> SEQUENCE: 3172

000

<210> SEQ ID NO 3173

<400> SEQUENCE: 3173

000

<210> SEQ ID NO 3174

<400> SEQUENCE: 3174

000

<210> SEQ ID NO 3175

<400> SEQUENCE: 3175

000

<210> SEQ ID NO 3176

<400> SEQUENCE: 3176

000

<210> SEQ ID NO 3177

<400> SEQUENCE: 3177

000

<210> SEQ ID NO 3178

<400> SEQUENCE: 3178

000

<210> SEQ ID NO 3179

<400> SEQUENCE: 3179

000

<210> SEQ ID NO 3180

<400> SEQUENCE: 3180

000

<210> SEQ ID NO 3181

<400> SEQUENCE: 3181

000

<210> SEQ ID NO 3182

<400> SEQUENCE: 3182

000

<210> SEQ ID NO 3183

<400> SEQUENCE: 3183

000

<210> SEQ ID NO 3184

<400> SEQUENCE: 3184

000

<210> SEQ ID NO 3185

<400> SEQUENCE: 3185

000

<210> SEQ ID NO 3186

<400> SEQUENCE: 3186

000

<210> SEQ ID NO 3187

<400> SEQUENCE: 3187

000

<210> SEQ ID NO 3188

<400> SEQUENCE: 3188

000

<210> SEQ ID NO 3189

<400> SEQUENCE: 3189

000

<210> SEQ ID NO 3190

<400> SEQUENCE: 3190

000

<210> SEQ ID NO 3191

<400> SEQUENCE: 3191

000

<210> SEQ ID NO 3192

<400> SEQUENCE: 3192

000

<210> SEQ ID NO 3193

<400> SEQUENCE: 3193

000

<210> SEQ ID NO 3194

<400> SEQUENCE: 3194

000

<210> SEQ ID NO 3195

<400> SEQUENCE: 3195

000

<210> SEQ ID NO 3196

<400> SEQUENCE: 3196

000

<210> SEQ ID NO 3197

<400> SEQUENCE: 3197

000

<210> SEQ ID NO 3198

<400> SEQUENCE: 3198

000

<210> SEQ ID NO 3199

<400> SEQUENCE: 3199

000

<210> SEQ ID NO 3200

<400> SEQUENCE: 3200

000

<210> SEQ ID NO 3201

<400> SEQUENCE: 3201

000

<210> SEQ ID NO 3202

<400> SEQUENCE: 3202

000

<210> SEQ ID NO 3203

<400> SEQUENCE: 3203

000

<210> SEQ ID NO 3204

<400> SEQUENCE: 3204

000

<210> SEQ ID NO 3205

<400> SEQUENCE: 3205

000

<210> SEQ ID NO 3206

<400> SEQUENCE: 3206

000

<210> SEQ ID NO 3207

<400> SEQUENCE: 3207

000

<210> SEQ ID NO 3208

<400> SEQUENCE: 3208

000

<210> SEQ ID NO 3209

<400> SEQUENCE: 3209

000

<210> SEQ ID NO 3210

<400> SEQUENCE: 3210

000

<210> SEQ ID NO 3211

<400> SEQUENCE: 3211

000

<210> SEQ ID NO 3212

<400> SEQUENCE: 3212

000

<210> SEQ ID NO 3213

<400> SEQUENCE: 3213

000

<210> SEQ ID NO 3214

<400> SEQUENCE: 3214

000

<210> SEQ ID NO 3215

<400> SEQUENCE: 3215

000

<210> SEQ ID NO 3216

<400> SEQUENCE: 3216

000

<210> SEQ ID NO 3217

<400> SEQUENCE: 3217

000

<210> SEQ ID NO 3218

<400> SEQUENCE: 3218

000

<210> SEQ ID NO 3219

<400> SEQUENCE: 3219

000

<210> SEQ ID NO 3220

<400> SEQUENCE: 3220

000

<210> SEQ ID NO 3221

<400> SEQUENCE: 3221

000

<210> SEQ ID NO 3222

<400> SEQUENCE: 3222

000

<210> SEQ ID NO 3223

<400> SEQUENCE: 3223

000

<210> SEQ ID NO 3224

<400> SEQUENCE: 3224

000

<210> SEQ ID NO 3225

<400> SEQUENCE: 3225

000

<210> SEQ ID NO 3226

<400> SEQUENCE: 3226

000

<210> SEQ ID NO 3227

<400> SEQUENCE: 3227

000

<210> SEQ ID NO 3228

<400> SEQUENCE: 3228

000

<210> SEQ ID NO 3229

<400> SEQUENCE: 3229

000

<210> SEQ ID NO 3230

<400> SEQUENCE: 3230

000

<210> SEQ ID NO 3231

<400> SEQUENCE: 3231

000

<210> SEQ ID NO 3232

<400> SEQUENCE: 3232

000

<210> SEQ ID NO 3233

<400> SEQUENCE: 3233

000

<210> SEQ ID NO 3234

<400> SEQUENCE: 3234

000

<210> SEQ ID NO 3235

<400> SEQUENCE: 3235

000

<210> SEQ ID NO 3236

<400> SEQUENCE: 3236

000

<210> SEQ ID NO 3237

<400> SEQUENCE: 3237

000

<210> SEQ ID NO 3238

<400> SEQUENCE: 3238

000

<210> SEQ ID NO 3239

<400> SEQUENCE: 3239

000

<210> SEQ ID NO 3240

<400> SEQUENCE: 3240

000

<210> SEQ ID NO 3241

<400> SEQUENCE: 3241

000

<210> SEQ ID NO 3242

<400> SEQUENCE: 3242

000

<210> SEQ ID NO 3243

<400> SEQUENCE: 3243

000

<210> SEQ ID NO 3244

<400> SEQUENCE: 3244

000

<210> SEQ ID NO 3245

<400> SEQUENCE: 3245

000

<210> SEQ ID NO 3246

<400> SEQUENCE: 3246

000

<210> SEQ ID NO 3247

<400> SEQUENCE: 3247

000

<210> SEQ ID NO 3248

<400> SEQUENCE: 3248

000

<210> SEQ ID NO 3249

<400> SEQUENCE: 3249

000

<210> SEQ ID NO 3250

<400> SEQUENCE: 3250

000

<210> SEQ ID NO 3251

<400> SEQUENCE: 3251

000

<210> SEQ ID NO 3252

<400> SEQUENCE: 3252

000

<210> SEQ ID NO 3253

<400> SEQUENCE: 3253

000

<210> SEQ ID NO 3254

<400> SEQUENCE: 3254

000

<210> SEQ ID NO 3255

<400> SEQUENCE: 3255

000

<210> SEQ ID NO 3256

<400> SEQUENCE: 3256

000

<210> SEQ ID NO 3257

<400> SEQUENCE: 3257

000

<210> SEQ ID NO 3258

<400> SEQUENCE: 3258

000

<210> SEQ ID NO 3259

<400> SEQUENCE: 3259

000

<210> SEQ ID NO 3260

<400> SEQUENCE: 3260

000

<210> SEQ ID NO 3261

<400> SEQUENCE: 3261

000

<210> SEQ ID NO 3262

<400> SEQUENCE: 3262

000

<210> SEQ ID NO 3263

<400> SEQUENCE: 3263

000

<210> SEQ ID NO 3264

<400> SEQUENCE: 3264

000

<210> SEQ ID NO 3265

<400> SEQUENCE: 3265

000

<210> SEQ ID NO 3266

<400> SEQUENCE: 3266

000

<210> SEQ ID NO 3267

<400> SEQUENCE: 3267

000

<210> SEQ ID NO 3268

<400> SEQUENCE: 3268

000

<210> SEQ ID NO 3269

<400> SEQUENCE: 3269

000

<210> SEQ ID NO 3270

<400> SEQUENCE: 3270

000

<210> SEQ ID NO 3271

<400> SEQUENCE: 3271

000

<210> SEQ ID NO 3272

<400> SEQUENCE: 3272

000

<210> SEQ ID NO 3273

<400> SEQUENCE: 3273

000

<210> SEQ ID NO 3274

<400> SEQUENCE: 3274

000

<210> SEQ ID NO 3275

<400> SEQUENCE: 3275

000

<210> SEQ ID NO 3276

<400> SEQUENCE: 3276

000

<210> SEQ ID NO 3277

<400> SEQUENCE: 3277

000

<210> SEQ ID NO 3278

<400> SEQUENCE: 3278

000

<210> SEQ ID NO 3279

<400> SEQUENCE: 3279

000

<210> SEQ ID NO 3280

<400> SEQUENCE: 3280

000

<210> SEQ ID NO 3281

<400> SEQUENCE: 3281

000

<210> SEQ ID NO 3282

<400> SEQUENCE: 3282

000

<210> SEQ ID NO 3283

<400> SEQUENCE: 3283

000

<210> SEQ ID NO 3284

<400> SEQUENCE: 3284

000

<210> SEQ ID NO 3285

<400> SEQUENCE: 3285

000

<210> SEQ ID NO 3286

<400> SEQUENCE: 3286

000

<210> SEQ ID NO 3287

<400> SEQUENCE: 3287

000

<210> SEQ ID NO 3288

<400> SEQUENCE: 3288

000

<210> SEQ ID NO 3289

<400> SEQUENCE: 3289

000

<210> SEQ ID NO 3290

<400> SEQUENCE: 3290

000

<210> SEQ ID NO 3291

<400> SEQUENCE: 3291

000

<210> SEQ ID NO 3292

<400> SEQUENCE: 3292

000

<210> SEQ ID NO 3293

<400> SEQUENCE: 3293

000

<210> SEQ ID NO 3294

<400> SEQUENCE: 3294

000

<210> SEQ ID NO 3295

<400> SEQUENCE: 3295

000

<210> SEQ ID NO 3296

<400> SEQUENCE: 3296

000

<210> SEQ ID NO 3297

<400> SEQUENCE: 3297

000

<210> SEQ ID NO 3298

<400> SEQUENCE: 3298

000

<210> SEQ ID NO 3299

<400> SEQUENCE: 3299

000

<210> SEQ ID NO 3300

<400> SEQUENCE: 3300

000

<210> SEQ ID NO 3301

<400> SEQUENCE: 3301

000

<210> SEQ ID NO 3302

<400> SEQUENCE: 3302

000

<210> SEQ ID NO 3303

<400> SEQUENCE: 3303

000

<210> SEQ ID NO 3304

<400> SEQUENCE: 3304

000

<210> SEQ ID NO 3305

<400> SEQUENCE: 3305

000

<210> SEQ ID NO 3306

<400> SEQUENCE: 3306

000

<210> SEQ ID NO 3307

<400> SEQUENCE: 3307

000

<210> SEQ ID NO 3308

<400> SEQUENCE: 3308

000

<210> SEQ ID NO 3309

<400> SEQUENCE: 3309

000

<210> SEQ ID NO 3310

<400> SEQUENCE: 3310

000

<210> SEQ ID NO 3311

<400> SEQUENCE: 3311

000

<210> SEQ ID NO 3312

<400> SEQUENCE: 3312

000

<210> SEQ ID NO 3313

<400> SEQUENCE: 3313

000

<210> SEQ ID NO 3314

<400> SEQUENCE: 3314

000

<210> SEQ ID NO 3315

<400> SEQUENCE: 3315

000

<210> SEQ ID NO 3316

<400> SEQUENCE: 3316

000

<210> SEQ ID NO 3317

<400> SEQUENCE: 3317

000

<210> SEQ ID NO 3318

<400> SEQUENCE: 3318

000

<210> SEQ ID NO 3319

<400> SEQUENCE: 3319

000

<210> SEQ ID NO 3320

<400> SEQUENCE: 3320

000

<210> SEQ ID NO 3321

<400> SEQUENCE: 3321

000

<210> SEQ ID NO 3322

<400> SEQUENCE: 3322

000

<210> SEQ ID NO 3323

<400> SEQUENCE: 3323

000

<210> SEQ ID NO 3324

<400> SEQUENCE: 3324

000

<210> SEQ ID NO 3325

<400> SEQUENCE: 3325

000

<210> SEQ ID NO 3326

<400> SEQUENCE: 3326

000

<210> SEQ ID NO 3327

<400> SEQUENCE: 3327

000

<210> SEQ ID NO 3328

<400> SEQUENCE: 3328

000

<210> SEQ ID NO 3329

<400> SEQUENCE: 3329

000

<210> SEQ ID NO 3330

<400> SEQUENCE: 3330

000

<210> SEQ ID NO 3331

<400> SEQUENCE: 3331

000

<210> SEQ ID NO 3332

<400> SEQUENCE: 3332

000

<210> SEQ ID NO 3333

<400> SEQUENCE: 3333

000

<210> SEQ ID NO 3334

<400> SEQUENCE: 3334

000

<210> SEQ ID NO 3335

<400> SEQUENCE: 3335

000

<210> SEQ ID NO 3336

<400> SEQUENCE: 3336

000

<210> SEQ ID NO 3337

<400> SEQUENCE: 3337

000

<210> SEQ ID NO 3338

<400> SEQUENCE: 3338

000

<210> SEQ ID NO 3339

<400> SEQUENCE: 3339

000

<210> SEQ ID NO 3340

<400> SEQUENCE: 3340

000

<210> SEQ ID NO 3341

<400> SEQUENCE: 3341

000

<210> SEQ ID NO 3342

<400> SEQUENCE: 3342

000

<210> SEQ ID NO 3343

<400> SEQUENCE: 3343

000

<210> SEQ ID NO 3344

<400> SEQUENCE: 3344

000

<210> SEQ ID NO 3345

<400> SEQUENCE: 3345

000

<210> SEQ ID NO 3346

<400> SEQUENCE: 3346

000

<210> SEQ ID NO 3347

<400> SEQUENCE: 3347

000

<210> SEQ ID NO 3348

<400> SEQUENCE: 3348

000

<210> SEQ ID NO 3349

<400> SEQUENCE: 3349

000

<210> SEQ ID NO 3350

<400> SEQUENCE: 3350

000

<210> SEQ ID NO 3351

<400> SEQUENCE: 3351

000

<210> SEQ ID NO 3352

<400> SEQUENCE: 3352

000

<210> SEQ ID NO 3353

<400> SEQUENCE: 3353

000

<210> SEQ ID NO 3354

<400> SEQUENCE: 3354

000

<210> SEQ ID NO 3355

<400> SEQUENCE: 3355

000

<210> SEQ ID NO 3356

<400> SEQUENCE: 3356

000

<210> SEQ ID NO 3357

<400> SEQUENCE: 3357

000

<210> SEQ ID NO 3358

<400> SEQUENCE: 3358

000

<210> SEQ ID NO 3359

<400> SEQUENCE: 3359

000

<210> SEQ ID NO 3360

<400> SEQUENCE: 3360

000

<210> SEQ ID NO 3361

<400> SEQUENCE: 3361

000

<210> SEQ ID NO 3362

<400> SEQUENCE: 3362

000

<210> SEQ ID NO 3363

<400> SEQUENCE: 3363

000

<210> SEQ ID NO 3364

<400> SEQUENCE: 3364

000

<210> SEQ ID NO 3365

<400> SEQUENCE: 3365

000

<210> SEQ ID NO 3366

<400> SEQUENCE: 3366

000

<210> SEQ ID NO 3367
<400> SEQUENCE: 3367
000

<210> SEQ ID NO 3368
<400> SEQUENCE: 3368
000

<210> SEQ ID NO 3369
<400> SEQUENCE: 3369
000

<210> SEQ ID NO 3370
<400> SEQUENCE: 3370
000

<210> SEQ ID NO 3371
<400> SEQUENCE: 3371
000

<210> SEQ ID NO 3372
<400> SEQUENCE: 3372
000

<210> SEQ ID NO 3373
<400> SEQUENCE: 3373
000

<210> SEQ ID NO 3374
<400> SEQUENCE: 3374
000

<210> SEQ ID NO 3375
<400> SEQUENCE: 3375
000

<210> SEQ ID NO 3376
<400> SEQUENCE: 3376
000

<210> SEQ ID NO 3377
<400> SEQUENCE: 3377
000

<210> SEQ ID NO 3378

<400> SEQUENCE: 3378

000

<210> SEQ ID NO 3379

<400> SEQUENCE: 3379

000

<210> SEQ ID NO 3380

<400> SEQUENCE: 3380

000

<210> SEQ ID NO 3381

<400> SEQUENCE: 3381

000

<210> SEQ ID NO 3382

<400> SEQUENCE: 3382

000

<210> SEQ ID NO 3383

<400> SEQUENCE: 3383

000

<210> SEQ ID NO 3384

<400> SEQUENCE: 3384

000

<210> SEQ ID NO 3385

<400> SEQUENCE: 3385

000

<210> SEQ ID NO 3386

<400> SEQUENCE: 3386

000

<210> SEQ ID NO 3387

<400> SEQUENCE: 3387

000

<210> SEQ ID NO 3388

<400> SEQUENCE: 3388

000

<210> SEQ ID NO 3389

<400> SEQUENCE: 3389

000

<210> SEQ ID NO 3390

<400> SEQUENCE: 3390

000

<210> SEQ ID NO 3391

<400> SEQUENCE: 3391

000

<210> SEQ ID NO 3392

<400> SEQUENCE: 3392

000

<210> SEQ ID NO 3393

<400> SEQUENCE: 3393

000

<210> SEQ ID NO 3394

<400> SEQUENCE: 3394

000

<210> SEQ ID NO 3395

<400> SEQUENCE: 3395

000

<210> SEQ ID NO 3396

<400> SEQUENCE: 3396

000

<210> SEQ ID NO 3397

<400> SEQUENCE: 3397

000

<210> SEQ ID NO 3398

<400> SEQUENCE: 3398

000

<210> SEQ ID NO 3399

<400> SEQUENCE: 3399

000

<210> SEQ ID NO 3400

<400> SEQUENCE: 3400

000

<210> SEQ ID NO 3401

<400> SEQUENCE: 3401

000

<210> SEQ ID NO 3402

<400> SEQUENCE: 3402

000

<210> SEQ ID NO 3403

<400> SEQUENCE: 3403

000

<210> SEQ ID NO 3404

<400> SEQUENCE: 3404

000

<210> SEQ ID NO 3405

<400> SEQUENCE: 3405

000

<210> SEQ ID NO 3406

<400> SEQUENCE: 3406

000

<210> SEQ ID NO 3407

<400> SEQUENCE: 3407

000

<210> SEQ ID NO 3408

<400> SEQUENCE: 3408

000

<210> SEQ ID NO 3409

<400> SEQUENCE: 3409

000

<210> SEQ ID NO 3410

<400> SEQUENCE: 3410

000

<210> SEQ ID NO 3411

<400> SEQUENCE: 3411

000

<210> SEQ ID NO 3412

<400> SEQUENCE: 3412

000

<210> SEQ ID NO 3413

<400> SEQUENCE: 3413

000

<210> SEQ ID NO 3414

<400> SEQUENCE: 3414

000

<210> SEQ ID NO 3415

<400> SEQUENCE: 3415

000

<210> SEQ ID NO 3416

<400> SEQUENCE: 3416

000

<210> SEQ ID NO 3417

<400> SEQUENCE: 3417

000

<210> SEQ ID NO 3418

<400> SEQUENCE: 3418

000

<210> SEQ ID NO 3419

<400> SEQUENCE: 3419

000

<210> SEQ ID NO 3420

<400> SEQUENCE: 3420

000

<210> SEQ ID NO 3421

<400> SEQUENCE: 3421

000

<210> SEQ ID NO 3422

<400> SEQUENCE: 3422

000

<210> SEQ ID NO 3423

<400> SEQUENCE: 3423

000

<210> SEQ ID NO 3424

<400> SEQUENCE: 3424

000

<210> SEQ ID NO 3425

<400> SEQUENCE: 3425

000

<210> SEQ ID NO 3426

<400> SEQUENCE: 3426

000

<210> SEQ ID NO 3427

<400> SEQUENCE: 3427

000

<210> SEQ ID NO 3428

<400> SEQUENCE: 3428

000

<210> SEQ ID NO 3429

<400> SEQUENCE: 3429

000

<210> SEQ ID NO 3430

<400> SEQUENCE: 3430

000

<210> SEQ ID NO 3431

<400> SEQUENCE: 3431

000

<210> SEQ ID NO 3432

<400> SEQUENCE: 3432

000

<210> SEQ ID NO 3433

<400> SEQUENCE: 3433

000

<210> SEQ ID NO 3434

<400> SEQUENCE: 3434

000

<210> SEQ ID NO 3435
<400> SEQUENCE: 3435
000

<210> SEQ ID NO 3436
<400> SEQUENCE: 3436
000

<210> SEQ ID NO 3437
<400> SEQUENCE: 3437
000

<210> SEQ ID NO 3438
<400> SEQUENCE: 3438
000

<210> SEQ ID NO 3439
<400> SEQUENCE: 3439
000

<210> SEQ ID NO 3440
<400> SEQUENCE: 3440
000

<210> SEQ ID NO 3441
<400> SEQUENCE: 3441
000

<210> SEQ ID NO 3442
<400> SEQUENCE: 3442
000

<210> SEQ ID NO 3443
<400> SEQUENCE: 3443
000

<210> SEQ ID NO 3444
<400> SEQUENCE: 3444
000

<210> SEQ ID NO 3445
<400> SEQUENCE: 3445
000

<210> SEQ ID NO 3446

<400> SEQUENCE: 3446

000

<210> SEQ ID NO 3447

<400> SEQUENCE: 3447

000

<210> SEQ ID NO 3448

<400> SEQUENCE: 3448

000

<210> SEQ ID NO 3449

<400> SEQUENCE: 3449

000

<210> SEQ ID NO 3450

<400> SEQUENCE: 3450

000

<210> SEQ ID NO 3451

<400> SEQUENCE: 3451

000

<210> SEQ ID NO 3452

<400> SEQUENCE: 3452

000

<210> SEQ ID NO 3453

<400> SEQUENCE: 3453

000

<210> SEQ ID NO 3454

<400> SEQUENCE: 3454

000

<210> SEQ ID NO 3455

<400> SEQUENCE: 3455

000

<210> SEQ ID NO 3456

<400> SEQUENCE: 3456

000

<210> SEQ ID NO 3457

<400> SEQUENCE: 3457

000

<210> SEQ ID NO 3458

<400> SEQUENCE: 3458

000

<210> SEQ ID NO 3459

<400> SEQUENCE: 3459

000

<210> SEQ ID NO 3460

<400> SEQUENCE: 3460

000

<210> SEQ ID NO 3461

<400> SEQUENCE: 3461

000

<210> SEQ ID NO 3462

<400> SEQUENCE: 3462

000

<210> SEQ ID NO 3463

<400> SEQUENCE: 3463

000

<210> SEQ ID NO 3464

<400> SEQUENCE: 3464

000

<210> SEQ ID NO 3465

<400> SEQUENCE: 3465

000

<210> SEQ ID NO 3466

<400> SEQUENCE: 3466

000

<210> SEQ ID NO 3467

<400> SEQUENCE: 3467

000

<210> SEQ ID NO 3468

<400> SEQUENCE: 3468

000

<210> SEQ ID NO 3469

<400> SEQUENCE: 3469

000

<210> SEQ ID NO 3470

<400> SEQUENCE: 3470

000

<210> SEQ ID NO 3471

<400> SEQUENCE: 3471

000

<210> SEQ ID NO 3472

<400> SEQUENCE: 3472

000

<210> SEQ ID NO 3473

<400> SEQUENCE: 3473

000

<210> SEQ ID NO 3474

<400> SEQUENCE: 3474

000

<210> SEQ ID NO 3475

<400> SEQUENCE: 3475

000

<210> SEQ ID NO 3476

<400> SEQUENCE: 3476

000

<210> SEQ ID NO 3477

<400> SEQUENCE: 3477

000

<210> SEQ ID NO 3478

<400> SEQUENCE: 3478

000

<210> SEQ ID NO 3479

<400> SEQUENCE: 3479

000

<210> SEQ ID NO 3480

<400> SEQUENCE: 3480

000

<210> SEQ ID NO 3481

<400> SEQUENCE: 3481

000

<210> SEQ ID NO 3482

<400> SEQUENCE: 3482

000

<210> SEQ ID NO 3483

<400> SEQUENCE: 3483

000

<210> SEQ ID NO 3484

<400> SEQUENCE: 3484

000

<210> SEQ ID NO 3485

<400> SEQUENCE: 3485

000

<210> SEQ ID NO 3486

<400> SEQUENCE: 3486

000

<210> SEQ ID NO 3487

<400> SEQUENCE: 3487

000

<210> SEQ ID NO 3488

<400> SEQUENCE: 3488

000

<210> SEQ ID NO 3489

<400> SEQUENCE: 3489

000

<210> SEQ ID NO 3490

<400> SEQUENCE: 3490

000

<210> SEQ ID NO 3491

<400> SEQUENCE: 3491

000

<210> SEQ ID NO 3492

<400> SEQUENCE: 3492

000

<210> SEQ ID NO 3493

<400> SEQUENCE: 3493

000

<210> SEQ ID NO 3494

<400> SEQUENCE: 3494

000

<210> SEQ ID NO 3495

<400> SEQUENCE: 3495

000

<210> SEQ ID NO 3496

<400> SEQUENCE: 3496

000

<210> SEQ ID NO 3497

<400> SEQUENCE: 3497

000

<210> SEQ ID NO 3498

<400> SEQUENCE: 3498

000

<210> SEQ ID NO 3499

<400> SEQUENCE: 3499

000

<210> SEQ ID NO 3500

<400> SEQUENCE: 3500

000

<210> SEQ ID NO 3501

<400> SEQUENCE: 3501

000

<210> SEQ ID NO 3502

<400> SEQUENCE: 3502

000

<210> SEQ ID NO 3503

<400> SEQUENCE: 3503

000

<210> SEQ ID NO 3504

<400> SEQUENCE: 3504

000

<210> SEQ ID NO 3505

<400> SEQUENCE: 3505

000

<210> SEQ ID NO 3506

<400> SEQUENCE: 3506

000

<210> SEQ ID NO 3507

<400> SEQUENCE: 3507

000

<210> SEQ ID NO 3508

<400> SEQUENCE: 3508

000

<210> SEQ ID NO 3509

<400> SEQUENCE: 3509

000

<210> SEQ ID NO 3510

<400> SEQUENCE: 3510

000

<210> SEQ ID NO 3511

<400> SEQUENCE: 3511

000

<210> SEQ ID NO 3512

<400> SEQUENCE: 3512

000

<210> SEQ ID NO 3513

<400> SEQUENCE: 3513

000

<210> SEQ ID NO 3514
<400> SEQUENCE: 3514
000

<210> SEQ ID NO 3515
<400> SEQUENCE: 3515
000

<210> SEQ ID NO 3516
<400> SEQUENCE: 3516
000

<210> SEQ ID NO 3517
<400> SEQUENCE: 3517
000

<210> SEQ ID NO 3518
<400> SEQUENCE: 3518
000

<210> SEQ ID NO 3519
<400> SEQUENCE: 3519
000

<210> SEQ ID NO 3520
<400> SEQUENCE: 3520
000

<210> SEQ ID NO 3521
<400> SEQUENCE: 3521
000

<210> SEQ ID NO 3522
<400> SEQUENCE: 3522
000

<210> SEQ ID NO 3523
<400> SEQUENCE: 3523
000

<210> SEQ ID NO 3524
<400> SEQUENCE: 3524
000

<210> SEQ ID NO 3525

<400> SEQUENCE: 3525

000

<210> SEQ ID NO 3526

<400> SEQUENCE: 3526

000

<210> SEQ ID NO 3527

<400> SEQUENCE: 3527

000

<210> SEQ ID NO 3528

<400> SEQUENCE: 3528

000

<210> SEQ ID NO 3529

<400> SEQUENCE: 3529

000

<210> SEQ ID NO 3530

<400> SEQUENCE: 3530

000

<210> SEQ ID NO 3531

<400> SEQUENCE: 3531

000

<210> SEQ ID NO 3532

<400> SEQUENCE: 3532

000

<210> SEQ ID NO 3533

<400> SEQUENCE: 3533

000

<210> SEQ ID NO 3534

<400> SEQUENCE: 3534

000

<210> SEQ ID NO 3535

<400> SEQUENCE: 3535

000

<210> SEQ ID NO 3536

<400> SEQUENCE: 3536

000

<210> SEQ ID NO 3537

<400> SEQUENCE: 3537

000

<210> SEQ ID NO 3538

<400> SEQUENCE: 3538

000

<210> SEQ ID NO 3539

<400> SEQUENCE: 3539

000

<210> SEQ ID NO 3540

<400> SEQUENCE: 3540

000

<210> SEQ ID NO 3541

<400> SEQUENCE: 3541

000

<210> SEQ ID NO 3542

<400> SEQUENCE: 3542

000

<210> SEQ ID NO 3543

<400> SEQUENCE: 3543

000

<210> SEQ ID NO 3544

<400> SEQUENCE: 3544

000

<210> SEQ ID NO 3545

<400> SEQUENCE: 3545

000

<210> SEQ ID NO 3546

<400> SEQUENCE: 3546

000

<210> SEQ ID NO 3547

<400> SEQUENCE: 3547

000

<210> SEQ ID NO 3548

<400> SEQUENCE: 3548

000

<210> SEQ ID NO 3549

<400> SEQUENCE: 3549

000

<210> SEQ ID NO 3550

<400> SEQUENCE: 3550

000

<210> SEQ ID NO 3551

<400> SEQUENCE: 3551

000

<210> SEQ ID NO 3552

<400> SEQUENCE: 3552

000

<210> SEQ ID NO 3553

<400> SEQUENCE: 3553

000

<210> SEQ ID NO 3554

<400> SEQUENCE: 3554

000

<210> SEQ ID NO 3555

<400> SEQUENCE: 3555

000

<210> SEQ ID NO 3556

<400> SEQUENCE: 3556

000

<210> SEQ ID NO 3557

<400> SEQUENCE: 3557

000

<210> SEQ ID NO 3558

<400> SEQUENCE: 3558

-continued

000

<210> SEQ ID NO 3559

<400> SEQUENCE: 3559

000

<210> SEQ ID NO 3560

<400> SEQUENCE: 3560

000

<210> SEQ ID NO 3561

<400> SEQUENCE: 3561

000

<210> SEQ ID NO 3562

<400> SEQUENCE: 3562

000

<210> SEQ ID NO 3563

<400> SEQUENCE: 3563

000

<210> SEQ ID NO 3564

<400> SEQUENCE: 3564

000

<210> SEQ ID NO 3565

<400> SEQUENCE: 3565

000

<210> SEQ ID NO 3566

<400> SEQUENCE: 3566

000

<210> SEQ ID NO 3567

<400> SEQUENCE: 3567

000

<210> SEQ ID NO 3568

<400> SEQUENCE: 3568

000

<210> SEQ ID NO 3569

<400> SEQUENCE: 3569

000

<210> SEQ ID NO 3570

<400> SEQUENCE: 3570

000

<210> SEQ ID NO 3571

<400> SEQUENCE: 3571

000

<210> SEQ ID NO 3572

<400> SEQUENCE: 3572

000

<210> SEQ ID NO 3573

<400> SEQUENCE: 3573

000

<210> SEQ ID NO 3574

<400> SEQUENCE: 3574

000

<210> SEQ ID NO 3575

<400> SEQUENCE: 3575

000

<210> SEQ ID NO 3576

<400> SEQUENCE: 3576

000

<210> SEQ ID NO 3577

<400> SEQUENCE: 3577

000

<210> SEQ ID NO 3578

<400> SEQUENCE: 3578

000

<210> SEQ ID NO 3579

<400> SEQUENCE: 3579

000

<210> SEQ ID NO 3580

<400> SEQUENCE: 3580

000

<210> SEQ ID NO 3581

<400> SEQUENCE: 3581

000

<210> SEQ ID NO 3582

<400> SEQUENCE: 3582

000

<210> SEQ ID NO 3583

<400> SEQUENCE: 3583

000

<210> SEQ ID NO 3584

<400> SEQUENCE: 3584

000

<210> SEQ ID NO 3585

<400> SEQUENCE: 3585

000

<210> SEQ ID NO 3586

<400> SEQUENCE: 3586

000

<210> SEQ ID NO 3587

<400> SEQUENCE: 3587

000

<210> SEQ ID NO 3588

<400> SEQUENCE: 3588

000

<210> SEQ ID NO 3589

<400> SEQUENCE: 3589

000

<210> SEQ ID NO 3590

<400> SEQUENCE: 3590

000

<210> SEQ ID NO 3591

<400> SEQUENCE: 3591

000

<210> SEQ ID NO 3592

<400> SEQUENCE: 3592

000

<210> SEQ ID NO 3593
<400> SEQUENCE: 3593
000

<210> SEQ ID NO 3594
<400> SEQUENCE: 3594
000

<210> SEQ ID NO 3595
<400> SEQUENCE: 3595
000

<210> SEQ ID NO 3596
<400> SEQUENCE: 3596
000

<210> SEQ ID NO 3597
<400> SEQUENCE: 3597
000

<210> SEQ ID NO 3598
<400> SEQUENCE: 3598
000

<210> SEQ ID NO 3599
<400> SEQUENCE: 3599
000

<210> SEQ ID NO 3600
<400> SEQUENCE: 3600
000

<210> SEQ ID NO 3601
<400> SEQUENCE: 3601
000

<210> SEQ ID NO 3602
<400> SEQUENCE: 3602
000

<210> SEQ ID NO 3603
<400> SEQUENCE: 3603
000

<210> SEQ ID NO 3604

<400> SEQUENCE: 3604

000

<210> SEQ ID NO 3605

<400> SEQUENCE: 3605

000

<210> SEQ ID NO 3606

<400> SEQUENCE: 3606

000

<210> SEQ ID NO 3607

<400> SEQUENCE: 3607

000

<210> SEQ ID NO 3608

<400> SEQUENCE: 3608

000

<210> SEQ ID NO 3609

<400> SEQUENCE: 3609

000

<210> SEQ ID NO 3610

<400> SEQUENCE: 3610

000

<210> SEQ ID NO 3611

<400> SEQUENCE: 3611

000

<210> SEQ ID NO 3612

<400> SEQUENCE: 3612

000

<210> SEQ ID NO 3613

<400> SEQUENCE: 3613

000

<210> SEQ ID NO 3614

<400> SEQUENCE: 3614

000

<210> SEQ ID NO 3615

<400> SEQUENCE: 3615

000

<210> SEQ ID NO 3616

<400> SEQUENCE: 3616

000

<210> SEQ ID NO 3617

<400> SEQUENCE: 3617

000

<210> SEQ ID NO 3618

<400> SEQUENCE: 3618

000

<210> SEQ ID NO 3619

<400> SEQUENCE: 3619

000

<210> SEQ ID NO 3620

<400> SEQUENCE: 3620

000

<210> SEQ ID NO 3621

<400> SEQUENCE: 3621

000

<210> SEQ ID NO 3622

<400> SEQUENCE: 3622

000

<210> SEQ ID NO 3623

<400> SEQUENCE: 3623

000

<210> SEQ ID NO 3624

<400> SEQUENCE: 3624

000

<210> SEQ ID NO 3625

<400> SEQUENCE: 3625

000

<210> SEQ ID NO 3626

<400> SEQUENCE: 3626

000

<210> SEQ ID NO 3627

<400> SEQUENCE: 3627

000

<210> SEQ ID NO 3628

<400> SEQUENCE: 3628

000

<210> SEQ ID NO 3629

<400> SEQUENCE: 3629

000

<210> SEQ ID NO 3630

<400> SEQUENCE: 3630

000

<210> SEQ ID NO 3631

<400> SEQUENCE: 3631

000

<210> SEQ ID NO 3632

<400> SEQUENCE: 3632

000

<210> SEQ ID NO 3633

<400> SEQUENCE: 3633

000

<210> SEQ ID NO 3634

<400> SEQUENCE: 3634

000

<210> SEQ ID NO 3635

<400> SEQUENCE: 3635

000

<210> SEQ ID NO 3636

<400> SEQUENCE: 3636

000

<210> SEQ ID NO 3637

<400> SEQUENCE: 3637

000

<210> SEQ ID NO 3638

<400> SEQUENCE: 3638

000

<210> SEQ ID NO 3639

<400> SEQUENCE: 3639

000

<210> SEQ ID NO 3640

<400> SEQUENCE: 3640

000

<210> SEQ ID NO 3641

<400> SEQUENCE: 3641

000

<210> SEQ ID NO 3642

<400> SEQUENCE: 3642

000

<210> SEQ ID NO 3643

<400> SEQUENCE: 3643

000

<210> SEQ ID NO 3644

<400> SEQUENCE: 3644

000

<210> SEQ ID NO 3645

<400> SEQUENCE: 3645

000

<210> SEQ ID NO 3646

<400> SEQUENCE: 3646

000

<210> SEQ ID NO 3647

<400> SEQUENCE: 3647

000

<210> SEQ ID NO 3648

<400> SEQUENCE: 3648

000

<210> SEQ ID NO 3649

<400> SEQUENCE: 3649

000

<210> SEQ ID NO 3650

<400> SEQUENCE: 3650

000

<210> SEQ ID NO 3651

<400> SEQUENCE: 3651

000

<210> SEQ ID NO 3652

<400> SEQUENCE: 3652

000

<210> SEQ ID NO 3653

<400> SEQUENCE: 3653

000

<210> SEQ ID NO 3654

<400> SEQUENCE: 3654

000

<210> SEQ ID NO 3655

<400> SEQUENCE: 3655

000

<210> SEQ ID NO 3656

<400> SEQUENCE: 3656

000

<210> SEQ ID NO 3657

<400> SEQUENCE: 3657

000

<210> SEQ ID NO 3658

<400> SEQUENCE: 3658

000

<210> SEQ ID NO 3659

<400> SEQUENCE: 3659

000

<210> SEQ ID NO 3660

<400> SEQUENCE: 3660

000

<210> SEQ ID NO 3661

<400> SEQUENCE: 3661

000

<210> SEQ ID NO 3662

<400> SEQUENCE: 3662

000

<210> SEQ ID NO 3663

<400> SEQUENCE: 3663

000

<210> SEQ ID NO 3664

<400> SEQUENCE: 3664

000

<210> SEQ ID NO 3665

<400> SEQUENCE: 3665

000

<210> SEQ ID NO 3666

<400> SEQUENCE: 3666

000

<210> SEQ ID NO 3667

<400> SEQUENCE: 3667

000

<210> SEQ ID NO 3668

<400> SEQUENCE: 3668

000

<210> SEQ ID NO 3669

<400> SEQUENCE: 3669

000

<210> SEQ ID NO 3670

<400> SEQUENCE: 3670

000

<210> SEQ ID NO 3671

<400> SEQUENCE: 3671

000

<210> SEQ ID NO 3672
<400> SEQUENCE: 3672
000

<210> SEQ ID NO 3673
<400> SEQUENCE: 3673
000

<210> SEQ ID NO 3674
<400> SEQUENCE: 3674
000

<210> SEQ ID NO 3675
<400> SEQUENCE: 3675
000

<210> SEQ ID NO 3676
<400> SEQUENCE: 3676
000

<210> SEQ ID NO 3677
<400> SEQUENCE: 3677
000

<210> SEQ ID NO 3678
<400> SEQUENCE: 3678
000

<210> SEQ ID NO 3679
<400> SEQUENCE: 3679
000

<210> SEQ ID NO 3680
<400> SEQUENCE: 3680
000

<210> SEQ ID NO 3681
<400> SEQUENCE: 3681
000

<210> SEQ ID NO 3682
<400> SEQUENCE: 3682
000

<210> SEQ ID NO 3683

<400> SEQUENCE: 3683

000

<210> SEQ ID NO 3684

<400> SEQUENCE: 3684

000

<210> SEQ ID NO 3685

<400> SEQUENCE: 3685

000

<210> SEQ ID NO 3686

<400> SEQUENCE: 3686

000

<210> SEQ ID NO 3687

<400> SEQUENCE: 3687

000

<210> SEQ ID NO 3688

<400> SEQUENCE: 3688

000

<210> SEQ ID NO 3689

<400> SEQUENCE: 3689

000

<210> SEQ ID NO 3690

<400> SEQUENCE: 3690

000

<210> SEQ ID NO 3691

<400> SEQUENCE: 3691

000

<210> SEQ ID NO 3692

<400> SEQUENCE: 3692

000

<210> SEQ ID NO 3693

<400> SEQUENCE: 3693

000

<210> SEQ ID NO 3694

<400> SEQUENCE: 3694

000

<210> SEQ ID NO 3695

<400> SEQUENCE: 3695

000

<210> SEQ ID NO 3696

<400> SEQUENCE: 3696

000

<210> SEQ ID NO 3697

<400> SEQUENCE: 3697

000

<210> SEQ ID NO 3698

<400> SEQUENCE: 3698

000

<210> SEQ ID NO 3699

<400> SEQUENCE: 3699

000

<210> SEQ ID NO 3700

<400> SEQUENCE: 3700

000

<210> SEQ ID NO 3701

<400> SEQUENCE: 3701

000

<210> SEQ ID NO 3702

<400> SEQUENCE: 3702

000

<210> SEQ ID NO 3703

<400> SEQUENCE: 3703

000

<210> SEQ ID NO 3704

<400> SEQUENCE: 3704

000

<210> SEQ ID NO 3705

<400> SEQUENCE: 3705

000

<210> SEQ ID NO 3706

<400> SEQUENCE: 3706

000

<210> SEQ ID NO 3707

<400> SEQUENCE: 3707

000

<210> SEQ ID NO 3708

<400> SEQUENCE: 3708

000

<210> SEQ ID NO 3709

<400> SEQUENCE: 3709

000

<210> SEQ ID NO 3710

<400> SEQUENCE: 3710

000

<210> SEQ ID NO 3711

<400> SEQUENCE: 3711

000

<210> SEQ ID NO 3712

<400> SEQUENCE: 3712

000

<210> SEQ ID NO 3713

<400> SEQUENCE: 3713

000

<210> SEQ ID NO 3714

<400> SEQUENCE: 3714

000

<210> SEQ ID NO 3715

<400> SEQUENCE: 3715

000

<210> SEQ ID NO 3716

<400> SEQUENCE: 3716

000

<210> SEQ ID NO 3717

<400> SEQUENCE: 3717

000

<210> SEQ ID NO 3718

<400> SEQUENCE: 3718

000

<210> SEQ ID NO 3719

<400> SEQUENCE: 3719

000

<210> SEQ ID NO 3720

<400> SEQUENCE: 3720

000

<210> SEQ ID NO 3721

<400> SEQUENCE: 3721

000

<210> SEQ ID NO 3722

<400> SEQUENCE: 3722

000

<210> SEQ ID NO 3723

<400> SEQUENCE: 3723

000

<210> SEQ ID NO 3724

<400> SEQUENCE: 3724

000

<210> SEQ ID NO 3725

<400> SEQUENCE: 3725

000

<210> SEQ ID NO 3726

<400> SEQUENCE: 3726

000

<210> SEQ ID NO 3727

<400> SEQUENCE: 3727

000

<210> SEQ ID NO 3728

<400> SEQUENCE: 3728

000

<210> SEQ ID NO 3729

<400> SEQUENCE: 3729

000

<210> SEQ ID NO 3730

<400> SEQUENCE: 3730

000

<210> SEQ ID NO 3731

<400> SEQUENCE: 3731

000

<210> SEQ ID NO 3732

<400> SEQUENCE: 3732

000

<210> SEQ ID NO 3733

<400> SEQUENCE: 3733

000

<210> SEQ ID NO 3734

<400> SEQUENCE: 3734

000

<210> SEQ ID NO 3735

<400> SEQUENCE: 3735

000

<210> SEQ ID NO 3736

<400> SEQUENCE: 3736

000

<210> SEQ ID NO 3737

<400> SEQUENCE: 3737

000

<210> SEQ ID NO 3738

<400> SEQUENCE: 3738

000

<210> SEQ ID NO 3739

<400> SEQUENCE: 3739

000

<210> SEQ ID NO 3740

<400> SEQUENCE: 3740

000

<210> SEQ ID NO 3741

<400> SEQUENCE: 3741

000

<210> SEQ ID NO 3742

<400> SEQUENCE: 3742

000

<210> SEQ ID NO 3743

<400> SEQUENCE: 3743

000

<210> SEQ ID NO 3744

<400> SEQUENCE: 3744

000

<210> SEQ ID NO 3745

<400> SEQUENCE: 3745

000

<210> SEQ ID NO 3746

<400> SEQUENCE: 3746

000

<210> SEQ ID NO 3747

<400> SEQUENCE: 3747

000

<210> SEQ ID NO 3748

<400> SEQUENCE: 3748

000

<210> SEQ ID NO 3749

<400> SEQUENCE: 3749

000

<210> SEQ ID NO 3750

<400> SEQUENCE: 3750

000

<210> SEQ ID NO 3751
<400> SEQUENCE: 3751
000

<210> SEQ ID NO 3752
<400> SEQUENCE: 3752
000

<210> SEQ ID NO 3753
<400> SEQUENCE: 3753
000

<210> SEQ ID NO 3754
<400> SEQUENCE: 3754
000

<210> SEQ ID NO 3755
<400> SEQUENCE: 3755
000

<210> SEQ ID NO 3756
<400> SEQUENCE: 3756
000

<210> SEQ ID NO 3757
<400> SEQUENCE: 3757
000

<210> SEQ ID NO 3758
<400> SEQUENCE: 3758
000

<210> SEQ ID NO 3759
<400> SEQUENCE: 3759
000

<210> SEQ ID NO 3760
<400> SEQUENCE: 3760
000

<210> SEQ ID NO 3761
<400> SEQUENCE: 3761
000

<210> SEQ ID NO 3762

<400> SEQUENCE: 3762

000

<210> SEQ ID NO 3763

<400> SEQUENCE: 3763

000

<210> SEQ ID NO 3764

<400> SEQUENCE: 3764

000

<210> SEQ ID NO 3765

<400> SEQUENCE: 3765

000

<210> SEQ ID NO 3766

<400> SEQUENCE: 3766

000

<210> SEQ ID NO 3767

<400> SEQUENCE: 3767

000

<210> SEQ ID NO 3768

<400> SEQUENCE: 3768

000

<210> SEQ ID NO 3769

<400> SEQUENCE: 3769

000

<210> SEQ ID NO 3770

<400> SEQUENCE: 3770

000

<210> SEQ ID NO 3771

<400> SEQUENCE: 3771

000

<210> SEQ ID NO 3772

<400> SEQUENCE: 3772

000

<210> SEQ ID NO 3773

<400> SEQUENCE: 3773

000

<210> SEQ ID NO 3774

<400> SEQUENCE: 3774

000

<210> SEQ ID NO 3775

<400> SEQUENCE: 3775

000

<210> SEQ ID NO 3776

<400> SEQUENCE: 3776

000

<210> SEQ ID NO 3777

<400> SEQUENCE: 3777

000

<210> SEQ ID NO 3778

<400> SEQUENCE: 3778

000

<210> SEQ ID NO 3779

<400> SEQUENCE: 3779

000

<210> SEQ ID NO 3780

<400> SEQUENCE: 3780

000

<210> SEQ ID NO 3781

<400> SEQUENCE: 3781

000

<210> SEQ ID NO 3782

<400> SEQUENCE: 3782

000

<210> SEQ ID NO 3783

<400> SEQUENCE: 3783

000

<210> SEQ ID NO 3784

<400> SEQUENCE: 3784

000

<210> SEQ ID NO 3785

<400> SEQUENCE: 3785

000

<210> SEQ ID NO 3786

<400> SEQUENCE: 3786

000

<210> SEQ ID NO 3787

<400> SEQUENCE: 3787

000

<210> SEQ ID NO 3788

<400> SEQUENCE: 3788

000

<210> SEQ ID NO 3789

<400> SEQUENCE: 3789

000

<210> SEQ ID NO 3790

<400> SEQUENCE: 3790

000

<210> SEQ ID NO 3791

<400> SEQUENCE: 3791

000

<210> SEQ ID NO 3792

<400> SEQUENCE: 3792

000

<210> SEQ ID NO 3793

<400> SEQUENCE: 3793

000

<210> SEQ ID NO 3794

<400> SEQUENCE: 3794

000

<210> SEQ ID NO 3795

<400> SEQUENCE: 3795

000

<210> SEQ ID NO 3796

<400> SEQUENCE: 3796

000

<210> SEQ ID NO 3797

<400> SEQUENCE: 3797

000

<210> SEQ ID NO 3798

<400> SEQUENCE: 3798

000

<210> SEQ ID NO 3799

<400> SEQUENCE: 3799

000

<210> SEQ ID NO 3800

<400> SEQUENCE: 3800

000

<210> SEQ ID NO 3801

<400> SEQUENCE: 3801

000

<210> SEQ ID NO 3802

<400> SEQUENCE: 3802

000

<210> SEQ ID NO 3803

<400> SEQUENCE: 3803

000

<210> SEQ ID NO 3804

<400> SEQUENCE: 3804

000

<210> SEQ ID NO 3805

<400> SEQUENCE: 3805

000

<210> SEQ ID NO 3806

<400> SEQUENCE: 3806

000

<210> SEQ ID NO 3807

<400> SEQUENCE: 3807

000

<210> SEQ ID NO 3808

<400> SEQUENCE: 3808

000

<210> SEQ ID NO 3809

<400> SEQUENCE: 3809

000

<210> SEQ ID NO 3810

<400> SEQUENCE: 3810

000

<210> SEQ ID NO 3811

<400> SEQUENCE: 3811

000

<210> SEQ ID NO 3812

<400> SEQUENCE: 3812

000

<210> SEQ ID NO 3813

<400> SEQUENCE: 3813

000

<210> SEQ ID NO 3814

<400> SEQUENCE: 3814

000

<210> SEQ ID NO 3815

<400> SEQUENCE: 3815

000

<210> SEQ ID NO 3816

<400> SEQUENCE: 3816

000

<210> SEQ ID NO 3817

<400> SEQUENCE: 3817

000

<210> SEQ ID NO 3818

<400> SEQUENCE: 3818

000

<210> SEQ ID NO 3819

<400> SEQUENCE: 3819

000

<210> SEQ ID NO 3820

<400> SEQUENCE: 3820

000

<210> SEQ ID NO 3821

<400> SEQUENCE: 3821

000

<210> SEQ ID NO 3822

<400> SEQUENCE: 3822

000

<210> SEQ ID NO 3823

<400> SEQUENCE: 3823

000

<210> SEQ ID NO 3824

<400> SEQUENCE: 3824

000

<210> SEQ ID NO 3825

<400> SEQUENCE: 3825

000

<210> SEQ ID NO 3826

<400> SEQUENCE: 3826

000

<210> SEQ ID NO 3827

<400> SEQUENCE: 3827

000

<210> SEQ ID NO 3828

<400> SEQUENCE: 3828

000

<210> SEQ ID NO 3829

<400> SEQUENCE: 3829

000

<210> SEQ ID NO 3830
<400> SEQUENCE: 3830
000

<210> SEQ ID NO 3831
<400> SEQUENCE: 3831
000

<210> SEQ ID NO 3832
<400> SEQUENCE: 3832
000

<210> SEQ ID NO 3833
<400> SEQUENCE: 3833
000

<210> SEQ ID NO 3834
<400> SEQUENCE: 3834
000

<210> SEQ ID NO 3835
<400> SEQUENCE: 3835
000

<210> SEQ ID NO 3836
<400> SEQUENCE: 3836
000

<210> SEQ ID NO 3837
<400> SEQUENCE: 3837
000

<210> SEQ ID NO 3838
<400> SEQUENCE: 3838
000

<210> SEQ ID NO 3839
<400> SEQUENCE: 3839
000

<210> SEQ ID NO 3840
<400> SEQUENCE: 3840
000

<210> SEQ ID NO 3841

<400> SEQUENCE: 3841

000

<210> SEQ ID NO 3842

<400> SEQUENCE: 3842

000

<210> SEQ ID NO 3843

<400> SEQUENCE: 3843

000

<210> SEQ ID NO 3844

<400> SEQUENCE: 3844

000

<210> SEQ ID NO 3845

<400> SEQUENCE: 3845

000

<210> SEQ ID NO 3846

<400> SEQUENCE: 3846

000

<210> SEQ ID NO 3847

<400> SEQUENCE: 3847

000

<210> SEQ ID NO 3848

<400> SEQUENCE: 3848

000

<210> SEQ ID NO 3849

<400> SEQUENCE: 3849

000

<210> SEQ ID NO 3850

<400> SEQUENCE: 3850

000

<210> SEQ ID NO 3851

<400> SEQUENCE: 3851

000

<210> SEQ ID NO 3852

<400> SEQUENCE: 3852

000

<210> SEQ ID NO 3853

<400> SEQUENCE: 3853

000

<210> SEQ ID NO 3854

<400> SEQUENCE: 3854

000

<210> SEQ ID NO 3855

<400> SEQUENCE: 3855

000

<210> SEQ ID NO 3856

<400> SEQUENCE: 3856

000

<210> SEQ ID NO 3857

<400> SEQUENCE: 3857

000

<210> SEQ ID NO 3858

<400> SEQUENCE: 3858

000

<210> SEQ ID NO 3859

<400> SEQUENCE: 3859

000

<210> SEQ ID NO 3860

<400> SEQUENCE: 3860

000

<210> SEQ ID NO 3861

<400> SEQUENCE: 3861

000

<210> SEQ ID NO 3862

<400> SEQUENCE: 3862

000

<210> SEQ ID NO 3863

<400> SEQUENCE: 3863

000

<210> SEQ ID NO 3864

<400> SEQUENCE: 3864

000

<210> SEQ ID NO 3865

<400> SEQUENCE: 3865

000

<210> SEQ ID NO 3866

<400> SEQUENCE: 3866

000

<210> SEQ ID NO 3867

<400> SEQUENCE: 3867

000

<210> SEQ ID NO 3868

<400> SEQUENCE: 3868

000

<210> SEQ ID NO 3869

<400> SEQUENCE: 3869

000

<210> SEQ ID NO 3870

<400> SEQUENCE: 3870

000

<210> SEQ ID NO 3871

<400> SEQUENCE: 3871

000

<210> SEQ ID NO 3872

<400> SEQUENCE: 3872

000

<210> SEQ ID NO 3873

<400> SEQUENCE: 3873

000

<210> SEQ ID NO 3874

<400> SEQUENCE: 3874

000

<210> SEQ ID NO 3875

<400> SEQUENCE: 3875

000

<210> SEQ ID NO 3876

<400> SEQUENCE: 3876

000

<210> SEQ ID NO 3877

<400> SEQUENCE: 3877

000

<210> SEQ ID NO 3878

<400> SEQUENCE: 3878

000

<210> SEQ ID NO 3879

<400> SEQUENCE: 3879

000

<210> SEQ ID NO 3880

<400> SEQUENCE: 3880

000

<210> SEQ ID NO 3881

<400> SEQUENCE: 3881

000

<210> SEQ ID NO 3882

<400> SEQUENCE: 3882

000

<210> SEQ ID NO 3883

<400> SEQUENCE: 3883

000

<210> SEQ ID NO 3884

<400> SEQUENCE: 3884

000

<210> SEQ ID NO 3885

<400> SEQUENCE: 3885

000

<210> SEQ ID NO 3886

<400> SEQUENCE: 3886

000

<210> SEQ ID NO 3887

<400> SEQUENCE: 3887

000

<210> SEQ ID NO 3888

<400> SEQUENCE: 3888

000

<210> SEQ ID NO 3889

<400> SEQUENCE: 3889

000

<210> SEQ ID NO 3890

<400> SEQUENCE: 3890

000

<210> SEQ ID NO 3891

<400> SEQUENCE: 3891

000

<210> SEQ ID NO 3892

<400> SEQUENCE: 3892

000

<210> SEQ ID NO 3893

<400> SEQUENCE: 3893

000

<210> SEQ ID NO 3894

<400> SEQUENCE: 3894

000

<210> SEQ ID NO 3895

<400> SEQUENCE: 3895

000

<210> SEQ ID NO 3896

<400> SEQUENCE: 3896

000

<210> SEQ ID NO 3897

<400> SEQUENCE: 3897

000

<210> SEQ ID NO 3898

<400> SEQUENCE: 3898

000

<210> SEQ ID NO 3899

<400> SEQUENCE: 3899

000

<210> SEQ ID NO 3900

<400> SEQUENCE: 3900

000

<210> SEQ ID NO 3901

<400> SEQUENCE: 3901

000

<210> SEQ ID NO 3902

<400> SEQUENCE: 3902

000

<210> SEQ ID NO 3903

<400> SEQUENCE: 3903

000

<210> SEQ ID NO 3904

<400> SEQUENCE: 3904

000

<210> SEQ ID NO 3905

<400> SEQUENCE: 3905

000

<210> SEQ ID NO 3906

<400> SEQUENCE: 3906

000

<210> SEQ ID NO 3907

<400> SEQUENCE: 3907

000

<210> SEQ ID NO 3908

<400> SEQUENCE: 3908

000

<210> SEQ ID NO 3909
<400> SEQUENCE: 3909
000

<210> SEQ ID NO 3910
<400> SEQUENCE: 3910
000

<210> SEQ ID NO 3911
<400> SEQUENCE: 3911
000

<210> SEQ ID NO 3912
<400> SEQUENCE: 3912
000

<210> SEQ ID NO 3913
<400> SEQUENCE: 3913
000

<210> SEQ ID NO 3914
<400> SEQUENCE: 3914
000

<210> SEQ ID NO 3915
<400> SEQUENCE: 3915
000

<210> SEQ ID NO 3916
<400> SEQUENCE: 3916
000

<210> SEQ ID NO 3917
<400> SEQUENCE: 3917
000

<210> SEQ ID NO 3918
<400> SEQUENCE: 3918
000

<210> SEQ ID NO 3919
<400> SEQUENCE: 3919
000

<210> SEQ ID NO 3920

<400> SEQUENCE: 3920

000

<210> SEQ ID NO 3921

<400> SEQUENCE: 3921

000

<210> SEQ ID NO 3922

<400> SEQUENCE: 3922

000

<210> SEQ ID NO 3923

<400> SEQUENCE: 3923

000

<210> SEQ ID NO 3924

<400> SEQUENCE: 3924

000

<210> SEQ ID NO 3925

<400> SEQUENCE: 3925

000

<210> SEQ ID NO 3926

<400> SEQUENCE: 3926

000

<210> SEQ ID NO 3927

<400> SEQUENCE: 3927

000

<210> SEQ ID NO 3928

<400> SEQUENCE: 3928

000

<210> SEQ ID NO 3929

<400> SEQUENCE: 3929

000

<210> SEQ ID NO 3930

<400> SEQUENCE: 3930

000

-continued

<210> SEQ ID NO 3931

<400> SEQUENCE: 3931

000

<210> SEQ ID NO 3932

<400> SEQUENCE: 3932

000

<210> SEQ ID NO 3933

<400> SEQUENCE: 3933

000

<210> SEQ ID NO 3934

<400> SEQUENCE: 3934

000

<210> SEQ ID NO 3935

<400> SEQUENCE: 3935

000

<210> SEQ ID NO 3936

<400> SEQUENCE: 3936

000

<210> SEQ ID NO 3937

<400> SEQUENCE: 3937

000

<210> SEQ ID NO 3938

<400> SEQUENCE: 3938

000

<210> SEQ ID NO 3939

<400> SEQUENCE: 3939

000

<210> SEQ ID NO 3940

<400> SEQUENCE: 3940

000

<210> SEQ ID NO 3941

<400> SEQUENCE: 3941

000

<210> SEQ ID NO 3942

<400> SEQUENCE: 3942

000

<210> SEQ ID NO 3943

<400> SEQUENCE: 3943

000

<210> SEQ ID NO 3944

<400> SEQUENCE: 3944

000

<210> SEQ ID NO 3945

<400> SEQUENCE: 3945

000

<210> SEQ ID NO 3946

<400> SEQUENCE: 3946

000

<210> SEQ ID NO 3947

<400> SEQUENCE: 3947

000

<210> SEQ ID NO 3948

<400> SEQUENCE: 3948

000

<210> SEQ ID NO 3949

<400> SEQUENCE: 3949

000

<210> SEQ ID NO 3950

<400> SEQUENCE: 3950

000

<210> SEQ ID NO 3951

<400> SEQUENCE: 3951

000

<210> SEQ ID NO 3952

<400> SEQUENCE: 3952

000

<210> SEQ ID NO 3953

<400> SEQUENCE: 3953

000

<210> SEQ ID NO 3954

<400> SEQUENCE: 3954

000

<210> SEQ ID NO 3955

<400> SEQUENCE: 3955

000

<210> SEQ ID NO 3956

<400> SEQUENCE: 3956

000

<210> SEQ ID NO 3957

<400> SEQUENCE: 3957

000

<210> SEQ ID NO 3958

<400> SEQUENCE: 3958

000

<210> SEQ ID NO 3959

<400> SEQUENCE: 3959

000

<210> SEQ ID NO 3960

<400> SEQUENCE: 3960

000

<210> SEQ ID NO 3961

<400> SEQUENCE: 3961

000

<210> SEQ ID NO 3962

<400> SEQUENCE: 3962

000

<210> SEQ ID NO 3963

<400> SEQUENCE: 3963

000

<210> SEQ ID NO 3964

<400> SEQUENCE: 3964

000

<210> SEQ ID NO 3965
<400> SEQUENCE: 3965
000

<210> SEQ ID NO 3966
<400> SEQUENCE: 3966
000

<210> SEQ ID NO 3967
<400> SEQUENCE: 3967
000

<210> SEQ ID NO 3968
<400> SEQUENCE: 3968
000

<210> SEQ ID NO 3969
<400> SEQUENCE: 3969
000

<210> SEQ ID NO 3970
<400> SEQUENCE: 3970
000

<210> SEQ ID NO 3971
<400> SEQUENCE: 3971
000

<210> SEQ ID NO 3972
<400> SEQUENCE: 3972
000

<210> SEQ ID NO 3973
<400> SEQUENCE: 3973
000

<210> SEQ ID NO 3974
<400> SEQUENCE: 3974
000

<210> SEQ ID NO 3975
<400> SEQUENCE: 3975
000

<210> SEQ ID NO 3976

<400> SEQUENCE: 3976

000

<210> SEQ ID NO 3977

<400> SEQUENCE: 3977

000

<210> SEQ ID NO 3978

<400> SEQUENCE: 3978

000

<210> SEQ ID NO 3979

<400> SEQUENCE: 3979

000

<210> SEQ ID NO 3980

<400> SEQUENCE: 3980

000

<210> SEQ ID NO 3981

<400> SEQUENCE: 3981

000

<210> SEQ ID NO 3982

<400> SEQUENCE: 3982

000

<210> SEQ ID NO 3983

<400> SEQUENCE: 3983

000

<210> SEQ ID NO 3984

<400> SEQUENCE: 3984

000

<210> SEQ ID NO 3985

<400> SEQUENCE: 3985

000

<210> SEQ ID NO 3986

<400> SEQUENCE: 3986

000

<210> SEQ ID NO 3987

<400> SEQUENCE: 3987

-continued

000

<210> SEQ ID NO 3988

<400> SEQUENCE: 3988

000

<210> SEQ ID NO 3989

<400> SEQUENCE: 3989

000

<210> SEQ ID NO 3990

<400> SEQUENCE: 3990

000

<210> SEQ ID NO 3991

<400> SEQUENCE: 3991

000

<210> SEQ ID NO 3992

<400> SEQUENCE: 3992

000

<210> SEQ ID NO 3993

<400> SEQUENCE: 3993

000

<210> SEQ ID NO 3994

<400> SEQUENCE: 3994

000

<210> SEQ ID NO 3995

<400> SEQUENCE: 3995

000

<210> SEQ ID NO 3996

<400> SEQUENCE: 3996

000

<210> SEQ ID NO 3997

<400> SEQUENCE: 3997

000

<210> SEQ ID NO 3998

<400> SEQUENCE: 3998

000

<210> SEQ ID NO 3999

<400> SEQUENCE: 3999

000

<210> SEQ ID NO 4000

<400> SEQUENCE: 4000

000

<210> SEQ ID NO 4001

<400> SEQUENCE: 4001

000

<210> SEQ ID NO 4002

<400> SEQUENCE: 4002

000

<210> SEQ ID NO 4003

<400> SEQUENCE: 4003

000

<210> SEQ ID NO 4004

<400> SEQUENCE: 4004

000

<210> SEQ ID NO 4005

<400> SEQUENCE: 4005

000

<210> SEQ ID NO 4006

<400> SEQUENCE: 4006

000

<210> SEQ ID NO 4007

<400> SEQUENCE: 4007

000

<210> SEQ ID NO 4008

<400> SEQUENCE: 4008

000

<210> SEQ ID NO 4009

<400> SEQUENCE: 4009

000

<210> SEQ ID NO 4010

<400> SEQUENCE: 4010

000

<210> SEQ ID NO 4011

<400> SEQUENCE: 4011

000

<210> SEQ ID NO 4012

<400> SEQUENCE: 4012

000

<210> SEQ ID NO 4013

<400> SEQUENCE: 4013

000

<210> SEQ ID NO 4014

<400> SEQUENCE: 4014

000

<210> SEQ ID NO 4015

<400> SEQUENCE: 4015

000

<210> SEQ ID NO 4016

<400> SEQUENCE: 4016

000

<210> SEQ ID NO 4017

<400> SEQUENCE: 4017

000

<210> SEQ ID NO 4018

<400> SEQUENCE: 4018

000

<210> SEQ ID NO 4019

<400> SEQUENCE: 4019

000

<210> SEQ ID NO 4020

<400> SEQUENCE: 4020

000

<210> SEQ ID NO 4021

<400> SEQUENCE: 4021

000

<210> SEQ ID NO 4022

<400> SEQUENCE: 4022

000

<210> SEQ ID NO 4023

<400> SEQUENCE: 4023

000

<210> SEQ ID NO 4024

<400> SEQUENCE: 4024

000

<210> SEQ ID NO 4025

<400> SEQUENCE: 4025

000

<210> SEQ ID NO 4026

<400> SEQUENCE: 4026

000

<210> SEQ ID NO 4027

<400> SEQUENCE: 4027

000

<210> SEQ ID NO 4028

<400> SEQUENCE: 4028

000

<210> SEQ ID NO 4029

<400> SEQUENCE: 4029

000

<210> SEQ ID NO 4030

<400> SEQUENCE: 4030

000

<210> SEQ ID NO 4031

<400> SEQUENCE: 4031

000

<210> SEQ ID NO 4032

<400> SEQUENCE: 4032

000

<210> SEQ ID NO 4033

<400> SEQUENCE: 4033

000

<210> SEQ ID NO 4034

<400> SEQUENCE: 4034

000

<210> SEQ ID NO 4035

<400> SEQUENCE: 4035

000

<210> SEQ ID NO 4036

<400> SEQUENCE: 4036

000

<210> SEQ ID NO 4037

<400> SEQUENCE: 4037

000

<210> SEQ ID NO 4038

<400> SEQUENCE: 4038

000

<210> SEQ ID NO 4039

<400> SEQUENCE: 4039

000

<210> SEQ ID NO 4040

<400> SEQUENCE: 4040

000

<210> SEQ ID NO 4041

<400> SEQUENCE: 4041

000

<210> SEQ ID NO 4042

<400> SEQUENCE: 4042

000

<210> SEQ ID NO 4043

<400> SEQUENCE: 4043

000

<210> SEQ ID NO 4044

<400> SEQUENCE: 4044

000

<210> SEQ ID NO 4045

<400> SEQUENCE: 4045

000

<210> SEQ ID NO 4046

<400> SEQUENCE: 4046

000

<210> SEQ ID NO 4047

<400> SEQUENCE: 4047

000

<210> SEQ ID NO 4048

<400> SEQUENCE: 4048

000

<210> SEQ ID NO 4049

<400> SEQUENCE: 4049

000

<210> SEQ ID NO 4050

<400> SEQUENCE: 4050

000

<210> SEQ ID NO 4051

<400> SEQUENCE: 4051

000

<210> SEQ ID NO 4052

<400> SEQUENCE: 4052

000

<210> SEQ ID NO 4053

<400> SEQUENCE: 4053

000

<210> SEQ ID NO 4054

<400> SEQUENCE: 4054

000

<210> SEQ ID NO 4055

<400> SEQUENCE: 4055

000

<210> SEQ ID NO 4056

<400> SEQUENCE: 4056

000

<210> SEQ ID NO 4057

<400> SEQUENCE: 4057

000

<210> SEQ ID NO 4058

<400> SEQUENCE: 4058

000

<210> SEQ ID NO 4059

<400> SEQUENCE: 4059

000

<210> SEQ ID NO 4060

<400> SEQUENCE: 4060

000

<210> SEQ ID NO 4061

<400> SEQUENCE: 4061

000

<210> SEQ ID NO 4062

<400> SEQUENCE: 4062

000

<210> SEQ ID NO 4063

<400> SEQUENCE: 4063

000

<210> SEQ ID NO 4064

<400> SEQUENCE: 4064

000

<210> SEQ ID NO 4065

<400> SEQUENCE: 4065

000

<210> SEQ ID NO 4066

<400> SEQUENCE: 4066

000

<210> SEQ ID NO 4067

<400> SEQUENCE: 4067

000

<210> SEQ ID NO 4068

<400> SEQUENCE: 4068

000

<210> SEQ ID NO 4069

<400> SEQUENCE: 4069

000

<210> SEQ ID NO 4070

<400> SEQUENCE: 4070

000

<210> SEQ ID NO 4071

<400> SEQUENCE: 4071

000

<210> SEQ ID NO 4072

<400> SEQUENCE: 4072

000

<210> SEQ ID NO 4073

<400> SEQUENCE: 4073

000

<210> SEQ ID NO 4074

<400> SEQUENCE: 4074

000

<210> SEQ ID NO 4075

<400> SEQUENCE: 4075

000

<210> SEQ ID NO 4076

<400> SEQUENCE: 4076

000

<210> SEQ ID NO 4077

<400> SEQUENCE: 4077

000

<210> SEQ ID NO 4078

<400> SEQUENCE: 4078

000

<210> SEQ ID NO 4079

<400> SEQUENCE: 4079

000

<210> SEQ ID NO 4080

<400> SEQUENCE: 4080

000

<210> SEQ ID NO 4081

<400> SEQUENCE: 4081

000

<210> SEQ ID NO 4082

<400> SEQUENCE: 4082

000

<210> SEQ ID NO 4083

<400> SEQUENCE: 4083

000

<210> SEQ ID NO 4084

<400> SEQUENCE: 4084

000

<210> SEQ ID NO 4085

<400> SEQUENCE: 4085

000

<210> SEQ ID NO 4086

<400> SEQUENCE: 4086

000

<210> SEQ ID NO 4087

<400> SEQUENCE: 4087

000

<210> SEQ ID NO 4088

<400> SEQUENCE: 4088

000

<210> SEQ ID NO 4089

<400> SEQUENCE: 4089

000

<210> SEQ ID NO 4090

<400> SEQUENCE: 4090

000

<210> SEQ ID NO 4091

<400> SEQUENCE: 4091

000

<210> SEQ ID NO 4092

<400> SEQUENCE: 4092

000

<210> SEQ ID NO 4093

<400> SEQUENCE: 4093

000

<210> SEQ ID NO 4094

<400> SEQUENCE: 4094

000

<210> SEQ ID NO 4095

<400> SEQUENCE: 4095

000

<210> SEQ ID NO 4096

<400> SEQUENCE: 4096

000

<210> SEQ ID NO 4097

<400> SEQUENCE: 4097

000

<210> SEQ ID NO 4098

<400> SEQUENCE: 4098

000

<210> SEQ ID NO 4099

<400> SEQUENCE: 4099

000

<210> SEQ ID NO 4100

<400> SEQUENCE: 4100

000

<210> SEQ ID NO 4101

<400> SEQUENCE: 4101

000

<210> SEQ ID NO 4102

<400> SEQUENCE: 4102

000

<210> SEQ ID NO 4103

<400> SEQUENCE: 4103

000

<210> SEQ ID NO 4104

<400> SEQUENCE: 4104

000

<210> SEQ ID NO 4105

<400> SEQUENCE: 4105

000

<210> SEQ ID NO 4106

<400> SEQUENCE: 4106

000

<210> SEQ ID NO 4107

<400> SEQUENCE: 4107

000

<210> SEQ ID NO 4108

<400> SEQUENCE: 4108

000

<210> SEQ ID NO 4109

<400> SEQUENCE: 4109

000

<210> SEQ ID NO 4110

<400> SEQUENCE: 4110

000

<210> SEQ ID NO 4111

<400> SEQUENCE: 4111

000

<210> SEQ ID NO 4112

<400> SEQUENCE: 4112

000

<210> SEQ ID NO 4113

<400> SEQUENCE: 4113

000

<210> SEQ ID NO 4114

<400> SEQUENCE: 4114

000

<210> SEQ ID NO 4115

<400> SEQUENCE: 4115

000

<210> SEQ ID NO 4116

<400> SEQUENCE: 4116

000

<210> SEQ ID NO 4117

<400> SEQUENCE: 4117

000

<210> SEQ ID NO 4118

<400> SEQUENCE: 4118

000

<210> SEQ ID NO 4119

<400> SEQUENCE: 4119

000

<210> SEQ ID NO 4120

<400> SEQUENCE: 4120

000

<210> SEQ ID NO 4121

<400> SEQUENCE: 4121

000

<210> SEQ ID NO 4122

<400> SEQUENCE: 4122

000

<210> SEQ ID NO 4123

<400> SEQUENCE: 4123

000

<210> SEQ ID NO 4124

<400> SEQUENCE: 4124

000

<210> SEQ ID NO 4125

<400> SEQUENCE: 4125

000

<210> SEQ ID NO 4126

<400> SEQUENCE: 4126

000

<210> SEQ ID NO 4127

<400> SEQUENCE: 4127

000

<210> SEQ ID NO 4128

<400> SEQUENCE: 4128

000

<210> SEQ ID NO 4129

<400> SEQUENCE: 4129

000

<210> SEQ ID NO 4130

<400> SEQUENCE: 4130

000

<210> SEQ ID NO 4131

<400> SEQUENCE: 4131

000

<210> SEQ ID NO 4132

<400> SEQUENCE: 4132

000

<210> SEQ ID NO 4133

<400> SEQUENCE: 4133

000

<210> SEQ ID NO 4134

<400> SEQUENCE: 4134

000

<210> SEQ ID NO 4135

<400> SEQUENCE: 4135

000

<210> SEQ ID NO 4136

<400> SEQUENCE: 4136

000

<210> SEQ ID NO 4137

<400> SEQUENCE: 4137

000

<210> SEQ ID NO 4138

<400> SEQUENCE: 4138

000

<210> SEQ ID NO 4139

<400> SEQUENCE: 4139

000

<210> SEQ ID NO 4140

<400> SEQUENCE: 4140

000

<210> SEQ ID NO 4141

<400> SEQUENCE: 4141

000

<210> SEQ ID NO 4142

<400> SEQUENCE: 4142

000

<210> SEQ ID NO 4143

<400> SEQUENCE: 4143

000

<210> SEQ ID NO 4144

<400> SEQUENCE: 4144

000

<210> SEQ ID NO 4145

<400> SEQUENCE: 4145

-continued

000

<210> SEQ ID NO 4146
<400> SEQUENCE: 4146
000

<210> SEQ ID NO 4147
<400> SEQUENCE: 4147
000

<210> SEQ ID NO 4148
<400> SEQUENCE: 4148
000

<210> SEQ ID NO 4149
<400> SEQUENCE: 4149
000

<210> SEQ ID NO 4150
<400> SEQUENCE: 4150
000

<210> SEQ ID NO 4151
<400> SEQUENCE: 4151
000

<210> SEQ ID NO 4152
<400> SEQUENCE: 4152
000

<210> SEQ ID NO 4153
<400> SEQUENCE: 4153
000

<210> SEQ ID NO 4154
<400> SEQUENCE: 4154
000

<210> SEQ ID NO 4155
<400> SEQUENCE: 4155
000

<210> SEQ ID NO 4156
<400> SEQUENCE: 4156
000

<210> SEQ ID NO 4157

<400> SEQUENCE: 4157

000

<210> SEQ ID NO 4158

<400> SEQUENCE: 4158

000

<210> SEQ ID NO 4159

<400> SEQUENCE: 4159

000

<210> SEQ ID NO 4160

<400> SEQUENCE: 4160

000

<210> SEQ ID NO 4161

<400> SEQUENCE: 4161

000

<210> SEQ ID NO 4162

<400> SEQUENCE: 4162

000

<210> SEQ ID NO 4163

<400> SEQUENCE: 4163

000

<210> SEQ ID NO 4164

<400> SEQUENCE: 4164

000

<210> SEQ ID NO 4165

<400> SEQUENCE: 4165

000

<210> SEQ ID NO 4166

<400> SEQUENCE: 4166

000

<210> SEQ ID NO 4167

<400> SEQUENCE: 4167

000

<210> SEQ ID NO 4168

<400> SEQUENCE: 4168

000

<210> SEQ ID NO 4169

<400> SEQUENCE: 4169

000

<210> SEQ ID NO 4170

<400> SEQUENCE: 4170

000

<210> SEQ ID NO 4171

<400> SEQUENCE: 4171

000

<210> SEQ ID NO 4172

<400> SEQUENCE: 4172

000

<210> SEQ ID NO 4173

<400> SEQUENCE: 4173

000

<210> SEQ ID NO 4174

<400> SEQUENCE: 4174

000

<210> SEQ ID NO 4175

<400> SEQUENCE: 4175

000

<210> SEQ ID NO 4176

<400> SEQUENCE: 4176

000

<210> SEQ ID NO 4177

<400> SEQUENCE: 4177

000

<210> SEQ ID NO 4178

<400> SEQUENCE: 4178

000

<210> SEQ ID NO 4179

<400> SEQUENCE: 4179

000

<210> SEQ ID NO 4180

<400> SEQUENCE: 4180

000

<210> SEQ ID NO 4181

<400> SEQUENCE: 4181

000

<210> SEQ ID NO 4182

<400> SEQUENCE: 4182

000

<210> SEQ ID NO 4183

<400> SEQUENCE: 4183

000

<210> SEQ ID NO 4184

<400> SEQUENCE: 4184

000

<210> SEQ ID NO 4185

<400> SEQUENCE: 4185

000

<210> SEQ ID NO 4186

<400> SEQUENCE: 4186

000

<210> SEQ ID NO 4187

<400> SEQUENCE: 4187

000

<210> SEQ ID NO 4188

<400> SEQUENCE: 4188

000

<210> SEQ ID NO 4189

<400> SEQUENCE: 4189

000

<210> SEQ ID NO 4190

<400> SEQUENCE: 4190

000

<210> SEQ ID NO 4191

<400> SEQUENCE: 4191

000

<210> SEQ ID NO 4192

<400> SEQUENCE: 4192

000

<210> SEQ ID NO 4193

<400> SEQUENCE: 4193

000

<210> SEQ ID NO 4194

<400> SEQUENCE: 4194

000

<210> SEQ ID NO 4195

<400> SEQUENCE: 4195

000

<210> SEQ ID NO 4196

<400> SEQUENCE: 4196

000

<210> SEQ ID NO 4197

<400> SEQUENCE: 4197

000

<210> SEQ ID NO 4198

<400> SEQUENCE: 4198

000

<210> SEQ ID NO 4199

<400> SEQUENCE: 4199

000

<210> SEQ ID NO 4200

<400> SEQUENCE: 4200

000

<210> SEQ ID NO 4201

<400> SEQUENCE: 4201

000

<210> SEQ ID NO 4202

<400> SEQUENCE: 4202

000

<210> SEQ ID NO 4203

<400> SEQUENCE: 4203

000

<210> SEQ ID NO 4204

<400> SEQUENCE: 4204

000

<210> SEQ ID NO 4205

<400> SEQUENCE: 4205

000

<210> SEQ ID NO 4206

<400> SEQUENCE: 4206

000

<210> SEQ ID NO 4207

<400> SEQUENCE: 4207

000

<210> SEQ ID NO 4208

<400> SEQUENCE: 4208

000

<210> SEQ ID NO 4209

<400> SEQUENCE: 4209

000

<210> SEQ ID NO 4210

<400> SEQUENCE: 4210

000

<210> SEQ ID NO 4211

<400> SEQUENCE: 4211

000

<210> SEQ ID NO 4212

<400> SEQUENCE: 4212

000

<210> SEQ ID NO 4213

<400> SEQUENCE: 4213

000

<210> SEQ ID NO 4214

<400> SEQUENCE: 4214

000

<210> SEQ ID NO 4215

<400> SEQUENCE: 4215

000

<210> SEQ ID NO 4216

<400> SEQUENCE: 4216

000

<210> SEQ ID NO 4217

<400> SEQUENCE: 4217

000

<210> SEQ ID NO 4218

<400> SEQUENCE: 4218

000

<210> SEQ ID NO 4219

<400> SEQUENCE: 4219

000

<210> SEQ ID NO 4220

<400> SEQUENCE: 4220

000

<210> SEQ ID NO 4221

<400> SEQUENCE: 4221

000

<210> SEQ ID NO 4222

<400> SEQUENCE: 4222

000

<210> SEQ ID NO 4223

<400> SEQUENCE: 4223

000

<210> SEQ ID NO 4224

<400> SEQUENCE: 4224

000

<210> SEQ ID NO 4225

<400> SEQUENCE: 4225

000

<210> SEQ ID NO 4226

<400> SEQUENCE: 4226

000

<210> SEQ ID NO 4227

<400> SEQUENCE: 4227

000

<210> SEQ ID NO 4228

<400> SEQUENCE: 4228

000

<210> SEQ ID NO 4229

<400> SEQUENCE: 4229

000

<210> SEQ ID NO 4230

<400> SEQUENCE: 4230

000

<210> SEQ ID NO 4231

<400> SEQUENCE: 4231

000

<210> SEQ ID NO 4232

<400> SEQUENCE: 4232

000

<210> SEQ ID NO 4233

<400> SEQUENCE: 4233

000

<210> SEQ ID NO 4234

<400> SEQUENCE: 4234

000

<210> SEQ ID NO 4235

<400> SEQUENCE: 4235

000

<210> SEQ ID NO 4236

<400> SEQUENCE: 4236

000

<210> SEQ ID NO 4237

<400> SEQUENCE: 4237

000

<210> SEQ ID NO 4238

<400> SEQUENCE: 4238

000

<210> SEQ ID NO 4239

<400> SEQUENCE: 4239

000

<210> SEQ ID NO 4240

<400> SEQUENCE: 4240

000

<210> SEQ ID NO 4241

<400> SEQUENCE: 4241

000

<210> SEQ ID NO 4242

<400> SEQUENCE: 4242

000

<210> SEQ ID NO 4243

<400> SEQUENCE: 4243

000

<210> SEQ ID NO 4244

<400> SEQUENCE: 4244

000

<210> SEQ ID NO 4245

<400> SEQUENCE: 4245

000

<210> SEQ ID NO 4246

<400> SEQUENCE: 4246

000

<210> SEQ ID NO 4247

<400> SEQUENCE: 4247

000

<210> SEQ ID NO 4248

<400> SEQUENCE: 4248

000

<210> SEQ ID NO 4249

<400> SEQUENCE: 4249

000

<210> SEQ ID NO 4250

<400> SEQUENCE: 4250

000

<210> SEQ ID NO 4251

<400> SEQUENCE: 4251

000

<210> SEQ ID NO 4252

<400> SEQUENCE: 4252

000

<210> SEQ ID NO 4253

<400> SEQUENCE: 4253

000

<210> SEQ ID NO 4254

<400> SEQUENCE: 4254

000

<210> SEQ ID NO 4255

<400> SEQUENCE: 4255

000

<210> SEQ ID NO 4256

<400> SEQUENCE: 4256

000

<210> SEQ ID NO 4257

<400> SEQUENCE: 4257

000

<210> SEQ ID NO 4258

<400> SEQUENCE: 4258

000

<210> SEQ ID NO 4259

<400> SEQUENCE: 4259

000

<210> SEQ ID NO 4260

<400> SEQUENCE: 4260

000

<210> SEQ ID NO 4261

<400> SEQUENCE: 4261

000

<210> SEQ ID NO 4262

<400> SEQUENCE: 4262

000

<210> SEQ ID NO 4263

<400> SEQUENCE: 4263

000

<210> SEQ ID NO 4264

<400> SEQUENCE: 4264

000

<210> SEQ ID NO 4265

<400> SEQUENCE: 4265

000

<210> SEQ ID NO 4266

<400> SEQUENCE: 4266

000

<210> SEQ ID NO 4267

<400> SEQUENCE: 4267

000

<210> SEQ ID NO 4268

<400> SEQUENCE: 4268

000

<210> SEQ ID NO 4269

<400> SEQUENCE: 4269

000

<210> SEQ ID NO 4270

<400> SEQUENCE: 4270

000

<210> SEQ ID NO 4271

<400> SEQUENCE: 4271

000

<210> SEQ ID NO 4272

<400> SEQUENCE: 4272

000

<210> SEQ ID NO 4273

<400> SEQUENCE: 4273

000

<210> SEQ ID NO 4274

<400> SEQUENCE: 4274

000

<210> SEQ ID NO 4275

<400> SEQUENCE: 4275

000

<210> SEQ ID NO 4276

<400> SEQUENCE: 4276

000

<210> SEQ ID NO 4277

<400> SEQUENCE: 4277

000

<210> SEQ ID NO 4278

<400> SEQUENCE: 4278

000

<210> SEQ ID NO 4279

<400> SEQUENCE: 4279

000

<210> SEQ ID NO 4280

<400> SEQUENCE: 4280

000

<210> SEQ ID NO 4281

<400> SEQUENCE: 4281

000

<210> SEQ ID NO 4282

<400> SEQUENCE: 4282

000

<210> SEQ ID NO 4283

<400> SEQUENCE: 4283

000

<210> SEQ ID NO 4284

<400> SEQUENCE: 4284

000

<210> SEQ ID NO 4285

<400> SEQUENCE: 4285

000

<210> SEQ ID NO 4286

<400> SEQUENCE: 4286

000

<210> SEQ ID NO 4287

<400> SEQUENCE: 4287

000

<210> SEQ ID NO 4288

<400> SEQUENCE: 4288

000

<210> SEQ ID NO 4289

<400> SEQUENCE: 4289

000

<210> SEQ ID NO 4290

<400> SEQUENCE: 4290

000

<210> SEQ ID NO 4291

<400> SEQUENCE: 4291

000

<210> SEQ ID NO 4292

<400> SEQUENCE: 4292

000

<210> SEQ ID NO 4293

<400> SEQUENCE: 4293

000

<210> SEQ ID NO 4294

<400> SEQUENCE: 4294

000

<210> SEQ ID NO 4295

<400> SEQUENCE: 4295

000

<210> SEQ ID NO 4296

<400> SEQUENCE: 4296

000

<210> SEQ ID NO 4297

<400> SEQUENCE: 4297

000

<210> SEQ ID NO 4298

<400> SEQUENCE: 4298

000

<210> SEQ ID NO 4299

<400> SEQUENCE: 4299

000

<210> SEQ ID NO 4300

<400> SEQUENCE: 4300

000

<210> SEQ ID NO 4301

<400> SEQUENCE: 4301

000

<210> SEQ ID NO 4302

<400> SEQUENCE: 4302

000

<210> SEQ ID NO 4303

<400> SEQUENCE: 4303

000

<210> SEQ ID NO 4304

<400> SEQUENCE: 4304

000

<210> SEQ ID NO 4305

<400> SEQUENCE: 4305

000

<210> SEQ ID NO 4306

<400> SEQUENCE: 4306

000

<210> SEQ ID NO 4307

<400> SEQUENCE: 4307

000

<210> SEQ ID NO 4308

<400> SEQUENCE: 4308

000

<210> SEQ ID NO 4309

<400> SEQUENCE: 4309

000

<210> SEQ ID NO 4310

<400> SEQUENCE: 4310

000

<210> SEQ ID NO 4311

<400> SEQUENCE: 4311

000

<210> SEQ ID NO 4312

<400> SEQUENCE: 4312

000

<210> SEQ ID NO 4313

<400> SEQUENCE: 4313

000

<210> SEQ ID NO 4314

<400> SEQUENCE: 4314

000

<210> SEQ ID NO 4315

<400> SEQUENCE: 4315

000

<210> SEQ ID NO 4316

<400> SEQUENCE: 4316

000

<210> SEQ ID NO 4317

<400> SEQUENCE: 4317

000

<210> SEQ ID NO 4318

<400> SEQUENCE: 4318

000

<210> SEQ ID NO 4319

<400> SEQUENCE: 4319

000

<210> SEQ ID NO 4320

<400> SEQUENCE: 4320

000

<210> SEQ ID NO 4321

<400> SEQUENCE: 4321

000

<210> SEQ ID NO 4322

<400> SEQUENCE: 4322

000

<210> SEQ ID NO 4323

<400> SEQUENCE: 4323

000

<210> SEQ ID NO 4324

<400> SEQUENCE: 4324

000

<210> SEQ ID NO 4325

<400> SEQUENCE: 4325

000

<210> SEQ ID NO 4326

<400> SEQUENCE: 4326

000

<210> SEQ ID NO 4327

<400> SEQUENCE: 4327

000

<210> SEQ ID NO 4328

<400> SEQUENCE: 4328

000

<210> SEQ ID NO 4329

<400> SEQUENCE: 4329

000

<210> SEQ ID NO 4330

<400> SEQUENCE: 4330

000

<210> SEQ ID NO 4331

<400> SEQUENCE: 4331

000

<210> SEQ ID NO 4332

<400> SEQUENCE: 4332

000

<210> SEQ ID NO 4333

<400> SEQUENCE: 4333

000

<210> SEQ ID NO 4334

<400> SEQUENCE: 4334

000

<210> SEQ ID NO 4335

<400> SEQUENCE: 4335

000

<210> SEQ ID NO 4336

<400> SEQUENCE: 4336

000

<210> SEQ ID NO 4337

<400> SEQUENCE: 4337

000

<210> SEQ ID NO 4338

<400> SEQUENCE: 4338

000

<210> SEQ ID NO 4339

<400> SEQUENCE: 4339

000

<210> SEQ ID NO 4340

<400> SEQUENCE: 4340

000

<210> SEQ ID NO 4341

<400> SEQUENCE: 4341

000

<210> SEQ ID NO 4342

<400> SEQUENCE: 4342

000

<210> SEQ ID NO 4343

<400> SEQUENCE: 4343

000

<210> SEQ ID NO 4344

<400> SEQUENCE: 4344

000

<210> SEQ ID NO 4345

<400> SEQUENCE: 4345

000

<210> SEQ ID NO 4346

<400> SEQUENCE: 4346

000

<210> SEQ ID NO 4347

<400> SEQUENCE: 4347

000

<210> SEQ ID NO 4348

<400> SEQUENCE: 4348

-continued

000

<210> SEQ ID NO 4349

<400> SEQUENCE: 4349

000

<210> SEQ ID NO 4350

<400> SEQUENCE: 4350

000

<210> SEQ ID NO 4351

<400> SEQUENCE: 4351

000

<210> SEQ ID NO 4352

<400> SEQUENCE: 4352

000

<210> SEQ ID NO 4353

<400> SEQUENCE: 4353

000

<210> SEQ ID NO 4354

<400> SEQUENCE: 4354

000

<210> SEQ ID NO 4355

<400> SEQUENCE: 4355

000

<210> SEQ ID NO 4356

<400> SEQUENCE: 4356

000

<210> SEQ ID NO 4357

<400> SEQUENCE: 4357

000

<210> SEQ ID NO 4358

<400> SEQUENCE: 4358

000

<210> SEQ ID NO 4359

<400> SEQUENCE: 4359

000

<210> SEQ ID NO 4360

<400> SEQUENCE: 4360

000

<210> SEQ ID NO 4361

<400> SEQUENCE: 4361

000

<210> SEQ ID NO 4362

<400> SEQUENCE: 4362

000

<210> SEQ ID NO 4363

<400> SEQUENCE: 4363

000

<210> SEQ ID NO 4364

<400> SEQUENCE: 4364

000

<210> SEQ ID NO 4365

<400> SEQUENCE: 4365

000

<210> SEQ ID NO 4366

<400> SEQUENCE: 4366

000

<210> SEQ ID NO 4367

<400> SEQUENCE: 4367

000

<210> SEQ ID NO 4368

<400> SEQUENCE: 4368

000

<210> SEQ ID NO 4369

<400> SEQUENCE: 4369

000

<210> SEQ ID NO 4370

<400> SEQUENCE: 4370

000

<210> SEQ ID NO 4371

<400> SEQUENCE: 4371

000

<210> SEQ ID NO 4372

<400> SEQUENCE: 4372

000

<210> SEQ ID NO 4373

<400> SEQUENCE: 4373

000

<210> SEQ ID NO 4374

<400> SEQUENCE: 4374

000

<210> SEQ ID NO 4375

<400> SEQUENCE: 4375

000

<210> SEQ ID NO 4376

<400> SEQUENCE: 4376

000

<210> SEQ ID NO 4377

<400> SEQUENCE: 4377

000

<210> SEQ ID NO 4378

<400> SEQUENCE: 4378

000

<210> SEQ ID NO 4379

<400> SEQUENCE: 4379

000

<210> SEQ ID NO 4380

<400> SEQUENCE: 4380

000

<210> SEQ ID NO 4381

<400> SEQUENCE: 4381

000

<210> SEQ ID NO 4382

<400> SEQUENCE: 4382

000

<210> SEQ ID NO 4383
<400> SEQUENCE: 4383
000

<210> SEQ ID NO 4384
<400> SEQUENCE: 4384
000

<210> SEQ ID NO 4385
<400> SEQUENCE: 4385
000

<210> SEQ ID NO 4386
<400> SEQUENCE: 4386
000

<210> SEQ ID NO 4387
<400> SEQUENCE: 4387
000

<210> SEQ ID NO 4388
<400> SEQUENCE: 4388
000

<210> SEQ ID NO 4389
<400> SEQUENCE: 4389
000

<210> SEQ ID NO 4390
<400> SEQUENCE: 4390
000

<210> SEQ ID NO 4391
<400> SEQUENCE: 4391
000

<210> SEQ ID NO 4392
<400> SEQUENCE: 4392
000

<210> SEQ ID NO 4393
<400> SEQUENCE: 4393
000

<210> SEQ ID NO 4394

<400> SEQUENCE: 4394

000

<210> SEQ ID NO 4395

<400> SEQUENCE: 4395

000

<210> SEQ ID NO 4396

<400> SEQUENCE: 4396

000

<210> SEQ ID NO 4397

<400> SEQUENCE: 4397

000

<210> SEQ ID NO 4398

<400> SEQUENCE: 4398

000

<210> SEQ ID NO 4399

<400> SEQUENCE: 4399

000

<210> SEQ ID NO 4400

<400> SEQUENCE: 4400

000

<210> SEQ ID NO 4401

<400> SEQUENCE: 4401

000

<210> SEQ ID NO 4402

<400> SEQUENCE: 4402

000

<210> SEQ ID NO 4403

<400> SEQUENCE: 4403

000

<210> SEQ ID NO 4404

<400> SEQUENCE: 4404

000

<210> SEQ ID NO 4405

<400> SEQUENCE: 4405

000

<210> SEQ ID NO 4406

<400> SEQUENCE: 4406

000

<210> SEQ ID NO 4407

<400> SEQUENCE: 4407

000

<210> SEQ ID NO 4408

<400> SEQUENCE: 4408

000

<210> SEQ ID NO 4409

<400> SEQUENCE: 4409

000

<210> SEQ ID NO 4410

<400> SEQUENCE: 4410

000

<210> SEQ ID NO 4411

<400> SEQUENCE: 4411

000

<210> SEQ ID NO 4412

<400> SEQUENCE: 4412

000

<210> SEQ ID NO 4413

<400> SEQUENCE: 4413

000

<210> SEQ ID NO 4414

<400> SEQUENCE: 4414

000

<210> SEQ ID NO 4415

<400> SEQUENCE: 4415

000

<210> SEQ ID NO 4416

<400> SEQUENCE: 4416

000

<210> SEQ ID NO 4417

<400> SEQUENCE: 4417

000

<210> SEQ ID NO 4418

<400> SEQUENCE: 4418

000

<210> SEQ ID NO 4419

<400> SEQUENCE: 4419

000

<210> SEQ ID NO 4420

<400> SEQUENCE: 4420

000

<210> SEQ ID NO 4421

<400> SEQUENCE: 4421

000

<210> SEQ ID NO 4422

<400> SEQUENCE: 4422

000

<210> SEQ ID NO 4423

<400> SEQUENCE: 4423

000

<210> SEQ ID NO 4424

<400> SEQUENCE: 4424

000

<210> SEQ ID NO 4425

<400> SEQUENCE: 4425

000

<210> SEQ ID NO 4426

<400> SEQUENCE: 4426

000

<210> SEQ ID NO 4427

<400> SEQUENCE: 4427

000

<210> SEQ ID NO 4428

<400> SEQUENCE: 4428

000

<210> SEQ ID NO 4429

<400> SEQUENCE: 4429

000

<210> SEQ ID NO 4430

<400> SEQUENCE: 4430

000

<210> SEQ ID NO 4431

<400> SEQUENCE: 4431

000

<210> SEQ ID NO 4432

<400> SEQUENCE: 4432

000

<210> SEQ ID NO 4433

<400> SEQUENCE: 4433

000

<210> SEQ ID NO 4434

<400> SEQUENCE: 4434

000

<210> SEQ ID NO 4435

<400> SEQUENCE: 4435

000

<210> SEQ ID NO 4436

<400> SEQUENCE: 4436

000

<210> SEQ ID NO 4437

<400> SEQUENCE: 4437

000

<210> SEQ ID NO 4438

<400> SEQUENCE: 4438

000

<210> SEQ ID NO 4439

<400> SEQUENCE: 4439

000

<210> SEQ ID NO 4440

<400> SEQUENCE: 4440

000

<210> SEQ ID NO 4441

<400> SEQUENCE: 4441

000

<210> SEQ ID NO 4442

<400> SEQUENCE: 4442

000

<210> SEQ ID NO 4443

<400> SEQUENCE: 4443

000

<210> SEQ ID NO 4444

<400> SEQUENCE: 4444

000

<210> SEQ ID NO 4445

<400> SEQUENCE: 4445

000

<210> SEQ ID NO 4446

<400> SEQUENCE: 4446

000

<210> SEQ ID NO 4447

<400> SEQUENCE: 4447

000

<210> SEQ ID NO 4448

<400> SEQUENCE: 4448

000

<210> SEQ ID NO 4449

<400> SEQUENCE: 4449

000

<210> SEQ ID NO 4450

<400> SEQUENCE: 4450

000

<210> SEQ ID NO 4451

<400> SEQUENCE: 4451

000

<210> SEQ ID NO 4452

<400> SEQUENCE: 4452

000

<210> SEQ ID NO 4453

<400> SEQUENCE: 4453

000

<210> SEQ ID NO 4454

<400> SEQUENCE: 4454

000

<210> SEQ ID NO 4455

<400> SEQUENCE: 4455

000

<210> SEQ ID NO 4456

<400> SEQUENCE: 4456

000

<210> SEQ ID NO 4457

<400> SEQUENCE: 4457

000

<210> SEQ ID NO 4458

<400> SEQUENCE: 4458

000

<210> SEQ ID NO 4459

<400> SEQUENCE: 4459

000

<210> SEQ ID NO 4460

<400> SEQUENCE: 4460

000

<210> SEQ ID NO 4461

<400> SEQUENCE: 4461

000

<210> SEQ ID NO 4462

<400> SEQUENCE: 4462

000

<210> SEQ ID NO 4463

<400> SEQUENCE: 4463

000

<210> SEQ ID NO 4464

<400> SEQUENCE: 4464

000

<210> SEQ ID NO 4465

<400> SEQUENCE: 4465

000

<210> SEQ ID NO 4466

<400> SEQUENCE: 4466

000

<210> SEQ ID NO 4467

<400> SEQUENCE: 4467

000

<210> SEQ ID NO 4468

<400> SEQUENCE: 4468

000

<210> SEQ ID NO 4469

<400> SEQUENCE: 4469

000

<210> SEQ ID NO 4470

<400> SEQUENCE: 4470

000

<210> SEQ ID NO 4471

<400> SEQUENCE: 4471

000

<210> SEQ ID NO 4472

<400> SEQUENCE: 4472

000

<210> SEQ ID NO 4473

<400> SEQUENCE: 4473

000

<210> SEQ ID NO 4474

<400> SEQUENCE: 4474

000

<210> SEQ ID NO 4475

<400> SEQUENCE: 4475

000

<210> SEQ ID NO 4476

<400> SEQUENCE: 4476

000

<210> SEQ ID NO 4477

<400> SEQUENCE: 4477

000

<210> SEQ ID NO 4478

<400> SEQUENCE: 4478

000

<210> SEQ ID NO 4479

<400> SEQUENCE: 4479

000

<210> SEQ ID NO 4480

<400> SEQUENCE: 4480

000

<210> SEQ ID NO 4481

<400> SEQUENCE: 4481

000

<210> SEQ ID NO 4482

<400> SEQUENCE: 4482

000

<210> SEQ ID NO 4483

<400> SEQUENCE: 4483

000

<210> SEQ ID NO 4484

<400> SEQUENCE: 4484

000

<210> SEQ ID NO 4485

<400> SEQUENCE: 4485

000

<210> SEQ ID NO 4486

<400> SEQUENCE: 4486

000

<210> SEQ ID NO 4487

<400> SEQUENCE: 4487

000

<210> SEQ ID NO 4488

<400> SEQUENCE: 4488

000

<210> SEQ ID NO 4489

<400> SEQUENCE: 4489

000

<210> SEQ ID NO 4490

<400> SEQUENCE: 4490

000

<210> SEQ ID NO 4491

<400> SEQUENCE: 4491

000

<210> SEQ ID NO 4492

<400> SEQUENCE: 4492

000

<210> SEQ ID NO 4493

<400> SEQUENCE: 4493

000

<210> SEQ ID NO 4494

<400> SEQUENCE: 4494

000

<210> SEQ ID NO 4495

<400> SEQUENCE: 4495

000

<210> SEQ ID NO 4496

<400> SEQUENCE: 4496

000

<210> SEQ ID NO 4497

<400> SEQUENCE: 4497

000

<210> SEQ ID NO 4498

<400> SEQUENCE: 4498

000

<210> SEQ ID NO 4499

<400> SEQUENCE: 4499

000

<210> SEQ ID NO 4500

<400> SEQUENCE: 4500

000

<210> SEQ ID NO 4501

<400> SEQUENCE: 4501

000

<210> SEQ ID NO 4502

<400> SEQUENCE: 4502

000

<210> SEQ ID NO 4503

<400> SEQUENCE: 4503

000

<210> SEQ ID NO 4504

<400> SEQUENCE: 4504

000

<210> SEQ ID NO 4505

<400> SEQUENCE: 4505

000

<210> SEQ ID NO 4506

<400> SEQUENCE: 4506

000

<210> SEQ ID NO 4507

<400> SEQUENCE: 4507

000

<210> SEQ ID NO 4508

<400> SEQUENCE: 4508

000

<210> SEQ ID NO 4509

<400> SEQUENCE: 4509

000

<210> SEQ ID NO 4510

<400> SEQUENCE: 4510

000

<210> SEQ ID NO 4511

<400> SEQUENCE: 4511

000

<210> SEQ ID NO 4512

<400> SEQUENCE: 4512

000

<210> SEQ ID NO 4513

<400> SEQUENCE: 4513

000

<210> SEQ ID NO 4514

<400> SEQUENCE: 4514

000

<210> SEQ ID NO 4515

<400> SEQUENCE: 4515

000

<210> SEQ ID NO 4516

<400> SEQUENCE: 4516

000

<210> SEQ ID NO 4517

<400> SEQUENCE: 4517

000

<210> SEQ ID NO 4518

<400> SEQUENCE: 4518

000

<210> SEQ ID NO 4519

<400> SEQUENCE: 4519

000

<210> SEQ ID NO 4520

<400> SEQUENCE: 4520

000

<210> SEQ ID NO 4521

<400> SEQUENCE: 4521

000

<210> SEQ ID NO 4522

<400> SEQUENCE: 4522

000

<210> SEQ ID NO 4523

<400> SEQUENCE: 4523

000

<210> SEQ ID NO 4524

<400> SEQUENCE: 4524

000

<210> SEQ ID NO 4525

<400> SEQUENCE: 4525

000

<210> SEQ ID NO 4526

<400> SEQUENCE: 4526

000

<210> SEQ ID NO 4527

<400> SEQUENCE: 4527

000

<210> SEQ ID NO 4528

<400> SEQUENCE: 4528

000

<210> SEQ ID NO 4529

<400> SEQUENCE: 4529

000

<210> SEQ ID NO 4530

<400> SEQUENCE: 4530

000

<210> SEQ ID NO 4531

<400> SEQUENCE: 4531

000

<210> SEQ ID NO 4532

<400> SEQUENCE: 4532

000

<210> SEQ ID NO 4533

<400> SEQUENCE: 4533

000

<210> SEQ ID NO 4534

<400> SEQUENCE: 4534

000

<210> SEQ ID NO 4535

<400> SEQUENCE: 4535

000

<210> SEQ ID NO 4536

<400> SEQUENCE: 4536

000

<210> SEQ ID NO 4537

<400> SEQUENCE: 4537

000

<210> SEQ ID NO 4538

<400> SEQUENCE: 4538

000

<210> SEQ ID NO 4539

<400> SEQUENCE: 4539

000

<210> SEQ ID NO 4540

<400> SEQUENCE: 4540

-continued

000

<210> SEQ ID NO 4541

<400> SEQUENCE: 4541

000

<210> SEQ ID NO 4542

<400> SEQUENCE: 4542

000

<210> SEQ ID NO 4543

<400> SEQUENCE: 4543

000

<210> SEQ ID NO 4544

<400> SEQUENCE: 4544

000

<210> SEQ ID NO 4545

<400> SEQUENCE: 4545

000

<210> SEQ ID NO 4546

<400> SEQUENCE: 4546

000

<210> SEQ ID NO 4547

<400> SEQUENCE: 4547

000

<210> SEQ ID NO 4548

<400> SEQUENCE: 4548

000

<210> SEQ ID NO 4549

<400> SEQUENCE: 4549

000

<210> SEQ ID NO 4550

<400> SEQUENCE: 4550

000

<210> SEQ ID NO 4551

<400> SEQUENCE: 4551

000

<210> SEQ ID NO 4552

<400> SEQUENCE: 4552

000

<210> SEQ ID NO 4553

<400> SEQUENCE: 4553

000

<210> SEQ ID NO 4554

<400> SEQUENCE: 4554

000

<210> SEQ ID NO 4555

<400> SEQUENCE: 4555

000

<210> SEQ ID NO 4556

<400> SEQUENCE: 4556

000

<210> SEQ ID NO 4557

<400> SEQUENCE: 4557

000

<210> SEQ ID NO 4558

<400> SEQUENCE: 4558

000

<210> SEQ ID NO 4559

<400> SEQUENCE: 4559

000

<210> SEQ ID NO 4560

<400> SEQUENCE: 4560

000

<210> SEQ ID NO 4561

<400> SEQUENCE: 4561

000

<210> SEQ ID NO 4562

<400> SEQUENCE: 4562

000

<210> SEQ ID NO 4563

<400> SEQUENCE: 4563

000

<210> SEQ ID NO 4564

<400> SEQUENCE: 4564

000

<210> SEQ ID NO 4565

<400> SEQUENCE: 4565

000

<210> SEQ ID NO 4566

<400> SEQUENCE: 4566

000

<210> SEQ ID NO 4567

<400> SEQUENCE: 4567

000

<210> SEQ ID NO 4568

<400> SEQUENCE: 4568

000

<210> SEQ ID NO 4569

<400> SEQUENCE: 4569

000

<210> SEQ ID NO 4570

<400> SEQUENCE: 4570

000

<210> SEQ ID NO 4571

<400> SEQUENCE: 4571

000

<210> SEQ ID NO 4572

<400> SEQUENCE: 4572

000

<210> SEQ ID NO 4573

<400> SEQUENCE: 4573

000

<210> SEQ ID NO 4574

<400> SEQUENCE: 4574

000

<210> SEQ ID NO 4575

<400> SEQUENCE: 4575

000

<210> SEQ ID NO 4576

<400> SEQUENCE: 4576

000

<210> SEQ ID NO 4577

<400> SEQUENCE: 4577

000

<210> SEQ ID NO 4578

<400> SEQUENCE: 4578

000

<210> SEQ ID NO 4579

<400> SEQUENCE: 4579

000

<210> SEQ ID NO 4580

<400> SEQUENCE: 4580

000

<210> SEQ ID NO 4581

<400> SEQUENCE: 4581

000

<210> SEQ ID NO 4582

<400> SEQUENCE: 4582

000

<210> SEQ ID NO 4583

<400> SEQUENCE: 4583

000

<210> SEQ ID NO 4584

<400> SEQUENCE: 4584

000

<210> SEQ ID NO 4585

<400> SEQUENCE: 4585

000

<210> SEQ ID NO 4586

<400> SEQUENCE: 4586

000

<210> SEQ ID NO 4587

<400> SEQUENCE: 4587

000

<210> SEQ ID NO 4588

<400> SEQUENCE: 4588

000

<210> SEQ ID NO 4589

<400> SEQUENCE: 4589

000

<210> SEQ ID NO 4590

<400> SEQUENCE: 4590

000

<210> SEQ ID NO 4591

<400> SEQUENCE: 4591

000

<210> SEQ ID NO 4592

<400> SEQUENCE: 4592

000

<210> SEQ ID NO 4593

<400> SEQUENCE: 4593

000

<210> SEQ ID NO 4594

<400> SEQUENCE: 4594

000

<210> SEQ ID NO 4595

<400> SEQUENCE: 4595

000

<210> SEQ ID NO 4596

<400> SEQUENCE: 4596

000

<210> SEQ ID NO 4597

<400> SEQUENCE: 4597

000

<210> SEQ ID NO 4598

<400> SEQUENCE: 4598

000

<210> SEQ ID NO 4599

<400> SEQUENCE: 4599

000

<210> SEQ ID NO 4600

<400> SEQUENCE: 4600

000

<210> SEQ ID NO 4601

<400> SEQUENCE: 4601

000

<210> SEQ ID NO 4602

<400> SEQUENCE: 4602

000

<210> SEQ ID NO 4603

<400> SEQUENCE: 4603

000

<210> SEQ ID NO 4604

<400> SEQUENCE: 4604

000

<210> SEQ ID NO 4605

<400> SEQUENCE: 4605

000

<210> SEQ ID NO 4606

<400> SEQUENCE: 4606

000

<210> SEQ ID NO 4607

<400> SEQUENCE: 4607

000

<210> SEQ ID NO 4608

<400> SEQUENCE: 4608

000

<210> SEQ ID NO 4609

<400> SEQUENCE: 4609

000

<210> SEQ ID NO 4610

<400> SEQUENCE: 4610

000

<210> SEQ ID NO 4611

<400> SEQUENCE: 4611

000

<210> SEQ ID NO 4612

<400> SEQUENCE: 4612

000

<210> SEQ ID NO 4613

<400> SEQUENCE: 4613

000

<210> SEQ ID NO 4614

<400> SEQUENCE: 4614

000

<210> SEQ ID NO 4615

<400> SEQUENCE: 4615

000

<210> SEQ ID NO 4616

<400> SEQUENCE: 4616

000

<210> SEQ ID NO 4617

<400> SEQUENCE: 4617

000

<210> SEQ ID NO 4618

<400> SEQUENCE: 4618

000

<210> SEQ ID NO 4619

<400> SEQUENCE: 4619

-continued

000

<210> SEQ ID NO 4620

<400> SEQUENCE: 4620

000

<210> SEQ ID NO 4621

<400> SEQUENCE: 4621

000

<210> SEQ ID NO 4622

<400> SEQUENCE: 4622

000

<210> SEQ ID NO 4623

<400> SEQUENCE: 4623

000

<210> SEQ ID NO 4624

<400> SEQUENCE: 4624

000

<210> SEQ ID NO 4625

<400> SEQUENCE: 4625

000

<210> SEQ ID NO 4626

<400> SEQUENCE: 4626

000

<210> SEQ ID NO 4627

<400> SEQUENCE: 4627

000

<210> SEQ ID NO 4628

<400> SEQUENCE: 4628

000

<210> SEQ ID NO 4629

<400> SEQUENCE: 4629

000

<210> SEQ ID NO 4630

<400> SEQUENCE: 4630

000

<210> SEQ ID NO 4631

<400> SEQUENCE: 4631

000

<210> SEQ ID NO 4632

<400> SEQUENCE: 4632

000

<210> SEQ ID NO 4633

<400> SEQUENCE: 4633

000

<210> SEQ ID NO 4634

<400> SEQUENCE: 4634

000

<210> SEQ ID NO 4635

<400> SEQUENCE: 4635

000

<210> SEQ ID NO 4636

<400> SEQUENCE: 4636

000

<210> SEQ ID NO 4637

<400> SEQUENCE: 4637

000

<210> SEQ ID NO 4638

<400> SEQUENCE: 4638

000

<210> SEQ ID NO 4639

<400> SEQUENCE: 4639

000

<210> SEQ ID NO 4640

<400> SEQUENCE: 4640

000

<210> SEQ ID NO 4641

<400> SEQUENCE: 4641

000

<210> SEQ ID NO 4642

<400> SEQUENCE: 4642

000

<210> SEQ ID NO 4643

<400> SEQUENCE: 4643

000

<210> SEQ ID NO 4644

<400> SEQUENCE: 4644

000

<210> SEQ ID NO 4645

<400> SEQUENCE: 4645

000

<210> SEQ ID NO 4646

<400> SEQUENCE: 4646

000

<210> SEQ ID NO 4647

<400> SEQUENCE: 4647

000

<210> SEQ ID NO 4648

<400> SEQUENCE: 4648

000

<210> SEQ ID NO 4649

<400> SEQUENCE: 4649

000

<210> SEQ ID NO 4650

<400> SEQUENCE: 4650

000

<210> SEQ ID NO 4651

<400> SEQUENCE: 4651

000

<210> SEQ ID NO 4652

<400> SEQUENCE: 4652

000

<210> SEQ ID NO 4653

<400> SEQUENCE: 4653

000

<210> SEQ ID NO 4654

<400> SEQUENCE: 4654

000

<210> SEQ ID NO 4655

<400> SEQUENCE: 4655

000

<210> SEQ ID NO 4656

<400> SEQUENCE: 4656

000

<210> SEQ ID NO 4657

<400> SEQUENCE: 4657

000

<210> SEQ ID NO 4658

<400> SEQUENCE: 4658

000

<210> SEQ ID NO 4659

<400> SEQUENCE: 4659

000

<210> SEQ ID NO 4660

<400> SEQUENCE: 4660

000

<210> SEQ ID NO 4661

<400> SEQUENCE: 4661

000

<210> SEQ ID NO 4662

<400> SEQUENCE: 4662

000

<210> SEQ ID NO 4663

<400> SEQUENCE: 4663

000

<210> SEQ ID NO 4664

<400> SEQUENCE: 4664

000

<210> SEQ ID NO 4665

<400> SEQUENCE: 4665

000

<210> SEQ ID NO 4666

<400> SEQUENCE: 4666

000

<210> SEQ ID NO 4667

<400> SEQUENCE: 4667

000

<210> SEQ ID NO 4668

<400> SEQUENCE: 4668

000

<210> SEQ ID NO 4669

<400> SEQUENCE: 4669

000

<210> SEQ ID NO 4670

<400> SEQUENCE: 4670

000

<210> SEQ ID NO 4671

<400> SEQUENCE: 4671

000

<210> SEQ ID NO 4672

<400> SEQUENCE: 4672

000

<210> SEQ ID NO 4673

<400> SEQUENCE: 4673

000

<210> SEQ ID NO 4674

<400> SEQUENCE: 4674

000

<210> SEQ ID NO 4675

<400> SEQUENCE: 4675

000

<210> SEQ ID NO 4676

<400> SEQUENCE: 4676

000

<210> SEQ ID NO 4677

<400> SEQUENCE: 4677

000

<210> SEQ ID NO 4678

<400> SEQUENCE: 4678

000

<210> SEQ ID NO 4679

<400> SEQUENCE: 4679

000

<210> SEQ ID NO 4680

<400> SEQUENCE: 4680

000

<210> SEQ ID NO 4681

<400> SEQUENCE: 4681

000

<210> SEQ ID NO 4682

<400> SEQUENCE: 4682

000

<210> SEQ ID NO 4683

<400> SEQUENCE: 4683

000

<210> SEQ ID NO 4684

<400> SEQUENCE: 4684

000

<210> SEQ ID NO 4685

<400> SEQUENCE: 4685

000

<210> SEQ ID NO 4686

<400> SEQUENCE: 4686

000

<210> SEQ ID NO 4687

<400> SEQUENCE: 4687

000

<210> SEQ ID NO 4688

<400> SEQUENCE: 4688

000

<210> SEQ ID NO 4689

<400> SEQUENCE: 4689

000

<210> SEQ ID NO 4690

<400> SEQUENCE: 4690

000

<210> SEQ ID NO 4691

<400> SEQUENCE: 4691

000

<210> SEQ ID NO 4692

<400> SEQUENCE: 4692

000

<210> SEQ ID NO 4693

<400> SEQUENCE: 4693

000

<210> SEQ ID NO 4694

<400> SEQUENCE: 4694

000

<210> SEQ ID NO 4695

<400> SEQUENCE: 4695

000

<210> SEQ ID NO 4696

<400> SEQUENCE: 4696

000

<210> SEQ ID NO 4697

<400> SEQUENCE: 4697

000

<210> SEQ ID NO 4698

<400> SEQUENCE: 4698

000

<210> SEQ ID NO 4699

<400> SEQUENCE: 4699

000

<210> SEQ ID NO 4700

<400> SEQUENCE: 4700

000

<210> SEQ ID NO 4701

<400> SEQUENCE: 4701

000

<210> SEQ ID NO 4702

<400> SEQUENCE: 4702

000

<210> SEQ ID NO 4703

<400> SEQUENCE: 4703

000

<210> SEQ ID NO 4704

<400> SEQUENCE: 4704

000

<210> SEQ ID NO 4705

<400> SEQUENCE: 4705

000

<210> SEQ ID NO 4706

<400> SEQUENCE: 4706

000

<210> SEQ ID NO 4707

<400> SEQUENCE: 4707

000

<210> SEQ ID NO 4708

<400> SEQUENCE: 4708

000

<210> SEQ ID NO 4709

<400> SEQUENCE: 4709

000

<210> SEQ ID NO 4710

<400> SEQUENCE: 4710

000

<210> SEQ ID NO 4711

<400> SEQUENCE: 4711

000

<210> SEQ ID NO 4712

<400> SEQUENCE: 4712

000

<210> SEQ ID NO 4713

<400> SEQUENCE: 4713

000

<210> SEQ ID NO 4714

<400> SEQUENCE: 4714

000

<210> SEQ ID NO 4715

<400> SEQUENCE: 4715

000

<210> SEQ ID NO 4716

<400> SEQUENCE: 4716

000

<210> SEQ ID NO 4717

<400> SEQUENCE: 4717

000

<210> SEQ ID NO 4718

<400> SEQUENCE: 4718

000

<210> SEQ ID NO 4719

<400> SEQUENCE: 4719

000

<210> SEQ ID NO 4720

<400> SEQUENCE: 4720

000

<210> SEQ ID NO 4721

<400> SEQUENCE: 4721

000

<210> SEQ ID NO 4722

<400> SEQUENCE: 4722

000

<210> SEQ ID NO 4723

<400> SEQUENCE: 4723

000

<210> SEQ ID NO 4724

<400> SEQUENCE: 4724

000

<210> SEQ ID NO 4725

<400> SEQUENCE: 4725

000

<210> SEQ ID NO 4726

<400> SEQUENCE: 4726

000

<210> SEQ ID NO 4727

<400> SEQUENCE: 4727

000

<210> SEQ ID NO 4728

<400> SEQUENCE: 4728

000

<210> SEQ ID NO 4729

<400> SEQUENCE: 4729

000

<210> SEQ ID NO 4730

<400> SEQUENCE: 4730

000

<210> SEQ ID NO 4731

<400> SEQUENCE: 4731

000

<210> SEQ ID NO 4732

<400> SEQUENCE: 4732

000

<210> SEQ ID NO 4733

<400> SEQUENCE: 4733

000

<210> SEQ ID NO 4734

<400> SEQUENCE: 4734

000

<210> SEQ ID NO 4735

<400> SEQUENCE: 4735

000

<210> SEQ ID NO 4736

<400> SEQUENCE: 4736

000

<210> SEQ ID NO 4737

<400> SEQUENCE: 4737

000

<210> SEQ ID NO 4738

<400> SEQUENCE: 4738

000

<210> SEQ ID NO 4739

<400> SEQUENCE: 4739

000

<210> SEQ ID NO 4740

<400> SEQUENCE: 4740

000

<210> SEQ ID NO 4741

<400> SEQUENCE: 4741

000

<210> SEQ ID NO 4742

<400> SEQUENCE: 4742

000

<210> SEQ ID NO 4743

<400> SEQUENCE: 4743

000

<210> SEQ ID NO 4744

<400> SEQUENCE: 4744

000

<210> SEQ ID NO 4745

<400> SEQUENCE: 4745

000

<210> SEQ ID NO 4746

<400> SEQUENCE: 4746

000

<210> SEQ ID NO 4747

<400> SEQUENCE: 4747

000

<210> SEQ ID NO 4748

<400> SEQUENCE: 4748

000

<210> SEQ ID NO 4749

<400> SEQUENCE: 4749

000

<210> SEQ ID NO 4750

<400> SEQUENCE: 4750

000

<210> SEQ ID NO 4751

<400> SEQUENCE: 4751

000

<210> SEQ ID NO 4752

<400> SEQUENCE: 4752

000

<210> SEQ ID NO 4753

<400> SEQUENCE: 4753

000

<210> SEQ ID NO 4754

<400> SEQUENCE: 4754

000

-continued

<210> SEQ ID NO 4755

<400> SEQUENCE: 4755

000

<210> SEQ ID NO 4756

<400> SEQUENCE: 4756

000

<210> SEQ ID NO 4757

<400> SEQUENCE: 4757

000

<210> SEQ ID NO 4758

<400> SEQUENCE: 4758

000

<210> SEQ ID NO 4759

<400> SEQUENCE: 4759

000

<210> SEQ ID NO 4760

<400> SEQUENCE: 4760

000

<210> SEQ ID NO 4761

<400> SEQUENCE: 4761

000

<210> SEQ ID NO 4762

<400> SEQUENCE: 4762

000

<210> SEQ ID NO 4763

<400> SEQUENCE: 4763

000

<210> SEQ ID NO 4764

<400> SEQUENCE: 4764

000

<210> SEQ ID NO 4765

<400> SEQUENCE: 4765

000

<210> SEQ ID NO 4766

<400> SEQUENCE: 4766

000

<210> SEQ ID NO 4767

<400> SEQUENCE: 4767

000

<210> SEQ ID NO 4768

<400> SEQUENCE: 4768

000

<210> SEQ ID NO 4769

<400> SEQUENCE: 4769

000

<210> SEQ ID NO 4770

<400> SEQUENCE: 4770

000

<210> SEQ ID NO 4771

<400> SEQUENCE: 4771

000

<210> SEQ ID NO 4772

<400> SEQUENCE: 4772

000

<210> SEQ ID NO 4773

<400> SEQUENCE: 4773

000

<210> SEQ ID NO 4774

<400> SEQUENCE: 4774

000

<210> SEQ ID NO 4775

<400> SEQUENCE: 4775

000

<210> SEQ ID NO 4776

<400> SEQUENCE: 4776

000

<210> SEQ ID NO 4777

<400> SEQUENCE: 4777

000

<210> SEQ ID NO 4778

<400> SEQUENCE: 4778

000

<210> SEQ ID NO 4779

<400> SEQUENCE: 4779

000

<210> SEQ ID NO 4780

<400> SEQUENCE: 4780

000

<210> SEQ ID NO 4781

<400> SEQUENCE: 4781

000

<210> SEQ ID NO 4782

<400> SEQUENCE: 4782

000

<210> SEQ ID NO 4783

<400> SEQUENCE: 4783

000

<210> SEQ ID NO 4784

<400> SEQUENCE: 4784

000

<210> SEQ ID NO 4785

<400> SEQUENCE: 4785

000

<210> SEQ ID NO 4786

<400> SEQUENCE: 4786

000

<210> SEQ ID NO 4787

<400> SEQUENCE: 4787

000

<210> SEQ ID NO 4788

<400> SEQUENCE: 4788

000

<210> SEQ ID NO 4789

<400> SEQUENCE: 4789

000

<210> SEQ ID NO 4790

<400> SEQUENCE: 4790

000

<210> SEQ ID NO 4791

<400> SEQUENCE: 4791

000

<210> SEQ ID NO 4792

<400> SEQUENCE: 4792

000

<210> SEQ ID NO 4793

<400> SEQUENCE: 4793

000

<210> SEQ ID NO 4794

<400> SEQUENCE: 4794

000

<210> SEQ ID NO 4795

<400> SEQUENCE: 4795

000

<210> SEQ ID NO 4796

<400> SEQUENCE: 4796

000

<210> SEQ ID NO 4797

<400> SEQUENCE: 4797

000

<210> SEQ ID NO 4798

<400> SEQUENCE: 4798

000

<210> SEQ ID NO 4799

<400> SEQUENCE: 4799

000

<210> SEQ ID NO 4800

<400> SEQUENCE: 4800

000

<210> SEQ ID NO 4801

<400> SEQUENCE: 4801

000

<210> SEQ ID NO 4802

<400> SEQUENCE: 4802

000

<210> SEQ ID NO 4803

<400> SEQUENCE: 4803

000

<210> SEQ ID NO 4804

<400> SEQUENCE: 4804

000

<210> SEQ ID NO 4805

<400> SEQUENCE: 4805

000

<210> SEQ ID NO 4806

<400> SEQUENCE: 4806

000

<210> SEQ ID NO 4807

<400> SEQUENCE: 4807

000

<210> SEQ ID NO 4808

<400> SEQUENCE: 4808

000

<210> SEQ ID NO 4809

<400> SEQUENCE: 4809

000

<210> SEQ ID NO 4810

<400> SEQUENCE: 4810

000

<210> SEQ ID NO 4811

<400> SEQUENCE: 4811

000

<210> SEQ ID NO 4812

<400> SEQUENCE: 4812

000

<210> SEQ ID NO 4813

<400> SEQUENCE: 4813

000

<210> SEQ ID NO 4814

<400> SEQUENCE: 4814

000

<210> SEQ ID NO 4815

<400> SEQUENCE: 4815

000

<210> SEQ ID NO 4816

<400> SEQUENCE: 4816

000

<210> SEQ ID NO 4817

<400> SEQUENCE: 4817

000

<210> SEQ ID NO 4818

<400> SEQUENCE: 4818

000

<210> SEQ ID NO 4819

<400> SEQUENCE: 4819

000

<210> SEQ ID NO 4820

<400> SEQUENCE: 4820

000

<210> SEQ ID NO 4821

<400> SEQUENCE: 4821

000

<210> SEQ ID NO 4822

<400> SEQUENCE: 4822

000

<210> SEQ ID NO 4823

<400> SEQUENCE: 4823

000

<210> SEQ ID NO 4824

<400> SEQUENCE: 4824

000

<210> SEQ ID NO 4825

<400> SEQUENCE: 4825

000

<210> SEQ ID NO 4826

<400> SEQUENCE: 4826

000

<210> SEQ ID NO 4827

<400> SEQUENCE: 4827

000

<210> SEQ ID NO 4828

<400> SEQUENCE: 4828

000

<210> SEQ ID NO 4829

<400> SEQUENCE: 4829

000

<210> SEQ ID NO 4830

<400> SEQUENCE: 4830

000

<210> SEQ ID NO 4831

<400> SEQUENCE: 4831

000

<210> SEQ ID NO 4832

<400> SEQUENCE: 4832

000

<210> SEQ ID NO 4833

<400> SEQUENCE: 4833

000

<210> SEQ ID NO 4834

<400> SEQUENCE: 4834

000

<210> SEQ ID NO 4835

<400> SEQUENCE: 4835

000

<210> SEQ ID NO 4836

<400> SEQUENCE: 4836

000

<210> SEQ ID NO 4837

<400> SEQUENCE: 4837

000

<210> SEQ ID NO 4838

<400> SEQUENCE: 4838

000

<210> SEQ ID NO 4839

<400> SEQUENCE: 4839

000

<210> SEQ ID NO 4840

<400> SEQUENCE: 4840

000

<210> SEQ ID NO 4841

<400> SEQUENCE: 4841

000

<210> SEQ ID NO 4842

<400> SEQUENCE: 4842

000

<210> SEQ ID NO 4843

<400> SEQUENCE: 4843

000

<210> SEQ ID NO 4844

<400> SEQUENCE: 4844

000

<210> SEQ ID NO 4845

<400> SEQUENCE: 4845

000

<210> SEQ ID NO 4846

<400> SEQUENCE: 4846

000

<210> SEQ ID NO 4847

<400> SEQUENCE: 4847

000

<210> SEQ ID NO 4848

<400> SEQUENCE: 4848

000

<210> SEQ ID NO 4849

<400> SEQUENCE: 4849

000

<210> SEQ ID NO 4850

<400> SEQUENCE: 4850

000

<210> SEQ ID NO 4851

<400> SEQUENCE: 4851

000

<210> SEQ ID NO 4852

<400> SEQUENCE: 4852

000

<210> SEQ ID NO 4853

<400> SEQUENCE: 4853

000

<210> SEQ ID NO 4854

<400> SEQUENCE: 4854

000

<210> SEQ ID NO 4855

<400> SEQUENCE: 4855

000

<210> SEQ ID NO 4856

<400> SEQUENCE: 4856

-continued

000

<210> SEQ ID NO 4857
<400> SEQUENCE: 4857
000

<210> SEQ ID NO 4858
<400> SEQUENCE: 4858
000

<210> SEQ ID NO 4859
<400> SEQUENCE: 4859
000

<210> SEQ ID NO 4860
<400> SEQUENCE: 4860
000

<210> SEQ ID NO 4861
<400> SEQUENCE: 4861
000

<210> SEQ ID NO 4862
<400> SEQUENCE: 4862
000

<210> SEQ ID NO 4863
<400> SEQUENCE: 4863
000

<210> SEQ ID NO 4864
<400> SEQUENCE: 4864
000

<210> SEQ ID NO 4865
<400> SEQUENCE: 4865
000

<210> SEQ ID NO 4866
<400> SEQUENCE: 4866
000

<210> SEQ ID NO 4867
<400> SEQUENCE: 4867
000

<210> SEQ ID NO 4868

<400> SEQUENCE: 4868

000

<210> SEQ ID NO 4869

<400> SEQUENCE: 4869

000

<210> SEQ ID NO 4870

<400> SEQUENCE: 4870

000

<210> SEQ ID NO 4871

<400> SEQUENCE: 4871

000

<210> SEQ ID NO 4872

<400> SEQUENCE: 4872

000

<210> SEQ ID NO 4873

<400> SEQUENCE: 4873

000

<210> SEQ ID NO 4874

<400> SEQUENCE: 4874

000

<210> SEQ ID NO 4875

<400> SEQUENCE: 4875

000

<210> SEQ ID NO 4876

<400> SEQUENCE: 4876

000

<210> SEQ ID NO 4877

<400> SEQUENCE: 4877

000

<210> SEQ ID NO 4878

<400> SEQUENCE: 4878

000

<210> SEQ ID NO 4879

<400> SEQUENCE: 4879

000

<210> SEQ ID NO 4880

<400> SEQUENCE: 4880

000

<210> SEQ ID NO 4881

<400> SEQUENCE: 4881

000

<210> SEQ ID NO 4882

<400> SEQUENCE: 4882

000

<210> SEQ ID NO 4883

<400> SEQUENCE: 4883

000

<210> SEQ ID NO 4884

<400> SEQUENCE: 4884

000

<210> SEQ ID NO 4885

<400> SEQUENCE: 4885

000

<210> SEQ ID NO 4886

<400> SEQUENCE: 4886

000

<210> SEQ ID NO 4887

<400> SEQUENCE: 4887

000

<210> SEQ ID NO 4888

<400> SEQUENCE: 4888

000

<210> SEQ ID NO 4889

<400> SEQUENCE: 4889

000

<210> SEQ ID NO 4890

<400> SEQUENCE: 4890

000

<210> SEQ ID NO 4891

<400> SEQUENCE: 4891

000

<210> SEQ ID NO 4892

<400> SEQUENCE: 4892

000

<210> SEQ ID NO 4893

<400> SEQUENCE: 4893

000

<210> SEQ ID NO 4894

<400> SEQUENCE: 4894

000

<210> SEQ ID NO 4895

<400> SEQUENCE: 4895

000

<210> SEQ ID NO 4896

<400> SEQUENCE: 4896

000

<210> SEQ ID NO 4897

<400> SEQUENCE: 4897

000

<210> SEQ ID NO 4898

<400> SEQUENCE: 4898

000

<210> SEQ ID NO 4899

<400> SEQUENCE: 4899

000

<210> SEQ ID NO 4900

<400> SEQUENCE: 4900

000

<210> SEQ ID NO 4901

<400> SEQUENCE: 4901

000

<210> SEQ ID NO 4902

<400> SEQUENCE: 4902

000

<210> SEQ ID NO 4903

<400> SEQUENCE: 4903

000

<210> SEQ ID NO 4904

<400> SEQUENCE: 4904

000

<210> SEQ ID NO 4905

<400> SEQUENCE: 4905

000

<210> SEQ ID NO 4906

<400> SEQUENCE: 4906

000

<210> SEQ ID NO 4907

<400> SEQUENCE: 4907

000

<210> SEQ ID NO 4908

<400> SEQUENCE: 4908

000

<210> SEQ ID NO 4909

<400> SEQUENCE: 4909

000

<210> SEQ ID NO 4910

<400> SEQUENCE: 4910

000

<210> SEQ ID NO 4911

<400> SEQUENCE: 4911

000

<210> SEQ ID NO 4912

<400> SEQUENCE: 4912

000

<210> SEQ ID NO 4913

<400> SEQUENCE: 4913

000

<210> SEQ ID NO 4914

<400> SEQUENCE: 4914

000

<210> SEQ ID NO 4915

<400> SEQUENCE: 4915

000

<210> SEQ ID NO 4916

<400> SEQUENCE: 4916

000

<210> SEQ ID NO 4917

<400> SEQUENCE: 4917

000

<210> SEQ ID NO 4918

<400> SEQUENCE: 4918

000

<210> SEQ ID NO 4919

<400> SEQUENCE: 4919

000

<210> SEQ ID NO 4920

<400> SEQUENCE: 4920

000

<210> SEQ ID NO 4921

<400> SEQUENCE: 4921

000

<210> SEQ ID NO 4922

<400> SEQUENCE: 4922

000

<210> SEQ ID NO 4923

<400> SEQUENCE: 4923

000

<210> SEQ ID NO 4924

<400> SEQUENCE: 4924

000

<210> SEQ ID NO 4925

<400> SEQUENCE: 4925

000

<210> SEQ ID NO 4926

<400> SEQUENCE: 4926

000

<210> SEQ ID NO 4927

<400> SEQUENCE: 4927

000

<210> SEQ ID NO 4928

<400> SEQUENCE: 4928

000

<210> SEQ ID NO 4929

<400> SEQUENCE: 4929

000

<210> SEQ ID NO 4930

<400> SEQUENCE: 4930

000

<210> SEQ ID NO 4931

<400> SEQUENCE: 4931

000

<210> SEQ ID NO 4932

<400> SEQUENCE: 4932

000

<210> SEQ ID NO 4933

<400> SEQUENCE: 4933

000

<210> SEQ ID NO 4934

<400> SEQUENCE: 4934

000

<210> SEQ ID NO 4935

<400> SEQUENCE: 4935

000

<210> SEQ ID NO 4936

<400> SEQUENCE: 4936

000

<210> SEQ ID NO 4937

<400> SEQUENCE: 4937

000

<210> SEQ ID NO 4938

<400> SEQUENCE: 4938

000

<210> SEQ ID NO 4939

<400> SEQUENCE: 4939

000

<210> SEQ ID NO 4940

<400> SEQUENCE: 4940

000

<210> SEQ ID NO 4941

<400> SEQUENCE: 4941

000

<210> SEQ ID NO 4942

<400> SEQUENCE: 4942

000

<210> SEQ ID NO 4943

<400> SEQUENCE: 4943

000

<210> SEQ ID NO 4944

<400> SEQUENCE: 4944

000

<210> SEQ ID NO 4945

<400> SEQUENCE: 4945

000

<210> SEQ ID NO 4946

<400> SEQUENCE: 4946

000

<210> SEQ ID NO 4947

<400> SEQUENCE: 4947

000

<210> SEQ ID NO 4948

<400> SEQUENCE: 4948

000

<210> SEQ ID NO 4949

<400> SEQUENCE: 4949

000

<210> SEQ ID NO 4950

<400> SEQUENCE: 4950

000

<210> SEQ ID NO 4951

<400> SEQUENCE: 4951

000

<210> SEQ ID NO 4952

<400> SEQUENCE: 4952

000

<210> SEQ ID NO 4953

<400> SEQUENCE: 4953

000

<210> SEQ ID NO 4954

<400> SEQUENCE: 4954

000

<210> SEQ ID NO 4955

<400> SEQUENCE: 4955

000

<210> SEQ ID NO 4956

<400> SEQUENCE: 4956

000

<210> SEQ ID NO 4957

<400> SEQUENCE: 4957

000

<210> SEQ ID NO 4958

<400> SEQUENCE: 4958

000

<210> SEQ ID NO 4959

<400> SEQUENCE: 4959

000

<210> SEQ ID NO 4960

<400> SEQUENCE: 4960

000

<210> SEQ ID NO 4961

<400> SEQUENCE: 4961

000

<210> SEQ ID NO 4962

<400> SEQUENCE: 4962

000

<210> SEQ ID NO 4963

<400> SEQUENCE: 4963

000

<210> SEQ ID NO 4964

<400> SEQUENCE: 4964

000

<210> SEQ ID NO 4965

<400> SEQUENCE: 4965

000

<210> SEQ ID NO 4966

<400> SEQUENCE: 4966

000

<210> SEQ ID NO 4967

<400> SEQUENCE: 4967

000

<210> SEQ ID NO 4968

<400> SEQUENCE: 4968

000

<210> SEQ ID NO 4969

<400> SEQUENCE: 4969

000

<210> SEQ ID NO 4970

<400> SEQUENCE: 4970

000

<210> SEQ ID NO 4971

<400> SEQUENCE: 4971

000

<210> SEQ ID NO 4972

<400> SEQUENCE: 4972

000

<210> SEQ ID NO 4973

<400> SEQUENCE: 4973

000

<210> SEQ ID NO 4974

<400> SEQUENCE: 4974

000

<210> SEQ ID NO 4975

<400> SEQUENCE: 4975

000

<210> SEQ ID NO 4976

<400> SEQUENCE: 4976

000

<210> SEQ ID NO 4977

<400> SEQUENCE: 4977

000

<210> SEQ ID NO 4978

<400> SEQUENCE: 4978

000

<210> SEQ ID NO 4979

<400> SEQUENCE: 4979

000

<210> SEQ ID NO 4980

<400> SEQUENCE: 4980

000

<210> SEQ ID NO 4981

<400> SEQUENCE: 4981

000

<210> SEQ ID NO 4982

<400> SEQUENCE: 4982

000

<210> SEQ ID NO 4983

<400> SEQUENCE: 4983

000

<210> SEQ ID NO 4984

<400> SEQUENCE: 4984

000

<210> SEQ ID NO 4985

<400> SEQUENCE: 4985

000

<210> SEQ ID NO 4986

<400> SEQUENCE: 4986

000

<210> SEQ ID NO 4987

<400> SEQUENCE: 4987

000

<210> SEQ ID NO 4988

<400> SEQUENCE: 4988

000

<210> SEQ ID NO 4989

<400> SEQUENCE: 4989

000

<210> SEQ ID NO 4990

<400> SEQUENCE: 4990

000

<210> SEQ ID NO 4991

<400> SEQUENCE: 4991

000

<210> SEQ ID NO 4992

<400> SEQUENCE: 4992

000

<210> SEQ ID NO 4993

<400> SEQUENCE: 4993

000

<210> SEQ ID NO 4994

<400> SEQUENCE: 4994

000

<210> SEQ ID NO 4995

<400> SEQUENCE: 4995

000

<210> SEQ ID NO 4996

<400> SEQUENCE: 4996

000

<210> SEQ ID NO 4997

<400> SEQUENCE: 4997

000

<210> SEQ ID NO 4998

<400> SEQUENCE: 4998

000

<210> SEQ ID NO 4999

<400> SEQUENCE: 4999

000

<210> SEQ ID NO 5000

<400> SEQUENCE: 5000

000

<210> SEQ ID NO 5001

<400> SEQUENCE: 5001

000

<210> SEQ ID NO 5002

<400> SEQUENCE: 5002

000

<210> SEQ ID NO 5003

<400> SEQUENCE: 5003

000

<210> SEQ ID NO 5004

<400> SEQUENCE: 5004

000

<210> SEQ ID NO 5005

<400> SEQUENCE: 5005

000

<210> SEQ ID NO 5006

<400> SEQUENCE: 5006

000

<210> SEQ ID NO 5007

<400> SEQUENCE: 5007

000

<210> SEQ ID NO 5008

<400> SEQUENCE: 5008

000

<210> SEQ ID NO 5009

<400> SEQUENCE: 5009

000

<210> SEQ ID NO 5010

<400> SEQUENCE: 5010

000

<210> SEQ ID NO 5011

<400> SEQUENCE: 5011

000

<210> SEQ ID NO 5012

<400> SEQUENCE: 5012

000

<210> SEQ ID NO 5013

<400> SEQUENCE: 5013

000

<210> SEQ ID NO 5014

<400> SEQUENCE: 5014

000

<210> SEQ ID NO 5015
<400> SEQUENCE: 5015
000

<210> SEQ ID NO 5016
<400> SEQUENCE: 5016
000

<210> SEQ ID NO 5017
<400> SEQUENCE: 5017
000

<210> SEQ ID NO 5018
<400> SEQUENCE: 5018
000

<210> SEQ ID NO 5019
<400> SEQUENCE: 5019
000

<210> SEQ ID NO 5020
<400> SEQUENCE: 5020
000

<210> SEQ ID NO 5021
<400> SEQUENCE: 5021
000

<210> SEQ ID NO 5022
<400> SEQUENCE: 5022
000

<210> SEQ ID NO 5023
<400> SEQUENCE: 5023
000

<210> SEQ ID NO 5024
<400> SEQUENCE: 5024
000

<210> SEQ ID NO 5025
<400> SEQUENCE: 5025
000

<210> SEQ ID NO 5026

<400> SEQUENCE: 5026

000

<210> SEQ ID NO 5027

<400> SEQUENCE: 5027

000

<210> SEQ ID NO 5028

<400> SEQUENCE: 5028

000

<210> SEQ ID NO 5029

<400> SEQUENCE: 5029

000

<210> SEQ ID NO 5030

<400> SEQUENCE: 5030

000

<210> SEQ ID NO 5031

<400> SEQUENCE: 5031

000

<210> SEQ ID NO 5032

<400> SEQUENCE: 5032

000

<210> SEQ ID NO 5033

<400> SEQUENCE: 5033

000

<210> SEQ ID NO 5034

<400> SEQUENCE: 5034

000

<210> SEQ ID NO 5035

<400> SEQUENCE: 5035

000

<210> SEQ ID NO 5036
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 5036
ggccgctgca catcgtcctg 20

<210> SEQ ID NO 5037
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5037
gcggggtctg ccatgggtcg 20

<210> SEQ ID NO 5038
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5038
agttgctcat gcaggatttc 20

<210> SEQ ID NO 5039
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5039
aagtcatggt aggggagctt 20

<210> SEQ ID NO 5040
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5040
agtcatggta ggggagcttg 20

<210> SEQ ID NO 5041
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5041
attgcactca tcagagctac 20

<210> SEQ ID NO 5042
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5042
cctagagtga agagattcat 20

<210> SEQ ID NO 5043
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5043
ccaatgaatc tcttcactct 20

<210> SEQ ID NO 5044
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5044
aaagtcatgg taggggagct 20

<210> SEQ ID NO 5045
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5045
gtgagcaatc ccccgggcga 20

<210> SEQ ID NO 5046
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5046
gtcgttcttc acgaggatat 20

<210> SEQ ID NO 5047
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5047
gccgcgtcag gtactcctgt 20

<210> SEQ ID NO 5048
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5048
gacgcggcat gtcatcagct 20

<210> SEQ ID NO 5049
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5049
gcttctgctg ccggttaacg 20

<210> SEQ ID NO 5050
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5050
gtggatgacc tggctaacag 20

<210> SEQ ID NO 5051
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5051
gtgatcacac tccatgtggg 20

<210> SEQ ID NO 5052
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5052
gcccattgag ctggacaccc 20

<210> SEQ ID NO 5053
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5053
gcggtcatct tccaggatga 20

<210> SEQ ID NO 5054
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5054
gggagctgcc cagcttgcgc 20

<210> SEQ ID NO 5055
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5055
gttgatgttg ttggcacacg 20

<210> SEQ ID NO 5056
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5056
ggcatcttgg gcctcccaca 20

<210> SEQ ID NO 5057
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5057
gcggcatgtc atcagctggg 20

<210> SEQ ID NO 5058
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5058
gctcctcagc cgtcaggaac 20

<210> SEQ ID NO 5059

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5059
gctggtgtta tattctgatg 20

<210> SEQ ID NO 5060
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5060
ccgacttctg aacgtgcggt 20

<210> SEQ ID NO 5061
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5061
tgctggcgat acgcgtccac 20

<210> SEQ ID NO 5062
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5062
cccgacttct gaacgtgcgg 20

<210> SEQ ID NO 5063
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5063
ccaccgcacg ttcagaagtc 20

<210> SEQ ID NO 5064
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5064
tcacccgact tctgaacgtg 20

<210> SEQ ID NO 5065
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5065
cccaccgcac gttcagaagt 20

<210> SEQ ID NO 5066
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5066
cgagcagcgg ggtctgccat 20

<210> SEQ ID NO 5067
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5067
acgagcagcg gggtctgcca 20

<210> SEQ ID NO 5068
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5068
agcggggtct gccatgggtc 20

<210> SEQ ID NO 5069
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5069
cctgagcagc ccccgaccca 20

<210> SEQ ID NO 5070
<211> LENGTH: 20
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic oligonucleotide"

<400> SEQUENCE: 5070
aacgtgcggt gggatcgtgc 20

<210> SEQ ID NO 5071
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5071
ggacgatgtg cagcggccac 20

<210> SEQ ID NO 5072
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5072
gtccacagga cgatgtgcag 20

<210> SEQ ID NO 5073
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5073
catgggtcgg gggctgctca 20

<210> SEQ ID NO 5074
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5074
ccatgggtcg ggggctgctc 20

<210> SEQ ID NO 5075
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5075
cagcggggtc tgccatgggt 20

<210> SEQ ID NO 5076
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5076
atgggtcggg ggctgctcag 20

<210> SEQ ID NO 5077
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5077
cggggtctgc catgggtcgg 20

<210> SEQ ID NO 5078
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5078
aggaagtctg tgtggctgta 20

<210> SEQ ID NO 5079
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5079
ctccatctgt gagaagccac 20

<210> SEQ ID NO 5080
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5080
atgatagtca ctgacaacaa 20

<210> SEQ ID NO 5081
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5081
gatgctgcag ttgctcatgc 20

<210> SEQ ID NO 5082
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5082
acagccacac agacttcctg 20

<210> SEQ ID NO 5083
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5083
gaagccacag gaagtctgtg 20

<210> SEQ ID NO 5084
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5084
ttcctgtggc ttctcacaga 20

<210> SEQ ID NO 5085
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5085
ctgtggcttc tcacagatgg 20

<210> SEQ ID NO 5086
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5086
tcacaaaatt tacacagttg 20

<210> SEQ ID NO 5087
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5087
cccctaccat gactttattc 20

<210> SEQ ID NO 5088
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5088
ccagaataaa gtcatggtag 20

<210> SEQ ID NO 5089
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5089
gacaacatca tcttctcaga 20

<210> SEQ ID NO 5090
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5090
tccagaataa agtcatggta 20

<210> SEQ ID NO 5091
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5091
ggtaggggag cttggggtca 20

<210> SEQ ID NO 5092
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 5092
ttctccaaag tgcattatga 20

```
<210> SEQ ID NO 5093
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5093

catcttccag aataaagtca                                                20


<210> SEQ ID NO 5094
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5094

cacatgaaga aagtctcacc                                                20


<210> SEQ ID NO 5095
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5095

ttccagaata aagtcatggt                                                20


<210> SEQ ID NO 5096
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5096

ttttccttca taatgcactt                                                20


<210> SEQ ID NO 5097
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(10)
<223> OTHER INFORMATION: /note="This sequence may encompass 1-10
      nucleotides"

<400> SEQUENCE: 5097

aaaaaaaaaa                                                           10


<210> SEQ ID NO 5098
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="This sequence may encompass 10-20
      nucleotides"

<400> SEQUENCE: 5098

aaaaaaaaaa aaaaaaaaaa                                                   20


<210> SEQ ID NO 5099
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(200)
<223> OTHER INFORMATION: /note="This sequence may encompass 25-200
      nucleotides"

<400> SEQUENCE: 5099

aaaaaaaaaa aaaaaaaaaa aaaaaaaaaa aaaaaaaaaa aaaaaaaaaa aaaaaaaaaa       60

aaaaaaaaaa aaaaaaaaaa aaaaaaaaaa aaaaaaaaaa aaaaaaaaaa aaaaaaaaaa      120

aaaaaaaaaa aaaaaaaaaa aaaaaaaaaa aaaaaaaaaa aaaaaaaaaa aaaaaaaaaa      180

aaaaaaaaaa aaaaaaaaaa                                                  200


<210> SEQ ID NO 5100
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5100

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Pro
            20                  25                  30


<210> SEQ ID NO 5101
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5101

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Pro
        35
```

```
<210> SEQ ID NO 5102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5102

Gly Ser Ala Asp Asp Ala Lys Lys Asp Ala Ala Lys Lys Asp Gly Lys
1               5                   10                  15

Ser
```